(12) United States Patent
Wong et al.

(10) Patent No.: US 11,491,224 B2
(45) Date of Patent: Nov. 8, 2022

(54) BLADDER CANCER PHOTODYNAMIC THERAPEUTIC AGENTS WITH OFF-ON MAGNETIC RESONANCE IMAGING ENHANCEMENT

(71) Applicant: Hong Kong Baptist University, Hong Kong (CN)

(72) Inventors: Ka Leung Wong, Hong Kong (CN); Wai Kwok Wong, Hong Kong (CN); Ho Fai Chau, Hong Kong (CN)

(73) Assignee: Hong Kong Baptist University, Hong Kong (HK)

( * ) Notice: Subject to any disclaimer, the term of this patent is extended or adjusted under 35 U.S.C. 154(b) by 667 days.

(21) Appl. No.: 16/372,492

(22) Filed: Apr. 2, 2019

(65) Prior Publication Data

US 2019/0298832 A1    Oct. 3, 2019

Related U.S. Application Data

(60) Provisional application No. 62/652,302, filed on Apr. 3, 2018.

(51) Int. Cl.
| | | |
|---|---|---|
| A61K 9/00 | (2006.01) | |
| A61K 41/00 | (2020.01) | |
| A61K 33/244 | (2019.01) | |
| G01R 33/56 | (2006.01) | |
| C07F 5/00 | (2006.01) | |
| A61B 5/055 | (2006.01) | |
| A61P 35/00 | (2006.01) | |

(52) U.S. Cl.
CPC .......... *A61K 41/0076* (2013.01); *A61B 5/055* (2013.01); *A61K 33/244* (2019.01); *A61P 35/00* (2018.01); *C07F 5/003* (2013.01); *G01R 33/5601* (2013.01)

(58) Field of Classification Search
CPC ................................................ A61K 41/0076
See application file for complete search history.

(56) References Cited

U.S. PATENT DOCUMENTS 5,284,647 A * 2/1994 Niedballa ............ C07D 487/22
                                                    424/9.362
2016/0130284 A1    5/2016  Wong et al.

FOREIGN PATENT DOCUMENTS

CN        107109219 A      8/2017

OTHER PUBLICATIONS

International Search Report and Written Opinion of PCT application No. PCT/CN2019/081313 issued from the International Search Authority dated Jul. 4, 2019.
(Continued)

*Primary Examiner* — Paul W Dickinson
(74) *Attorney, Agent, or Firm* — Spruson & Ferguson (Hong Kong) Limited

(57) ABSTRACT

Provided herein are porphyrinato-lanthanide complexes useful as theranostic agents and methods of preparation and use thereof. The porphyrinato-lanthanide complexes are useful in the treatment and imaging of cancer.

19 Claims, 90 Drawing Sheets

Specification includes a Sequence Listing.

(56) References Cited

OTHER PUBLICATIONS

Zhang J.X. et al. A potential water-soluble ytterbium-based porphyrin-cyclen dual bio-probe for Golgi apparatus imaging and photodynamic therapy. Chem Commun. Aug. 9, 2012, vol. 48, pp. 9646-9648.
Zhou Y. et al. avß3-Isoform specific erbium complexes highly specific for bladder cancer imaging and photodynamic therapy. Chem Commun. Dec. 6, 2016, vol. 53, pp. 5557-5560.
Zhang et al. In vivo selective cancer-tracking gadolinium eradicator as new-generation photodynamic therapy against PNAS 01, Dec. 2014, No. 51, vol. 111, pp. E5492-E597.

* cited by examiner

D

| Photo-IC$_{50}$/μM (Dark-IC$_{50}$/μM) Photodynamic therapeutic index | T24 | HeLa | MRC5 |
|---|---|---|---|
| NLPor-Gd-L$_1$R$_1$ | 31 (902) 29.1 | 302 (2065) 6.8 | 406 (2124) 5.2 |
| NLPor-Gd-L$_1$R$_2$ | 27 (1061) 39 | 236 (3221) 13.6 | 541 (2794) 5.2 |
| NLPor-Gd-L$_1$R$_3$ | 8.2 (1632) 199 | 463 (2762) 6.0 | 442 (1842) 4.17 |

FIG. 5 (Continued)

| Photo-IC$_{50}$/μM (Dark-IC$_{50}$/μM) Photodynamic Therapeutic Index | HeLa | HK1 | MRC5 |
|---|---|---|---|
| Zn-NLPorB$_2$-Cyc-Gd-L$_2$A$_1$ | 0.66 (270) 409 | 0.85 (266) 313 | 0.88 (226) 256 |
| Zn-NLPorB$_2$-Cyc-Gd-L$_2$A$_2$ | 0.25 (337) 1348 | 0.71 (478) 673 | 0.45 (231) 512 |
| ALA | 264 (257) 1.03 | 250 (494) 1.98 | 261 (287) 0.91 |

FIG. 8

NLPor-Gd-L₁Rₙ  n = 3 : RRrKcGRLKEKKC

| Photo-IC$_{50}$/μM (Dark-IC$_{50}$/μM) Photodynamic therapeutic index | T24 | HeLa | MRC5 |
|---|---|---|---|
| NLPor-Gd-L$_1$R$_1$ | 31 (902) 29.1 | 302 (2065) 6.8 | 406 (2124) 5.2 |
| NLPor-Gd-L$_1$R$_2$ | 27 (1061) 39 | 236 (3221) 13.6 | 541 (2794) 5.2 |
| NLPor-Gd-L$_1$R$_3$ | 8.2 (1632) 199 | 463 (2762) 6.0 | 442 (1842) 4.17 |

FIG. 19 a

| Photo-IC$_{50}$/mM (Dark-IC$_{50}$/mM) Photodynamic therapeutic index | T24 | HeLa | MRC-5 |
|---|---|---|---|
| Er-R$_1$ | 38 (817) 21.5 | 271 (937) 3.5 | 489 (922) 1.9 |
| Yb-R$_1$ | 63 (1414) 22.4 | 287 (1297) 4.5 | 264 (1382) 5.23 |
| Er-R$_2$ | 35 (932) 22.6 | 392 (1184) 3.0 | 497 (1073) 2.2 |
| Yb-R$_2$ | 60 (1551) 25.9 | 499 (1422) 2.8 | 434 (1601) 3.7 |
| Er-R$_3$ | 31 (1044) 33.7 | 343 (1302) 3.8 | 345 (1127) 3.3 |
| Yb-R$_3$ | 56 (1766) 31.5 | 393 (1683) 4.3 | 473 (1884) 4.0 |
| ALA | 260 (929) 3.6 | 375 (1043) 2.8 | 744 (1547) 2.1 | b

FIG. 19 (Continued)

| Compound | Absorption($\lambda_{max}$)[nm] Log(ε[dm³·mol⁻¹·cm⁻¹])[a] | Emission($\lambda_{max}$)[nm] ($\Phi_{em}$)[b] | $\Phi_\Delta$[c] in PBS buffer by absorption | $\Phi_\Delta$[d] in CHCl₃ by emission |
|---|---|---|---|---|
| NLPor-Gd-L₁R₁ | 425(5.35), 554(4.07) | 608, 658, 720(0.016) | 0.39 | 0.47 |
| NLPor-Gd-L₁R₂ | 425(5.33), 554(4.14) | 608, 658, 720(0.017) | 0.39 | 0.47 |
| NLPor-Gd-L₁R₃ | 425(5.24), 554(4.08) | 608, 658, 720(0.017) | 0.40 | 0.48 |

FIG. 35

|  | Conc.[a] | $T_1(s)$[b] Slice 01 | $T_1(s)$[b] Slice 02 | $T_1(s)$ average[b] | $R_1(S^{-1})$[c] |
|---|---|---|---|---|---|
| Blank | 0.000 | 2.520 | 2.470 | 2.495 | 0.000 |
| GdDOTA | 1.000 | 0.168 | 0.170 | 0.169 | 5.522 |
|  | 0.750 | 0.206 | 0.207 | 0.207 | 4.442 |
|  | 0.500 | 0.300 | 0.302 | 0.301 | 2.919 |
|  | 0.250 | 0.536 | 0.534 | 0.535 | 1.468 |
| NLPor-Gd-L$_1$R$_3$ | 0.750 | 1.623 | 1.615 | 1.619 | 0.217 |
|  | 0.500 | 1.876 | 1.886 | 1.881 | 0.131 |
|  | 0.250 | 2.136 | 2.086 | 2.111 | 0.073 |
|  | 0.125 | 2.327 | 2.295 | 2.311 | 0.032 |

FIG. 36

| Time /min | 0.05% HCOOH in water /% | 0.05% HCOOH in MeOH /% |
|---|---|---|
| 0 | 50 | 50 |
| 5 | 20 | 80 |
| 15 | 10 | 90 |
| 20 | 0 | 100 |
| 30 | 20 | 80 |
| 35 | 50 | 50 |

FIG. 39

| Time /min | 0.05% HCOOH in water /% | 0.05% HCOOH in MeOH /% |
|---|---|---|
| 0 | 50 | 50 |
| 5 | 20 | 80 |
| 15 | 10 | 90 |
| 20 | 0 | 100 |
| 30 | 20 | 80 |
| 35 | 50 | 50 |

FIG. 45

| Compound | Absorption ($\lambda_{max}$) [nm] Log($\epsilon$[dm³mol⁻¹cm⁻¹]) | Emission ($\lambda_{max}$) | $\Phi_D$ in DCM | Photo-IC50/μM (Dark-IC50/μM) Photodynamic Therapeutic Index | | |
|---|---|---|---|---|---|---|
| | | | | HeLa | T24 | MRC5 |
| Zn-NLPorB₂-Cyc-L₂A₂ | 430 (2.17), 550 (1.00) | 650, 720 | 0.22 | 0.66 (270) 409 | 0.85 (266) 313 | 0.88 (226) 256 |
| Zn-NLPorB₂-Cyc-GdL₂A₂ | 430 (2.13), 550 (0.94) | 650, 720 | 0.21 | 0.25 (337) 1348 | 0.45 (478) 1062 | 0.71 (231) 330 |
| ALA | - | - | - | 204 (257) 1.28 | 250 (494) 1.98 | 259 (287) 1.11 |

FIG. 50 b

BLADDER CANCER PHOTODYNAMIC THERAPEUTIC AGENTS WITH OFF-ON MAGNETIC RESONANCE IMAGING ENHANCEMENT

CROSS-REFERENCE TO RELATED APPLICATIONS

This application claims the benefit of priority of U.S. Provisional Application No. 62/652,302, filed on Apr. 3, 2018, the contents of which are hereby incorporated by reference in their entirety for all purposes.

TECHNICAL FIELD

Provided herein are porphyrinato-lanthanide complexes useful as theranostic agents and methods of preparation and use thereof.

BACKGROUND

Despite photodynamic therapy (PDT) providing an efficient strategy in medical treatment, scientists are keen to progress from single-function PDT agents to more elaborate drugs. The recently introduced term 'theranostic' characterizes a new class of multifunctional compounds with both therapeutic and diagnostic functions. In particular, combination of PDT with magnetic resonance imaging (MRI) are promising developmental candidates, especially agents capable of two-photon excitation.

Porphyrin-based complexes are well known photosensitizers for use in PDT. Upon excitation, porphyrin-based complexes can undergo ground singlet state to excited triplet state electronic transitions by intersystem crossing. Cancer cell killing singlet oxygen ($^1O_2$) can be produced when the triplet excited state photosensitizer reacts with molecular oxygen present at the tumor site. Many porphyrin based photosensitizers have been reported with cancer cell killing properties. Nevertheless, spatial and temporal control of the photosensitizer still limit the use of porphyrin-based complexes for PDT. Moreover, there is a need for photosensitizers having reduced dark cytotoxicity, but high photo cytotoxicity, and good selectivity for cancer cells.

Magnetic Resonance imaging (MRI) is one of the most effective imaging techniques for early-stage disease diagnosis. It offers various advantages in the detection of tumors, such as the provision of high spatial resolution images and clear tissue contrast. Moreover, it is unnecessary to use harmful high energy radiation, which is another crucial advantage over other imaging methods, such as positron emission tomography (PET), single-photon emission computed tomography (SPECT) and X-ray computer tomography. The signal to noise ratio in MRI can be enhanced with the use of a contrast agent. Gadolinium-based contrast agent have been used in clinic for many decades. However, there are a very limited number of clinically approved gadolinium-based contrast agents that demonstrate high longitudinal relaxation time (T1 signal). Furthermore, there is a rising concern about the safety of gadolinium-based contrast agents. Accordingly, there is a need to develop safer and more effective gadolinium-based contrast agents, which can be administered at a lower dose.

Gadolinium-based bi-functional theranostic agents have attracted a good deal of attention. However, the balance between the dose of the gadolinium-based bi-functional theranostic agent for the imaging and therapeutic functions becomes an issue, because Gd(III)-based theranostic agents usually have a higher dose requirement for imaging than the dose required for therapeutic use of the theranostic agent.

The goal of minimizing therapeutic dose can be achieved by improving drug selectivity. Integrins are cell adhesion molecules consisting of dimeric non-covalently bound transmembrane alpha-v and beta-3 ($\alpha_V\beta_3$) sub-units. They act as receptors for various extracellular matrix proteins. Due to the overexpression of $\alpha_V\beta_3$-integrin in the neovasculature of bladder cancer, but not in the vessels of normal tissues, $\alpha_V\beta_3$-integrins have become attractive targets for both molecular imaging and PDT treatment of bladder cancer.

Diagnosis and local staging of bladder cancer is another important issue during anti-cancer treatment. MRI offers many advantages in providing high-resolution images for the accurate diagnosis of bladder cancer. In addition to multiplanar images, MRI is also capable of contrasting soft-tissues, which makes it a practical technique for monitoring bladder cancer, e.g., by clear differentiation between the wall layers of the bladder tissue. This technique has also been used to reveal intramural tumor invasion and extravesical extension of the tumor. Alongside this, the main disadvantage of conventional MRI contrast agents is the lack of targeting and, moreover, there is evidence that some previously commercially-available linear gadolinium-based MRI agents can induce adverse effects in patients with renal insufficiencies during the imaging process.

SUMMARY

Provided herein are porphyrinato-lanthanide metal complexes that can optionally be conjugated with a $\alpha_V\beta_3$ integrin-targeting peptides useful as imaging and/or therapeutic agents for cancer. The metal complexes provided herein can exhibit high T1 signal enhancement with T1 relaxivities, low dark cytotoxicity, high phototoxicity, and high photodynamic therapeutic index.

In a first aspect, provided herein is a metal complex comprising a compound of Formula I:

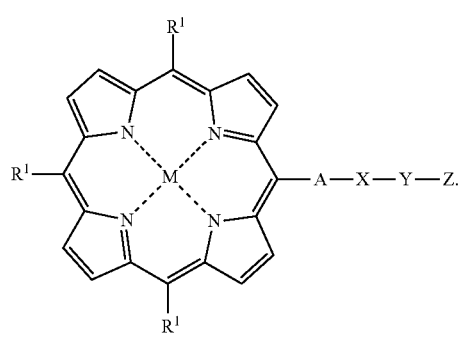

or a pharmaceutically acceptable salt thereof, wherein M is 2H or $Zn^{2+}$; or M has the structure:

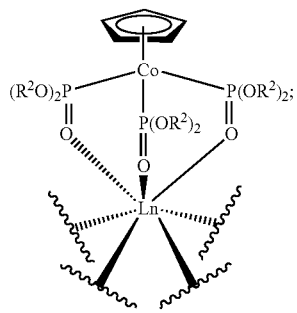

A is an optionally substituted phenyl;

X is absent,

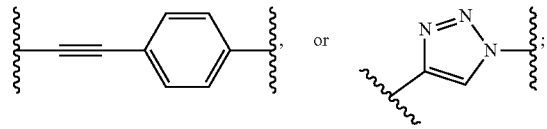 [SMILES: *C#Cc1ccc(*)cc1 ; *c1cn(*)nn1]

Y is —(CH₂)ₙ—, —(CH₂CH₂O)ₙCH₂—, —(CH₂CH₂O)ₙCH₂CH₂—, —(OCH₂CH₂O)ₙCH₂—, —(CH₂CH₂O)ₙCH₂CH₂—, —(CH₂CH₂O)ₙ—, —(OCH₂CH₂)ₙ—, or

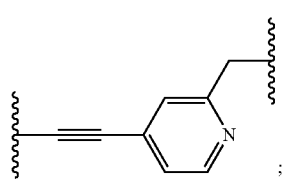 [SMILES: *C#Cc1ccnc(C*)c1]

Z is —(C=O)NHR³ or

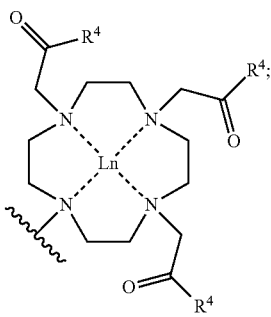

n is a whole number selected between 1-10;

Ln for each instance is independently a paramagnetic metal ion;

each R¹ is independently optionally substituted aryl;

each R² is independently alkyl;

R³ is SEQ ID NO:1, SEQ ID NO:2, or SEQ ID NO:3;

each R⁴ is independently O⁻, N(R⁵)₂, or NHR³; and each R⁵ is independently H or alkyl, with the proviso that at least one of M or Z comprises Ln.

In a first embodiment of the first aspect, provided herein is the metal complex of the first aspect, wherein Ln is selected from Gd(III).

In a second embodiment of the first aspect, provided herein is the metal complex of the first aspect, wherein M has the structure:

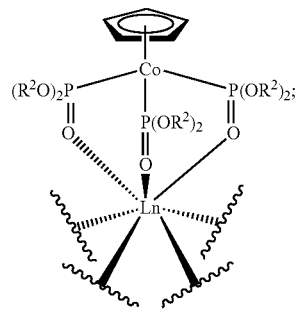

X is

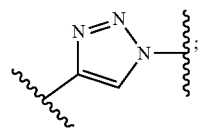 or 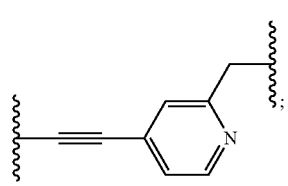 [SMILES: *C#Cc1ccnc(C*)c1]

Y is —(CH₂)ₙ—; —(CH₂CH₂O)ₙCH₂—; —(CH₂CH₂O)ₙ—; —(OCH₂CH₂)ₙ—; and

Z is —(C=O)NHR³; or

M is 2H or Zn²⁺; X is absent or

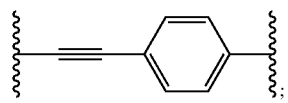

Y is —(OCH₂CH₂)ₙ—; or

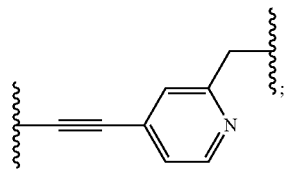

and Z is

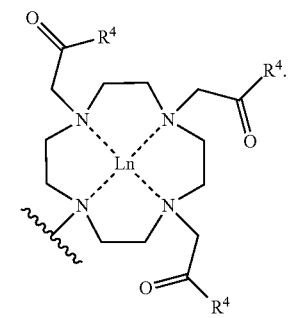

In a third embodiment of the first aspect, provided herein is the metal complex of the first aspect, wherein M has the structure:

X is

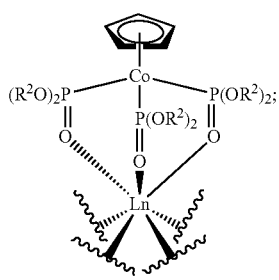

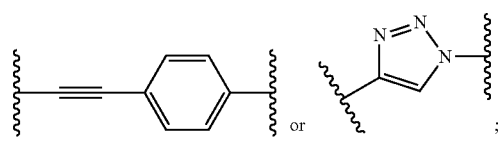 [SMILES: *C#Cc1ccc(*)cc1 ; *c1cn(*)nn1]

Y is —$(CH_2)_n$—; —$(CH_2CH_2O)_nCH_2$—; —$(CH_2CH_2O)_n$—; —$(OCH_2CH_2)_n$—; and Z is —$(C=O)NHR^3$.

In a fourth embodiment of the first aspect, provided herein is the metal complex of the third embodiment of the first aspect, wherein X is

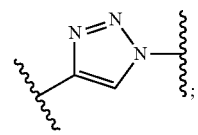 [SMILES: *c1cn(*)nn1]

Y is —$(CH_2CH_2O)_nCH_2$—; and $R^2 C_1$-$C_4$ alkyl.

In a fifth embodiment of the first aspect, provided herein is the metal complex of the third embodiment of the first aspect, wherein X is

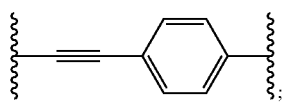

Y is —$(CH_2CH_2O)_n$—; and $R^2 C_1$-$C_4$ alkyl.

In a sixth embodiment of the first aspect, provided herein is the metal complex of the first aspect, wherein the compound of Formula I is selected from the group consisting of:

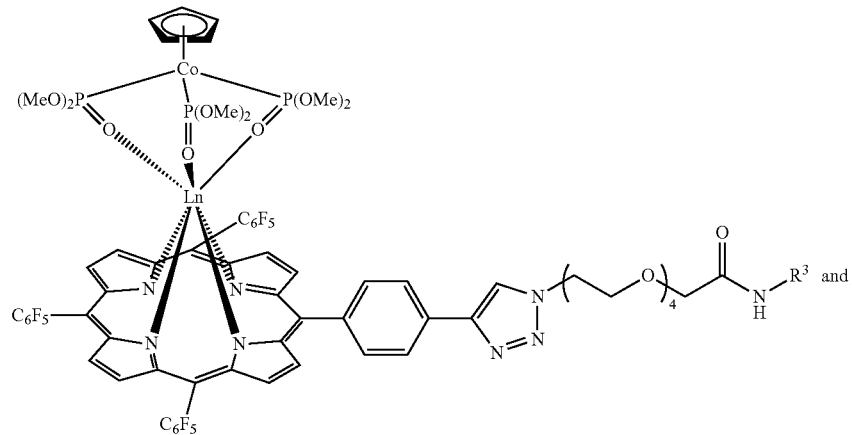

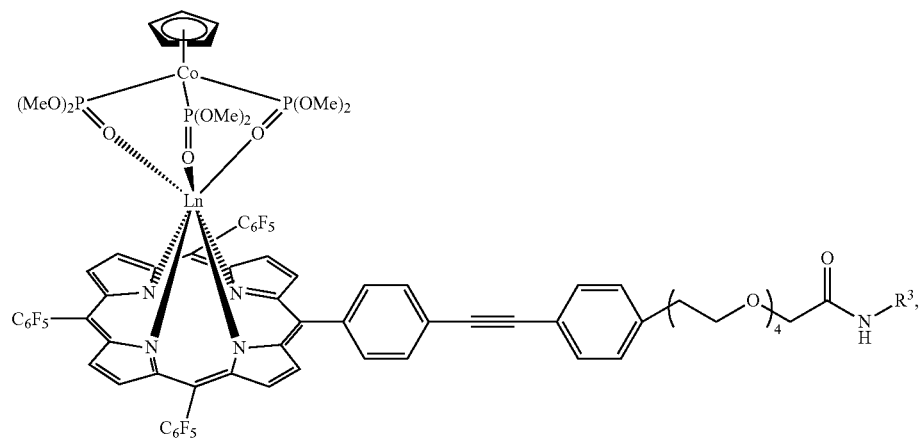

wherein Ln is Gd(III).

In a seventh embodiment of the first aspect, provided herein is the metal complex of the sixth embodiment of the first aspect, wherein M is 2H or Zn$^{2+}$; X is absent or

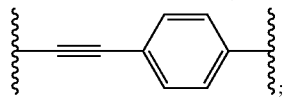 [SMILES: *C#Cc1ccc(*)cc1]

Y is —(OCH$_2$CH$_2$)$_n$—; or

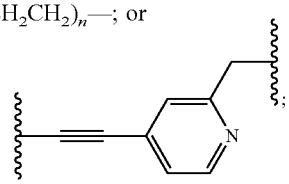

and Z is

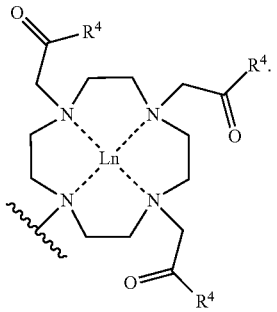

In an eighth embodiment of the first aspect, provided herein is the metal complex of the sixth embodiment of the seventh aspect, wherein X is absent; Y is

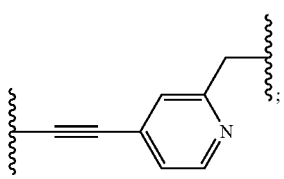

and R$^4$ is O— or NHR$^5$.

In an ninth embodiment of the first aspect, provided herein is the metal complex of the sixth embodiment of the seventh aspect, wherein X is absent; Y is —(OCH$_2$CH$_2$)$_n$—; two instance of R$^4$ are each N(R$^5$)$_2$; and one instance of R$^4$ is NHR$^3$.

In a tenth embodiment of the first aspect, provided herein is the metal complex of the first aspect, wherein the compound of Formula I is selected from the group consisting of:

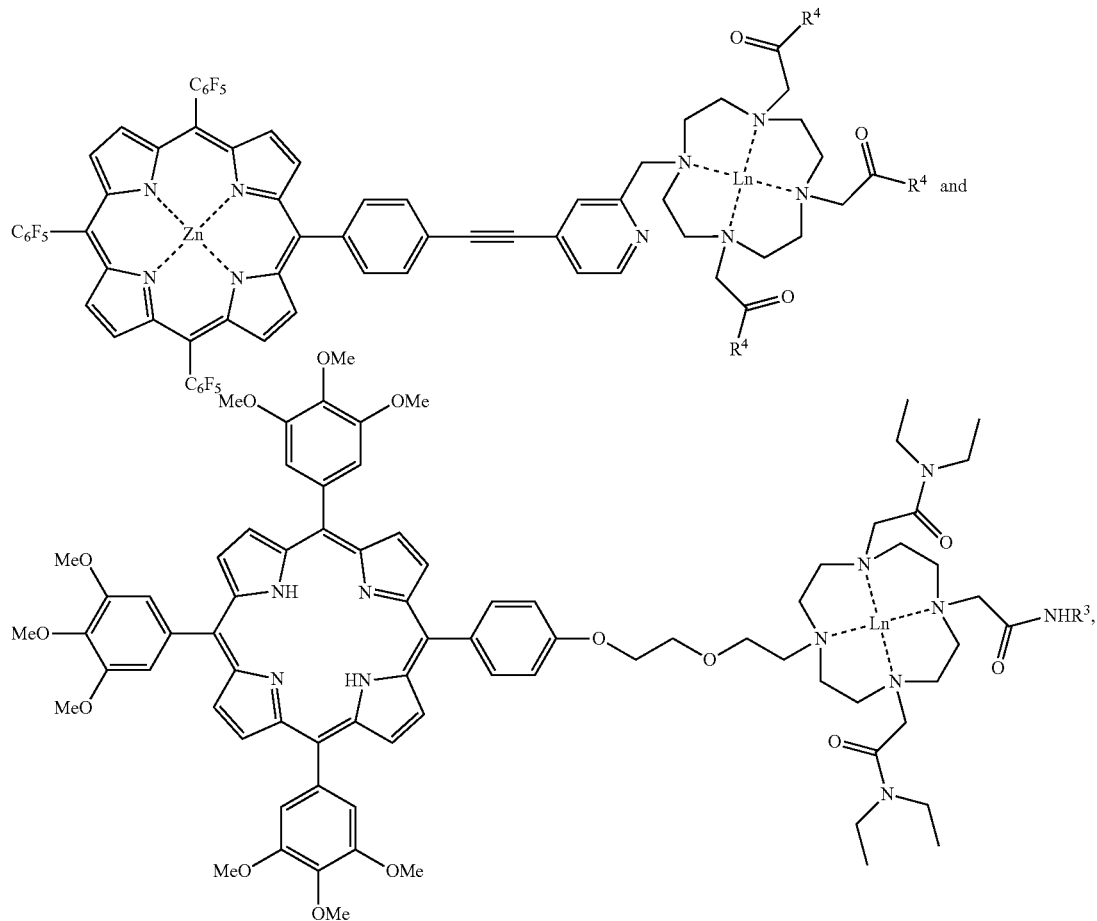

wherein Ln is Gd(III); and R$^4$ is O$^-$ or NH(tBu).

In a second aspect, provided herein is a pharmaceutical composition comprising the metal complex of the first aspect and at least one pharmaceutically acceptable excipient.

In a third aspect, provided herein is a method of imaging a subject by magnetic resonance imaging (MRI), the method comprising: administering a therapeutically effective amount of a metal complex of the first aspect to the subject; and imaging at least a portion of the subject by MRI.

In a first embodiment of the third aspect, provided herein is the method of the third aspect, wherein the metal complex is selected from the group consisting of:

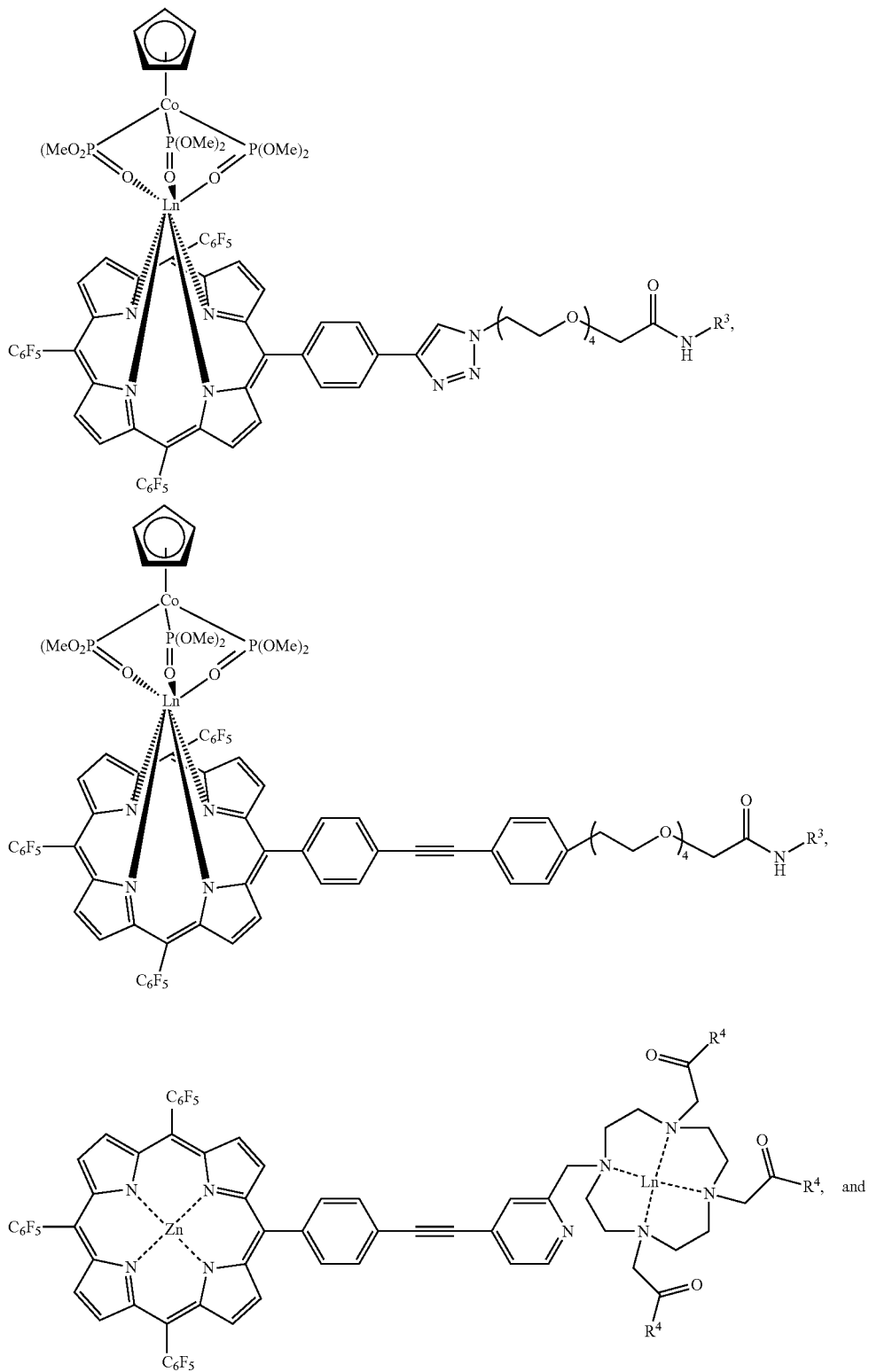

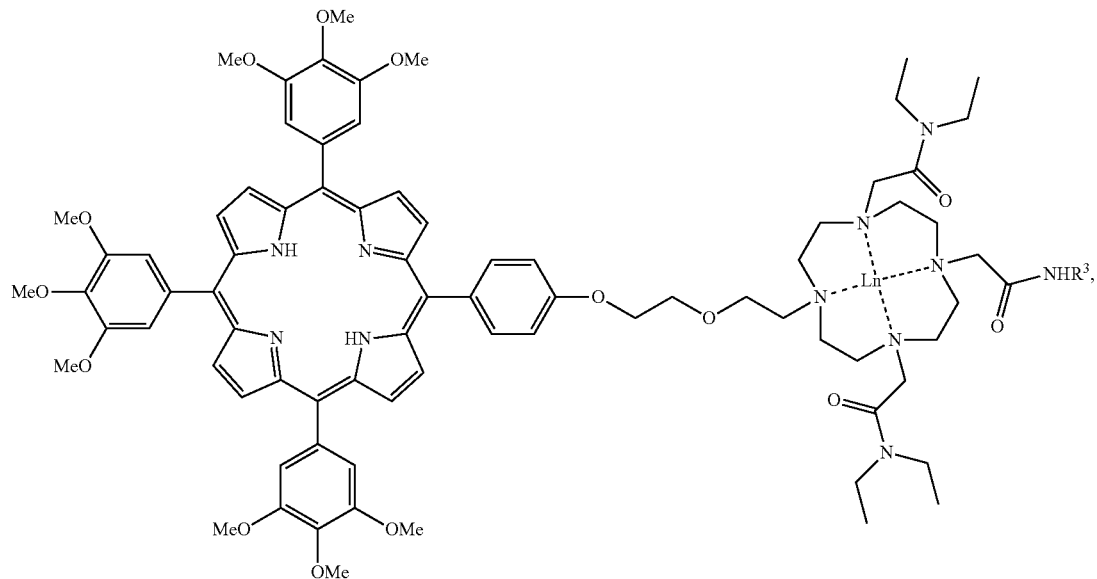

wherein Ln is Gd(III); and $R^4$ is $O^-$ or NH(tBu).

In a second embodiment of the third aspect, provided herein is the method of the third aspect further comprising the step of administering a therapeutically effective amount of a cancer therapeutic to the subject.

In a fourth aspect, provided herein is a method of treating cancer in a subject in need thereof, the method comprising administering a therapeutically effective amount of a metal complex of the first aspect; and irradiating a target tissue comprising the cancer with electromagnetic radiation having a wavelength within the activation wavelength of the metal complex.

In a first embodiment of the fourth aspect, provided herein is the method of the third aspect, wherein the cancer is bladder cancer.

In a second embodiment of the fourth aspect, provided herein is the method of the third aspect, wherein the metal complex is selected from the group consisting of:

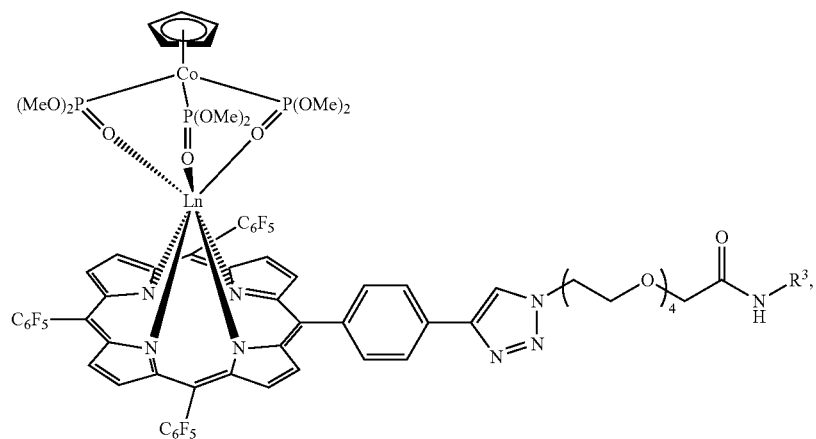

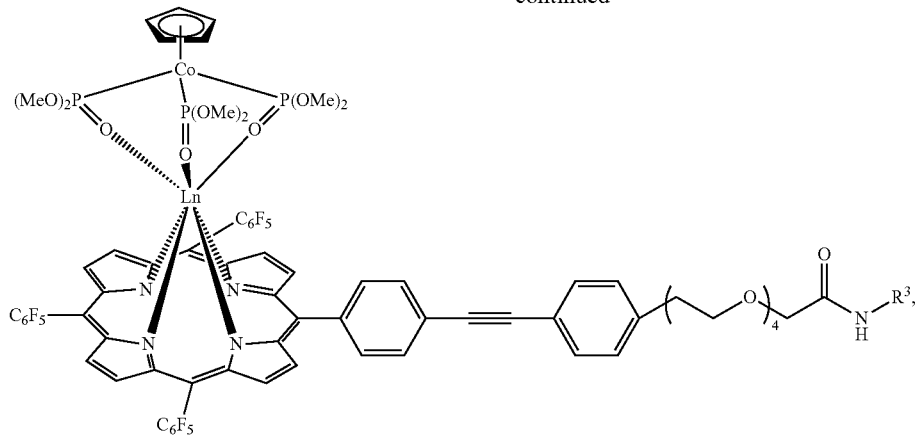

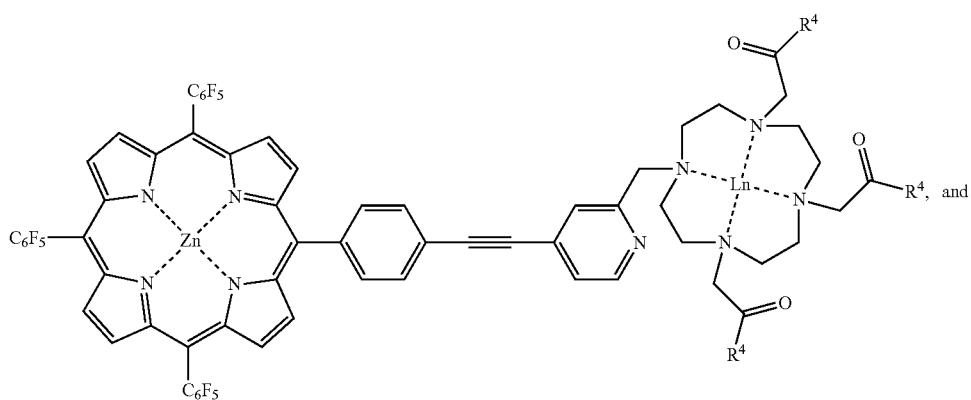

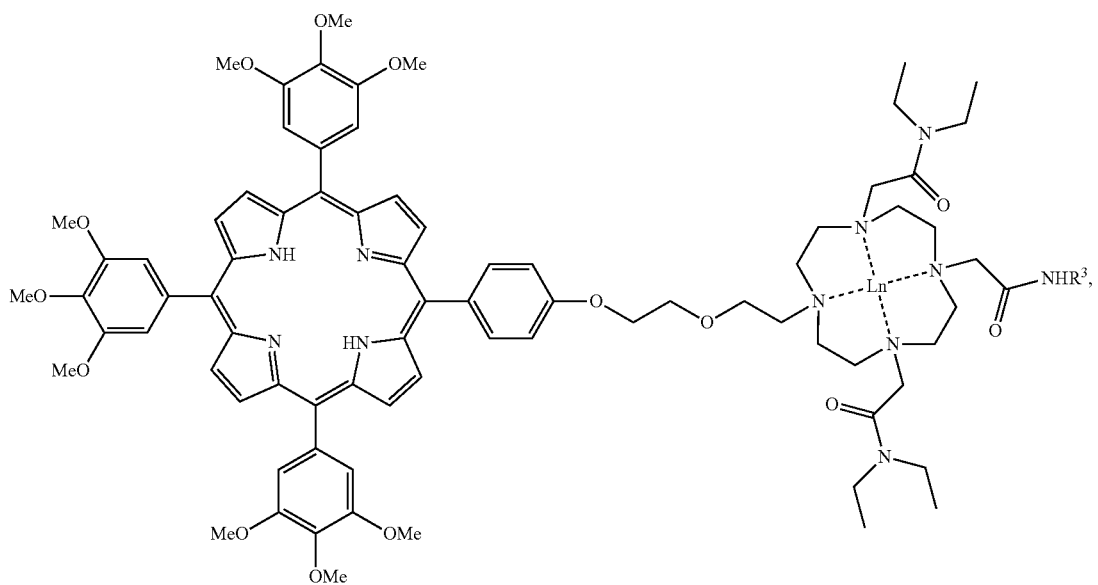

wherein Ln is Gd(III); and R⁴ is O⁻ or NH(tBu).

In a fifth aspect, provided herein is a method of imaging a subject by magnetic resonance imaging (MRI) and treating cancer in the subject, the method comprising: administering a therapeutically effective amount of a metal complex of claim 1 to the subject; irradiating a target tissue comprising the cancer with electromagnetic radiation having a wavelength within the activation wavelength of the metal complex; and imaging at least a portion of the subject by MRI.

In a first embodiment of the fifth aspect, provided herein is the method of the fifth aspect, wherein the metal complex is selected from the group consisting of:

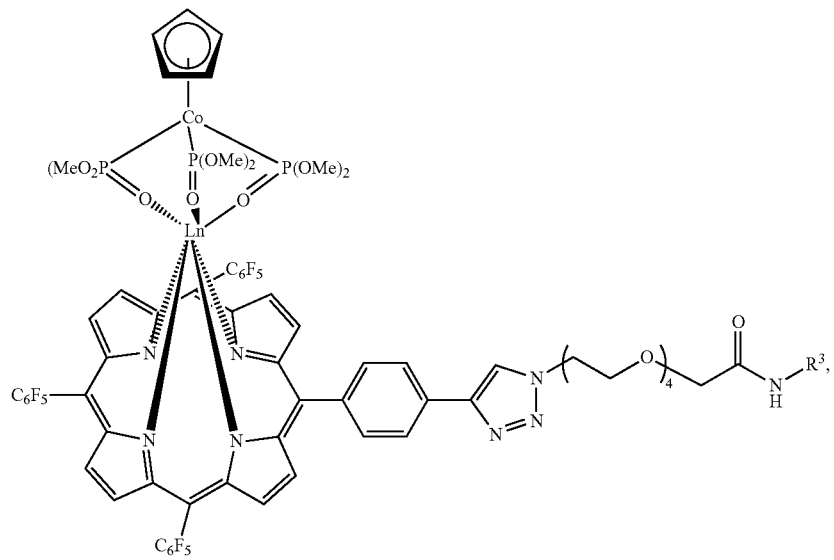
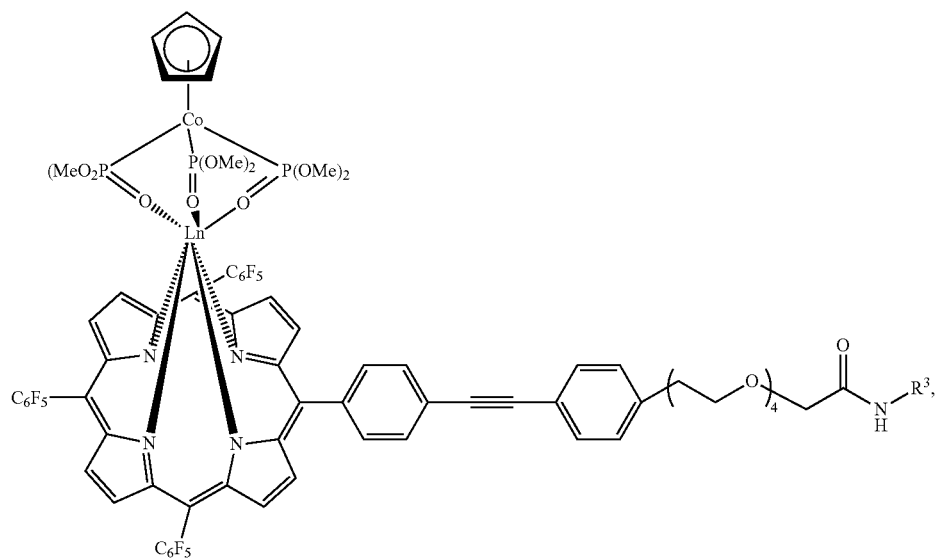
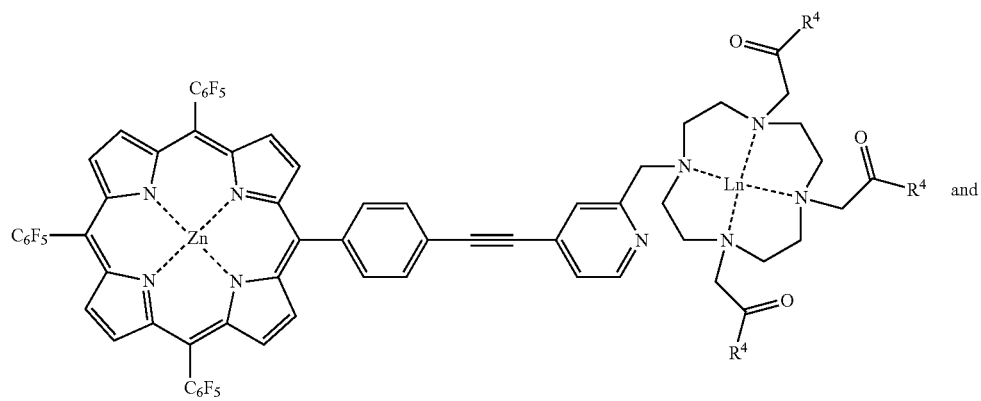

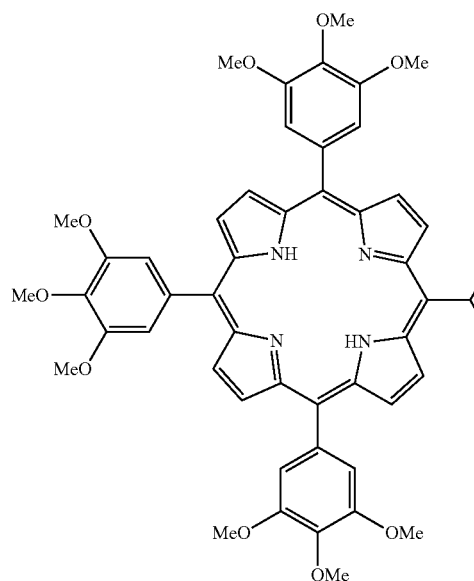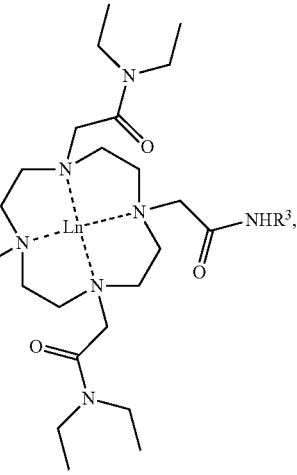

wherein Ln is Gd(III); and $R^4$ is $O^-$ or NH(tBu).

BRIEF DESCRIPTION OF THE DRAWINGS

The above and other objects and features of the present invention will become apparent from the following description of the invention, when taken in conjunction with the accompanying drawings, in which:

FIG. 8 shows In vitro photo-cytotoxicity of dark and photo IC$_{50}$ values Zn-NLPorB$_2$-Cyc-Gd-L$_2$A$_n$ (n=1 or 2) in HeLa, HK1, and MRC-5 cells.

FIG. 19 depicts (a) a table showing the photo IC$_{50}$, dark IC$_{50}$, and photodynamic therapeutic index for NLPor-Gd-L$_1$R$_1$, NLPor-Gd-L$_1$R$_2$, and NLPor-Gd-L$_1$R$_3$ against T24, HeLa, and MRC-5 cell lines; and (b) depicts a table showing the photo IC$_{50}$, dark IC$_{50}$ and photodynamic therapeutic index for Er—R$_1$, Yb—R$_1$, Er—R$_2$, Yb—R$_2$, Er—R$_3$, Yb—R$_3$ (disclosed in PCT Application No. PCT/CN2017/104492, which is herein incorporated by reference) and ALA against T24, HeLa and MRC-5 cell lines.

FIG. 35 depicts a table which shows the summary of photophysical measurements of NLPor-Gd-L$_1$R$_n$ (n=1-3) $^a$ Absorption and emission spectra were evaluated in aqueous solution at 298 K. $^b$ Emission quantum yield was measured by comparing to tetraphenylporphyrin (H$_2$TPP) in anhydrous DCM ($\Phi_{em}$=0.120). The singlet oxygen quantum yield was measured in PBS buffer by evaluating the absorbance changes of ABDA at 402 nm. $^d$ The singlet oxygen quantum yield was measured by comparing to the emission of tetraphenylporphyrin (H$_2$TPP) in anhydrous CHCl$_3$ ($\Phi_A$=0.55).

FIG. 36 depicts a table which shows the T$_1$ relaxivity of NLPor-Gd-L$_1$R$_3$ and Gd-DOTA. $^a$ The concentration of Gd(III) was corrected with ICP-MS. $^b$ The longitudinal relaxation time was measured twice for each sample and taken the average at 0.17T. $^c$ The longitudinal relaxivity, R$_1$=(1/T$_1$−1/T$_0$).

FIG. 39 shows the flow cytometry of NLPor-Gd-L$_1$R$_n$ (n=1-3) in T24 with 3 hr and 24 hr incubation.

FIG. 45 shows solvent gradient for analytical HPLC evaluating stability in different pH values.

FIG. 50 depicts a table that shows a summary of photophysical properties, singlet oxygen quantum yield of Zn-NLPorB$_2$-Cyc-L$_2$A$_2$ and Zn-NLPorB$_2$-Cyc-Gd-L$_2$A$_2$, Photo and Dark cytotoxicity of Zn-NLPorB$_2$-Cyc-L$_2$A$_2$, Zn-NLPorB$_2$-Cyc-Gd-L$_2$A$_2$ and ALA towards cancer cell lines HeLa, T24, normal cell line MRC5 under 1 J/cm$^2$ light irradiation ($\lambda_{ex}$=430 nm), MTT assay were carried out after 24 hours incubation at 37° C.

DETAILED DESCRIPTION

Definitions

Figure 1:
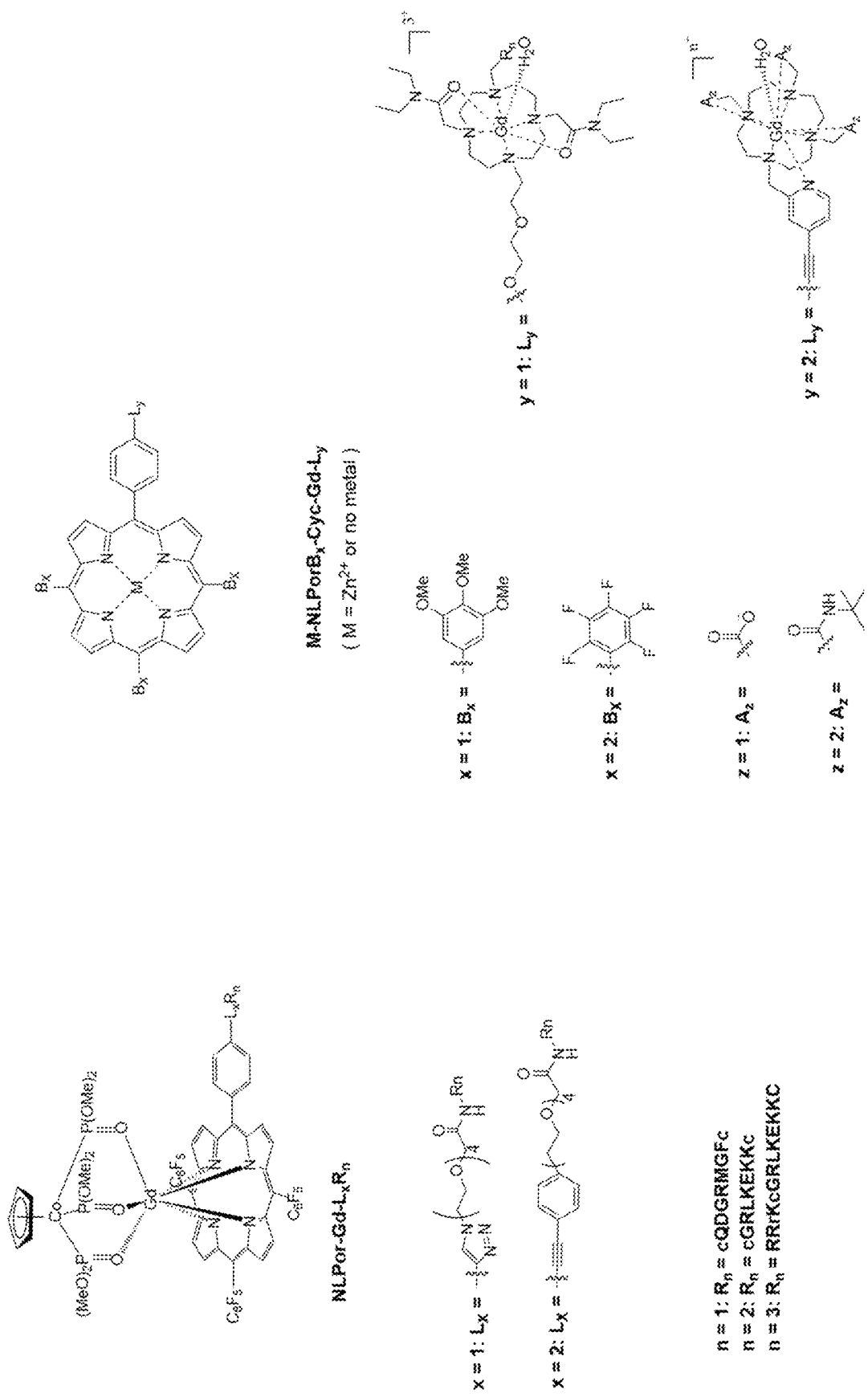
FIG. 1 shows eleven gadolinium complexes are synthesized for bladder cancer targeting magnetic resonance imaging (MRI) and photodynamic therapy (PDT).

The definitions of terms used herein are meant to incorporate the present state-of-the-art definitions recognized for each term in the field of biotechnology. Where appropriate, exemplification is provided. The definitions apply to the terms as they are used throughout this specification, unless otherwise limited in specific instances, either individually or as part of a larger group.

When trade names are used herein, applicants intend to independently include the trade name product formulation, the generic drug, and the active pharmaceutical ingredient(s) of the trade name product.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "optionally substituted" refers to a chemical group, such as alkyl, cycloalkyl aryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" and "sulfone" is art-recognized and refers to —SO$_2$—. "Halide" designates the corresponding anion of the halogens.

The term "pharmaceutically acceptable salt" or "salt" refers to a salt of one or more compounds. Suitable pharmaceutically acceptable salts of compounds include acid addition salts which may, for example, be formed by mixing a solution of the compound with a solution of a pharmaceutically acceptable acid, such as hydrochloric acid, hydrobromic acid, sulfuric acid, fumaric acid, oxalic acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

The term "subject" as used herein, refers to an animal, typically a mammal or a human, that will be or has been the object of treatment, observation, and/or experiment. When the term is used in conjunction with administration of a metal complex described herein and/or other therapeutic, then the subject has been the object of treatment, observation, and/or administration of the metal complex described herein or drug.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "therapeutically effective amount" as used herein, means that amount of active compound or pharmaceutical agent that elicits a biological, medicinal, or imaging response in a cell culture, tissue system, subject, animal, or human that is being sought by a researcher, veterinarian, clinician, or physician, which includes alleviation of the symptoms of the disease, condition, or disorder being treated and/or achieving the desired degree of magnetic resonance imaging contrast enhancement.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

Provided herein is a metal complex comprising a compound of the Formula I:

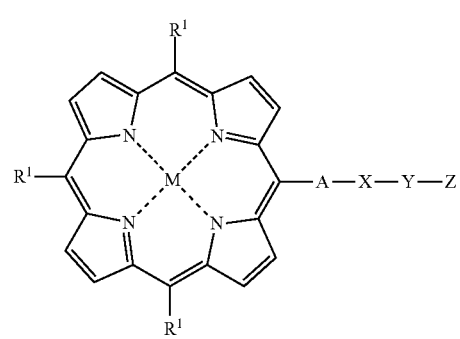

or a pharmaceutically acceptable thereof, wherein

M is 2H or Zn$^{2+}$; or M has the structure:

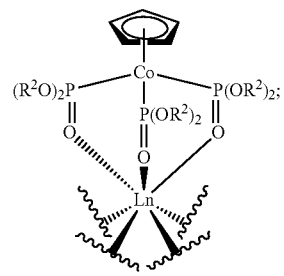

A is an optionally substituted phenyl;

X is absent,

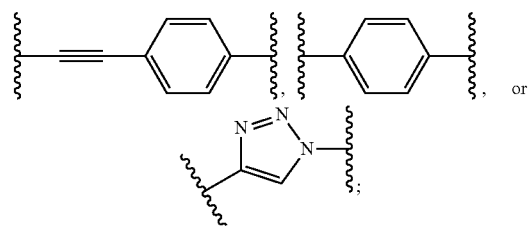

Y is —(CH$_2$)$_n$—, —(CH$_2$CH$_2$O)$_n$CH$_2$—, —(CH$_2$CH$_2$O)$_n$CH$_2$CH$_2$—, —(OCH$_2$CH$_2$O)$_n$CH$_2$—, (CH$_2$CH$_2$O)$_n$CH$_2$CH$_2$—, —(CH$_2$CH$_2$O)$_n$—, —(OCH$_2$CH$_2$)$_n$—, or

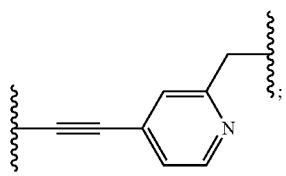 [SMILES: *C#Cc1ccnc(C*)c1]

Z is —(C=O)NHR³ or

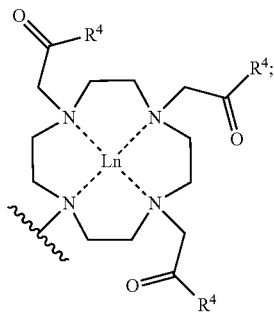

n is a whole number selected between 1-10;
Ln for each instance is independently a paramagnetic metal ion;
each R¹ is independently optionally substituted aryl;
each R² is independently alkyl;
R³ is SEQ ID NO:1 (Ahx D-Cys Gln Asp Gly Arg Met Gly Phe D-Cys, wherein Ahx is aminocaproic acid and D-Cys is the D-isomer of cysteine), SEQ ID NO:2 (Ahx D-Cys Gly Arg Leu Lys Glu Lys Lys D-Cys), or SEQ ID NO:3 (Ahx Arg Arg D-Arg Lys Xaa D-Cys Gly Arg Leu Lys Glu Lys Lys D-Cys);
each R⁴ is independently O⁻, N(R⁵)₂, or NHR³; and
each R⁵ is independently H or alkyl, with the proviso that at least one of M or Z comprises Ln.

In certain embodiments, the compound of Formula 1 can have an overall charge, e.g., of +1, +2, +3, or +4. In such cases, one or more counter anions can be present thereby yielding a charge neutral metal complex salt. Any substantially non-toxic anion can be used for the charge neutral metal complex salt. The selection of a suitable counter ion is well within the skill of a person of ordinary skill in the art. Exemplary anions include, but are not limited to, chloride, bromide, iodide, nitrate, sulfate, phosphate, carbonate, bicarbonate, tartrate, maleate, lactate, oxalate, formate, acetate, fumarate, maleate, mesylate, tosylate, adipate, caprate, caproate, caprylate, dodecylsulfate, glutarate, laurate, oleate, palmitate, citrate, hexaoate, glycolate, succinate, and the like. In certain embodiments, the metal complex is an oxalate salt.

In certain embodiments, each instance of Ln is a paramagnetic metal ion independently selected from the group consisting of the lanthanide series, e.g., having an atomic number of 57-70, and a transition metal of an atomic number of 21-29, 42, or 44.

In certain embodiments, each instance of Ln is independently selected from the group consisting of chromium(III), manganese(II), iron(III), iron(II), cobalt(II), nickel(II), copper(II), praseodymium(III), neodymium(III), samarium(III), ytterbium(III), gadolinium(III), terbium(III), dysprosium(III), holmium(III), erbium(III), lanthamium(III), gold(III), lead(II), bismuth(III), and europium(III). In certain embodiments, Ln is gadolinium(III).

In certain embodiments, n is a whole number selected from 1-9, 1-8, 1-7, 1-6, 2-6, 3-6, or 3-5.

A can be a divalent optionally substituted phenyl group which is covalently bound to porphyrin moiety and X in the 1 and 2 (ortho), 1 and 3 (meta), or 1 and 4 (para) positions of the phenyl group. In certain embodiments, A is a phenyl optionally substituted with 1, 2, 3, 4, or 5 substituents selected from the group consisting of fluoride, chloride, bromide, iodide, nitro, cyano, hydroxyl, alkyl, alkenyl, alkynyl, cycloalkyl, heterocyl, aryl, heteroaryl, —N(R)₂, —OR, —SR, —(S=O)R, —SO₂R, SO₂N(R)₂, —(C=O)R, —O(C=O)R, —(C=O)OR, —O(C=O)OR, —(C=O)N(R)₂, and —N(R)(C=O)(R), wherein R is hydrogen, alkyl, or aryl. In certain embodiments, A is selected from:

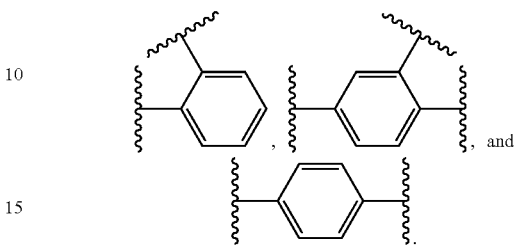

In instances in which X is absent, the metal complex of Formula I can be represented by the structure shown below:

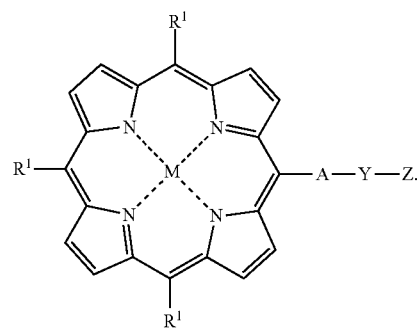

In certain embodiments, each R¹ is independently selected from optionally substituted phenyl, optionally substituted napthyl, optionally substituted furan, optionally substituted pyrrole, optionally substituted imidazole, optionally substituted thiazole, optionally substituted pyridine, optionally substituted pyrazine, and the like. In certain embodiments, R¹ is a phenyl optionally substituted with 1, 2, 3, 4, or 5 substituents selected from the group consisting of fluoride, chloride, bromide, iodide, nitro, cyano, hydroxyl, alkyl, alkenyl, alkynyl, cycloalkyl, heterocyl, aryl, heteroaryl, —N(R)₂, —OR, —SR, —(S=O)R, —SO₂R, —(C=O)R, —O(C=O)R, —(C=O)OR, —O(C=O)OR, —(C=O)N(R)₂, and —N(R)(C=O)(R), wherein R is hydrogen, alkyl, or aryl. In certain embodiments, R¹ is phenyl optionally substituted with 1, 2, 3, 4, or 5 substituents selected from the group consisting fluoride and —OR, wherein R is C₁-C₆ alkyl or C₁-C₃ alkyl.

In certain embodiments, R² is independently C₁-C₆ alkyl, C₁-C₅ alkyl, C₁-C₄ alkyl, or C₁-C₃ alkyl.

R³ can be a polypeptide sequence selected from the group consisting of SEQ ID NO:1, SEQ ID NO:2, and SEQ ID NO:3. The polypeptides are covalently bonded via the terminal amine.

In certain embodiments, each R⁵ is independently hydrogen, C₁-C₆ alkyl, C₁-C₅ alkyl, C₁-C₄ alkyl, or C₁-C₃ alkyl.

In certain embodiments, M has the structure:

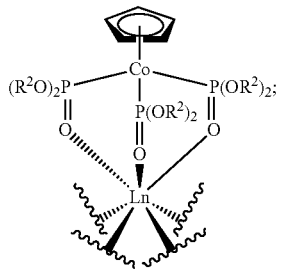

A is optionally substituted para phenyl;
R² is C₁-C₃ alkyl;
X is

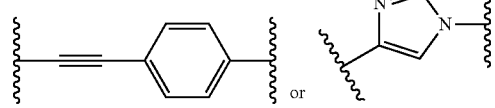

Y is —(CH₂)$_n$—; —(CH₂CH₂O)$_n$CH₂—; —(CH₂CH₂O)$_n$—; —(OCH₂CH₂)$_n$—, wherein n is a whole number selected from 3-5; and Z is —(C═O)NHR³.

In certain embodiments, M is 2H or Zn²⁺; A is optionally substituted para phenyl;

X is absent or

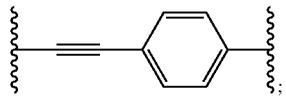

Y is —(OCH₂CH₂)$_n$—; or

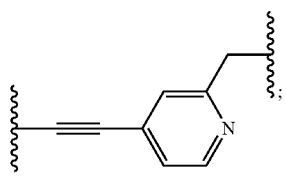 [SMILES: *C#Cc1ccnc(C*)c1]

and Z is

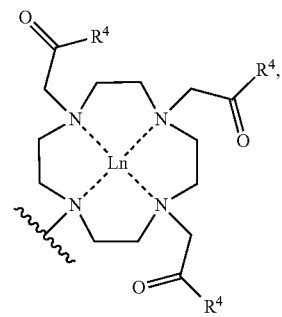

wherein R⁴ is O⁻, N(R⁵)₂, or NHR³; and each R⁵ is independently hydrogen or C₁-C₃ alkyl.

In certain embodiments, the compound of Formula I is selected from the group consisting of:

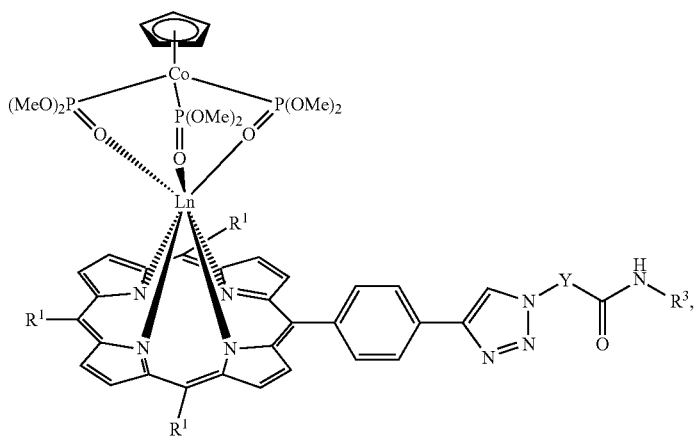

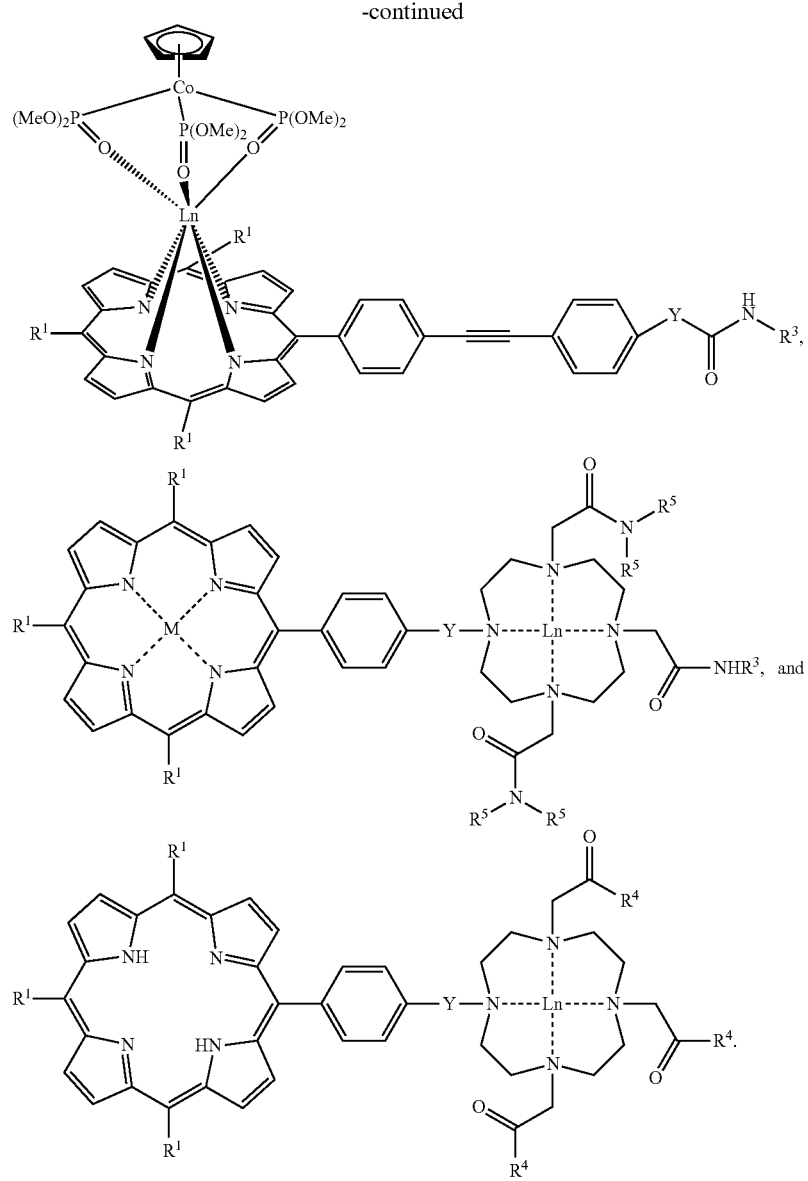

The present disclosure also provides a pharmaceutical composition comprising a metal complex described herein and at least one pharmaceutically acceptable excipient.

The metal complex described herein and their pharmaceutically acceptable salts can be administered to a mammalian subject either alone or in combination with pharmaceutically acceptable carriers or diluents in a pharmaceutical composition according to standard pharmaceutical practice. The metal complex can be administered orally or parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of one or more of the metal complexes described herein, formulated together with one or more pharmaceutically acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue. In certain embodiments, the method of administration of metal complexes of the present disclosure is parental administration (intravenous).

As set out herein, certain embodiments of the metal complexes described herein may contain a cationic complex, and are, thus, capable of forming pharmaceutically-acceptable salts with pharmaceutically-acceptable anions. The term "pharmaceutically-acceptable salts" in this respect, refers to the relatively non-toxic, inorganic and organic salts of compounds of the present disclosure. These salts can be prepared in situ in the administration vehicle or the dosage form manufacturing process, or by separately. Representative salts include the bromide, chloride, sulfate, bisulfate, nitrate, acetate, valerate, oleate, palmitate, stearate, laurate, benzoate, lactate, phosphate, tosylate, citrate, oxalate, maleate, fumarate, succinate, tartrate, napthylate, mesylate, glucoheptonate, lactobionate, and laurylsulphonate salts and the like.

The pharmaceutically acceptable salts of the metal complexes of the present disclosure include the conventional nontoxic salts or quaternary ammonium salts of the metal complexes, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic; phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the metal complexes described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present disclosure. These salts can likewise be prepared in situ in the administration vehicle or the dosage form manufacturing process, or by separately reacting the purified metal complexes in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing these formulations or compositions include the step of bringing into association a metal complex described herein with the carrier and, optionally, one or more accessory ingredients. In general, the formulations are prepared by uniformly and intimately bringing into association a compound of the present disclosure with liquid carriers (liquid formulation), liquid carriers followed by lyophylization (powder formulation for reconstitution with sterile water or the like), or finely divided solid carriers, or both, and then, if necessary, shaping or packaging the product.

Pharmaceutical compositions of the present disclosure suitable for parenteral administration comprise one or more metal complexes of the present disclosure in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents. In the examples, the active ingredients are brought together with the pharmaceutically acceptable carriers in solution and then lyophilized to yield a dry powder. The dry powder is packaged in unit dosage form and then reconstituted for parental administration by adding a sterile solution, such as water or normal saline, to the powder.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is, subject to metabolism and other like processes, for example, subcutaneous administration.

Also provided herein is a method of imaging a subject by magnetic resonance imaging (MRI), the method comprising: administering a therapeutically effective amount of a metal complex as described herein; and imaging at least a portion of the subject by MRI. In certain embodiments the at least a portion of the subject is suspected of having cancer. In certain embodiments, the at least a portion of the subject is the bladder of the subject.

In certain embodiments, the subject a canine, feline, bovine, equine, non-human primate, or human. In certain embodiments, the subject is a human.

Based on the MRI data collected, a clinician can diagnose whether the subject is suffering from cancer, e.g., bladder cancer. In the event that the subject is diagnosed with cancer based on the MRI data, the subject can be treated or the progression of the cancer can be monitored by the clinician. The cancer can be treated using any method known in the art, including, but not limited to radiotherapy, chemotherapy, surgery, and combinations thereof.

Accordingly, in certain embodiments, the method of imaging a subject further comprises the step of administering a therapeutically effective amount of a cancer therapeutic. In certain embodiments, the cancer therapeutic is a cancer therapeutic useful in the treatment of bladder cancer. Exemplary cancer therapeutic useful in the treatment of bladder cancer includes, but is not limited to, mitomycin, thiotepa, cisplatin, carboplatin, doxorubicin, gemcitabine, valrubicin, methotrexate, vinblastine, doxorubicin, and combinations thereof.

In certain embodiments, the method of imaging a subject further comprises the step of surgically removing the bladder cancer.

The metal complexes provided herein can also be used in connection with PDT of cancer. Thus, also provided is a method of treating cancer in a subject in need thereof, the method comprising administering a therapeutically effective amount of a metal complex described herein; and irradiating a target tissue comprising the cancer with electromagnetic radiation having a wavelength within the activation wavelength of the metal complex.

The target tissue in the subject can be irradiated from outside of the body at a site adjacent to the target tissue.

The activation wavelength is the wavelength at which the metal complex absorbs electromagnetic radiation and is able to transfer at least some of the energy absorbed to oxygen in the vicinity of the metal complex and convert the oxygen to reactive singlet oxygen. In certain embodiments, the activation wavelength is between 800-1,000 nm.

The metal complexes described herein can be administered according to therapeutic and/or imaging protocols well known in the art. It will be apparent to those skilled in the art that the administration of the compounds described herein can be varied depending on the disease being treated. Also, in accordance with the knowledge of the skilled clinician, the therapeutic protocols (e.g., dosage amounts and times of administration) can be varied in view of the observed effects of the administered metal complex on the subject, and in view of the observed responses of the disease to the administered therapeutic agents.

Eleven exemplary gadolinium complexes were prepared and tested for bladder cancer targeting magnetic resonance imaging and PDT (FIG. 1). The photophysical properties and binding affinity to the bladder cancer receptors—$\alpha_v\beta_3$ integrin/anionic membranes—phosphatidylcholine (DOPC) are shown in Table 1.

TABLE 1

The photophysical properties and binding affinity evaluation of proposed complexes in FIG. 1 for bladder cancer PDT.

| Gadolinium Complex | Emission Quantum Yield ($\lambda_{em}$ = 600-750 nm, $\lambda_{em}$ = 430 nm) | $^1O_2$ Quantum Yield ($\lambda_{em}$ = 430 nm) | Binding affinity to $\alpha_v\beta_3$ integrin/ DOPC (5: strongest and 1: weakest) |
|---|---|---|---|
| NLPor-Gd-$L_1R_1$ | 1.6% | 39% | 4 |
| NLPor-Gd-$L_1R_2$ | 1.6% | 40% | 4 |
| NLPor-Gd-$L_1R_3$ | 1.7% | 40% | 5 |
| NLPor-Gd-$L_2R_1$ | 1.6% | 39% | 2 |
| NLPor-Gd-$L_2R_2$ | 1.6% | 39% | 3 |
| NLPor-Gd-$L_2R_3$ | 1.7% | 40% | 3 |
| NLPorB$_1$-Cyc-$L_1R_1$ | 12% | 45% | 3 |
| NLPorB$_1$-Cyc-$L_1R_2$ | 11% | 46% | 3 |
| NLPorB$_1$-Cyc-$L_1R_3$ | 11% | 45% | 3 |
| Zn-NLPorB$_2$-Cyc-Gd-$L_2A_1$ | 7% | 41% | 4 |
| Zn-NLPorB$_2$-Cyc-Gd-$L_2A_2$ | 9% | 40% | 4 |

Figure 2:
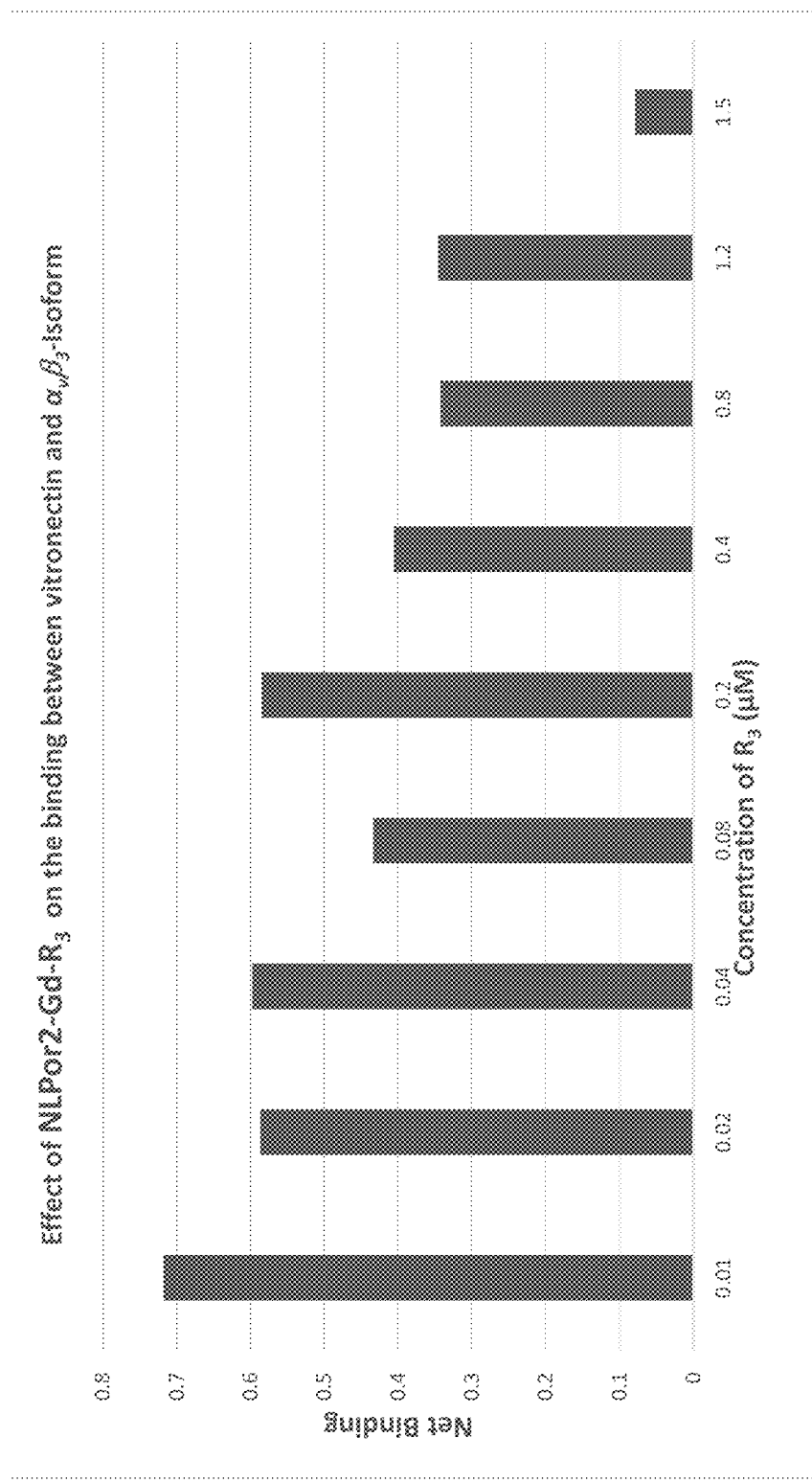
FIG. 2 shows relationship between the vitronectin—$α_vβ_3$ integrin net binding and concentration of NLPor-Gd-$L_1R_3$.
Figure 15:
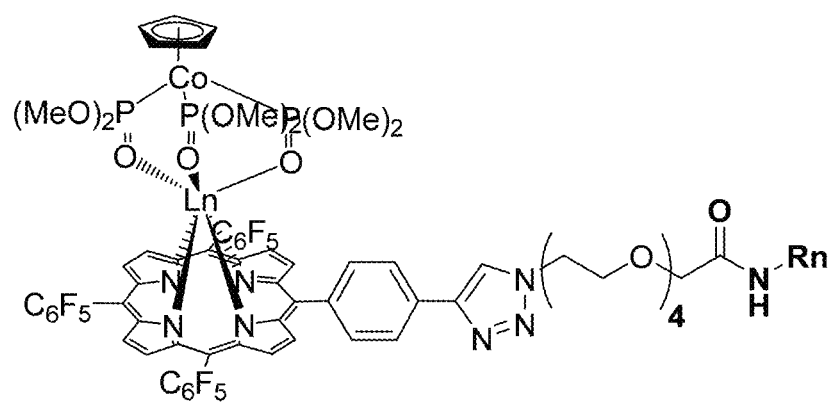
FIG. 15 shows the structure of NLPor-Gd-$L_1R_n$, n=3: AhxRRrKcGRLKEKKC (SEQ ID NO:3).

0.4 µg/mL of purified recombinant human $\alpha_v\beta_3$ integrin (derived from CHO cells, R&D Systems) was adsorbed onto a 96-well ELISA plate. The candidate ITG binding compound, NLPor-Gd-$L_1R_1$ was added to displace 0.25 µg/mL biotinylated vitronectin (a known ITG $\alpha_v\beta_3$ ligand, Abcam, Cambridge, England) from the recombinant $\alpha_v\beta_3$ integrin. The effect of NLPor-Gd-$L_1R_n$ and NLPor-Gd-$L_2R_n$ (n=1-3) (FIGS. 1 and 15) on the net binding of vitronectin and $\alpha_v\beta_3$ integrin was studied by evaluating the absorbance of the mixture at different concentrations of $R_n$. Generally, the lower the absorbance refers to the greater the effect of $R_n$ on hindering the binding between vitronectin and $\alpha_v\beta_3$ integrin. Since net binding was reduced as the concentration of NLPor-Gd-$L_1R_3$ increase (FIG. 2), it indicated NLPor-Gd-$L_1R_3$ might interact with the $\alpha_v\beta_3$ integrin and hence inhibit the binding between the $\alpha_v\beta_3$ integrin and biotinylated vitronectin.

Five of the exemplary gadolinium complexes were selected to test two criteria (1) water solubility; (2) strong cancer selectivity in term of binding with $\alpha_v\beta_3$ integrin (evaluated by western blot and integrin (ITG) binding activity assay for NLPor-Gd-$L_1R_n$ and NLPor-Gd-$L_2R_n$) and anionic membrane (by responsive signal with DOPC—M-NLPorB$_x$-Cyc-Gd-$L_y$).

Figure 3:
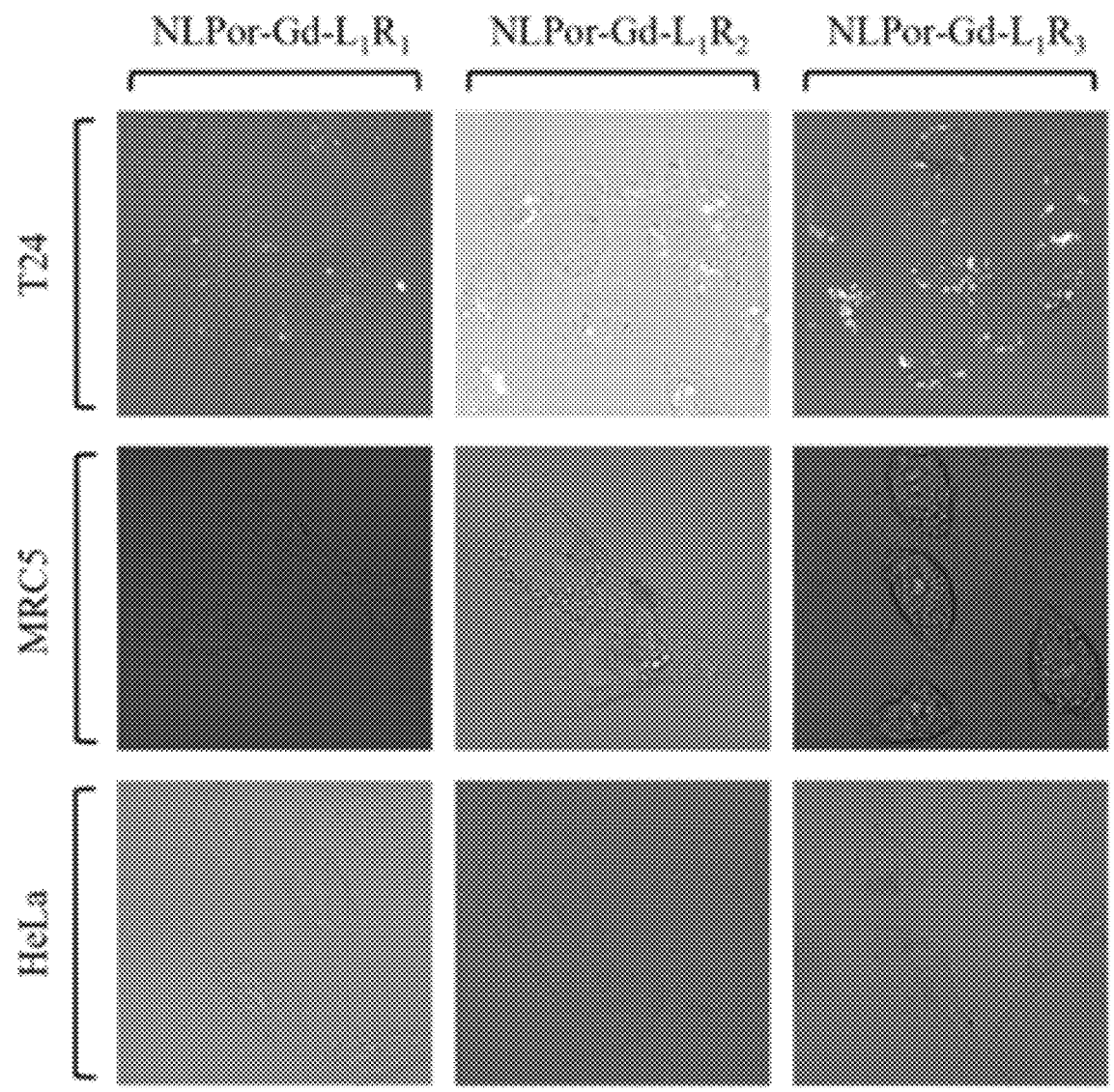
FIG. 3 shows in vitro imaging of NLPor-Gd-$L_1R_n$ (n=1-3) in human bladder cancer (T24), normal (MRC-5), and cervical carcinoma (HeLa) cells. (Dosed concentration: 5 μM, incubation time: 24 hours, $λ_{ex}$=561 nm).

The selected five exemplary gadolinium complexes were tested in vitro for bladder cancer cells selectivity by (1) confocal imaging, (2) selectivity for photodynamic index (bladder cancer cells vs normal cells) and $t_1$ relaxivity responsive signal to the cancer cells receptors/markers, i.e. $\alpha_v\beta_3$ integrin or DOPC. Comprehensive studies on in vitro imaging were performed on three different cell lines (T24: human bladder carcinoma cell line; HeLa: cervical cancer cell line; MRC-5: normal lung cell line). According to FIG. 3, red emission was observed from bladder cancer cells T24, where the emission could be generated from the chromophore moieties of porphyrins. In contrast, no light signal was obtained from HeLa and MRC-5 cells. This situation further confirmed the specific localization of NLPor-Gd-$L_xR_n$ (n=1-3) in bladder cancer cells. The selectivity of NLPoR-Gd-L1$R_n$ to the T24 bladder cancer cells might due to the binding of the compounds towards the overexpression of $\alpha_v\beta_3$ integrin on the T24 bladder cancer cells.

Bladder cancer peptide $R_3$ is more hydrophilic than $R_1$ and $R_2$. Therefore, the red emission of NLPor-Gd-$L_1R_3$ was of high emission intensity than NLPor-Gd-$L_1R_2$ and NLPor-Gd-$L_1R_1$, following the trends: NLPor-Gd-$L_1R_3$>NLPor-Gd-$L_1R_2$>NLPor-Gd-$L_1R_1$.

Figure 4:
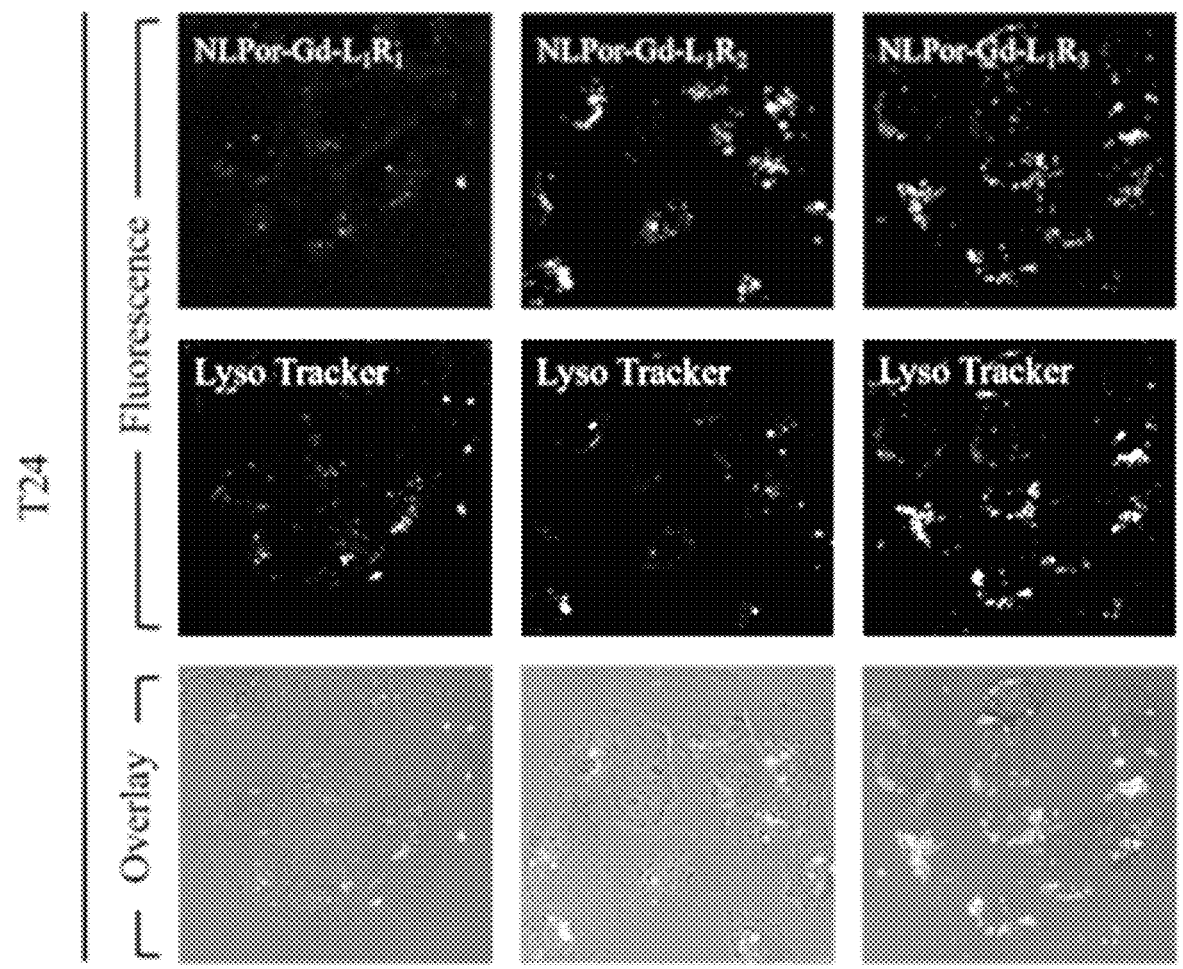
FIG. 4 shows subcellular localization of NLPor-Gd-$L_1R_n$ (n=1-3) by co-staining with lysotracker green in T24 cells. (Dosed con.: 5 μM, incubation time: 24 hours, $λ_{ex}$=561 nm).

After the investigation on the specific localization of NLPor-Gd-$L_1R_n$ (n=1-3) in bladder cancer cells, the co-staining experiments were performed to further identify the intracellular localization of NLPor-Gd-$L_1R_n$ (n=1-3) in bladder cancer cells. As shown in FIG. 4 (which has been converted to black and white from color), red emission (now white) was originated from NLPor-Gd-$L_1R_n$ complexes, and green emission (now white) was from the lysotracker. It is worth noting that the merged yellow (red plus green) (now white) co-staining emission showing in the overlay section could only be found in bladder cells incubated with NLPor-Gd-$L_1R_2$ and NLPor-Gd-$L_1R_3$. This observation proved the same staining positions of NLPor-Gd-$L_1R_2$/NLPor-Gd-$L_1R_3$ and lysotracker, which indicated the two complexes localized in the lysosome of bladder cancer cells T24. By contrast, no obvious overlap was found for NLPor-Gd-$L_1R_1$, which further indicated that NLPor-Gd-$L_1R_1$ localized on the membranes of bladder cancer cells T24.

Figure 5:
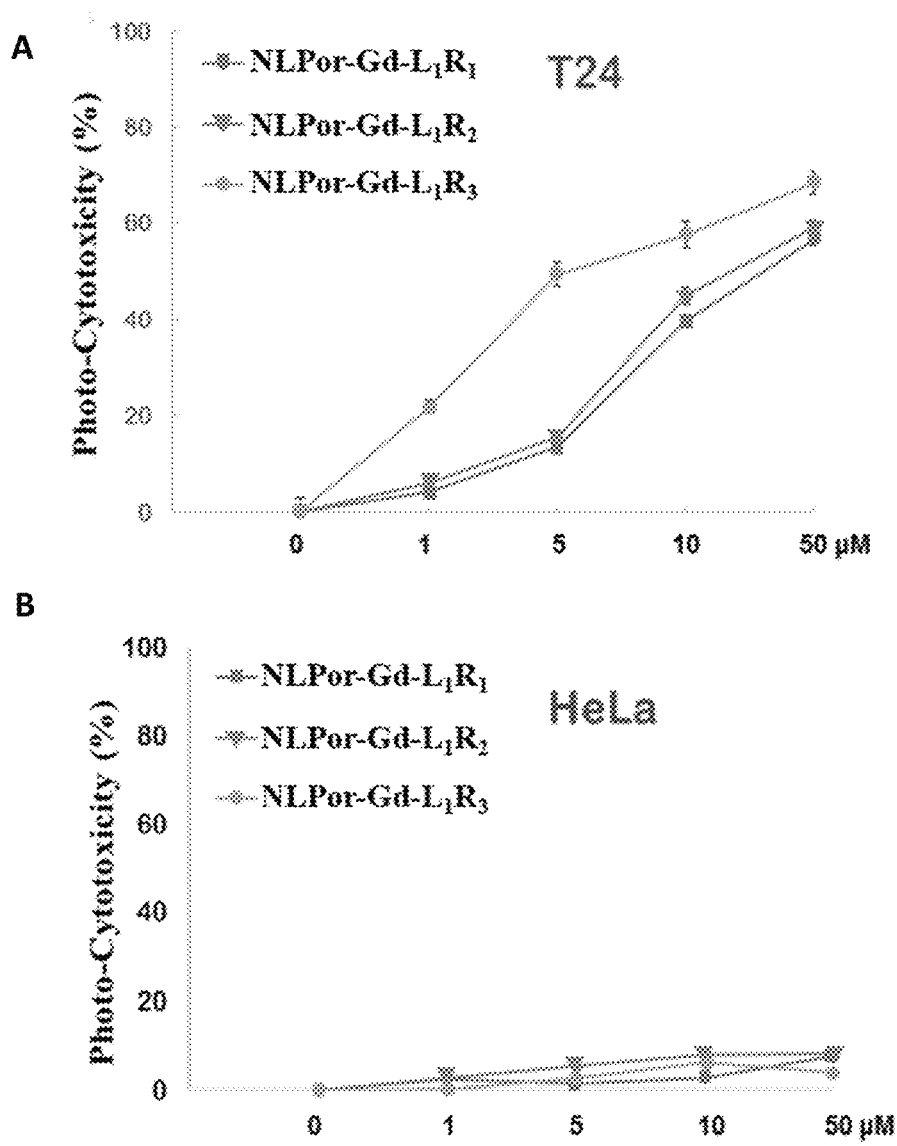
FIG. 5 (a) shows in vitro photo-cytotoxicity of NLPor-Gd-$L_1R_n$ (n=1-3) in T24 cells under 10 J cm$^{-2}$ irradiated with 550 nm long-pass filter; (b) shows in vitro photo-cytotoxicity of NLPor-Gd-$L_1R_n$ (n=1-3) in HeLa cells under 10 J cm$^{-2}$ irradiated with 550 nm long-pass filter; (c) shows in vitro photo-cytotoxicity of NLPor-Gd-$L_1R_n$ (n=1-3) in MRC-5 cells under 10 J cm$^{-2}$ irradiated with 550 nm long-pass filter; and (d) shows in vitro photo-cytotoxicity of NLPor-Gd-$L_1R_n$ (n=1-3) in dark and photo IC$_{50}$ values NLPor-Gd-$L_1R_n$ (n=1-3) in T24, HeLa, and MRC-5 cells.
Figure 5:
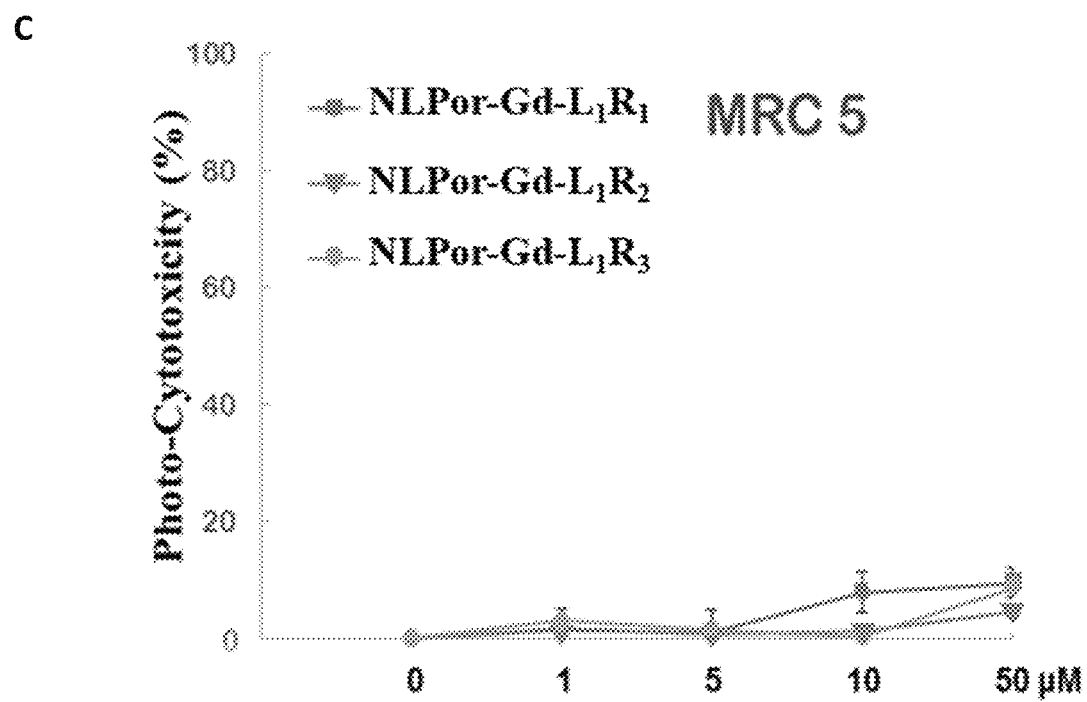

The cytotoxicity of NLPor-Gd-$L_1R_n$ (n=1-3) complexes in T24, HeLa, and MRC-5 cells was evaluated with or without light irradiation, respectively (FIG. 5). The photo-cytotoxicity of NLPor-Gd-$L_1R_n$ (n=1-3) in T24 was advantageously 10-fold more potent than that in HeLa and MRC-5 cells (for NLPor-Gd-$L_1R_3$, it was 50-fold more potent). In addition, with the increasing concentrations of the NLPor-Gd-$L_1R_n$ (n=1-3) complexes, the photo-cytotoxicity was also increased. The selectivity of the complexes for bladder cancer cells was also revealed by the difference in their cytotoxicity since the $IC_{50}$ values of NLPor-Gd-$L_1R_n$ (n=1-3) complexes in the T24 cells were lower than those in HeLa and MRC-5 cells. After light irradiation, the complexes could selectively kill bladder cancer cells but did not destroy the normal cells. The photocytotoxicity of NLPor-Gd-$L_1R_3$ was higher than NLPor-Gd-$L_1R_2$ and NLPor-Gd-$L_1R_1$. This observation could be attributed to the better solubility of NLPor-Gd-$L_1R_3$ in aqueous solution, which enhanced its cell permeability. As shown in FIG. 5, NLPor-Gd-$L_1R_3$ exhibited the highest PTI value among all the final products, followed by NLPor-Gd-$L_1R_2$>NLPor-Gd-$L_1R_1$.

Given that NLPor-Gd-$L_1R_3$ possessed the most potent photo-cytotoxicity ($IC_{50}$=8.2 µM), with the highest photodynamic therapy index (PTI, Light $IC_{50}$/dark $IC_{50}$) value (199), it could be considered as the most promising bladder cancer specific PDT agent among all tested samples.

Figure 6:
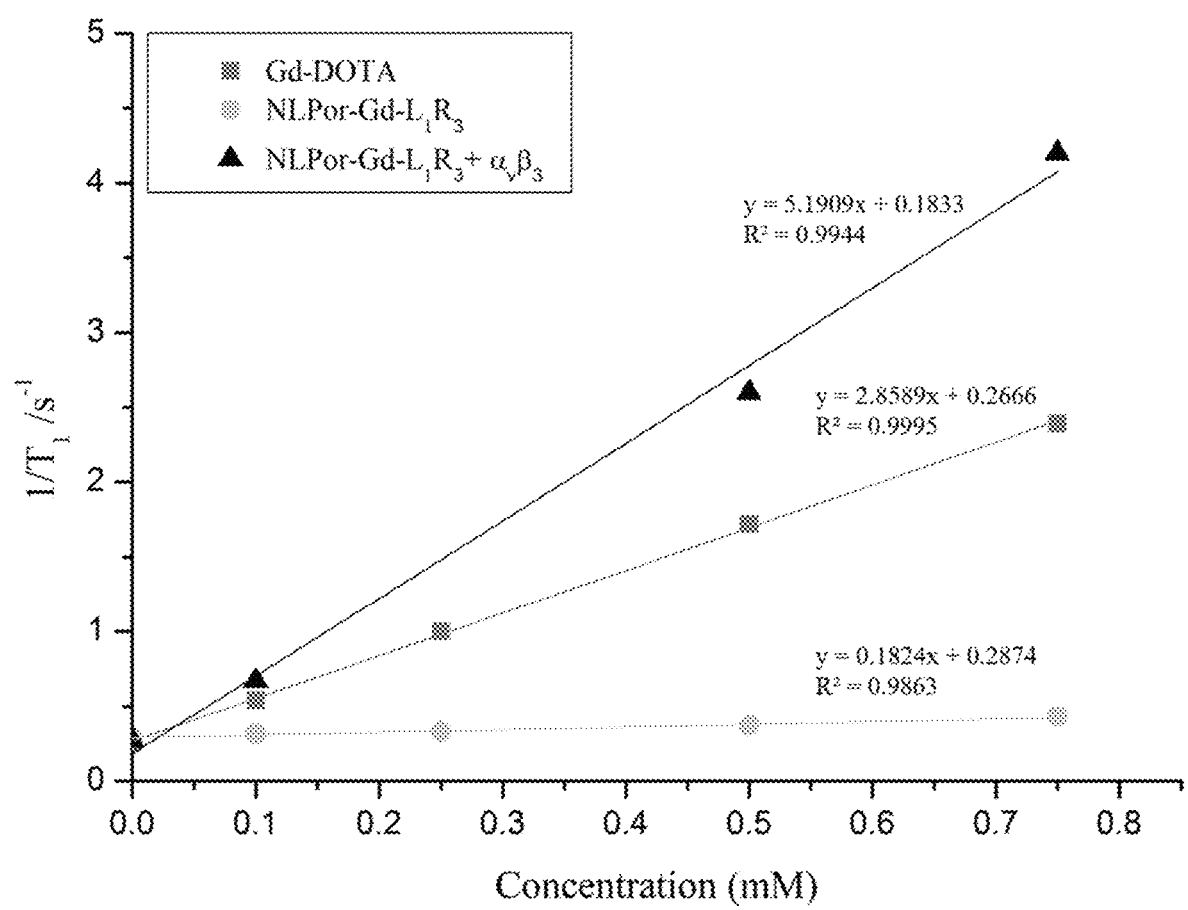
FIG. 6 shows the relationship between relativity (1/T$_1$) and the concentrations of Gd(III) (H$_2$O with 3% DMSO) in GdDOTA (control) and NLPor-Gd-L1R3 with the binding of $α_vβ_3$ integrin FIG. 7 (a) shows the confocal images of Zn-NLPorB$_2$-Cyc-Gd-L$_2$A$_2$ in HeLa and MRC5 cells. In normal cells—MRC5, the emission is found outside the cells, however in cancer cells—HeLa, the emission of Zn-NLPorB$_2$-Cyc-Gd-L$_2$A$_2$ is found in the membrane and cytoplasm; and (b) shows the co-localization of emission of Zn-NLPorB$_2$-Cyc-Gd-L$_2$A$_2$ in HeLa cells have been worked out with green lyso and mito tracker. ($λ_{ex}$=488 nm, conc. of Zn-NLPorB$_2$-Cyc-Gd-L$_2$A$_2$=10 μM, conc. of Lyso or Mito Tracker=50 nM, Zn-NLPorB$_2$-Cyc-Gd-L$_2$A$_2$ was firstly incubated in cells for 24 hours and took the image. After lyso or mito tracker was added and for further 30 min incubation)

$t_1$ relaxivity of the proposed MR-available PDT agent—NLPor-Gd-$L_1R_n$ (n=1 to 3) was measured. The relaxivity of NLPor-Gd-$L_1R_n$ (n=1 to 3) at 1.5 T in Water (3% DMSO) was 0.2847 $mM^{-1}s^{-1}$, which is lower than that of Gd-DOTA. Without wishing to be bound by theory, this difference in relaxivity could be due to the different coordinative numbers of them: for NLPor-Gd-$L_1R_n$, (n=1 to 3) the coordinative protection for the central $Gd^{3+}$ ion is better than that of Gd-DOTA, so the $Gd^{3+}$ ion in NLPor-Gd-$L_1R_n$ (n=1 to 3) has less chance to exchange with water protons compared to Gd-DOTA. The responsive $t_1$ of NLPor-Gd-$L_1R_n$ (n=1-3) have been evaluated with the addition of different concentrations of $α_vβ_3$ integrin. Since the solubility of NLPor-Gd-$L_1R_3$ in aqueous solution is higher than NLPor-Gd-$L_1R_2$ and NLPor-Gd-$L_1R_1$, the responsive $t_1$ relaxivity only can be observed from NLPor-Gd-$L_1R_3$ with $α_vβ_3$ integrin. (FIG. 6). When the $α_vβ_3$ integrin (targeting) binding might readily interact with two molecules and affect $t_1$ relaxivity from $2^{nd}$ or outer coordination spheres. The $t_1$ relaxivity of NLPor-Gd-$L_1R_3$ is enhanced from 0.2847 $mM^{-1}s^{-1}$ to 3.225 $mM^{-1}s^{-1}$ with the addition of $α_vβ_3$ integrin.

Figure 7:
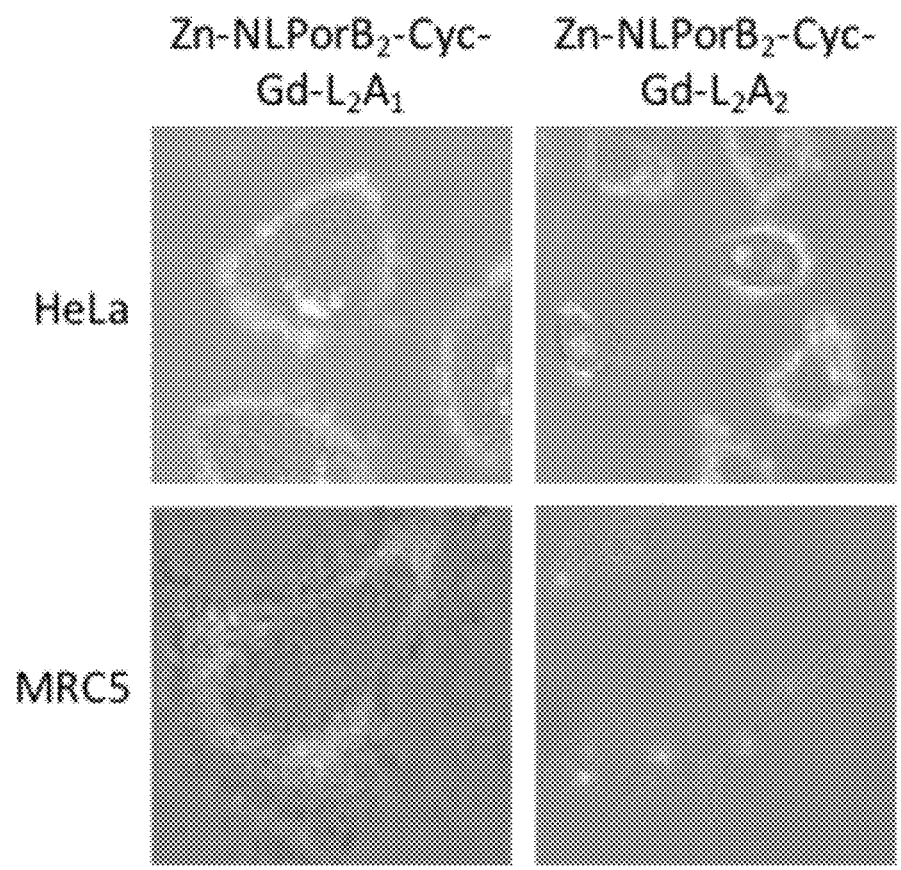
Figure 7:
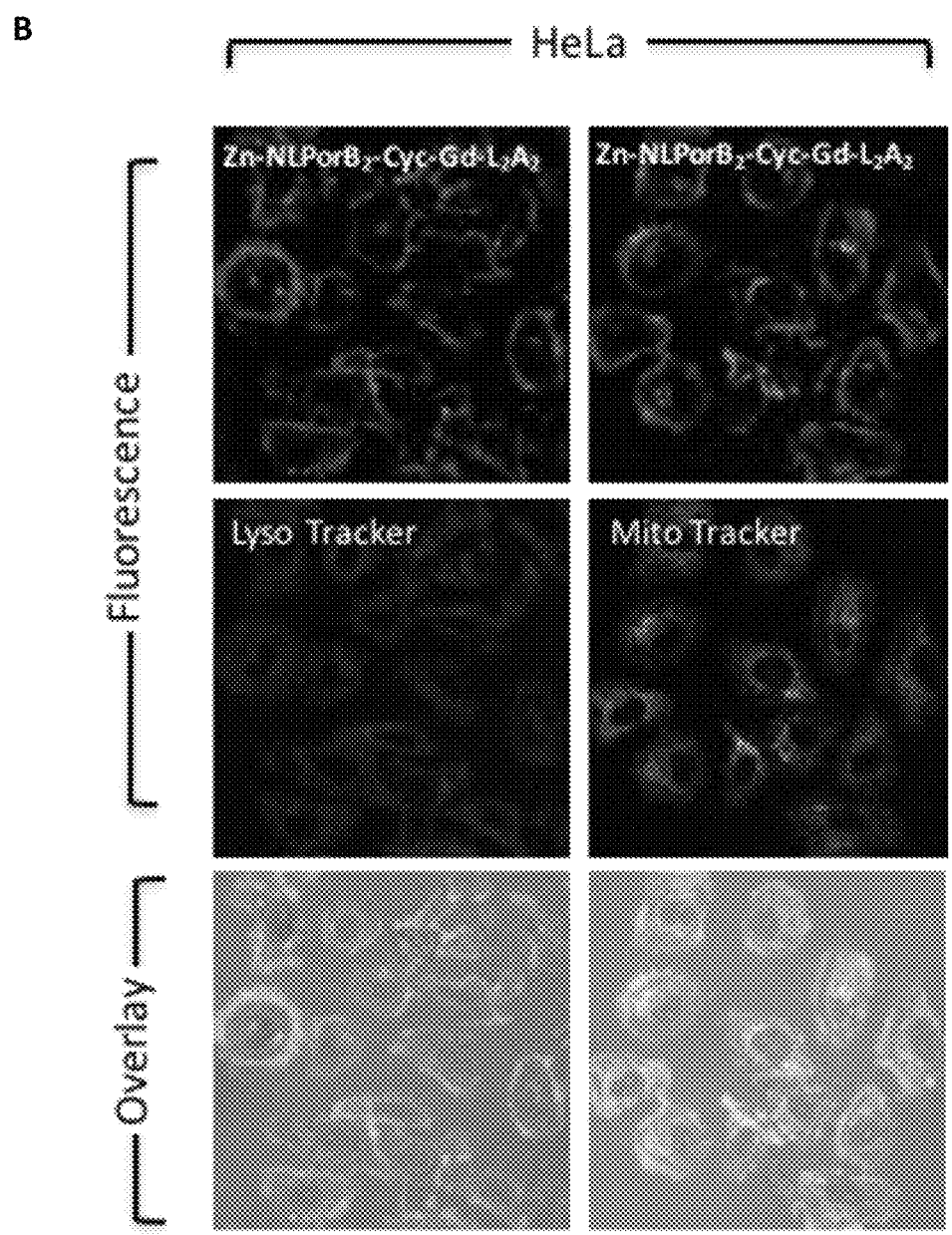

Comprehensive studies on in vitro imaging have been performed on three different cell lines (HK1: human nasopharyngeal carcinoma cell line; HeLa: cervical cancer cell line; MRC-5: normal lung cell line). According to FIG. 7a, red emission was observed from cancer cells anionic membrane and cytoplasm, where the emission could be generated from the chromophore moieties of porphyrins. In contrast, light signal was obtained from outside MRC-5 normal cells only. This situation further confirmed the specific localization of Zn-NLPor$B_2$-Cyc-Gd-$L_2A_2$ in cancer cells due to the charge and steric hindrance. Zn-NLPor$B_2$-Cyc-Gd-$L_2A_1$ shown the same subcellular localization in cancer cells and normal cells. Also, as shown in FIG. 7b (which has been converted to black and white from color), The red fluorescence (now white) of the confocal images on the first row are originated from the compound Zn-NLPorB2-Cyc-Gd-$L_2A_2$ in the HeLa cells. The green fluorescence (now white) of the confocal images on the second row are from the LysoTracker or MitoTracker which indicate the locations of the lysosomes and mitochondria in the HeLa cells. The overlay images showed some yellow color regions (now white). The yellow color regions indicate the overlap of the red and green fluorescence. The yellow regions indicate the compounds are located in the lysosomes and mitochondria of the HeLa cells.

The cytotoxicity of M-NLPor-Cyc-$L_2A_n$ (n=1 or 2) complexes in HK1, HeLa, and MRC-5 cells was evaluated with or without light irradiation, respectively (FIG. 8). The photo-cytotoxicity of NL-ZnPor-Cyc-Gd-$A_3$ is 1000 fold better than FDA approval PDT agent—ALA. (FIG. 8)

Figure 9:
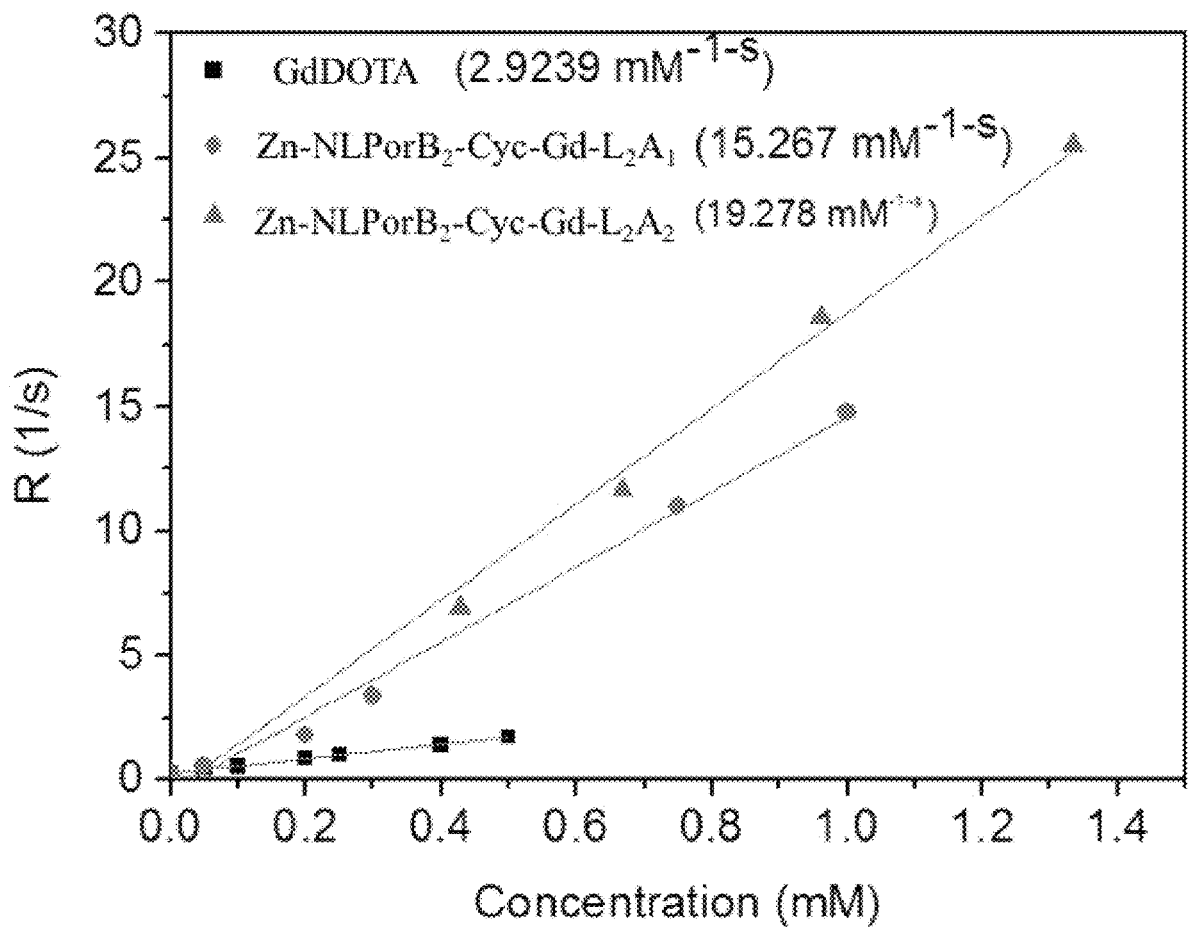
FIG. 9 shows the relationship between relativity (1/T$_1$) and the concentrations of Gd(III) (H$_2$O with 3% DMSO) in GdDOTA (control), Zn-NLPorB$_2$-Cyc-Gd-L$_2$A$_1$ and Zn-NLPorB$_2$-Cyc-Gd-L$_2$A$_2$.

$t_1$ relaxivity of the proposed MR-available PDT agent—M-NLPor-Cyc-$L_2A_n$ (n=1 or 2) was measured. The relaxivity of Zn-NLPor$B_2$-Cyc-Gd-$L_2A_1$ and Zn-NLPor$B_2$-Cyc-Gd-$L_2A_2$ at 1.5 T in water (3% DMSO) was 15.267 and 19.278 $mM^{-1}s^{-1}$ respectively which is much higher than that of Gd-DOTA. This difference in relaxivity could be due to stacking of porphyrin rings in aqueous solution, which results in an increase in apparent molecular weight and slowing rotational motion of whole complex with enhancement of $t_1$ relaxivity. (The q value of Zn-NLPor$B_2$-Cyc-Gd-$L_2A_n$ (n=1 or 2) (FIG. 9). However, there is no responsive $t_1$ relaxivity when Zn-NLPor$B_2$-Cyc-Gd-$L_2A_n$ (n=1 or 2) was binded with DOPC.

The five selected exemplary gadolinium complexes were evaluated in vitro for bladder cancer cells selectivity by (1) confocal imaging, (2) selectivity for photodynamic index (bladder cancer cells vs normal cells) and $t_1$ relaxivity responsive signal to the cancer cells receptors/markers, i.e. $α_vβ_3$ integrin or DOPC. One exemplary gadolinium complex was selected for MRI that was highly selectively for bladder cancer. Pharmacokinetics and biodistribution studies of NLPor-Gd-$L_1R_n$ and Zn-NLPor$B_2$-Cyc-Gd-$L_2A_n$ have been worked out in 100 mice (20 for each gadolinium complexes).

Figure 10:
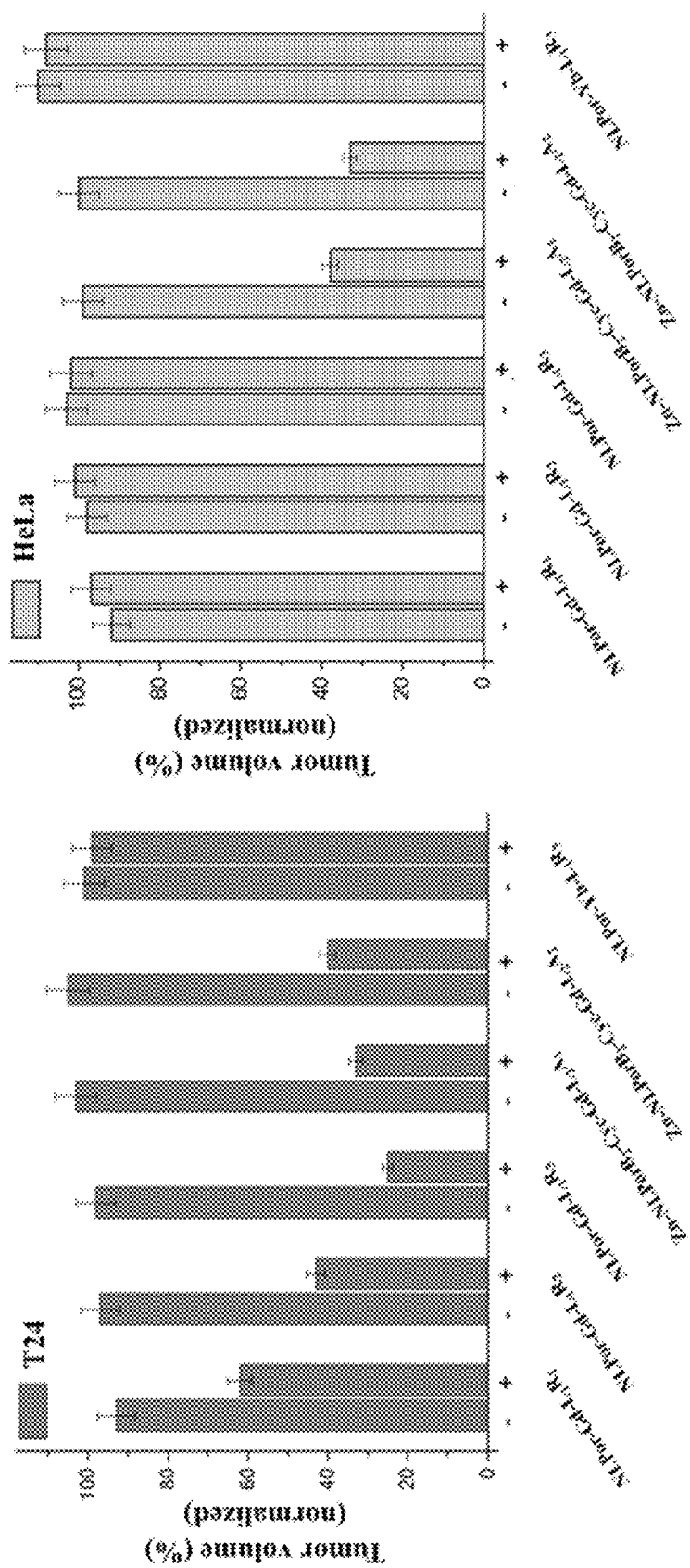
FIG. 10 shows the In vivo tumor inhibition via NLPor-Gd-$L_1R_n$ (n=1-3) and Zn-NLPorB$_2$-Cyc-L$_2$A$_n$ (n=1 or 2)-induced $^1O_2$ through caudal vein injection.

Mice with xenograft tumor were caudal vein injected with NLPor-Gd-$L_1R_n$ and Zn-NLPor$B_2$-Cyc-Gd-$L_2A_n$ (2.0 mg/kg body weight) and allowed for full circulation for 6 hours. Then tumors were irradiated with 860 nm light similarly as above. The tumor on the opposite side served as the control (light untreated). The treatments were repeated for three times in the following days in a one-time-per-day manner. Consistently, it was found that NLPor-Gd-$L_1R_3$ plus light treated tumors were inhibited in bladder cancer cells compared to their opposite flank controls of tumor or NLPor-Gd-$L_1R_n$ (n=1 or 2) and Zn-NLPor$B_2$-Cyc-Gd-$L_2A_n$ (n=1 or 2) groups. Pharmacokinetics analysis also showed that NLPor-Gd-$L_1R_3$ persisted in animals for a longer time with a larger MRT (mean resistance time) value, while NLPor-Gd-$L_1R_n$ (n=1, 2) and Zn-NLPor$B_2$-Cyc-Gd-$L_2A_n$ (n=1 or 2) was fast cleared (with MRT of 3.49 hours) (FIG. 10).

Figure 12:
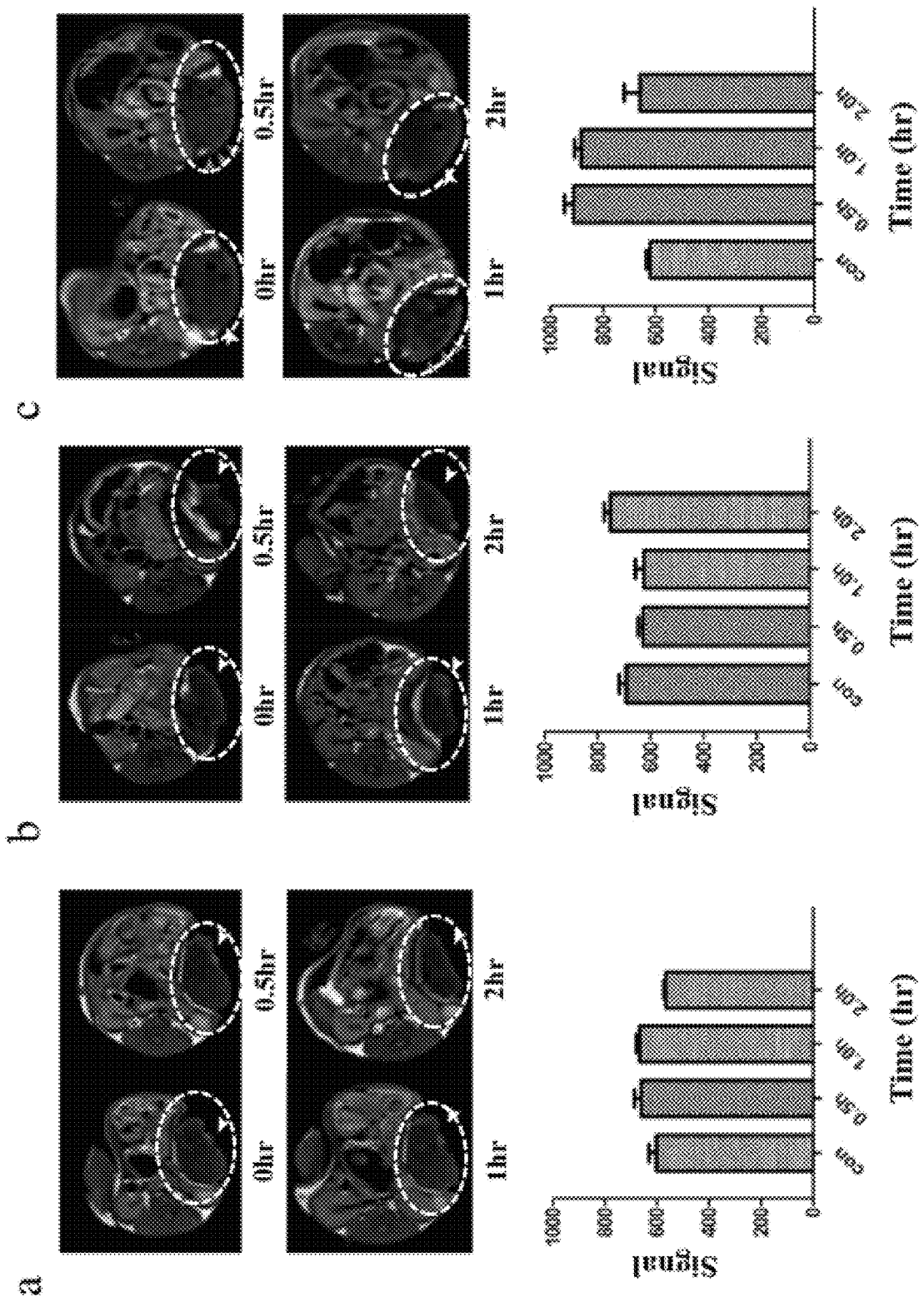
FIG. 12 shows (a) In vivo T1-weighted MR images of mouse tumor model before and after injection of GdDOTA at various time points; (b) In vivo T1-weighted MR images of mouse tumor model before and after injection of NLPor-Gd-L$_1$ at various time points; and (c) In vivo T1-weighted MR images of mouse tumor model before and after injection of NLPor-Gd-L$_1$R$_3$ at various time points.

After all these studies in previous session, NLPor-Gd-$L_1R_3$ is a potential dual bioprobe for bladder cancer specific MRI and PDT agent. Magnetic resonance imaging (MRI) is an advanced imaging technique which provides high-resolution pictures from deep tissue. In addition, MRI can offer 3D temporal-spatial resolution images. Gd-based materials are often used as contrast agents for MRI because of the paramagnetic property of Gadolinium. To study the working mechanism of NLPor-Gd-$L_1R_3$ in vivo, experiments were conducted BALB/c nude mice bearing T24 bladder cancer xenografts, and commonly used MRI contrast agent Gd-DOTA was chosen as the control. NLPor-Gd-$L_1R_3$ and Gd-DOTA were injected into the tail vein of the mice with T24 tumor respectively. MRI signal enhancement was assessed by performing in vivo MRI measurements in three BALB/c nude mice bearing T24 bladder cancer xenografts. Three tumor models were developed by subcutaneous injection of T24 bladder cancer cells. The injection doses of NLPor-Gd-L$_1$R$_3$, NLPor-Gd-L$_1$ (no R$_3$, only COOH group as control) and GdDOTA were 100 µmol/kg (2 µmol/mouse). MR images were acquired before and after tail vein injection of 200 µl of each sample at various time points. Strong MRI signal enhancement was observed at 0.5 hour and maintained for 1 hour after the injection NLPor-Gd-L$_1$R$_3$ while the signal decrease to the pre-injection level (FIG. 12c). Compared with NLPor-Gd-L$_1$R$_3$, NLPor-Gd-L$_1$ shows almost no post injection signal enhancement-within 2 hours (FIG. 12b), which proved the α$_v$β$_3$ integrin targeting function of R$_3$ is essential for providing MRI signal enhancement. Weak post injection signal enhancement observed in the MR images of GdDOTA injection (FIG. 12a) might related to the quick clearance properties of GdDOTA in the mice tumor model. MRI signal enhancement of NLPor-Gd-L$_1$R$_3$ injection is stronger than that of GdDOTA. It also demonstrated NLPor-Gd-L$_1$R$_3$ might have a longer clearance time than GdDOTA, which may due to the interaction between the R$_3$ and the α$_v$β$_3$ integrin in bladder cancer cells. Results show that NLPor-Gd-L$_1$R$_3$ can be a promising MRI contrasting agent for T24 bladder cancer.

Figure 13:
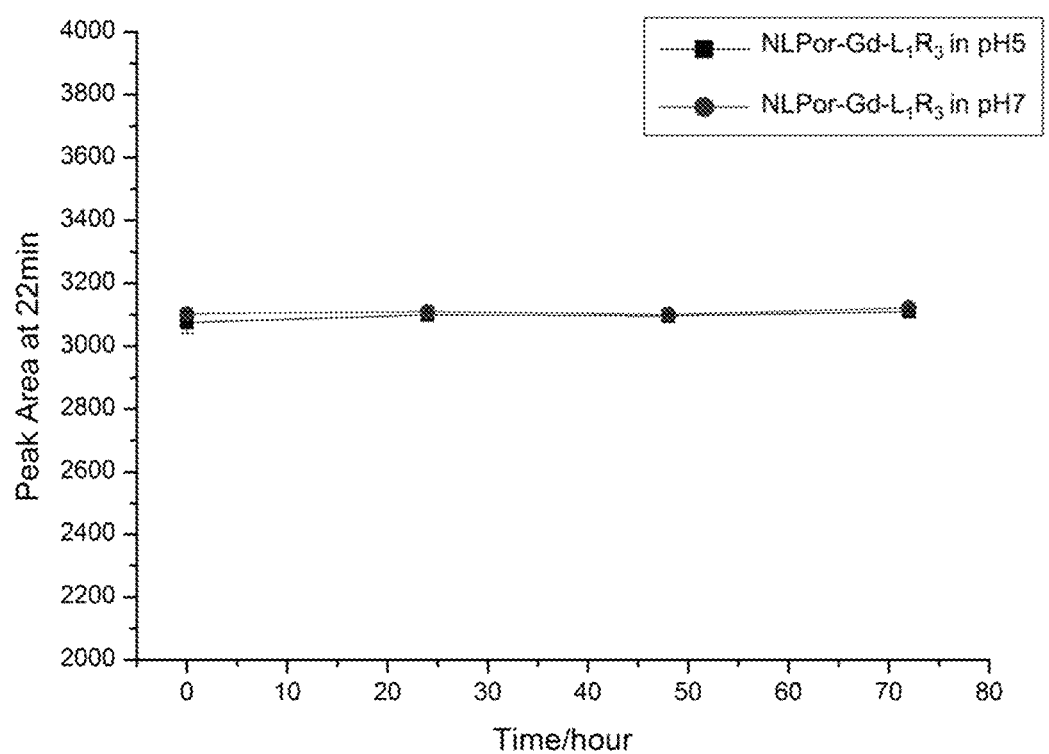
FIG. 13 shows change in peak area integration of NLPor-Gd-L$_1$R$_3$ (black) in pH7 buffer solution and (red) pH5 buffer solution over time.
Figure 14:
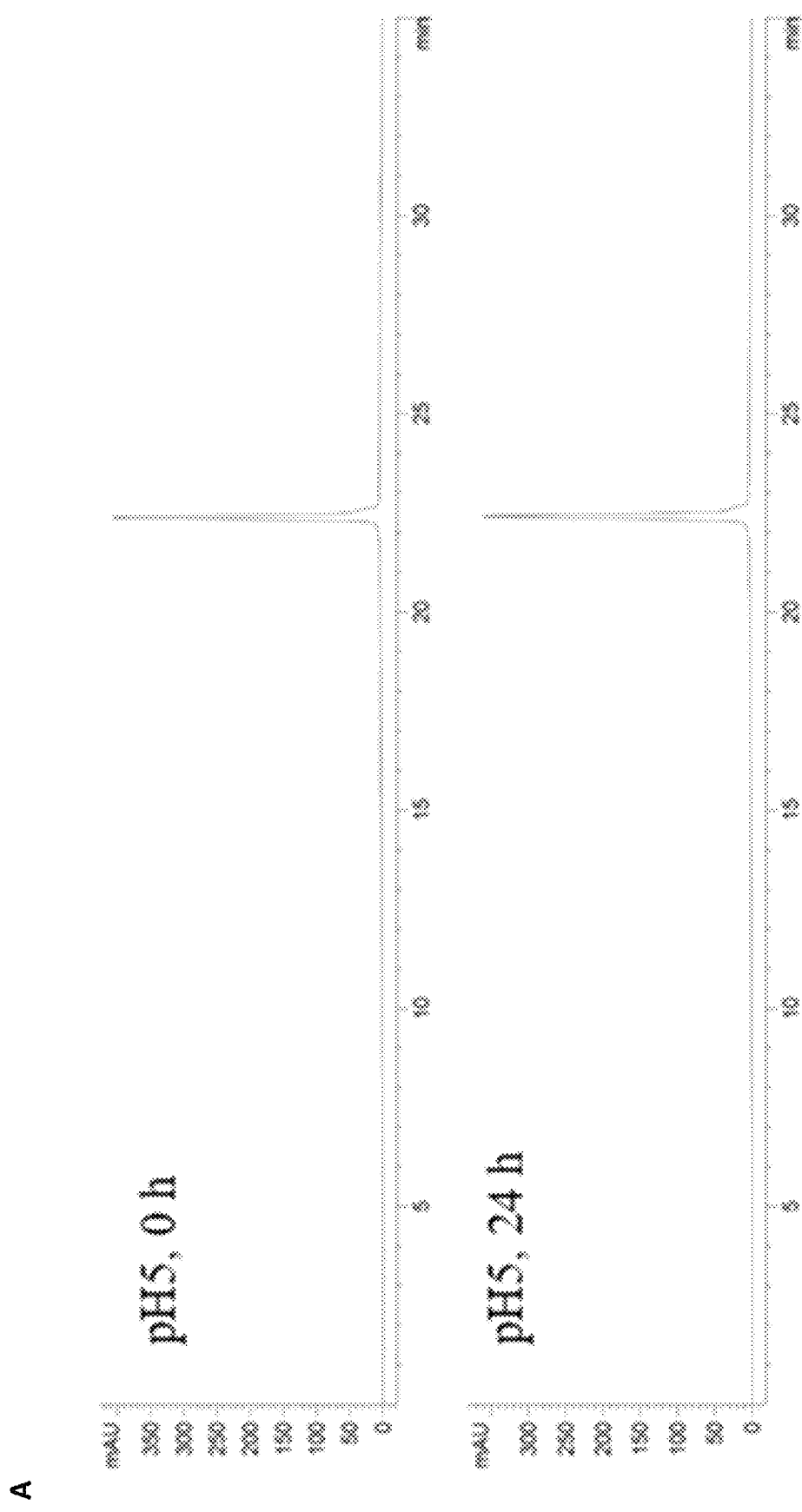
FIG. 14 (a) shows RP-HPLC chromatogram of NLPor-Gd-L$_1$R$_3$ in pH7 buffer solution over time; and (b) shows RP-HPLC chromatogram of NLPor-Gd-L$_1$R$_3$ in pH5 buffer solution over time.
Figure 14:
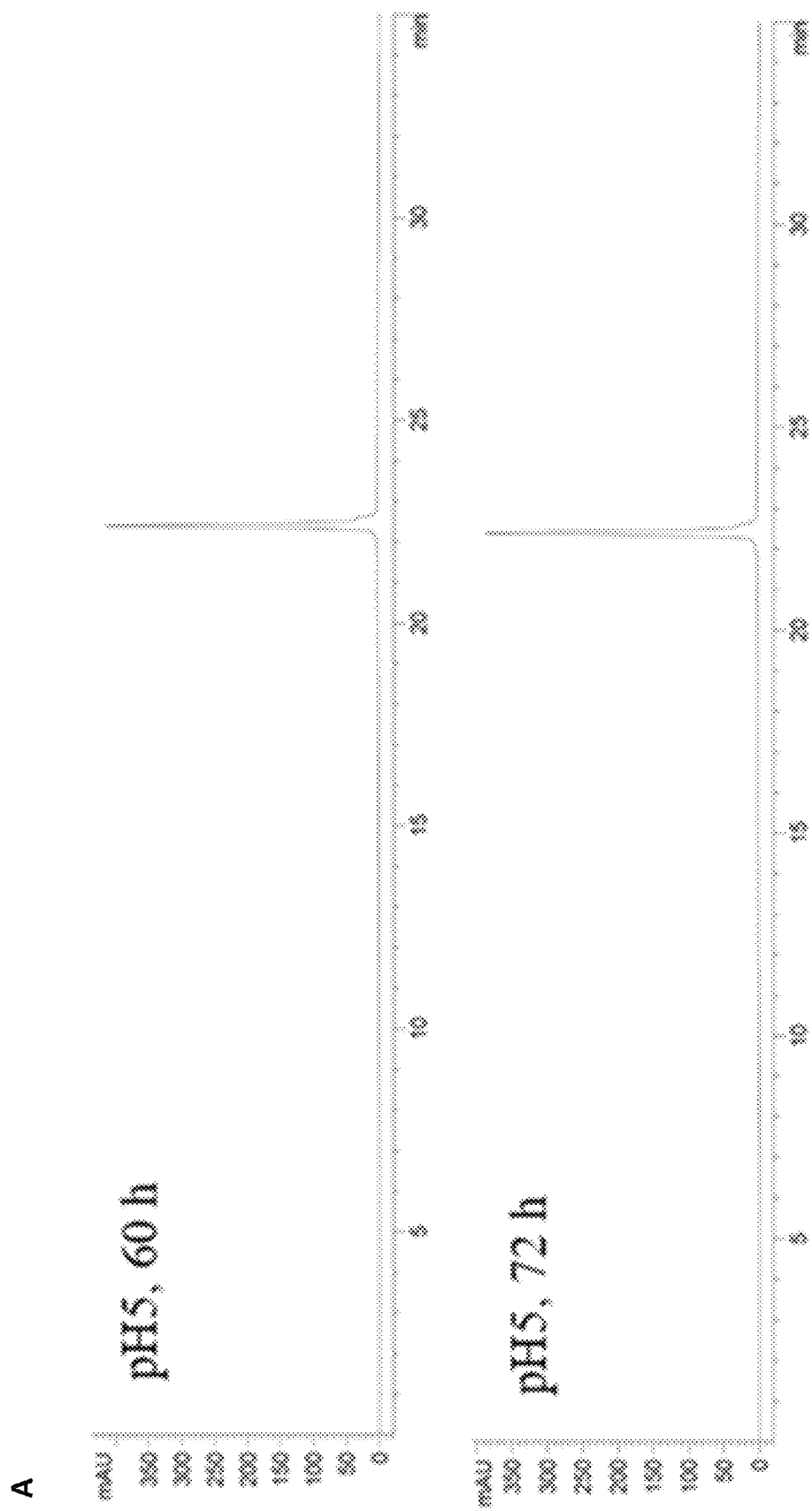
Figure 14:
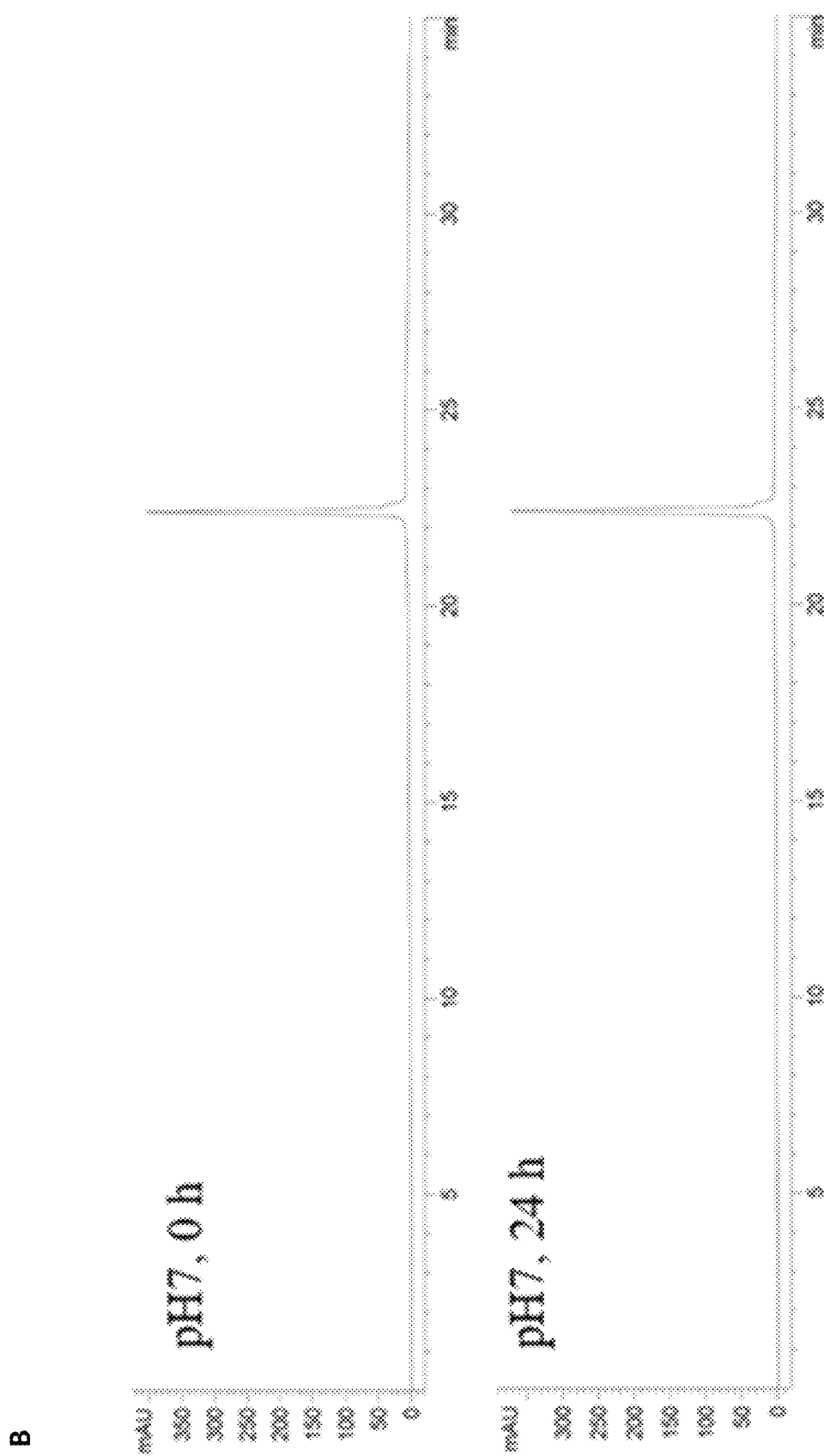
Figure 14:
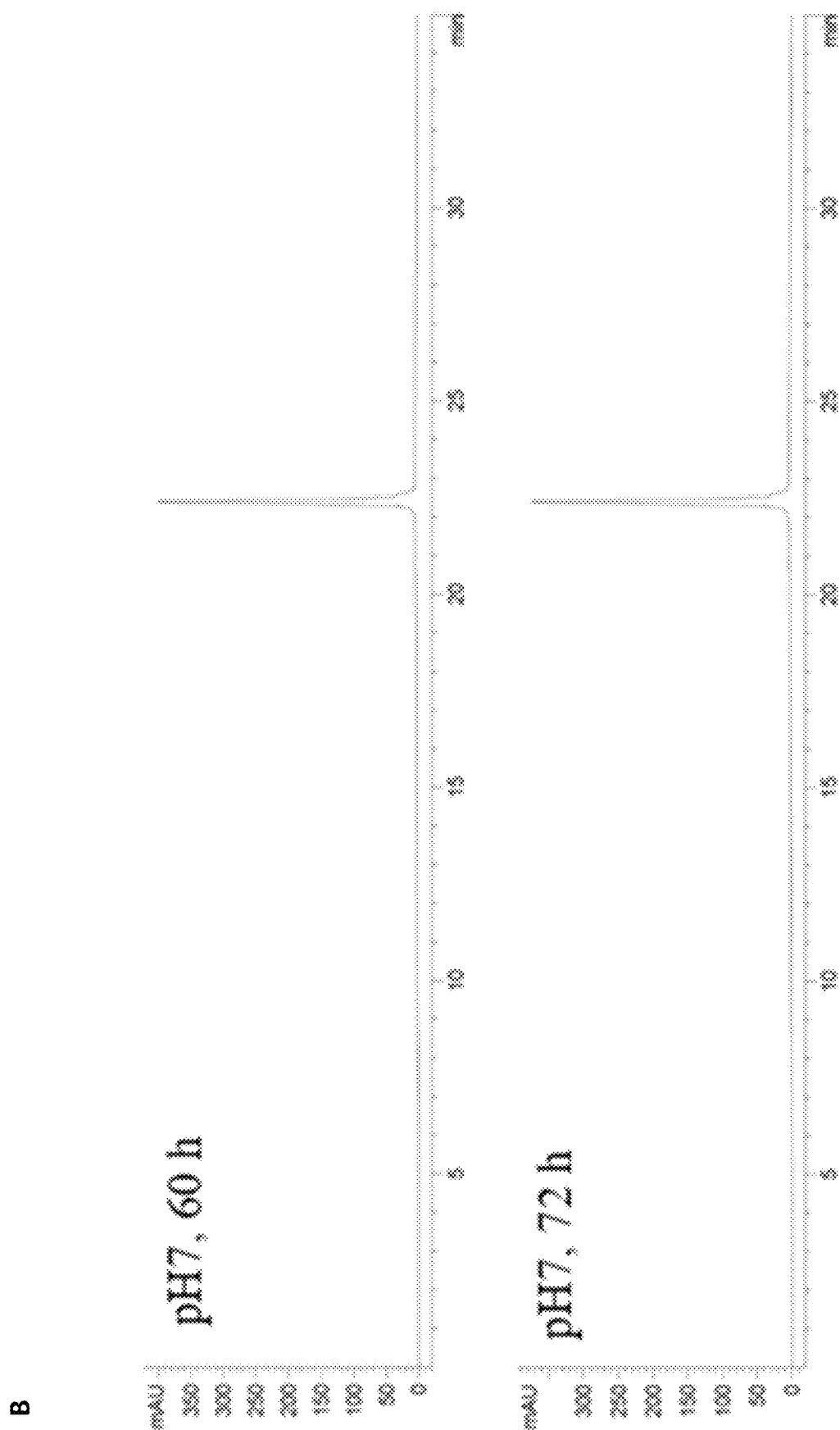

The stability of gadolinium based MRI contrasting agents is always an important parameter as free Gd$^{3+}$ ions are toxic as it has similar ionic radius as Ca$^{2+}$. Thus, free Gd$^{3+}$ ions may affect various voltage-gated calcium channels in the body. As the microenvironment of cancer cells is acidic, the kinetic stability of NLPor-Gd-L$_1$R$_3$ in both pH7 and pH5 buffered aqueous solution was analyzed by RP-HPLC. 200 µM NLPor-Gd-L$_1$R$_3$ was prepared and dissolved into pH7 and pH5 buffer aqueous solution respectively. RP-HPLC analysis of both samples were carried out in every 24 hours interval for 5 days. The integrated areas of the peak at t$_r$=23 min in different time intervals were obtained to determine the stability of NLPor-Gd-L$_1$R$_3$. The results indicated that there is a slight drop in the peak area integration after 24 hours in both pH7 and pH5 buffer solution. (FIGS. 13 and 14). Therefore, it can be concluded that the stability of NLPor-Gd-L$_1$R$_3$ in both pH7 and pH5 buffer solution can maintained for 24 hours.

Eleven porphyrinate gadolinium complexes were synthesized and NLPor-Gd-L$_1$R$_3$ was shown to target α$_v$β$_3$-integrin in cancer cells. NLPor-Gd-L$_1$R$_3$ can be applied in bladder cancer treatment and MR imaging. Three αvβ3-isoform targeting peptides were conjugated with porphyrinate lanthanide complexes, NLPor-Gd-L$_1$ demonstrated strong singlet oxygen quantum yield, 43%. NLPor-Gd-L$_1$R$_3$ was found to be able to penetrate into integrin α$_v$β$_3$ (+) expressive T24 cells but not α$_v$β$_3$ (−) expressive HeLa and MRC-5 cells by confocal imaging. NLPor-Gd-L$_1$R$_3$ exhibited the extreme inhibitory towards the T24 cells (IC$_{50}$=8.2 µM), with the highest PTI value (199) which is >20 folds higher than commercial available PDT agent ALA. NLPor-Gd-L$_1$R$_3$ was considered as the most promising bladder cancer specific PDT agent among all tested samples. It should be highlighted that NLPor-Gd-L$_1$R$_3$ is a novel highly bladder cancer cell specific therapeutic agent which kills tumor cells by the generation of $^1O_2$ from a porphyrin moiety and provides robust bimodal imaging (fluorescence and MRI contrast imaging). The imaging effect of NLPor-Gd-L$_1$R$_3$ was assessed by a range of in vitro and in vivo studies. This indicated that NLPor-Gd-L$_1$R$_3$ is a good candidate for MRI-guided bladder cancer PDT with high specificity.

Figure 49:
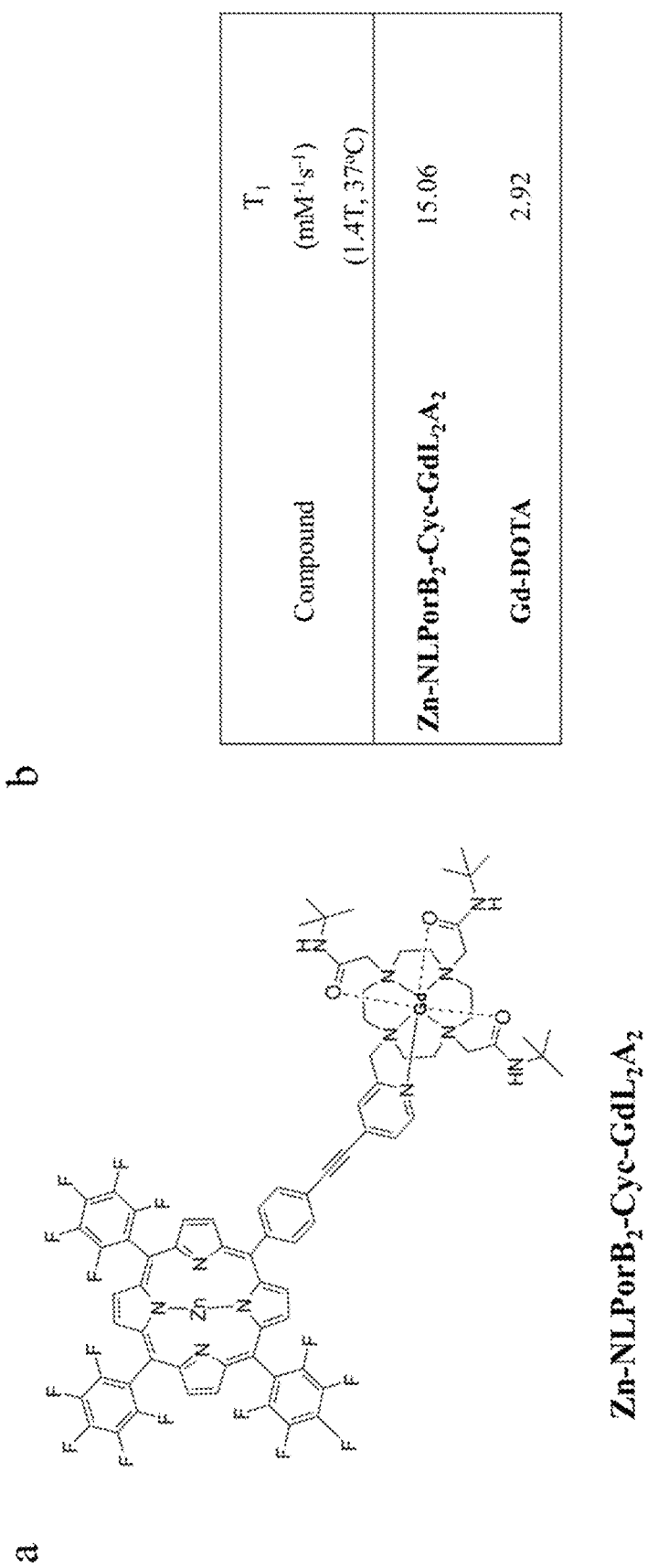
FIG. 49 shows (a) the structure of Zn-NLPorB$_2$-Cyc-Gd-L$_2$A$_2$; (b) T1 relaxivity at 1.4T, 37° C. of Zn-NLPorB$_2$-Cyc-Gd-L$_2$A$_2$ and Gd-DOTA.
Figure 54:
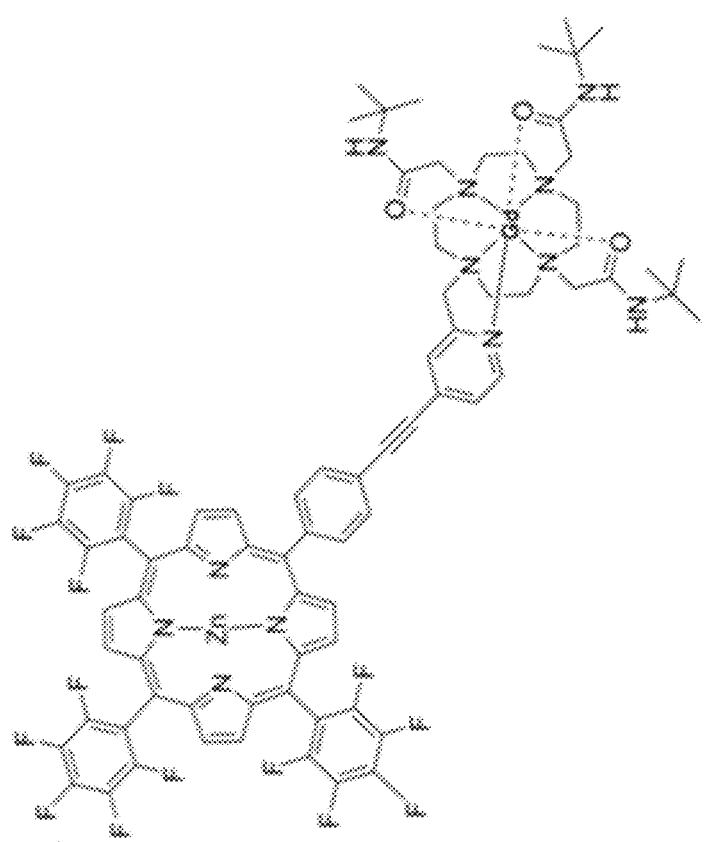
FIG. 54 shows (a) molecular structure of Zn-NLPorB$_2$-Cyc-Gd-L$_2$A$_2$, (b) Absorption spectra of Zn-NLPorB$_2$-Cyc-L$_2$A$_2$ and Zn-NLPorB$_2$-Cyc-Gd-L$_2$A$_2$, (c) Emission spectra of Zn-NLPorB$_2$-Cyc-L$_2$A$_2$ and Zn-NLPorB$_2$-Cyc-Gd-L$_2$A$_2$ under 430 nm excitation, (d) T1 relaxivity plot of Gd-DOTA and Zn-NLPorB$_2$-Cyc-Gd-L$_2$A$_2$ (1.4T, 37° C.).
Figure 54:
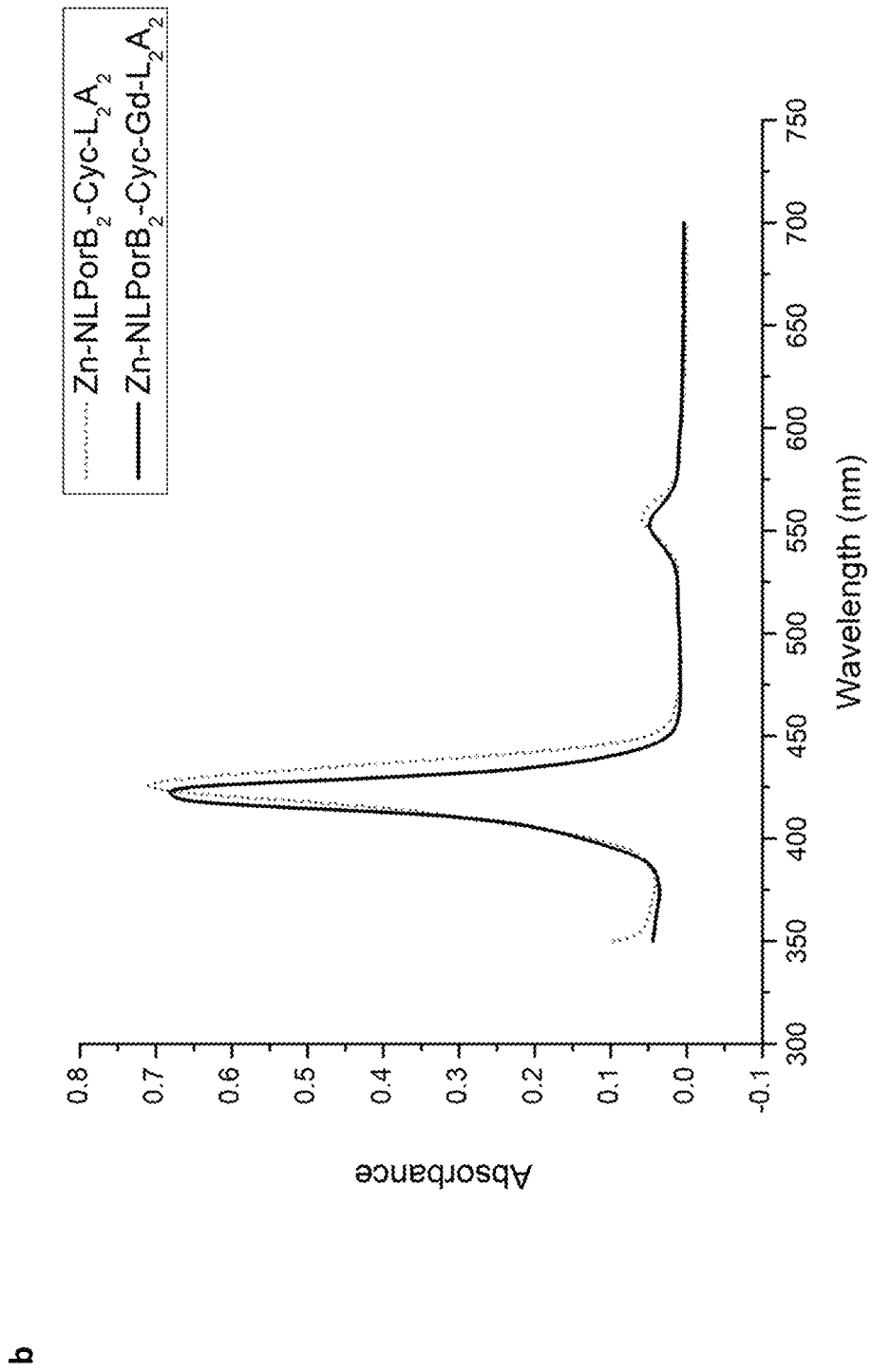
Figure 54:
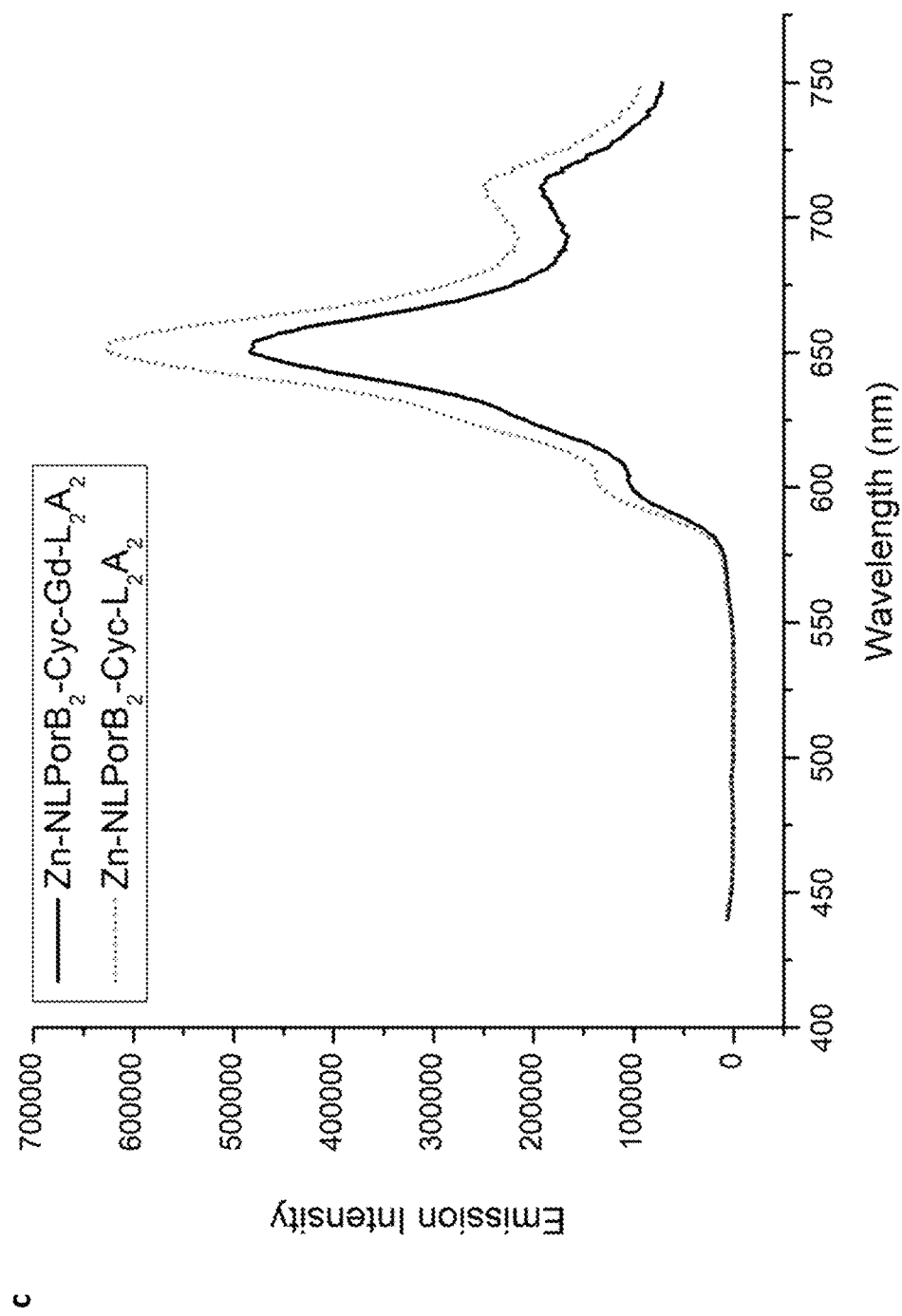
Figure 54:
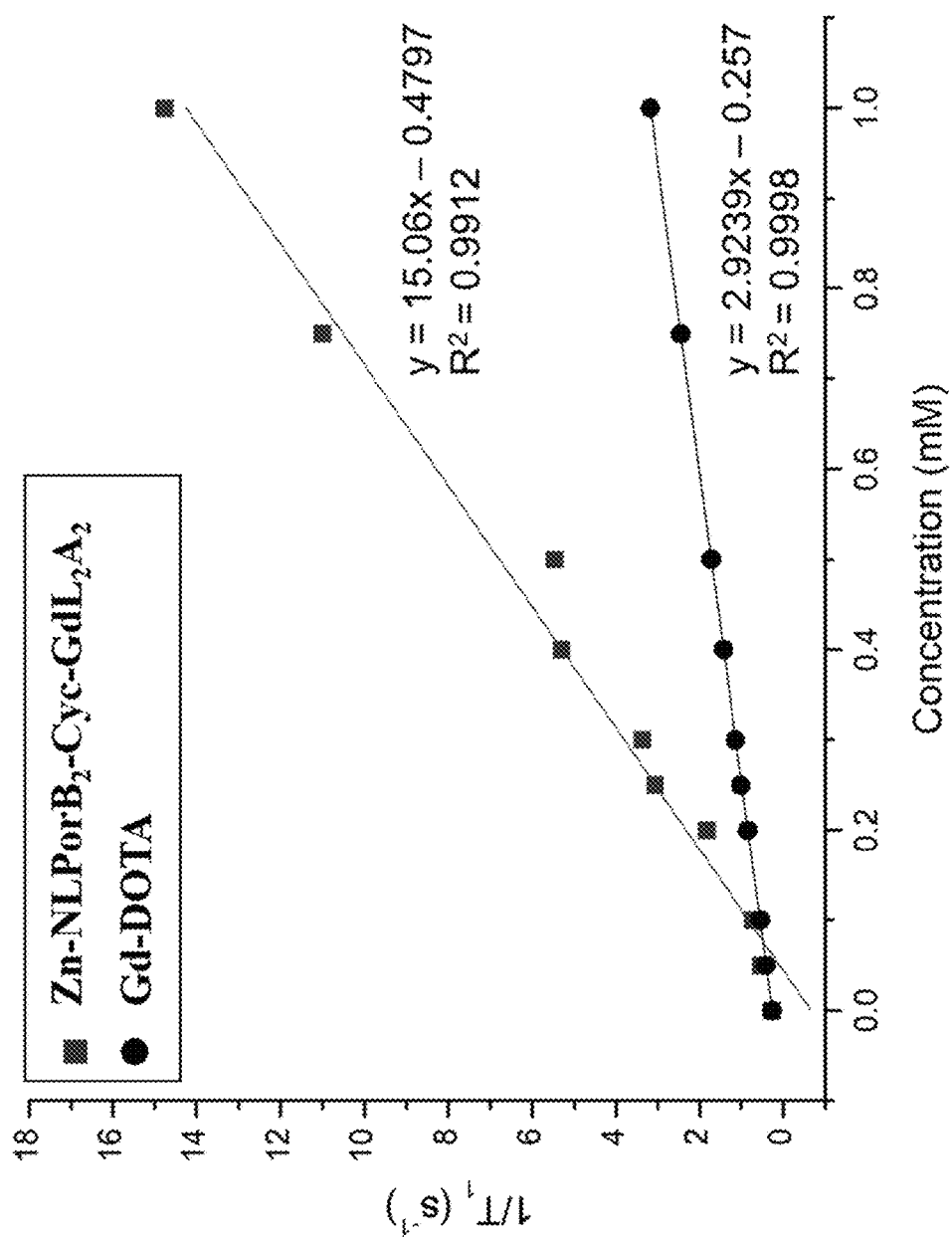

The absorption and emission spectra of Zn-NLPorB$_2$-Cyc-Gd-L$_2$A$_2$ and its precursor without Gd, Zn-NLPorB$_2$-Cyc-L$_2$A$_2$ were measured in aqueous solution (FIGS. 54b and 54c). Zn-NLPorB$_2$-Cyc-Gd-L$_2$A$_2$ and Zn-NLPorB$_2$-Cyc-L$_2$A$_2$ showed a Soret band at 420 nm which is corresponding to the transition of the ground state to the second excited state (S$_0$→S$_2$) and a Q band at 554 nm which is referring to the weak transition of the ground state to the first excited state (S$_0$→S$_1$). Zn-NLPorB$_2$-Cyc-Gd-L$_2$A$_2$ showed intense emission from 600 nm to 750 nm in aqueous solution with the excitation of 430 nm (FIG. 54c). Emission peaks at around 650 nm and 750 nm are originated from the transitions of the second excited state to the ground state (S$_2$→S$_0$) and from the first excited state to the ground state (S$_1$→S$_0$) of porphyrin respectively. The singlet oxygen quantum yields (Φ$_A$) of Zn-NLPorB$_2$-Cyc-Gd-L$_2$A$_2$ and Zn-NLPorB$_2$-Cyc-L$_2$A$_2$ were measured in CHCl$_3$ and calculated by comparing to a reference compound tetraphenylporphyrin, H$_2$TPP, (Φ$_A$=0.55 in CHCl$_3$). The singlet oxygen quantum yields of Zn-NLPorB$_2$-Cyc-Gd-L$_2$A$_2$ and Zn-NLPorB$_2$-Cyc-L$_2$A$_2$ are 0.21 and 0.27 respectively (FIG. 50). In the study of the T$_1$ relaxivity of Zn-NLPorB$_2$-Cyc-Gd-L$_2$A$_2$, clinical MRI contrasting agent Gd-DOTA was used as control for comparison. Zn-NLPorB$_2$-Cyc-Gd-L$_2$A$_2$ has a higher T$_1$ relaxivity of 15.06 mM$^{-1}$s$^{-1}$ while Gd-DOTA only shows 2.92 mM$^{-1}$s$^{-1}$ at 1.4T in water with 3% DMSO (FIG. 49). The high T$_1$ relaxivity of Zn-NLPorB$_2$-Cyc-Gd-L$_2$A$_2$ might attribute to the stacking of the porphyrin moiety in Zn-NLPorB$_2$-Cyc-Gd-L$_2$A$_2$ (FIG. 54a). It results in slowing down of the rotational motion of the complex and hence enhances the T$_1$ relaxivity of Zn-NLPorB$_2$-Cyc-Gd-L$_2$A$_2$.

The cytotoxicity assay of Zn-NLPorB$_2$-Cyc-Gd-L$_2$A$_2$ was performed on three different cell lines, HeLa (human cervical cancer cells), T24 (human bladder cancer cells) and MRC5 (human normal lung cells). Under the absence of light, the cytotoxicities of Zn-NLPorB$_2$-Cyc-Gd-L$_2$A$_2$ were very low in the three cell lines as shown in FIG. 50 (Dark-IC$_{50}$>200 µM). However, the cytotoxicity of the complex increased enormously upon light irradiation in all three cell lines. For instance, the IC$_{50}$ of Zn-NLPorB$_2$-Cyc-Gd-L$_2$A$_2$ in HeLa cells under darkness and light irradiation were 337 and 0.25 µM respectively. This proves the complex is highly safe without light irradiation while it is an effective PDT agent upon lighting, especially in cancer cell lines. This results in the high photodynamic therapeutic index (PDI) of HeLa and T24 cells (PDI were 1348 and 324 respectively). This also showed Zn-NLPorB$_2$-Cyc-Gd-L$_2$A$_2$ is a more efficient PDT agent when compared with the commercial PDT prodrug 5-aminolaevulinic acid (ALA). The cyototoxicity assay showed Zn-NLPorB$_2$-Cyc-Gd-L$_2$A$_2$ can also be a potential PDT prodrug in addition to the MRI contrasting agent.

Figure 51:
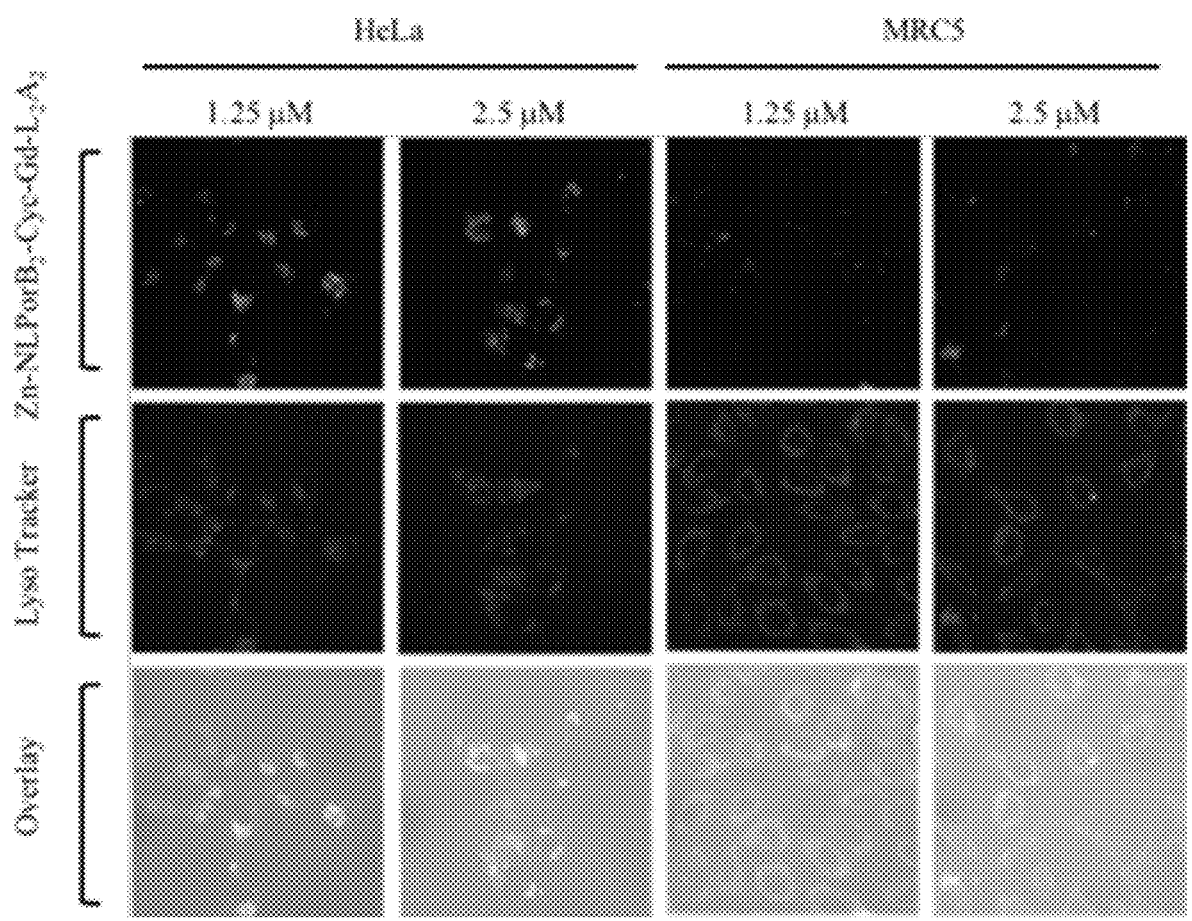
FIG. 51 shows co-stain confocal imaging of HeLa and MRC5 cells in LysoTracker Green and different concentration of Zn-NLPorB$_2$-Cyc-Gd-L$_2$A$_2$ under 480 nm laser excitation. (Zn-NLPorB$_2$-Cyc-Gd-L$_2$A$_2$ incubated in respective cell lines for 24 hours; 50 nM of LysoTracker Green was incubated in respective cell lines for 30 minutes).

In order to understand the cellular localization and selectivity of Zn-NLPorB$_2$-Cyc-Gd-L$_2$A$_2$ in cancer cells and normal cells, confocal imaging and co-staining experiments were carried out in cancer cells (HeLa) and normal cells (MRC5). As shown in FIG. 51 (which has been converted to black and white from color), the complex Zn-NLPorB$_2$-Cyc-Gd-L$_2$A$_2$ exhibited much stronger red emission (now white) in HeLa cells when comparing with MRC5 cells even under a low concentration. The red fluorescence of the confocal images on the first row are originated from the compound Zn-NLPorB$_2$-Cyc-Gd-L$_2$A$_2$ in the HeLa cells. The green fluorescence (now white) of the confocal images on the second row are from the LysoTrackeror and MitoTracker which indicate the locations of the lysosomes and mitochondria in the HeLa cells. The overlay images showed some yellow color regions (now white). The yellow color regions indicate the overlap of the red and green fluorescence. The yellow regions indicate the compounds are locate in the lysosomes and mitochondria of the HeLa cells after entering the cells. Another important message from the HeLa cancer cell images is the larger amount and more intense yellow regions can be found when the concentration of the Zn-NLPorB$_2$-Cyc-Gd-L$_2$A$_2$ increases from 1.25 µM to 2.5 µM. While in the MRC5 normal cells, there is much less yellow region found in the lower concentration of 1.25 µM. This result shows the uptake of the compound Zn-NLPorB$_2$-Cyc-Gd-L$_2$A$_2$ is much greater in the HeLa cancer cells than the MRC5 normal cells. It indicates the selectivity of Zn-NLPorB$_2$-Cyc-Gd-L$_2$A$_2$ towards cancer cells.

It represents faster and more intense cellular uptake of Zn-NLPorB$_2$-Cyc-Gd-L$_2$A$_2$ by cancer cells than normal cell lines. Co-staining experiments were performed to further evaluate the localization of Zn-NLPorB$_2$-Cyc-Gd-L$_2$A$_2$. The merged yellow emission showed in HeLa cells incubated with both Zn-NLPorB$_2$-Cyc-Gd-L$_2$A$_2$ and LysoTracker Green indicated the complex was located at the lysosome of HeLa cells. However, little or no red emission was found in MRC5 cells when only 2.5 and 1.25 µM Zn-NLPorB$_2$-Cyc-Gd-L$_2$A$_2$ was added into the cells. Only green emission was found in MRC5 cells, which represent the emission of the LysoTracker. The concentration-dependent cellular uptake of Zn-NLPorB$_2$-Cyc-Gd-L$_2$A$_2$ indicated our complex can selectively penetrate into the cancer cells but not to normal cells under a low concentration. As a low concentration (<2.5 µM) is sufficient to localize into the cancer cells, this can bring much less harm to other normal cells and therefore safer to be administrated.

Figure 11:
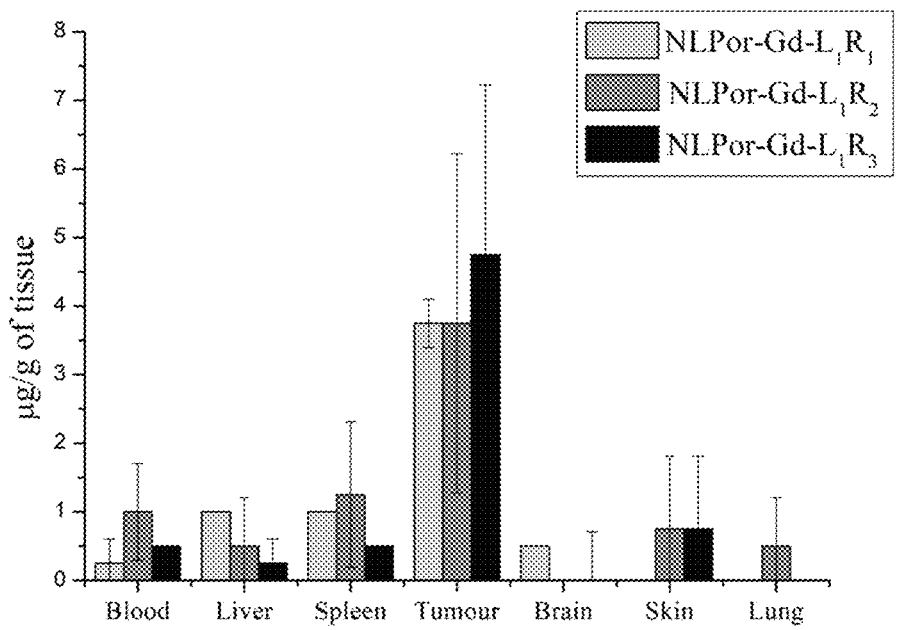
FIG. 11 shows Ex vivo biodistribution of NLPor-Gd-$L_1R_n$ (n=1-3) and Zn-NLPorB$_2$-Cyc-Gd-L$_2$A$_n$ (n=1 or 2) via ICP-MS studies in bladder cancer tumor and non bladder cancer tumor. (ppm/g, in tissue).
Figure 11:
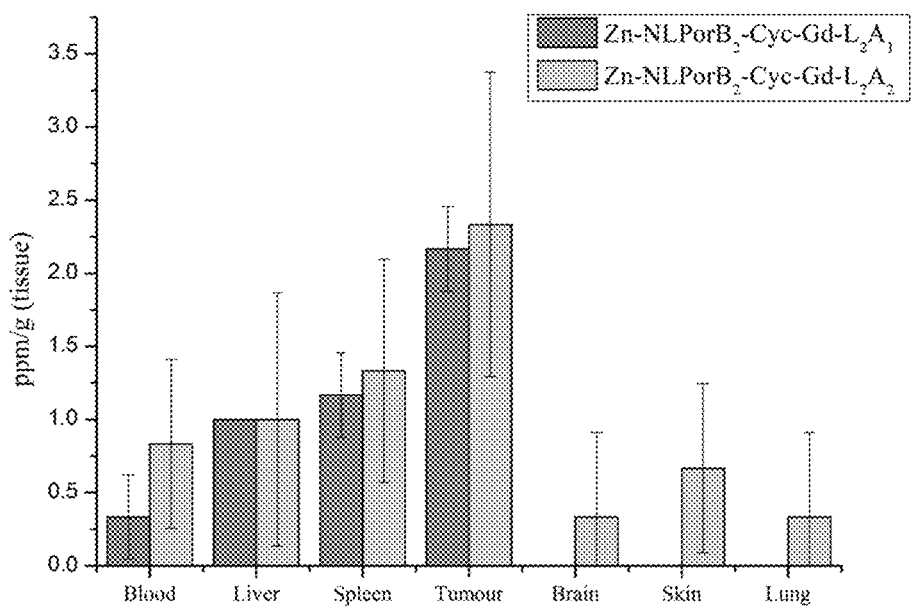
Figure 52:
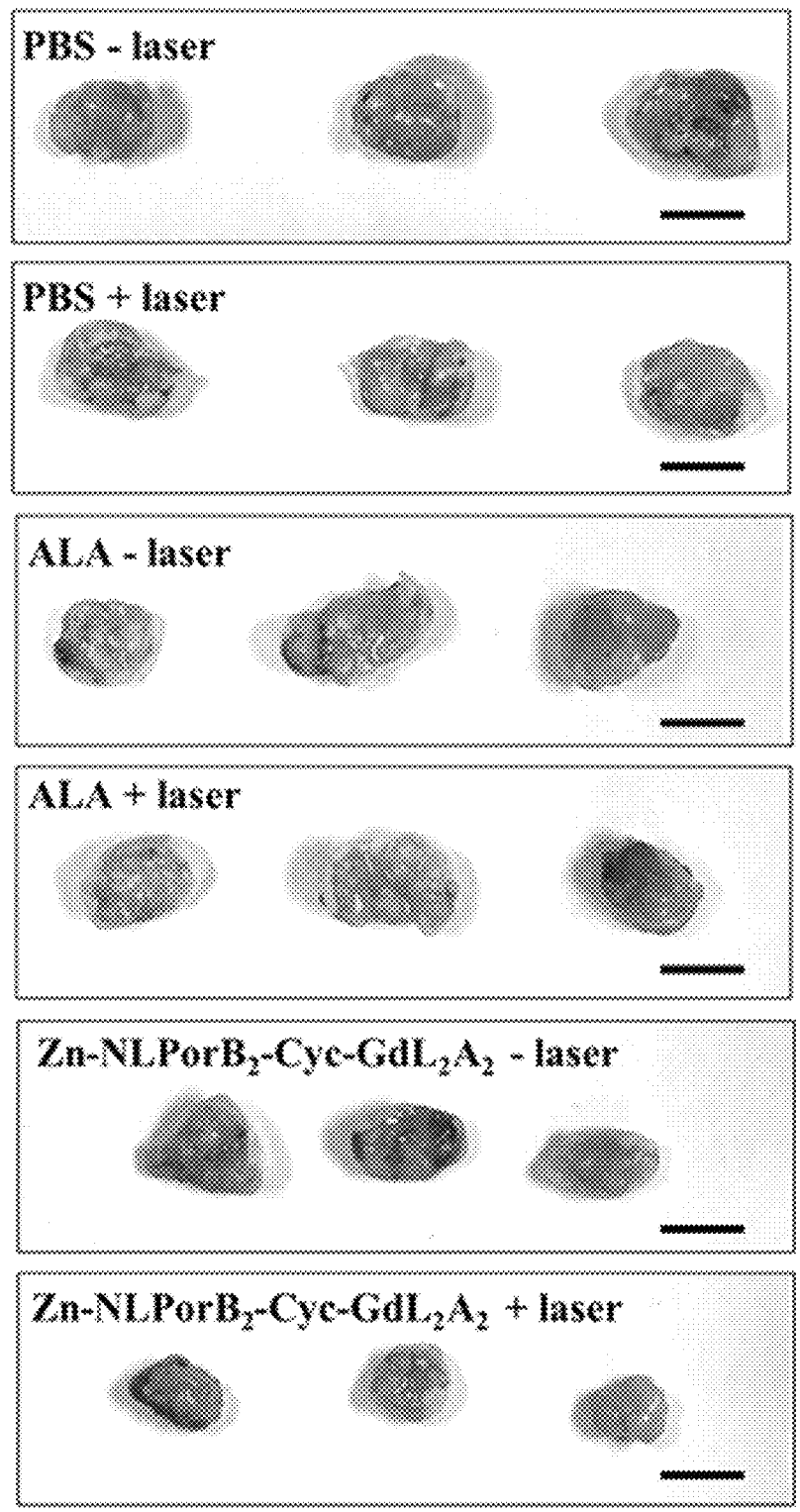
FIG. 52 shows (a) Representative images of tumors after PDT. (b) Change of tumor volume during the PDT treatment. (c) in vivo bio-distribution of Zn-NLPorB$_2$-Cyc-Gd-L$_2$A$_2$ at various time point
Figure 52:
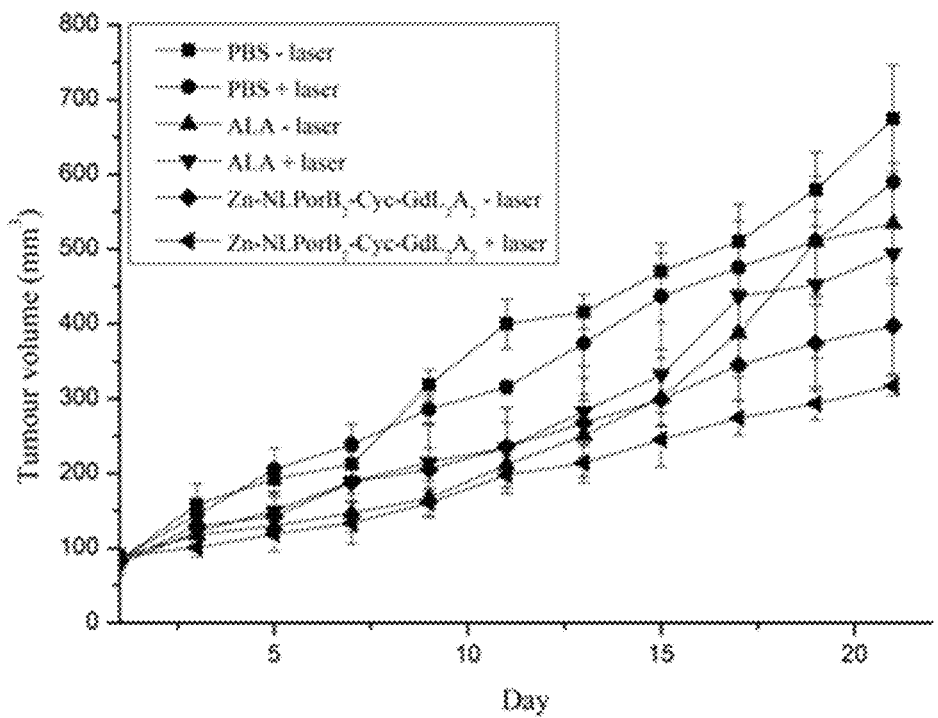
Figure 52:
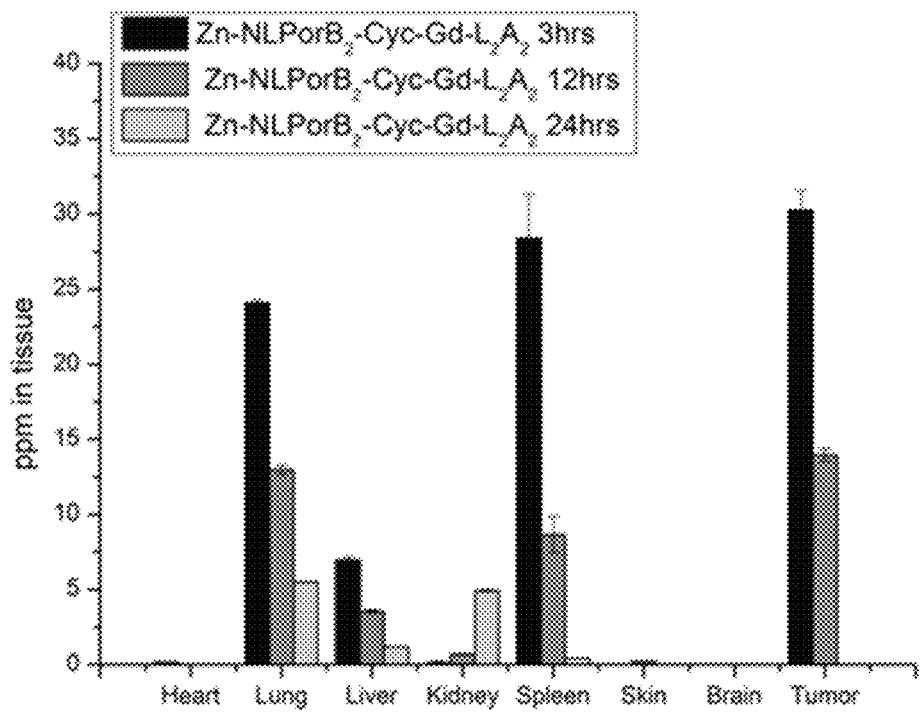

After the in vitro studies of Zn-NLPorB$_2$-Cyc-Gd-L$_2$A$_2$ in cancer cells and normal cell, in vivo experiment of finding out tumor inhibition efficiency of Zn-NLPorB$_2$-Cyc-Gd-L$_2$A$_2$ was carried out. HeLa xenograft mice models were divided into six groups for the tumor inhibition study (FIG. 52a). Zn-NLPorB$_2$-Cyc-Gd-L$_2$A$_2$ (3.46 mg/kg) and 5-aminoleeluvinc acid (ALA) (60 mg/kg) have been injected into different groups of HeLa tumors with the size of 200-350 mm$^3$ by intra-tumor injection with injecting PBS buffer as control. The PDT treatment group of tumors were irradiated with 808 nm laser for 2 hours after injections while the tumors on the opposite flank act as light untreated control. PDT treatment has been conducted once per day for 20 consecutive days. The total light dosage was 50 J/cm$^2$. Comparing with the PDT treatment of ALA, Zn-NLPorB$_2$-Cyc-Gd-L$_2$A$_2$ with 3.46 mg/kg body weight, same dosage as the in vivo MRI, demonstrated significant in vivo tumor inhibition effect after 20 days treatment (FIG. 52b). PDT treatment of HeLa tumor with Zn-NLPorB$_2$-Cyc-Gd-L$_2$A$_2$ showed a 62% decrease in volume after the 20 days treatment. The maintaining body weights of all groups of mice throughout the whole treatment proved the safety of compounds in vivo. In vivo biodistribution of Zn-NLPorB$_2$-Cyc-Gd-L$_2$A$_2$ in different time points were studied by ICP-MS. Zn-NLPorB$_2$-Cyc-Gd-L$_2$A$_2$ showed rapid accumulation at 3 hours and remain for 12 hours in the HeLa tumor site after the caudal vein injection (FIGS. 11 and 52c). Total clearance of Zn-NLPorB$_2$-Cyc-Gd-L$_2$A$_2$ from the mice body was observed after 48 hours post-injection.

Figure 53:
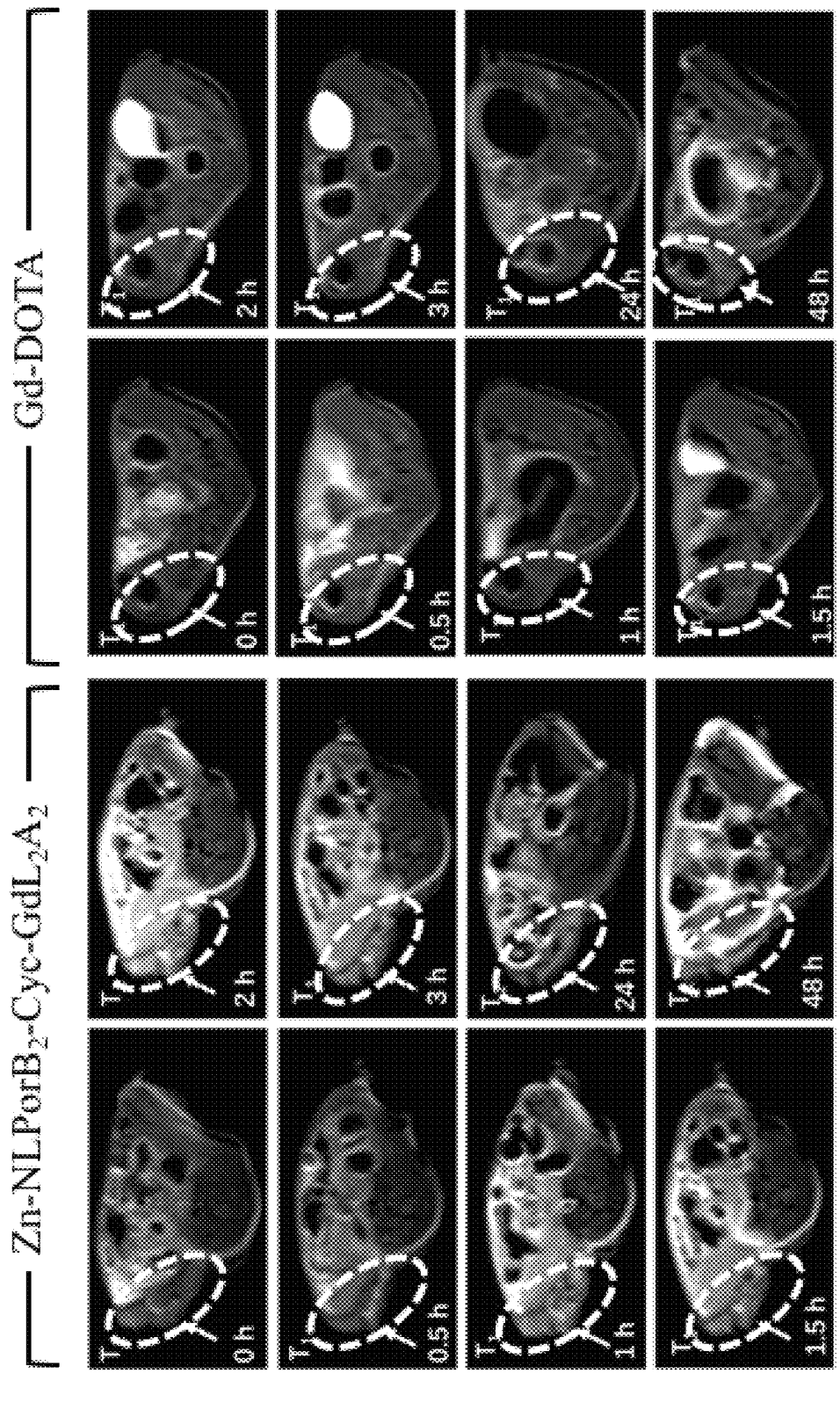
FIG. 53 shows (a) representative Magnetic Resonance Images of S18 xenograft mice cross section over time after the caudal vein injection of Zn-NLPorB$_2$-Cyc-Gd-L$_2$A$_2$ and Gd-DOTA. (b) T$_1$ signal enhancement produced by Zn-NLPorB$_2$-Cyc-Gd-L$_2$A$_2$ and Gd-DOTA over time. (c) Representative in vivo fluorescence images of S18 xenograft mice and normal mice over time.
Figure 53:
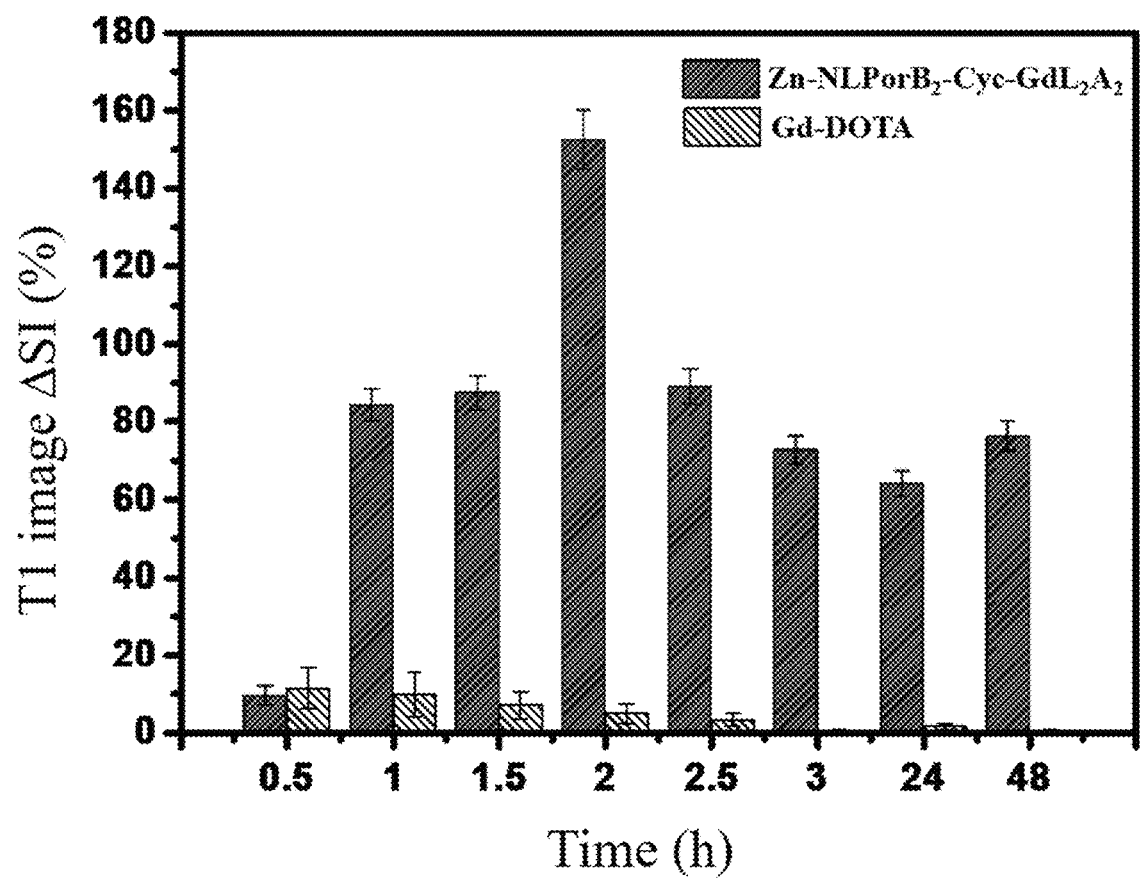
Figure 53:
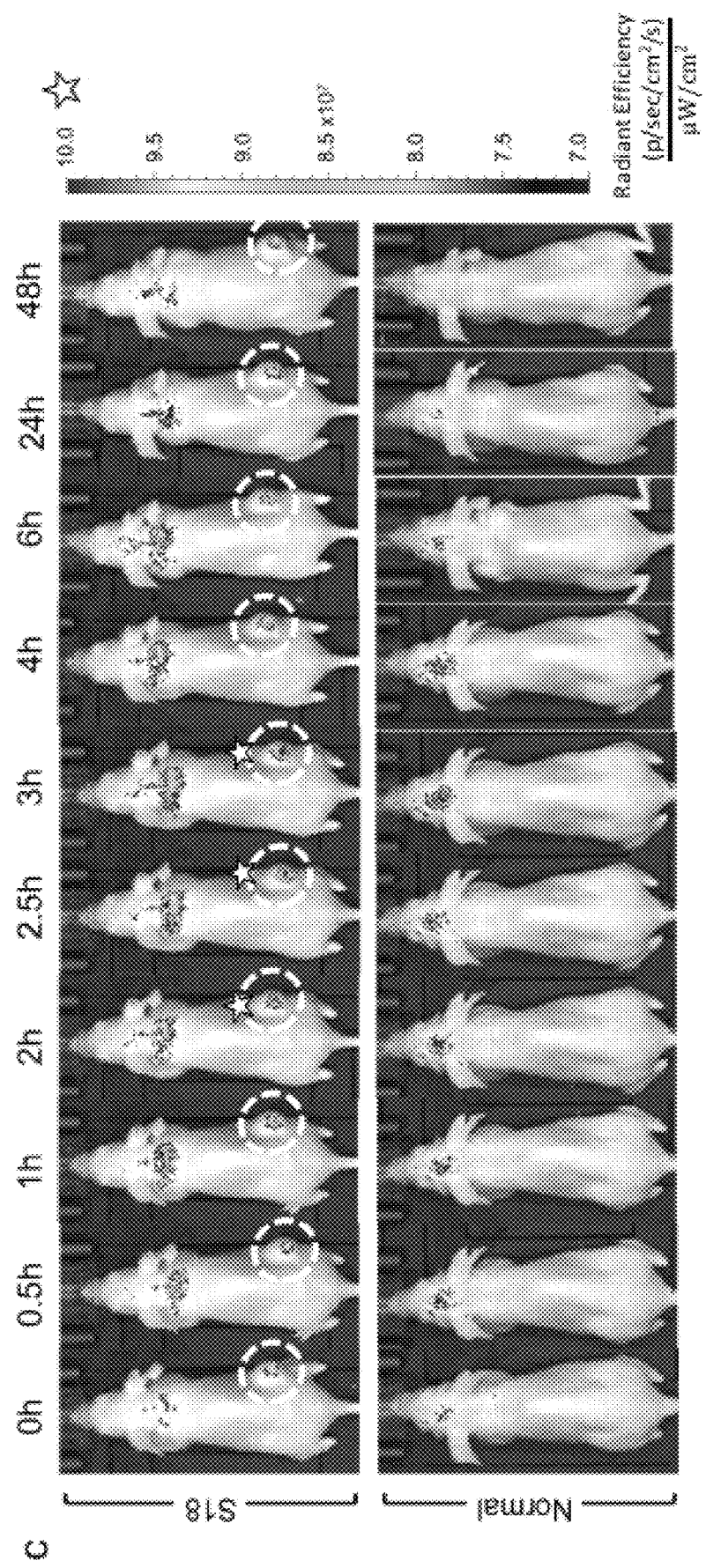

In addition to tumour inhibition efficiency of Zn-NLPorB$_2$-Cyc-Gd-L$_2$A$_2$, the MRI performance of Zn-NLPorB$_2$-Cyc-Gd-L$_2$A$_2$ was also evaluated by performing in vivo MRI in S18 xenograft mice models. Zn-NLPorB$_2$-Cyc-Gd-L$_2$A$_2$ (0.025 mmol/kg, ¼ dosage of Gd-DOTA) was injected into the S18 xenograft mice by caudal vein injection. T$_1$ images showed Zn-NLPorB$_2$-Cyc-Gd-L$_2$A$_2$ gave robust contrasting effect in vivo, the tumor site has been brightened up at the first hour after injection (FIG. 53a). The strongest signal enhancement was recorded at 2 hours after injection of Zn-NLPorB$_2$-Cyc-Gd-L$_2$A$_2$. Significant signal enhancement at the tumor site was found over 48 hours after injection compare with Gd-DOTA at the dosage of 0.1 mmol/kg body weight (FIG. 53b). Compared with Gd-DOTA, Zn-NLPorB$_2$-Cyc-Gd-L$_2$A$_2$ can reproduce stronger signal at a lower dosage. Therefore, clearer MR images with strong signal enhancement can be obtained to assist monitoring the anti-cancer treatment. In vivo fluorescence imaging has been carried out to further validate the accumulation phenomenon of Zn-NLPorB$_2$-Cyc-Gd-L$_2$A$_2$ at the tumor site. The result is consistent with the in vivo biodistribution results (FIG. 53d) that the highest amount of Zn-NLPorB$_2$-Cyc-Gd-L$_2$A$_2$ accumulation was discovered at the tumor site from 2 to 3 hours after injection while no obvious signal detected in normal mice (FIG. 53c). It explains for the strongest signal enhancement of the T$_1$ images at the same period of time.

In conclusion, a novel porphyrin-cyclen gadolinium based dual function bioprobe Zn-NLPorB$_2$-Cyc-Gd-L$_2$A$_2$ is introduced. With the impressive T$_1$ signal enhancement and higher T$_1$ reflexivity (15.06 mM$^{-1}$s$^{-1}$, 1.4T) when comparing with clinical approved MRI contrasting agent Gd-DOTA (T$_1$ relaxivity 2.92 mM$^{-1}$s$^{-1}$, 1.4T), it is believed that Zn-NLPorB$_2$-Cyc-Gd-L$_2$A$_2$ can be a good substitute of Gd-DOTA in MRI contrasting agent. In addition, it selectivity towards cancer cells under a very low concentration make it a much safer agent to be used. Its high PDT index also enable it to be a good photosensitizer which can carry out photodynamic therapy. This newly developed dual function bioprobe is believed to help us step into the new era of cancer treatment.

Figure 16:
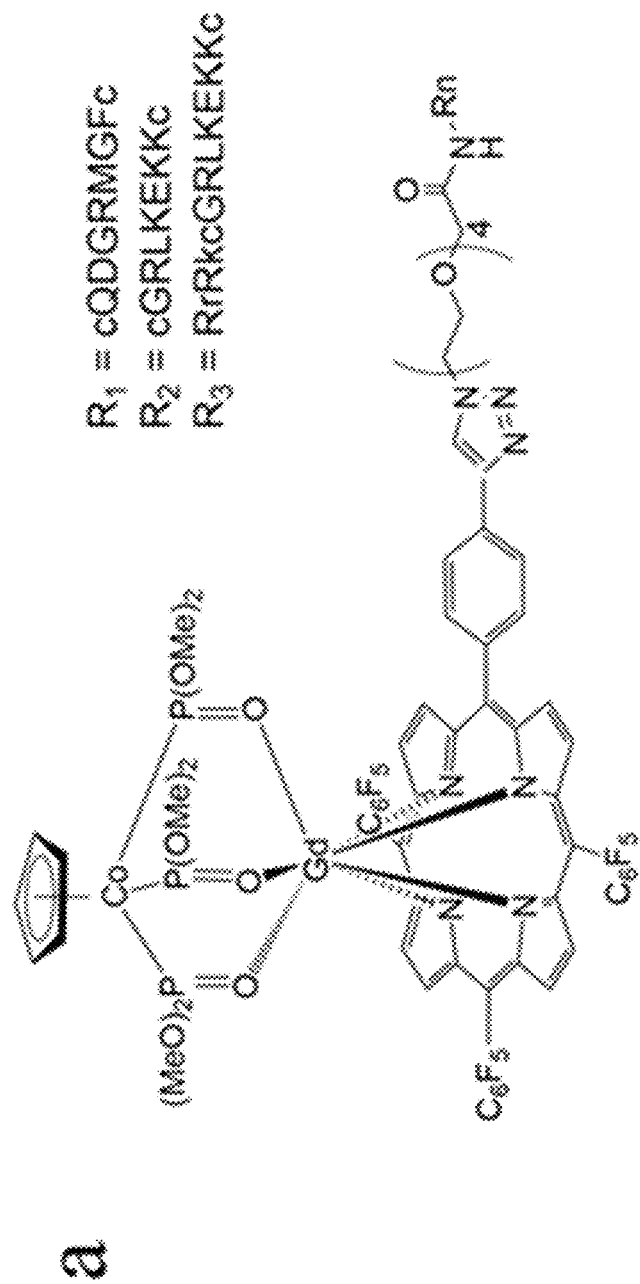
FIG. 16 shows (a) molecular structures of NLPor-Gd-L$_1$R$_n$ (n=1-3); (b) displacement percentages of the vitronectin—$α_Vβ_3$ integrin net binding at different concentrations of NLPor-Gd-L$_1$R$_n$; (c) RP-HPLC analysis results of the stability of 200 μM NLPor-Gd-L$_1$R$_3$ in pH 7 and pH 5 PBS buffer solutions.
Figure 16:
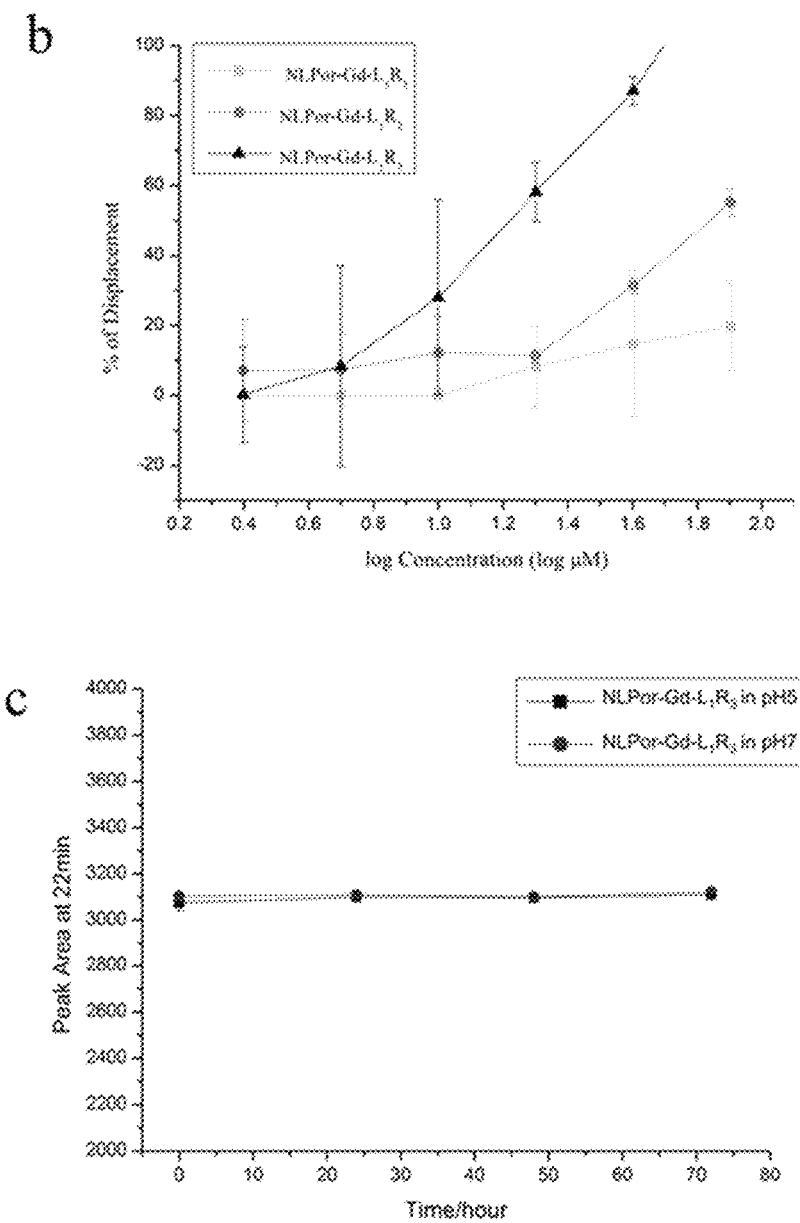

First, the integrin binding activity assay was conducted to evaluate the binding affinity of NLPor-Gd-L$_1$R$_n$ (FIG. 16a) to $\alpha_V\beta_3$ integrin. The conjugates acted as competing ligands to displace biotinylated vitronectin from the recombinant $\alpha_V\beta_3$ integrin. The effect of NLPor-Gd-L$_1$R$_n$ (n=1-3) on the net binding of vitronectin and $\alpha_V\beta_3$ integrin was revealed by evaluating the absorbance at 405 nm of the mixture at different concentrations of NLPor-Gd-L$_1$R$_n$. Decreasing absorbance indicated the competing effect of NLPor-Gd-L$_1$R$_n$ on vitronectin from $\alpha_V\beta_3$ integrin. The percentage displacement of vitronectin by either compound (FIG. 16b) clearly points to a reduction in net binding with increasing concentration of NLPor-Gd-L$_1$R$_n$, the effect being markedly larger with R$^3$. This is consistent with NLPor-Gd-L$_1$R$_n$ interacting with $\alpha_V\beta_3$ integrin and inhibiting the binding between the $\alpha_V\beta_3$ integrin and biotinylated vitronectin. The stability of Gd-based MRI contrast agents is always an important parameter since free Gd$^{3+}$ ions could be toxic due to their similar ionic radius to biologically-prevalent Ca$^{2+}$ ions, and thus free Gd$^{3+}$ ions may affect various voltage-gated calcium channels in the body. As the microenvironment of cancer cells is mildly acidic (pH 5-7), the kinetic stability of NLPor-Gd-L$_1$R$_3$ in both pH 7 and pH 5 buffered aqueous solutions was analyzed by reverse-phase high-performance liquid chromatography; 200 µM NLPor-Gd-L$_1$R$_3$ was prepared and dissolved in pH 7 and pH 5 phosphate buffered saline solutions and analyses were carried out every 24 h for 4 days. The areas of the peaks (at retention time t$_r$=23 min) after different time intervals were determined to assess the stability of NLPor-Gd-L$_1$R$_3$. The results showed no obvious decrease in peak areas after 24 h in both pH 7 and pH 5 solutions (FIG. 16c). Therefore, it can be concluded that the stability of NLPor-Gd-L$_1$R$_3$ in both pH 7 and pH 5 buffer solutions can be maintained for more than 24 h.

Figure 17:
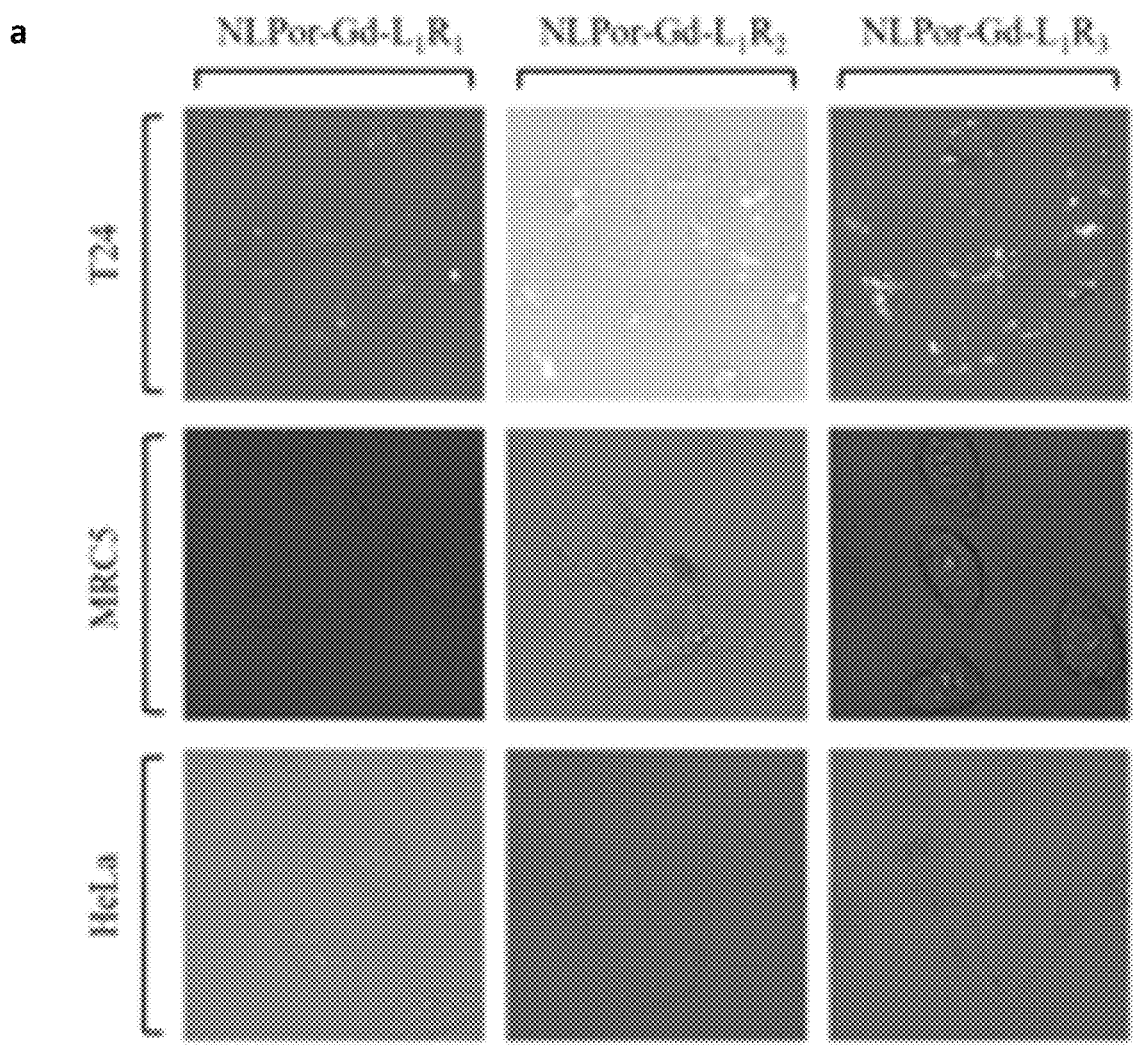
FIG. 17 shows in vitro imaging of (a) NLPor-Gd-$L_1R_n$ (n=1-3) in human bladder cancer (T24), normal (MRC-5), and cervical carcinoma (HeLa) cells and (b) subcellular localization of NLPor-Gd-L$_1$R$_n$ (n=1-3) by co-staining with lysotracker green in T24 cells. Dosage: 5 μM, incubation time: 24 h, $\lambda_{ex}$=561 nm.
Figure 17:
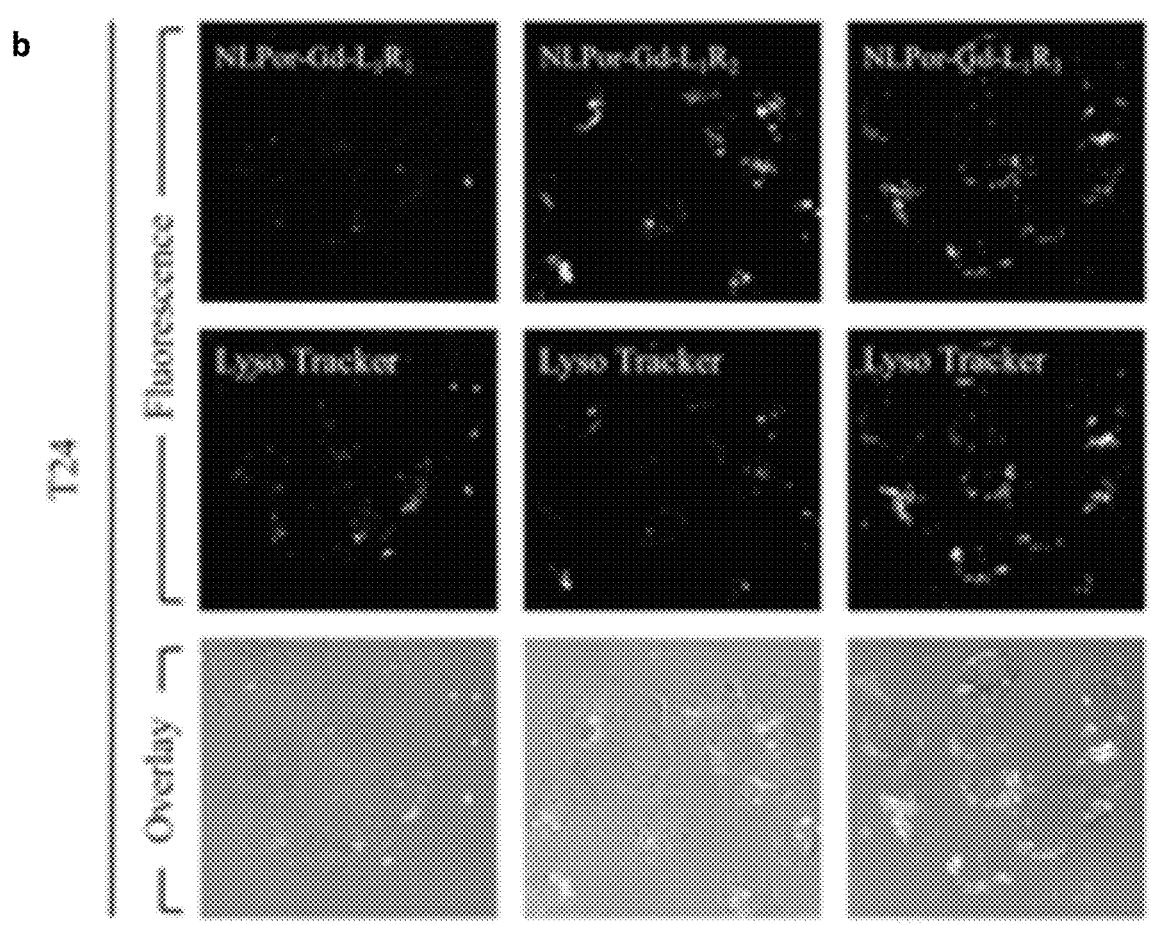

Next, studies on in vitro imaging with NLPor-Gd-L$_1$R$_n$ were performed on human bladder carcinoma (T24), cervical cancer (HeLa), and normal lung (MRC-5) cell lines. According to FIG. 17 (*a*) (which has been, converted to black and white from color), red emission generated (now white) by the porphyrinato chromophores was observed inside T24 bladder cancer cells while no signal was obtained from HeLa and MRC-5 cells. This is in line with specific localization of NLPor-Gd-L$_1$R$_n$ in bladder cancer cells. With peptide R$^3$ being more hydrophilic than R$^1$ and R$^2$, the R$^3$-conjugated compound has better solubility and biocompatibility. Therefore, more intense red emission from NLPor-Gd-L$_1$R$_3$ was observed. Co-staining experiments were performed with the green-emitting lysotracker dye to further investigate the intracellular localization of NLPor-Gd-L$_1$R$_n$. As shown in FIG. 17 (overlay section), both red and green emissions (now white) are seen and it is worth noting that the merged images show partial overlapping (yellow spots in overlay section (now white)) for R$^2$ and R$^3$: (Pearson's coefficients (ranging from −1 to 1): NLPor-Gd-L$_1$R$_2$=0.394; NLPor-Gd-L$_1$R$_3$=0.279).

Figure 18:
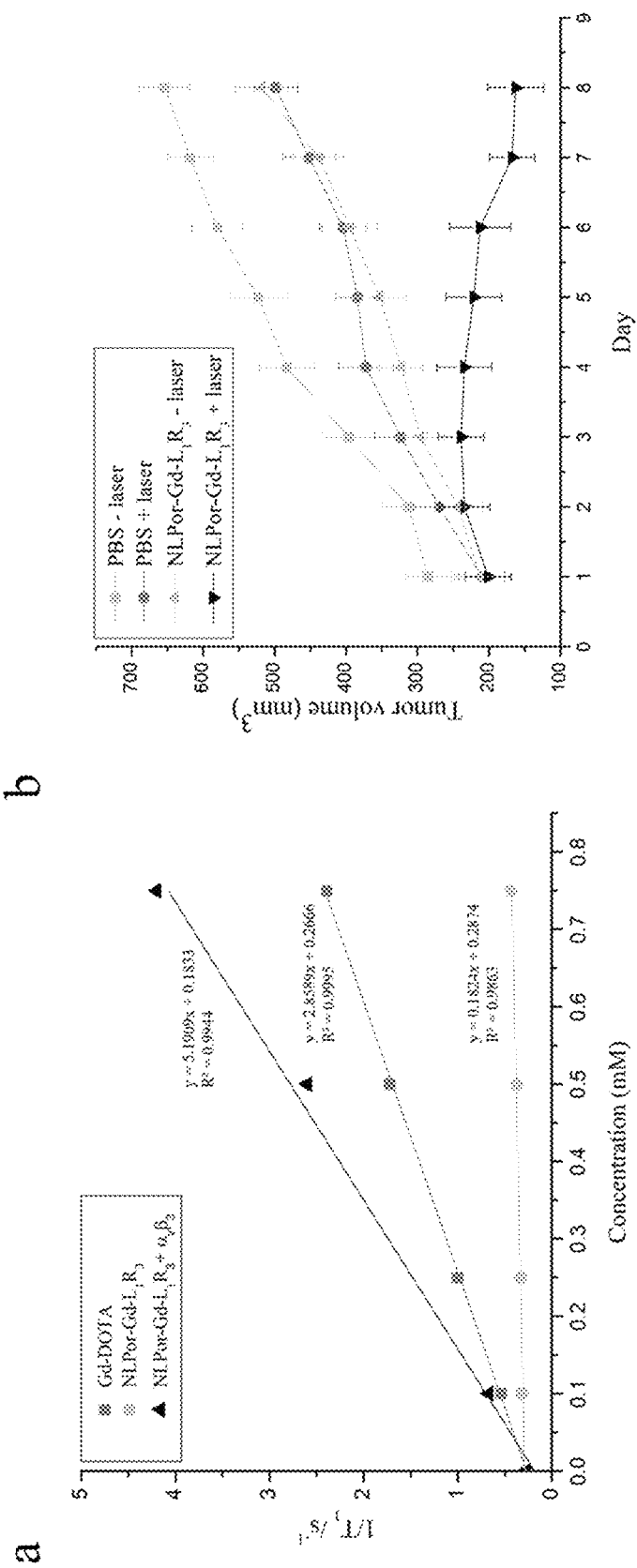
FIG. 18 shows (a) the relationship between T1 relaxivity and the concentration of Gd(III) (H$_2$O with 3% DMSO) in Gd-DOTA (control) or NLPor-Gd-L$_1$R$_3$ with/without the binding of α$_v$β$_3$ integrin; (b) Change of T24 tumor volume during in vivo PDT, data are expressed as mean±SEM. * referring to P<0.005 vs PBS-laser control, statistically significant difference; (c) Representative image of excised tumors after in vivo PDT; (d) bladder cancer xenograft—T24; and (e) non-bladder cancer xenograft—HeLa mice (□: no light, +: with light; $\lambda_{ex}$=808 nm, dose=50 J/cm$^2$).
Figure 18:
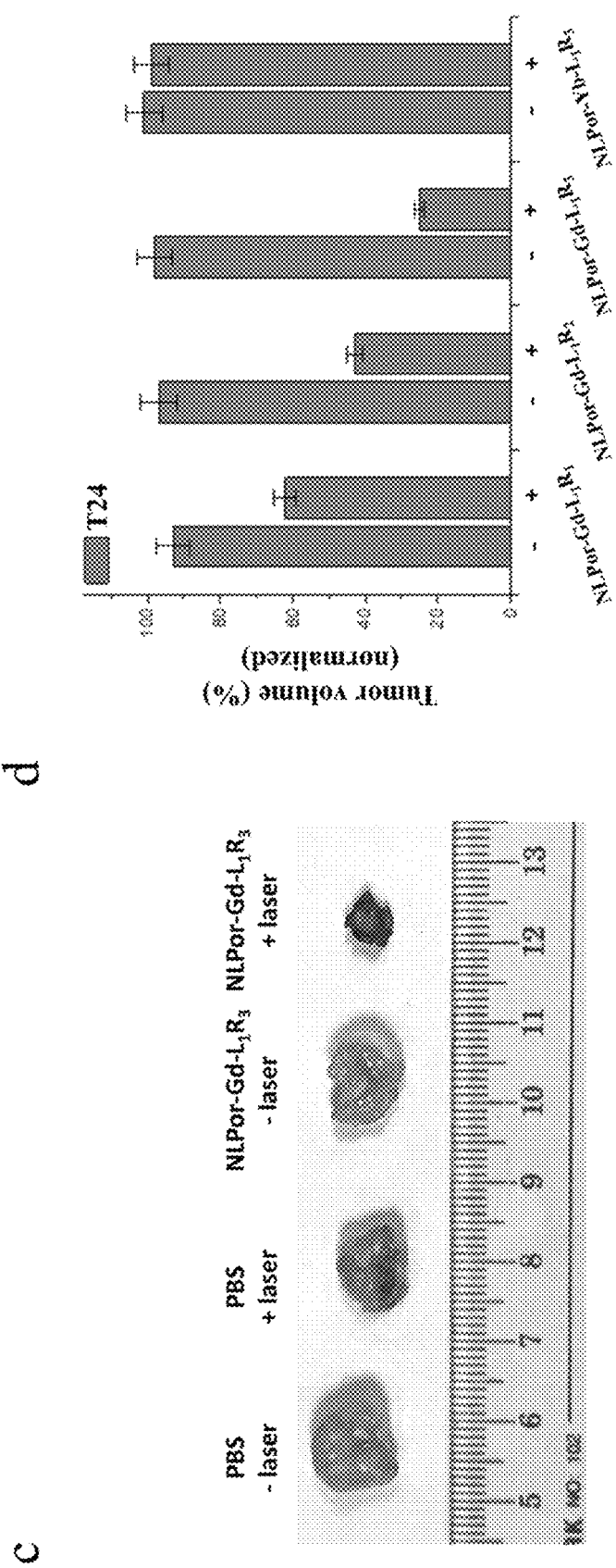
Figure 18:
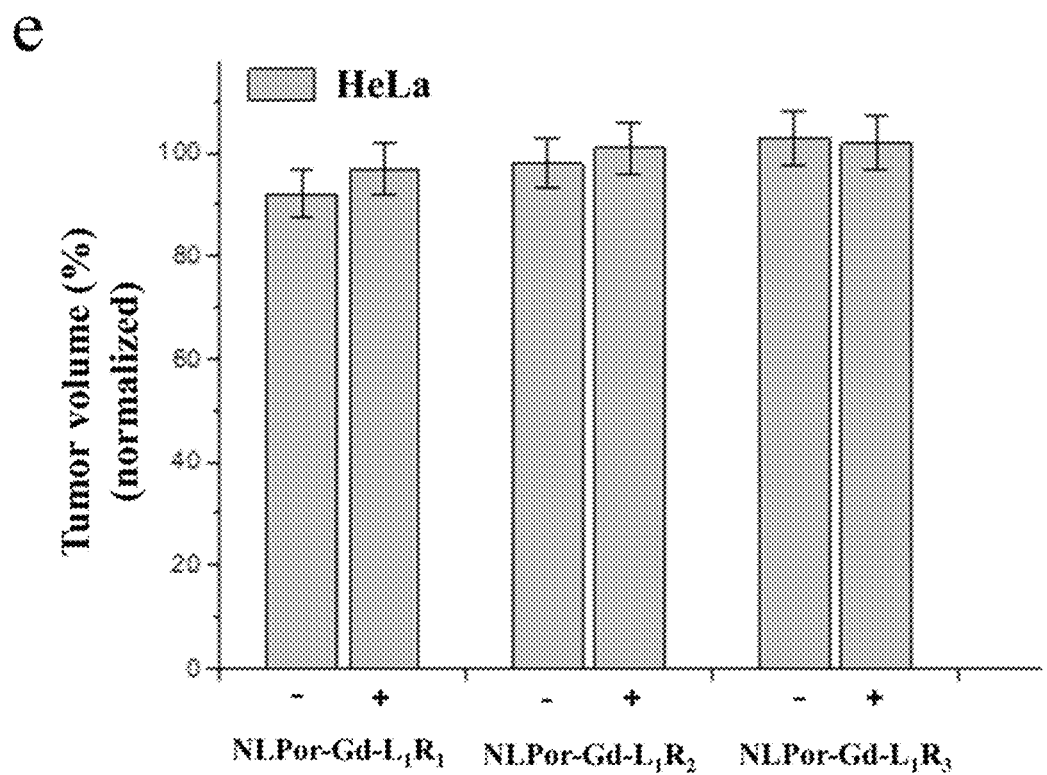
Figure 37:
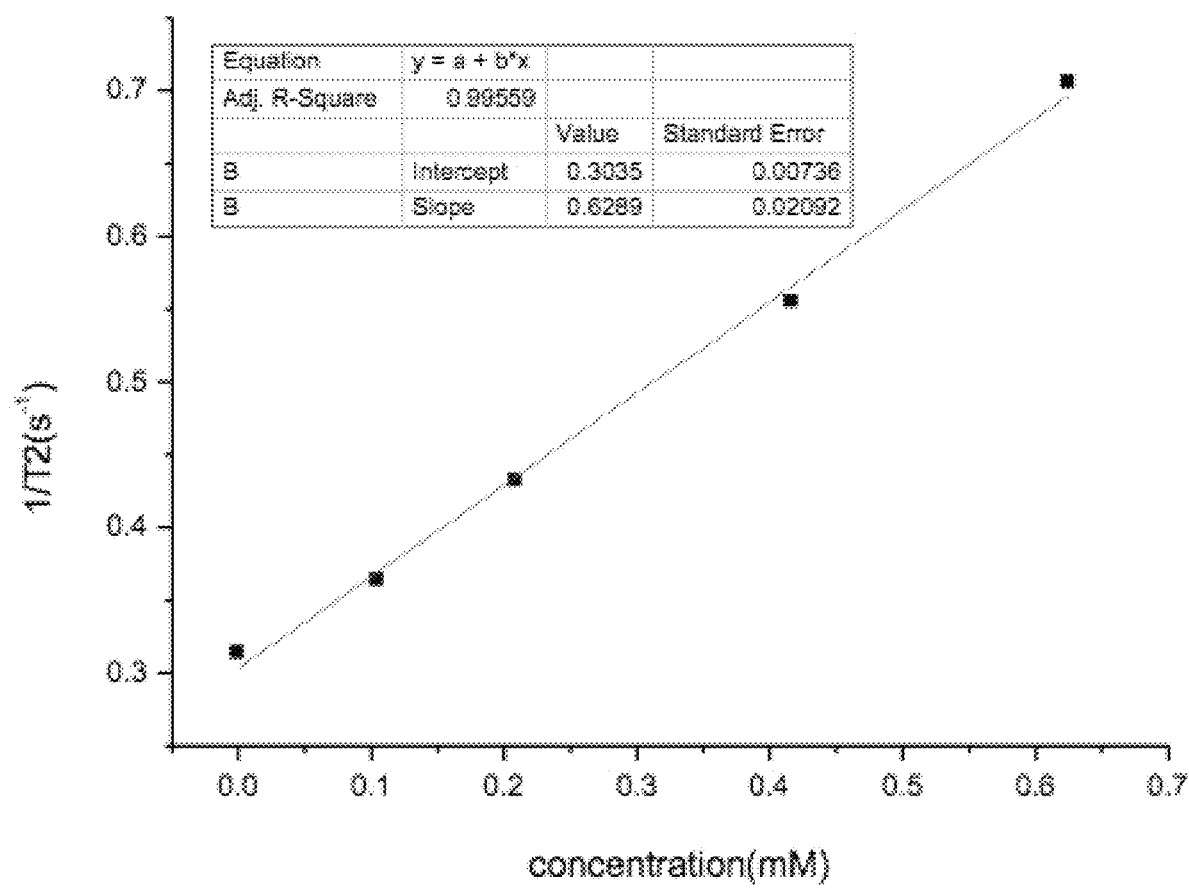
FIG. 37 shows the T$_2$ relativity of NLPor-Gd-L$_1$R$_3$ without the addition of α$_v$β$_3$.

The ability of NLPor-Gd-L$_1$R$_n$ (n=2, 3) to enhance MR imaging was assessed by determining their T$_1$ and T$_2$ relaxivities at 1.5 T in water (3% DMSO) and these data were confirmed with that for Gd-DOTA (Dotarem®). T$_1$ and T$_2$ relaxivity of NLPor-Gd-L$_1$R$_3$ were found to be r$_1$=0.182 mM$^{-1}$s$^{-1}$ (FIG. 18*a*) and r$_2$=0.6289 mM$^{-1}$s$^{-1}$ (FIG. 37). The T$_1$ relaxivity of NLPor-Gd-L$_1$R$_3$ is substantially lower than that of Gd-DOTA, 2.92 mM$^{-1}$s$^{-1}$ (FIG. 18*a*). This variation in relaxivity could result from a difference in hydration number since the NLPor-Gd-L$_1$R$_n$ complexes are probably devoid of coordinated water. However, it was found that NLPor-Gd-L$_1$R$_3$ showed responsive T$_1$ relaxivity after binding $\alpha_v\beta_3$ integrin, its r$_1$ relaxivity increasing to 3.225 mM$^{-1}$s$^{-1}$ (FIG. 18*a*, triangle data points). The responsive T$_1$ relaxivity could only be detected for this complex because it has higher water solubility than NLPor-Gd-L$_1$R$_1$ and NLPor-Gd-L$_1$R$_2$. The $\alpha_v\beta_3$ integrin might readily interact with two molecules of the Gd complex at the same time, and thus positively affect the T$_1$ relaxivity via second or outer coordination sphere interactions. The T$_1$ relaxivity enhancement could also be due to an increase in the apparent molecular weight of NLPor-Gd-L$_1$R$_3$ by interacting with $\alpha_v\beta_3$ integrin and hence slowing down the molecular rotation of the NLPor-Gd-L$_1$R$_3$.

After light irradiation, the NLPor-Gd-L$_1$R$_n$ complexes selectively kill bladder cancer cells, but also, and importantly, they do not affect normal cells as evidenced by cytotoxicity studies with T24, HeLa, and MRC-5 cells performed with and without light irradiation ($\lambda_{ex}$=430 nm, dose=10 J/cm$^2$). Results are shown in FIG. 19. Dark IC$_{50}$ values are only 1.1-3.0 smaller for T24 compared with HeLa or MRC-5 cells, but upon irradiation, IC$_{50}$ values become much smaller for T24: 10-13 times for R$^1$, 9-20 times for R$^2$ and a remarkable 55 times for R$^3$, This again is coherent with the large selectivity of the complexes for bladder cancer cells. The photocytotoxicity of NLPor-Gd-L$_1$R$_3$ for T24 cells (IC$_{50}$=8.2 µM) is much higher compared with NLPor-Gd-L$_1$R$_2$ and NLPor-Gd-L$_1$R$_1$, which could be attributed to its better solubility. NLPor-Gd-L$_1$R$_3$ also exhibits the highest photodynamic therapeutic index (PTI, dark IC$_{50}$/photo IC$_{50}$) amongst all three complexes i.e. a stunning value of 199, which is 20-fold higher than the well-known and commercially available PDT agent 5-aminolevulinic acid (ALA). This R$^3$-conjugated complex is, therefore, the most promising bladder cancer-specific PDT agent among the samples tested.

In vivo PDT studies have been carried out by laser irradiation at 808 nm (two-photon excitation) for 3 h after injecting the complex; the total light dosage was 50 J/cm$^2$, the treatment was performed three times a week with 3 nude mice bearing T24 bladder cancer xenografts for each group. Results show that NLPor-Gd-L$_1$R$_3$ at the same concentration as for in vivo MRI (100 µmol/kg body weight) has significant inhibition effect on the light-treated T24 tumors compared with the opposite flank dark controls and T24 tumors with PBS injection as control (FIGS. 18*b* and 18*c*). In another in vivo PDT experiment, NLPor-Gd-L$_1$R$_n$ (n=1-3; 100 µmol/kg body weight) showed obvious T24 tumor inhibition but nearly no inhibition effect was seen in HeLa tumors (FIGS. 18*d* and 18*e*). Most of the light energy absorbed by NLPor-Gd-L$_1$R$_n$ (n=1-3) is used for the generation of cytotoxic $^1$O$_2$ (1-photon quantum yields: 0.39-0.40, $\lambda_{ex}$=425 nm, PBS buffer) as proven by the control Yb-PEG-R$^3$ which has negligible cytotoxic effect since it does not generate $^1$O$_2$ due to the excitation energy being mainly transferred to the Yb(III) center for inducing NIR emission (FIG. 18*e*). Among all samples, NLPor-Gd-L$_1$R$_3$ presents the highest inhibitory effect to bladder T24 tumors. This is explained by the large $^1$O$_2$ quantum yield and strong $\alpha_v\beta_3$ integrin binding affinity properties of NLPor-Gd-L$_1$R$_3$.

Figure 20:
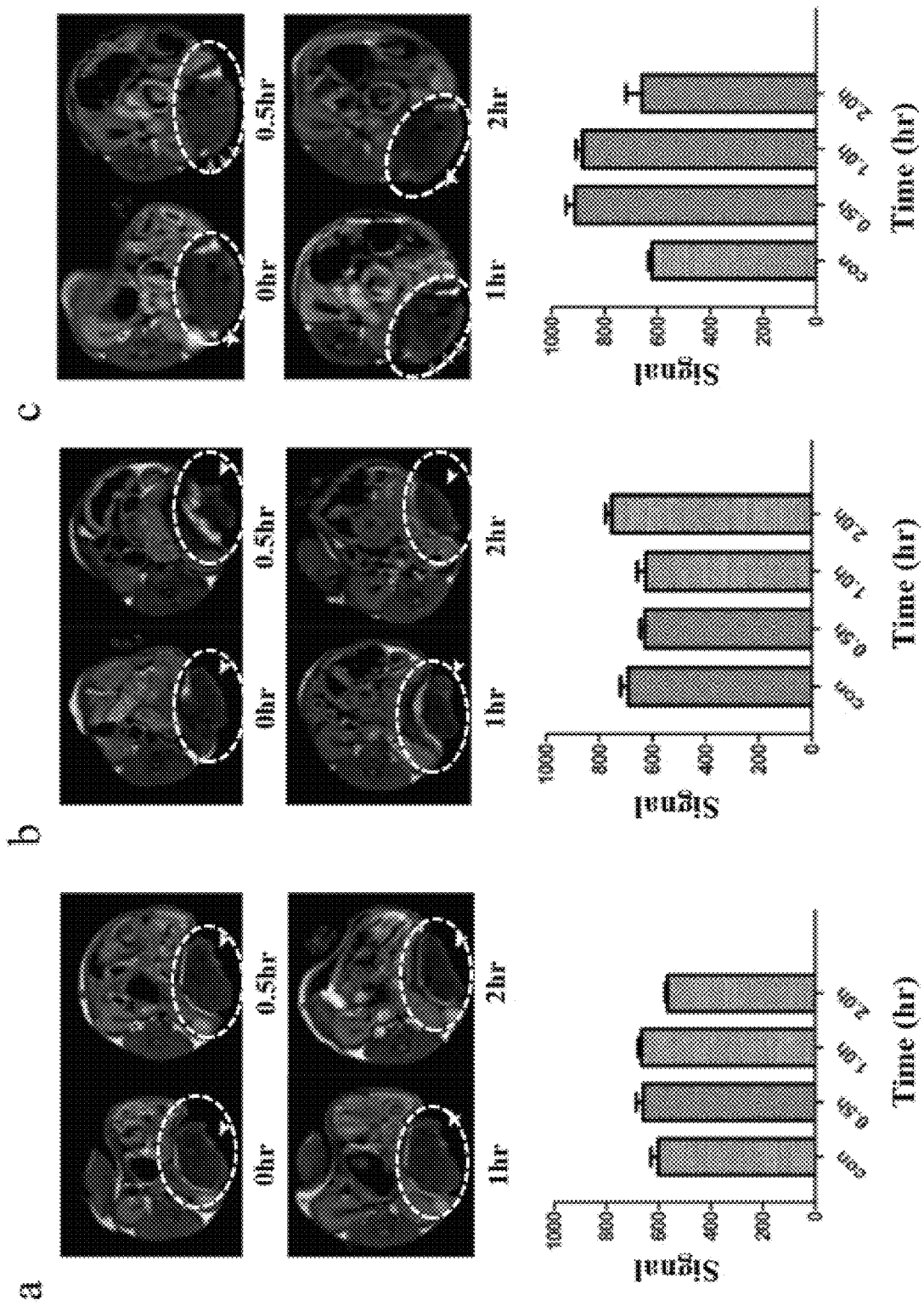
FIG. 20 shows in vivo T$_1$-weighted MR images of mouse T24 tumor model after injection of (a) GdDOTA; (b) NLPor-Gd-L$_1$; (c) NLPor-Gd-L$_1$R$_3$ at different times; (d) Ex vivo biodistribution of NLPor-Gd-L$_1$R$_n$ (n=1-3) via ICP-MS studies in bladder cancer tumor and non-bladder cancer tumor.
Figure 20:
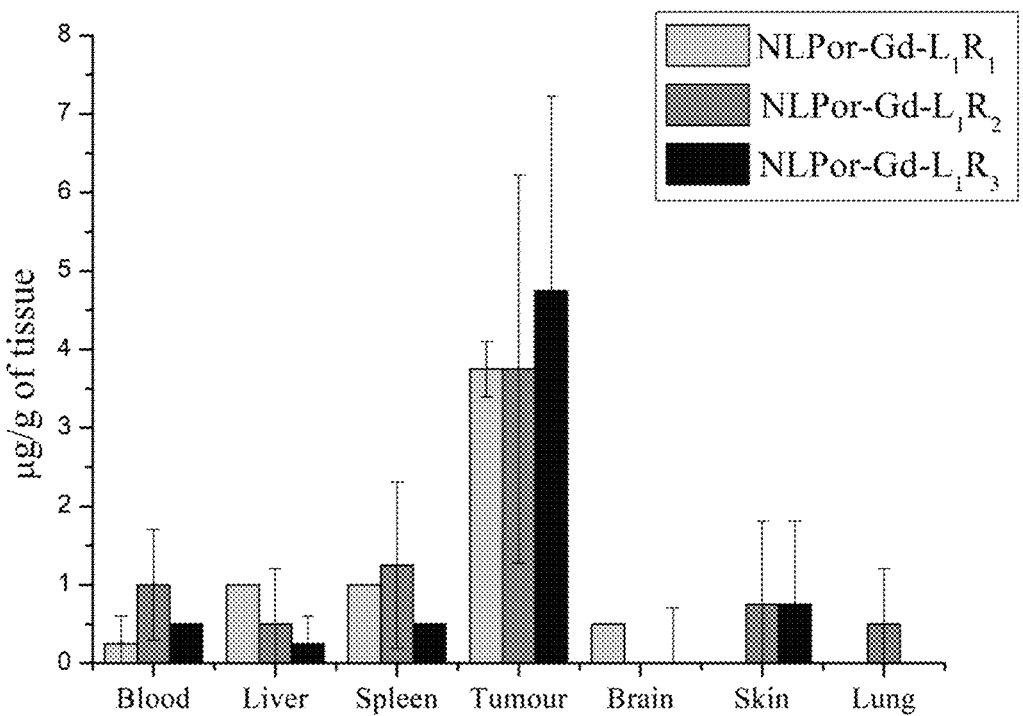

The above-described in-depth investigations indicate that NLPor-Gd-L$_1$R$_3$ can be regarded as a potential theranostic agent for PDT curing of bladder cancer. To study the potentiality of NLPor-Gd-L$_1$R$_3$ as an in vivo MRI contrast agent, experiments were conducted on BALB/c nude mice bearing T24 bladder cancer xenografts, while the commonly used MRI contrast agent Gd-DOTA was taken as control. The injection dose of NLPor-Gd-L$_1$R$_3$, Gd-PEG-COOH (carboxylic acid group instead of R$^3$ as control) and Gd-DOTA was 0.1 mmol/kg gadolinium (around 2 µmol/mouse). MR images were acquired before and after 200 µL tail vein injection of each subject at various times. Strong MRI signal enhancement was observed at 0.5 h and maintained for 1 h after injection (FIG. 20*c*). According to FIG. 20, the edge of the tumor treated with NLPor-Gd-L$_1$R$_3$ was comparatively clear to observe after 0.5 h and 1 h compared with Gd-PEG-COOH and Gd-DOTA controls; Gd-PEG-COOH showed nearly no post-injection signal enhancement within 2 h (FIG. 20*b* and FIG. 20*c*) which proved that the $\alpha_v\beta_3$ integrin targeting function of R$^3$ is essential for providing MRI signal enhancement. The weak post-injection signal enhancement observed in the MR images of mice injected with Gd-DOTA (FIG. 20*a*) may be a consequence of the rapid clearance of Gd-DOTA in this tumor model. The longer clearance time of NLPor-Gd-L$_1$R$_3$ compared with Gd-DOTA might result from the interaction between the R$^3$ peptides and the $\alpha_v\beta_3$ integrin in bladder cancer cells and this property could enable MRI studies over a long timescale.

A biodistribution study of NLPor-Gd-L$_1$R$_n$ (n=1-3) was carried out in T24 bladder cancer-bearing BALB/c nude mice. The complexes (100 µmol/kg) were injected into the caudal vein when the tumor xenograft attained a size of approximately 0.1 cm$^3$. Different tissues were collected 2 days after injection, and concentrations of NLPor-Gd-L$_1$R$_n$ (n=1-3) were quantified by ICP-MS. Results show the greatest enrichment of NLPor-Gd-L$_1$R$_n$ (n=1-3) in the tumors. It should be highlighted that both NLPor-Gd-L$_1$R$_2$ and NLPor-Gd-L$_1$R$_3$ are absent from the brains (FIGS. 11 and 20*d*). This is a marked advantage over some published Gd(III)-based theranostic agents, including Gd—N, which although exhibiting promising anti-cancer effects and imaging capability, was shown to penetrate the blood-brain barrier (concentration in brain ~1 ppm), potentially causing severe adverse effects.

In conclusion, among three synthesized porphyrinato-gadolinium complexes, extensive investigations revealed NLPor-Gd-$L_1R_3$ to be a potential $α_νβ_3$-integrin-specific theranostic agent for curing bladder cancer. This compound is indeed effective for PDT bladder cancer treatment and as a moderately efficient off-on MRI contrast agent. The PDT capability of NLPor-Gd-$L_1R_3$ comes from (i) its large specificity due to the inclusion of a carefully chosen targeting peptide; in particular the new agent does not penetrate into the brain, a definite advantage; (ii) its water solubility ($R^3$ substituent); (iii) it has high photo-cytotoxicity while remaining non-cytotoxic in dark (PTI=199) and in normal cells. The compound also exhibits 'off-on' responsive relaxivity with its low initial $T_1$ relaxivity increasing by over 10 times upon $α_νβ_3$ binding. The enhanced relaxivity is somewhat lower than values observed with commercially available MRI contrast agents but NLPor-Gd-$L_1R_3$ showed better bladder cancer imaging than Gd-DOTA under the same experimental conditions. In the near future, we envisage using this bespoken theranostic agent incorporated into various vectors to test its use in clinical practice.

EXPERIMENTAL DETAILS

I Synthesis of NLPor-Gd-$L_1R_3$

Figure 21:
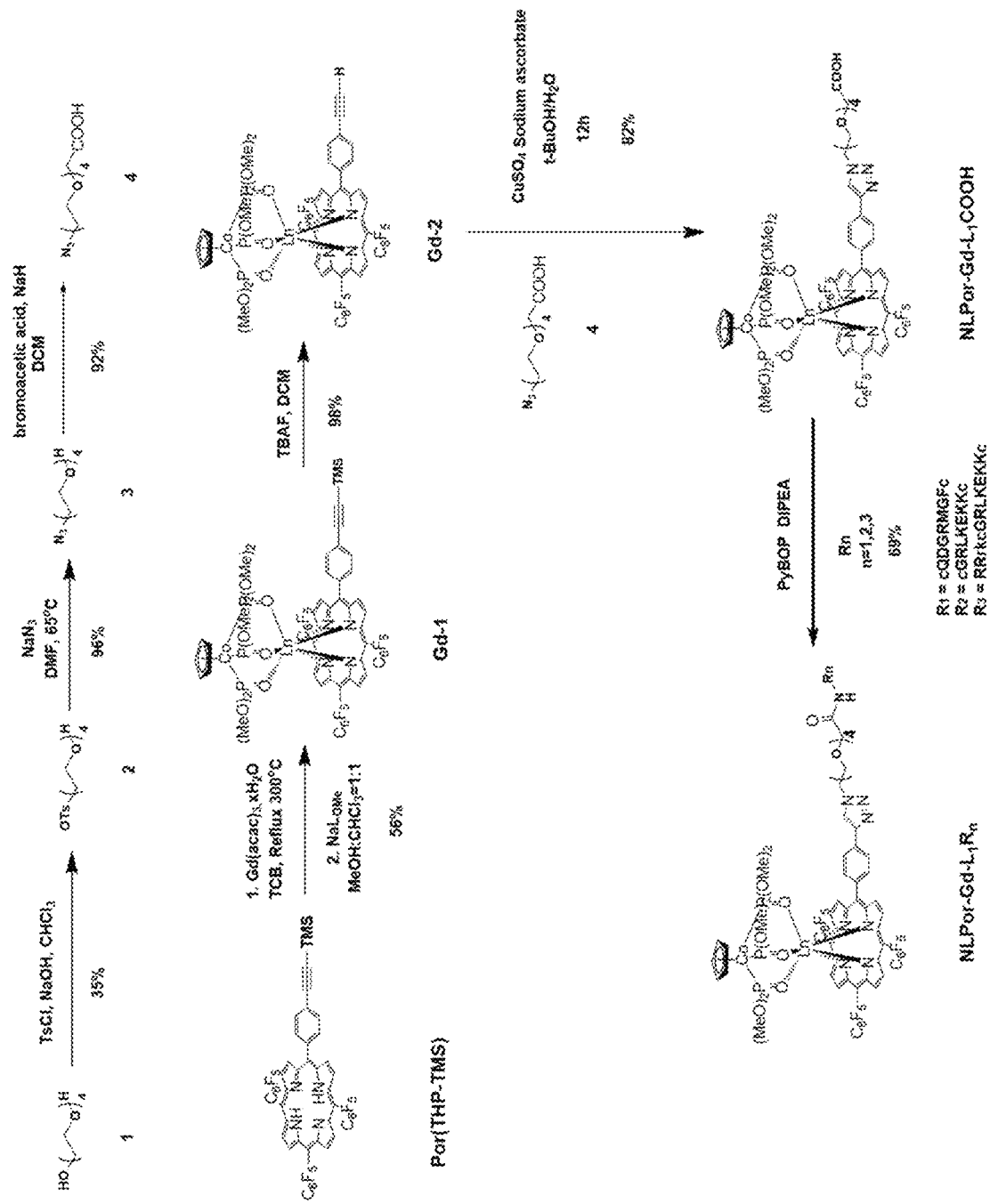
FIG. 21 depicts an exemplary schematic of the synthetic route of porphyrinate lanthanide complexes NLPor-Gd-L$_1$R$_n$ (n=1-3).
Figure 22:
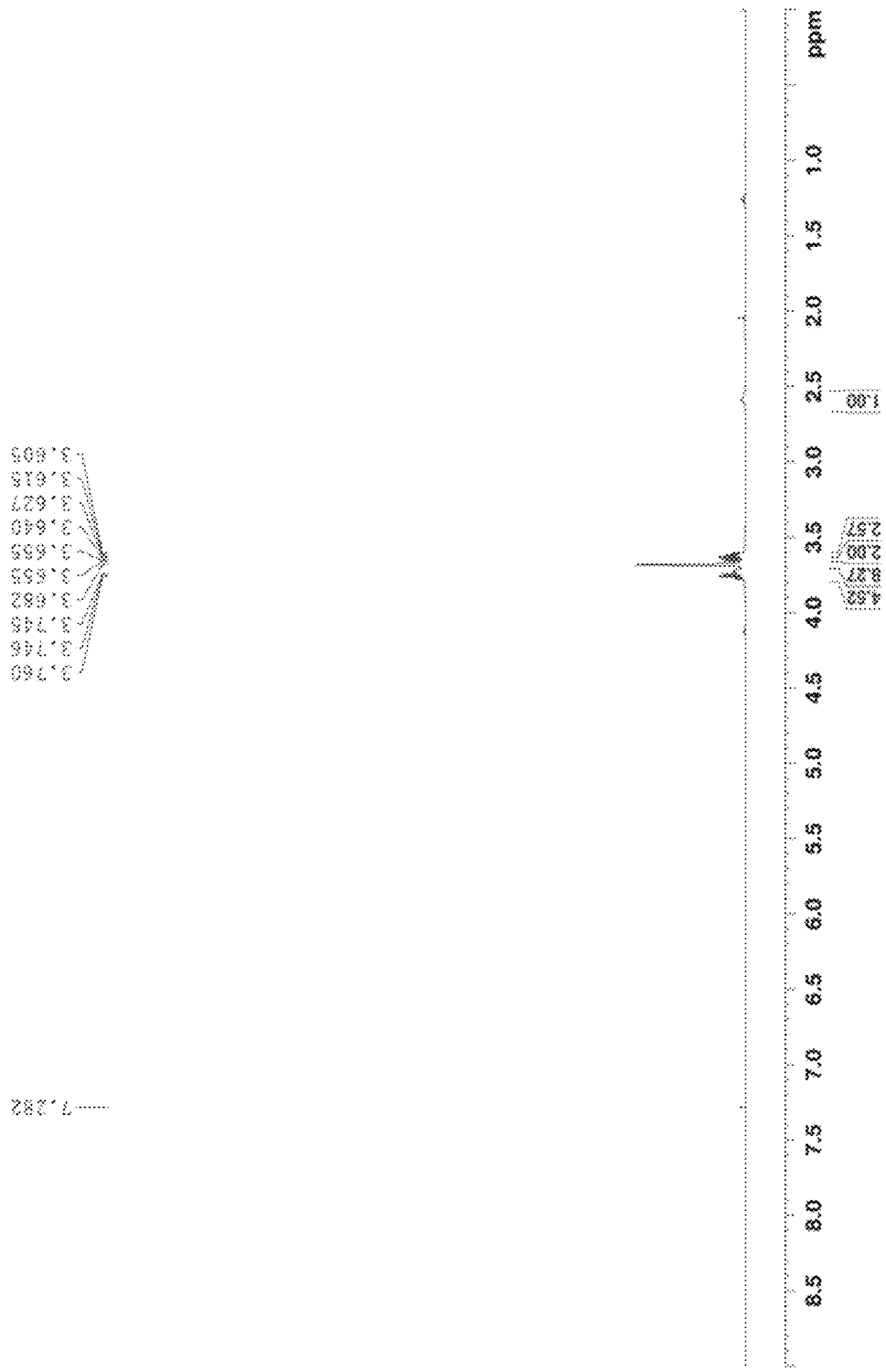
FIG. 22 shows the 400 MHz-$^1$H-NMR (CDCl$_3$) spectrum of compound 2.
Figure 23:
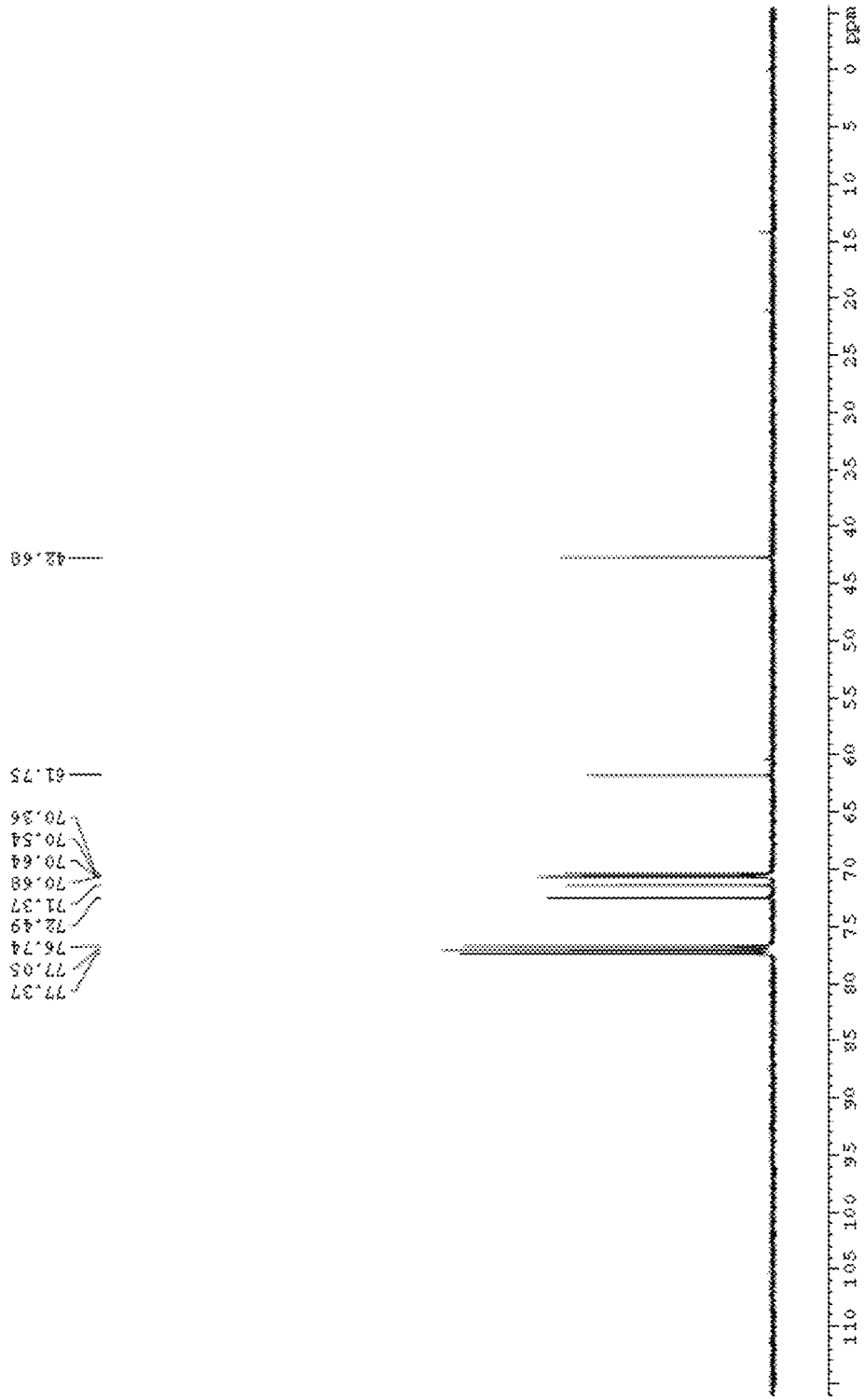
FIG. 23 shows the 400 MHz-$^{13}$C-NMR (CDCl$_3$) spectrum of compound 2.
Figure 24:
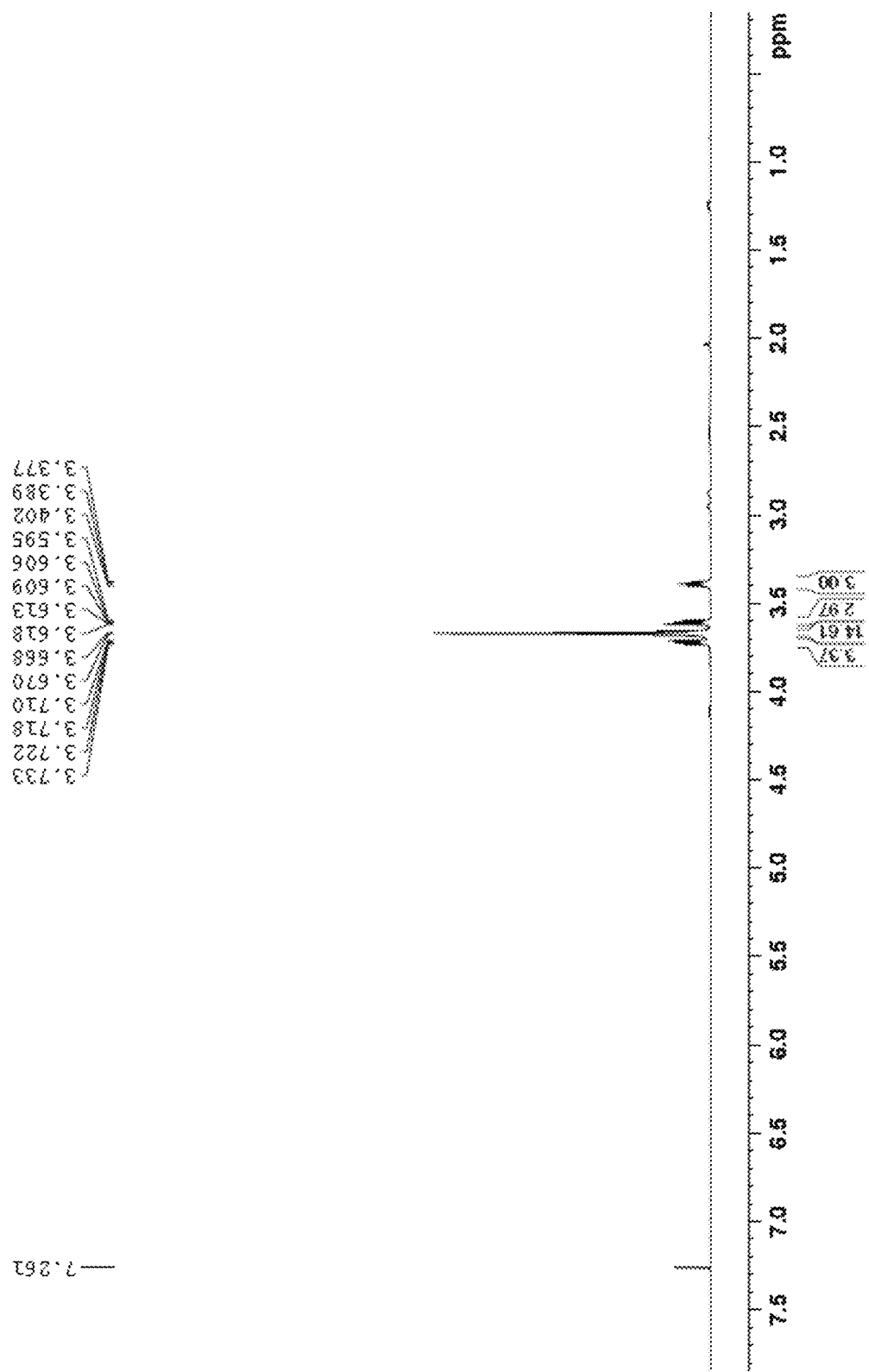
FIG. 24 shows the 400 MHz-$^{13}$C-NMR (CDCl$_3$) spectrum of compound 3.
Figure 25:
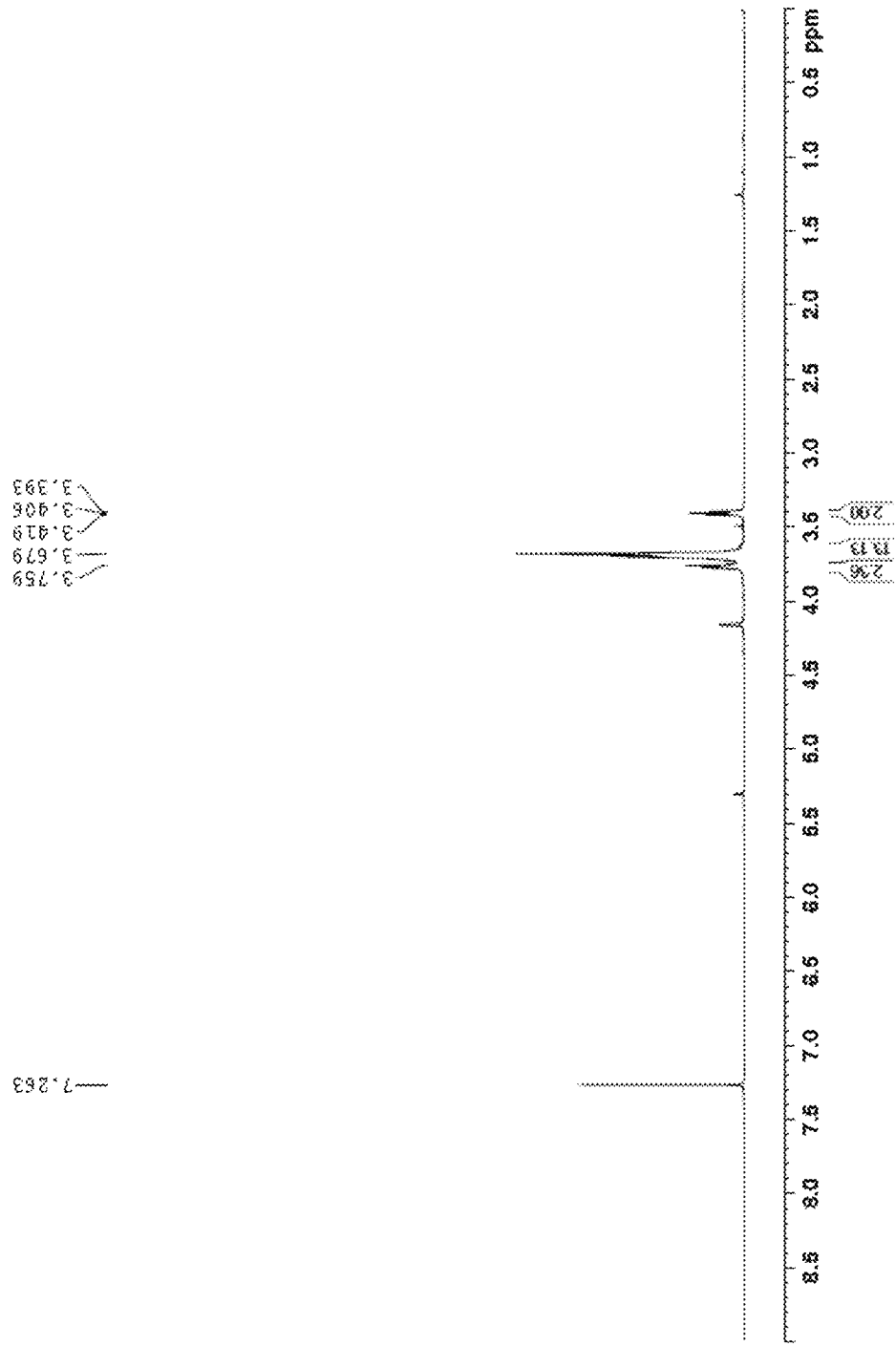
FIG. 25 shows the 400 MHz-$^1$H-NMR (CDCl$_3$) spectrum of compound 4.
Figure 26:
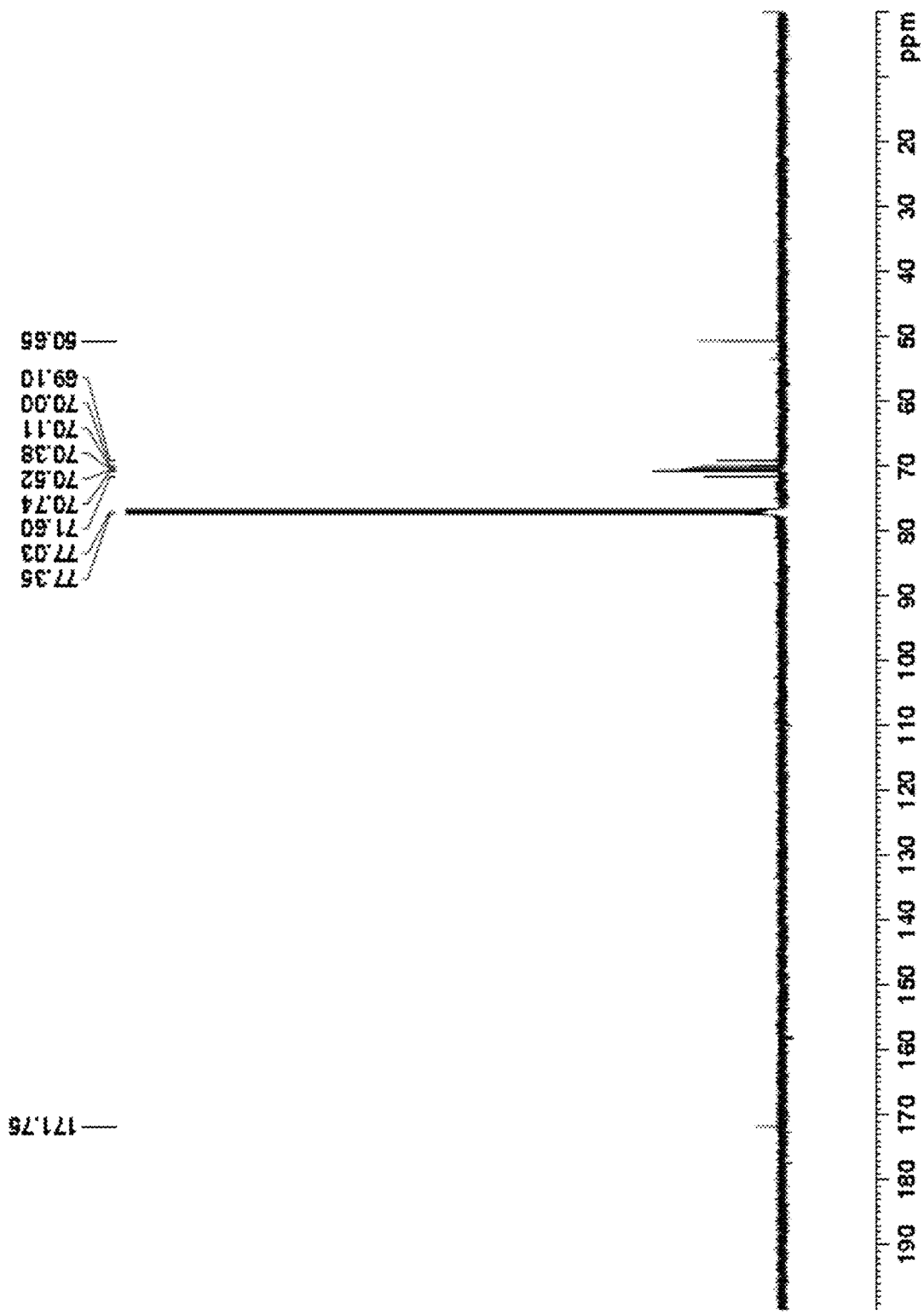
FIG. 26 shows the 400 MHz-$^{13}$C-NMR (CDCl$_3$) spectrum of compound 4
Figure 27:
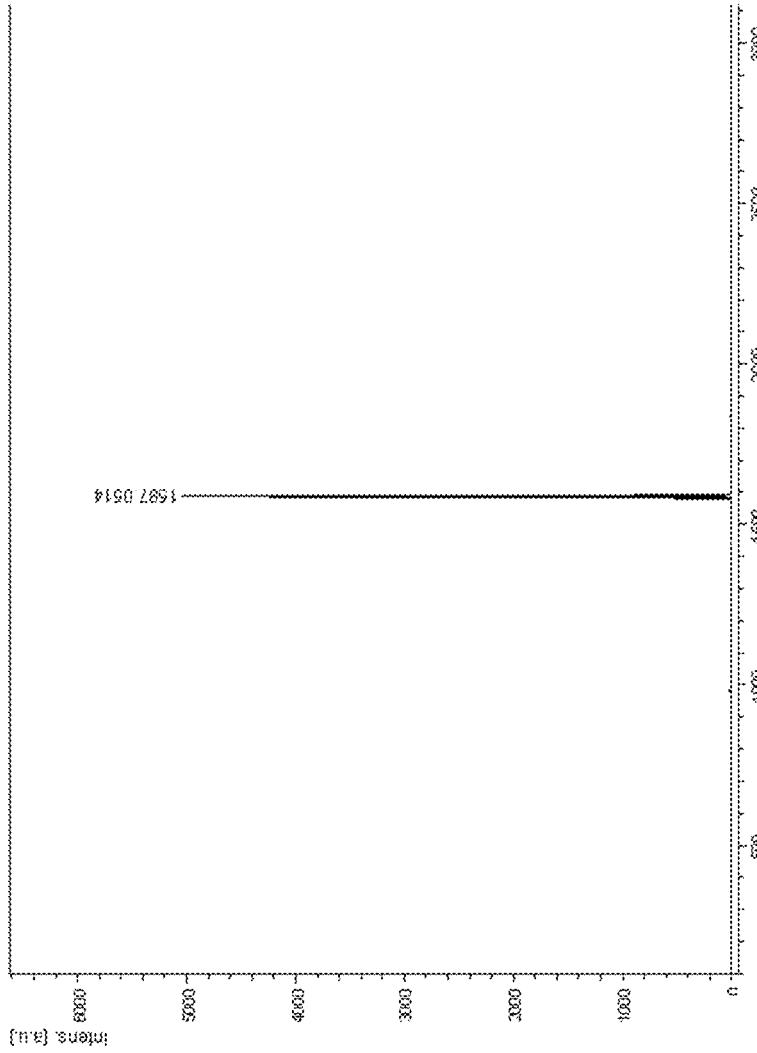
FIG. 27 shows the MS spectrum (MALDI-TOF) of Gd-1.
Figure 28:
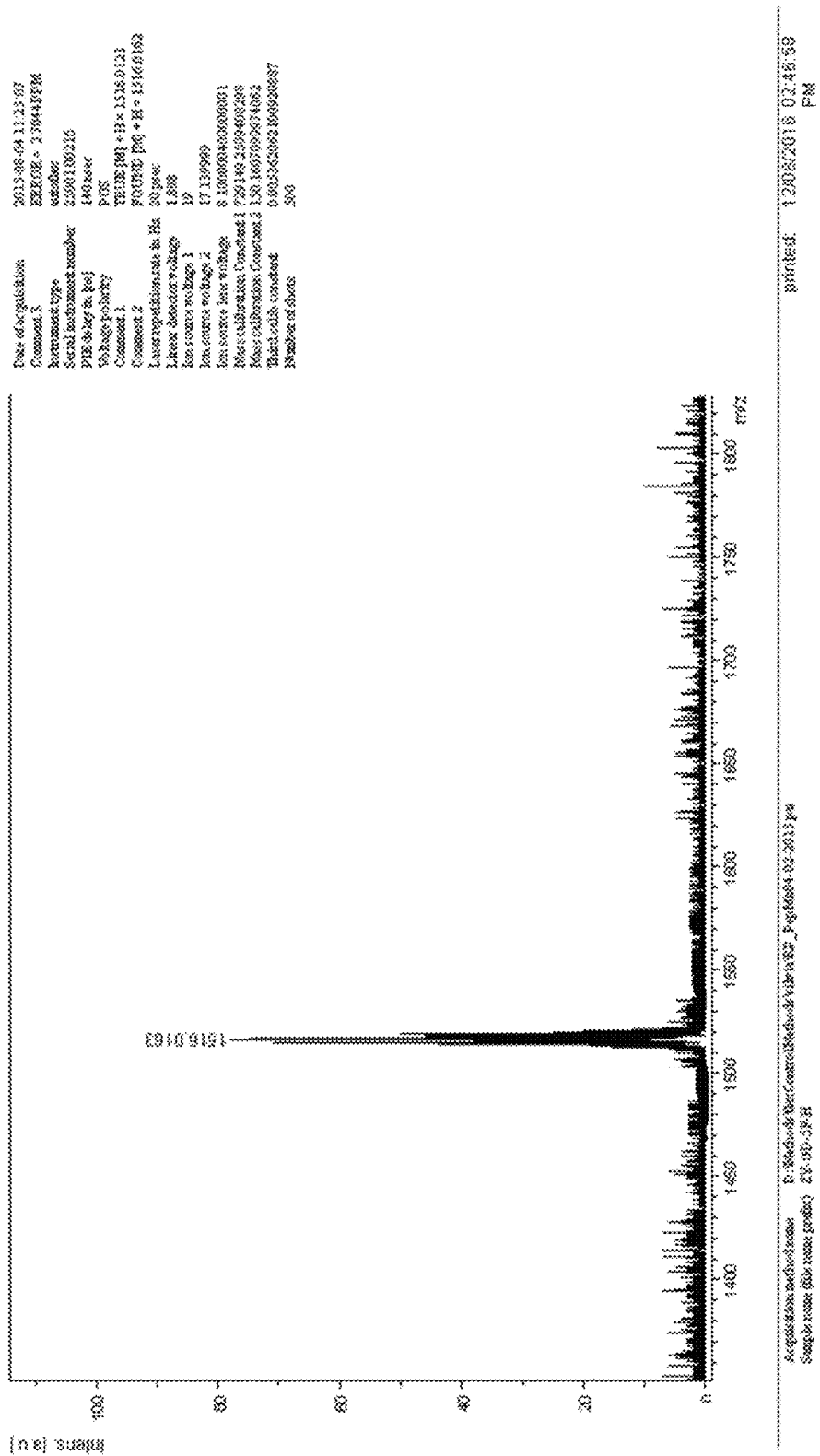
FIG. 28 shows the MS spectrum (MALDI-TOF) of Gd-2.

The synthetic route of NLPor-Gd-L1R3 is shown in FIG. 21, while FIG. 22-28 are the NMR spectra of the intermediate compounds and the final product. The spectra prove the purity of the compound and characteristic peaks shown in the spectra provide evidence that the desired compounds were synthesized successfully.

II Photophysical Properties of NLPor-Gd-$L_1R_3$ a) Electronic Absorption and Emission Spectra of NLPor-Gd-$L_1R_n$ (n=1-3)

Figure 29:
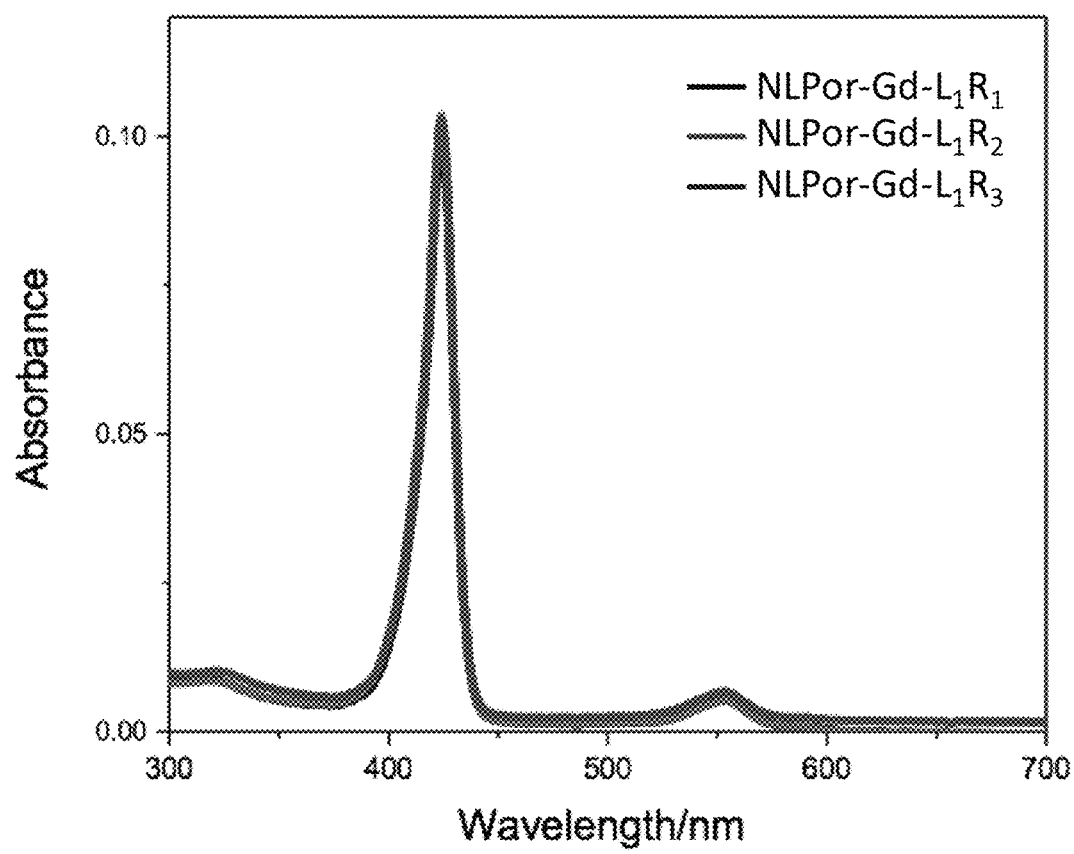
FIG. 29 shows the absorption spectra of NLPor-Gd-L$_1$R$_n$ (n=1-3) in aqueous solution at 298 K (Concentration: 1 μM).
Figure 30:
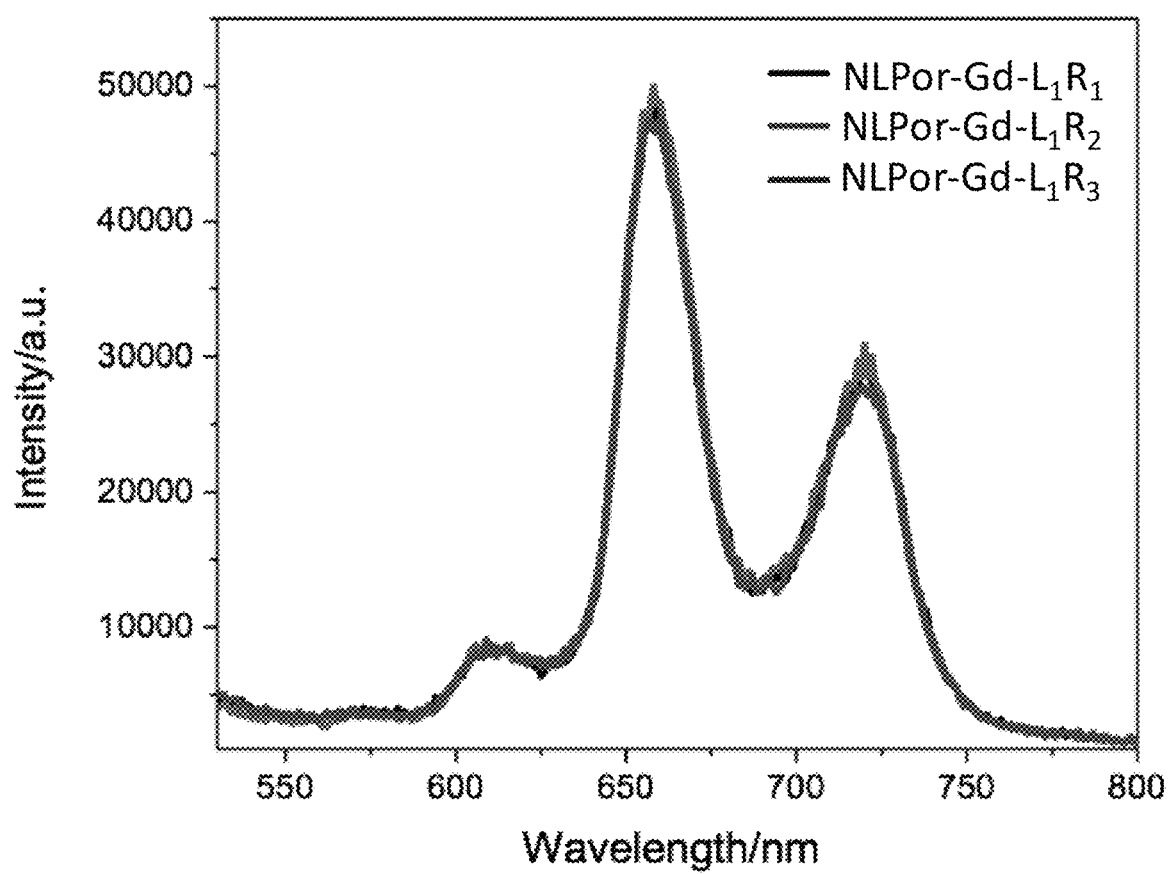
FIG. 30 shows the emission spectra of NLPor-Gd-L$_1$R$_n$ (n=1-3) in aqueous solution at 298 K (Concentration: 1 μM, $\lambda_{ex}$=430 nm).

The absorption and emission spectra of NLPor-Gd-$L_1R_n$ (n=1-3) are shown in FIGS. 29 and 30 respectively in aqueous solution. Three Gd complexes showed a strong Soret band at 425 nm attributed the $S_0 → S_2$ allowed the transition of porphyrin and one Q band at 554 nm attributed to the $S_0 → S_1$ forbidden transition of porphyrin. The emission spectra of NLPor-Gd-$L_1R_n$ (n=1-3) were measured in aqueous solution with the excitation of 430 nm, the intense emission bands found at 660 nm and 720 nm represented porphyrin's S (0, 0) and S (1, 0) emission.

b) Singlet Oxygen Quantum Yields

Singlet oxygen is one of the prime factors to evaluate the effectiveness of PDT agents. Considering many studies about the singlet oxygen quantum yields in the literature, there are two methods to determine the singlet oxygen quantum yields: comparing with the standard (1) emission of the generated singlet oxygen, (2) absorption of the photosensitizers. However, there are few examples to determine the singlet oxygen by combining two methods together, especially in aqueous solution. Herein, we measured the singlet oxygen quantum yields by two methods in $CHCl_3$ and aqueous solution respectively.

(1) The singlet oxygen quantum yield measurement by comparing the $^1O_2$ emission of NLPor-Gd-$L_xR_n$ (n=1-3) and standard $H_2TPP$ in $CHCl_3$.

The singlet oxygen quantum yields ($Φ_Δ$) of NLPor-Gd-$L_1R_n$ (n=1-3) were measured in $CHCl_3$ and calculated by comparing with a reference compound $H_2TPP$ ($Φ_Δ$=0.55 in $CHCl_3$).

Figure 31:
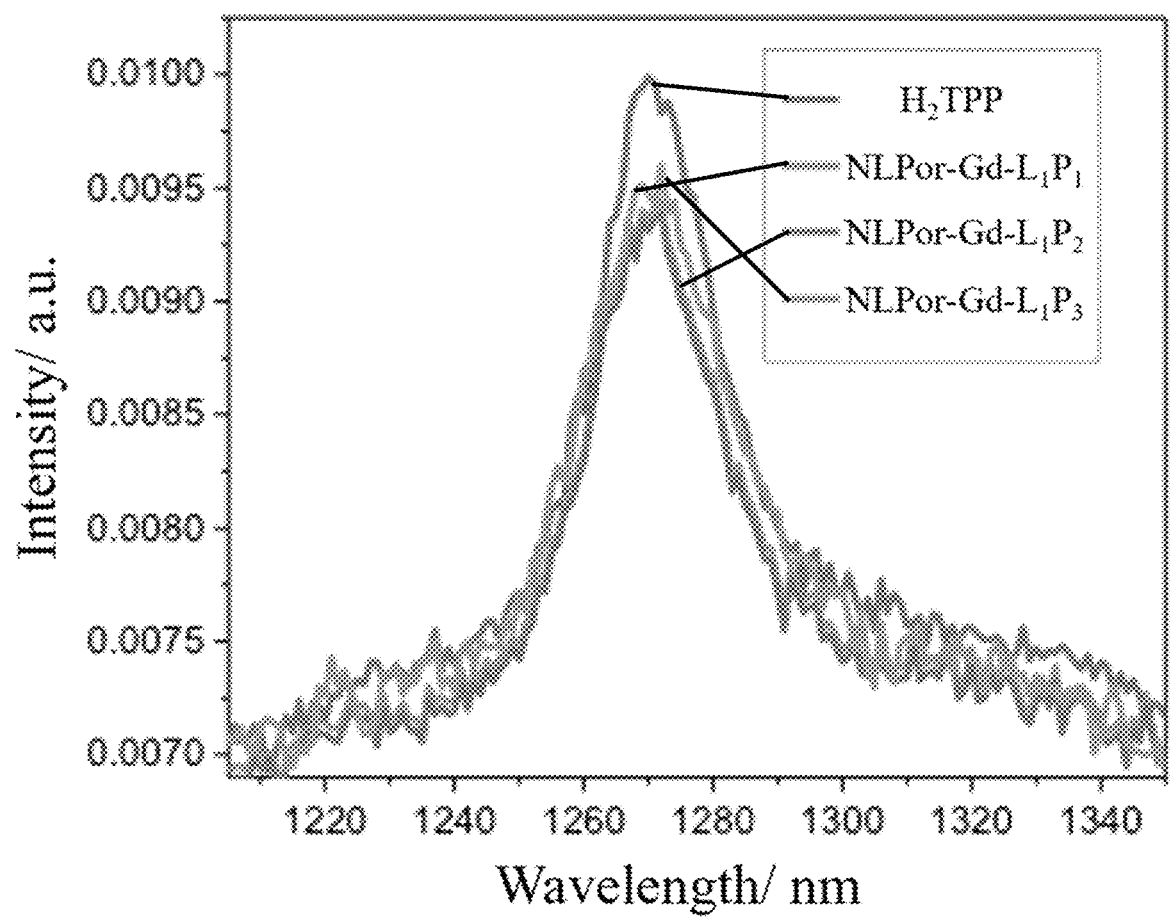
FIG. 31 shows the near-infrared $^1$O$_2$ phosphorescence spectra of NLPor-Gd-L$_1$R$_n$ (n=1-3) and the standard tetraphenylporphyrin (H$_2$TPP) in CHCl$_3$ (Abs=0.05, $\lambda_{ex}$=425 nm).
Figure 32:
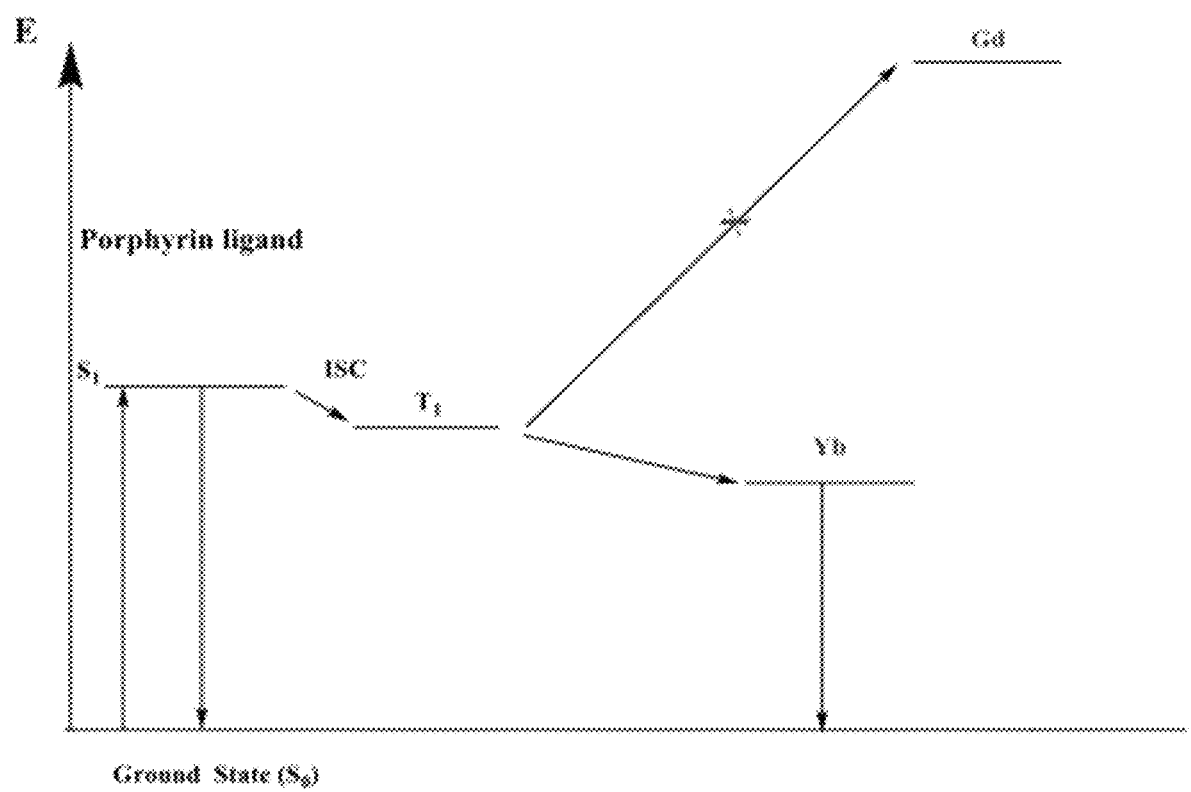
FIG. 32 shows the simplified diagram showing the energy transfer from the porphyrin to Yb$^{3+}$ and Gd$^{3+}$ ions.

The singlet oxygen quantum yields of NLPor-Gd-$L_1R_n$ (n=1-3) are 0.47, 0.47, 0.48, respectively (FIG. 31). Compared to Yb—R" (n=1-3), the singlet oxygen quantum yields of NLPor-Gd-$L_1R_n$ (n=1-3) are much higher because the $1^{st}$ excited state of Gd(III) is much higher than porphyrin's triplet state (FIG. 32), and the absorbed energy of the porphyrin can only transfer to the Gd(III) ion at a low possibility. Therefore, in porphyrin, most of the absorbed energy helps to convert $^3O_2$ to $^1O_2$.

(2) The singlet oxygen quantum yield measurements by evaluating the absorption changes of ABDA when mixed with NLPor-Gd-$L_1R_n$ (n=1-3) and standard Rose Bengal (RB) respectively in aqueous solution.

9,10-Anthracenediyl-bis(methylene)dimalonic acid (ABDA), a chemical-sensitive probe of reactive oxygen species, is commonly used to monitor the generation of singlet oxygen. After light irradiation, the absorbance of ABDA decreases because of the formation of its endoperoxide in the presence of $^1O_2$. The decreased amount of ABDA absorbance at 402 nm can be used to estimate the singlet oxygen quantum yield produced by the photosensitizers.

In this work, the singlet oxygen quantum yields ($Φ_Δ$) of NLPor-Gd-$L_1R_n$ (n=1-3) in Phosphate Buffered Saline (PBS) buffer was obtained using ABDA and RB ($Φ_{RB}$=0.75 in PBS buffer) as $^1O_2$ scavenger and reference respectively. NLPor-Gd-$L_1R_n$ (n=1-3) were incubated with ABDA, the mixtures were photo-activated by an LED lamp with power density 6 mWcm$^{-2}$. The generation of singlet oxygen was evaluated by recording the changes in ABDA absorbance at 402 nm. The singlet oxygen quantum yields of NLPor-Gd-$L_1R_n$ (n=1-3) ($Φ_{PS}$) were calculated by the following formula:

$$Φ_{PS} = Φ_{RB} \frac{K_{PS} * A_{RB}}{K_{RB} * A_{PS}}$$

Where $K_{PS}$ is the decomposition rate of ABDA when ABDA is mixed with NLPor-Gd-$L_1R_n$ (n=1-3). The $K_{RB}$ is the decomposition rate of ABDA when ABDA is mixed with RB after light irradiation. $A_{PS}$ is calculated by the absorption integration of NLPor-Gd-$L_1R_n$ (n=1-3) and $A_{RB}$ is determined by the absorption integration of RB in the range 400-700 nm.

Figure 33:
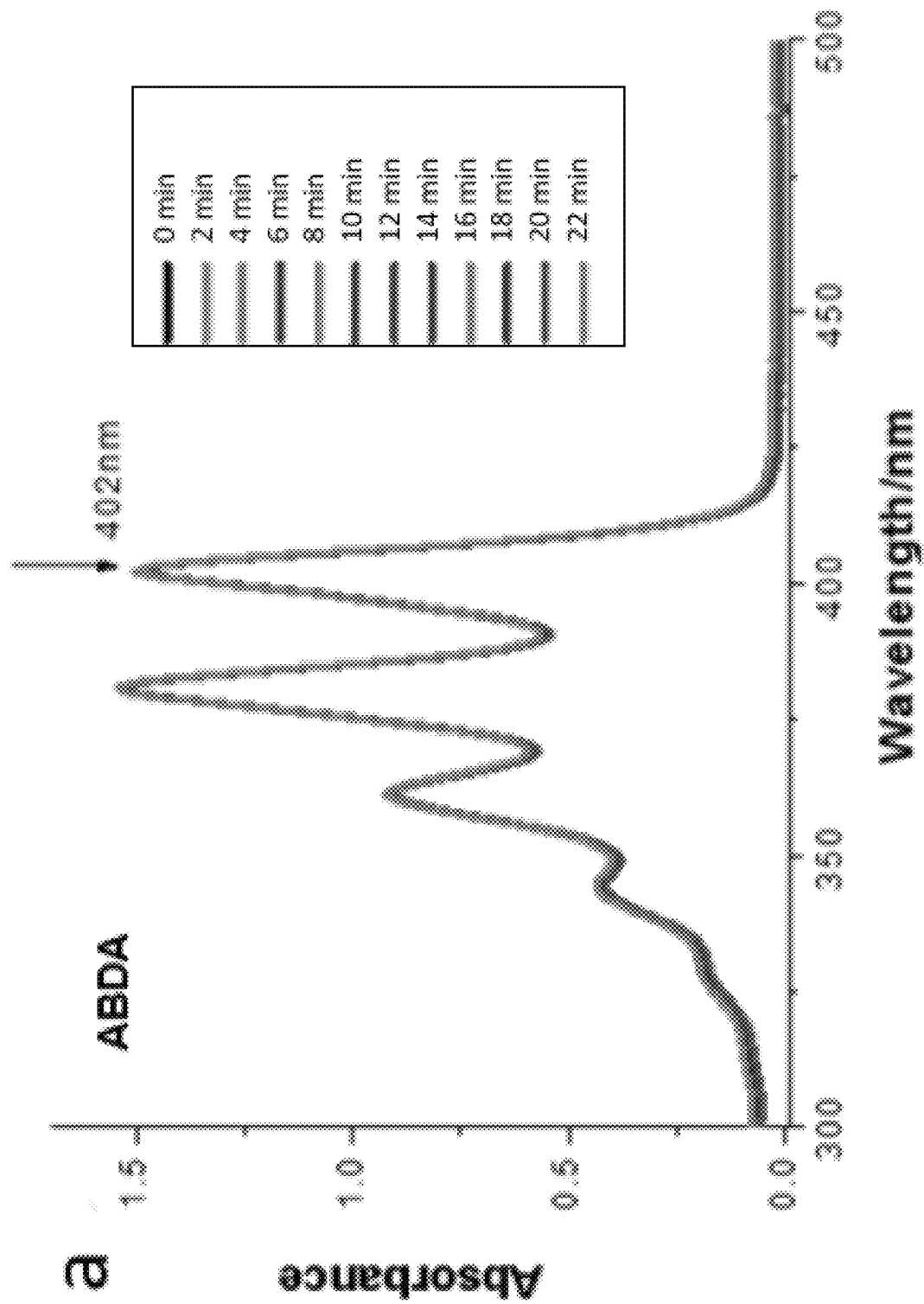
FIG. 33 shows the absorption spectra of 9,10-anthracenediylbis(methylene)dimalonic acid (ABDA, 200 μM) in the presence of the photosensitizers (10 μM) (a) Control group, (b) RB, (c) NLPor-Gd-L$_1$R$_1$, (d) NLPor-Gd-L$_1$R$_2$, and (e) NLPor-Gd-L$_1$R$_3$ in PBS buffer under different irradiation time, (LED lamp with power density 6 mW·cm$^{-2}$, equipped with 550 nm long pass filter).
Figure 33:
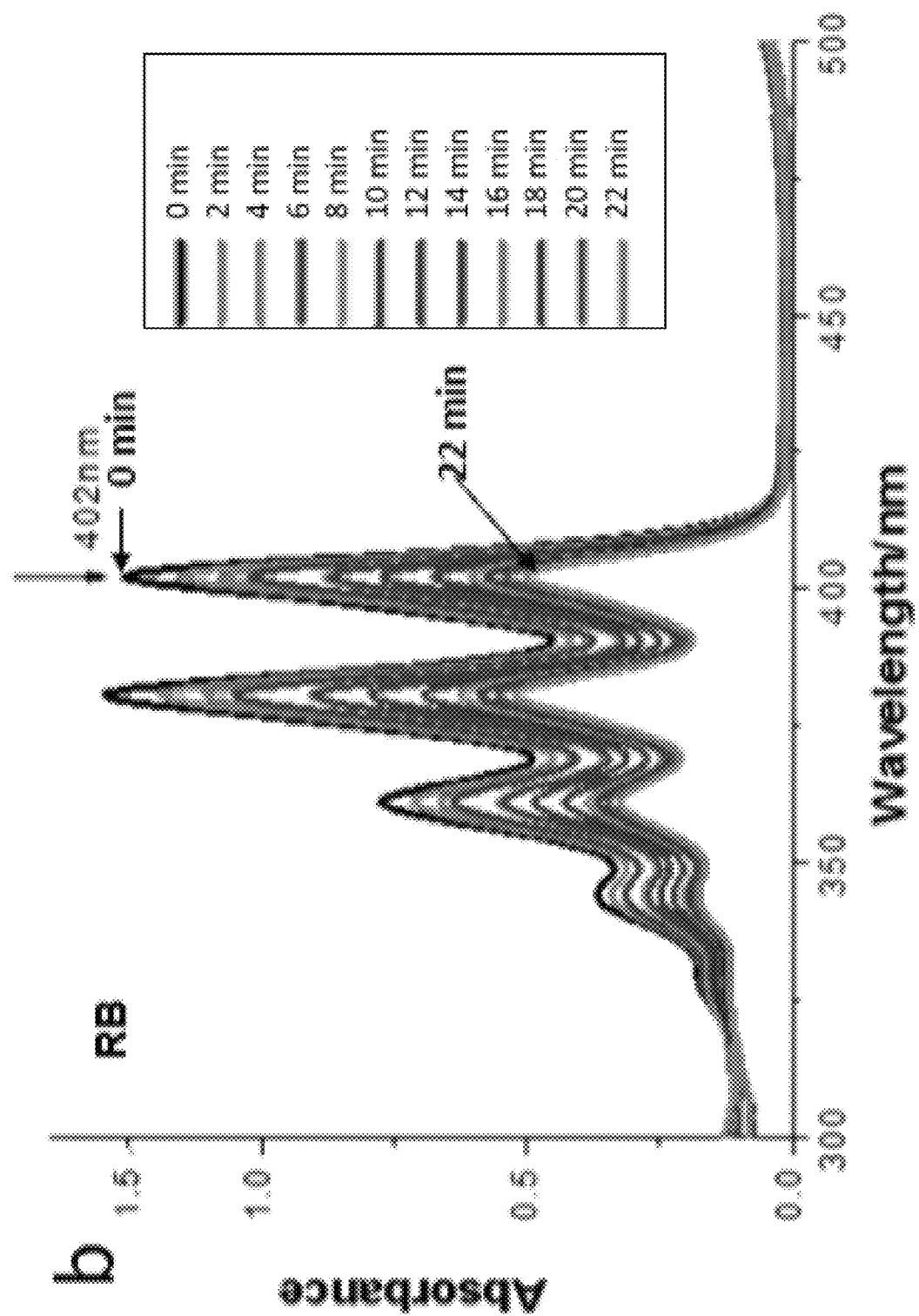
Figure 33:
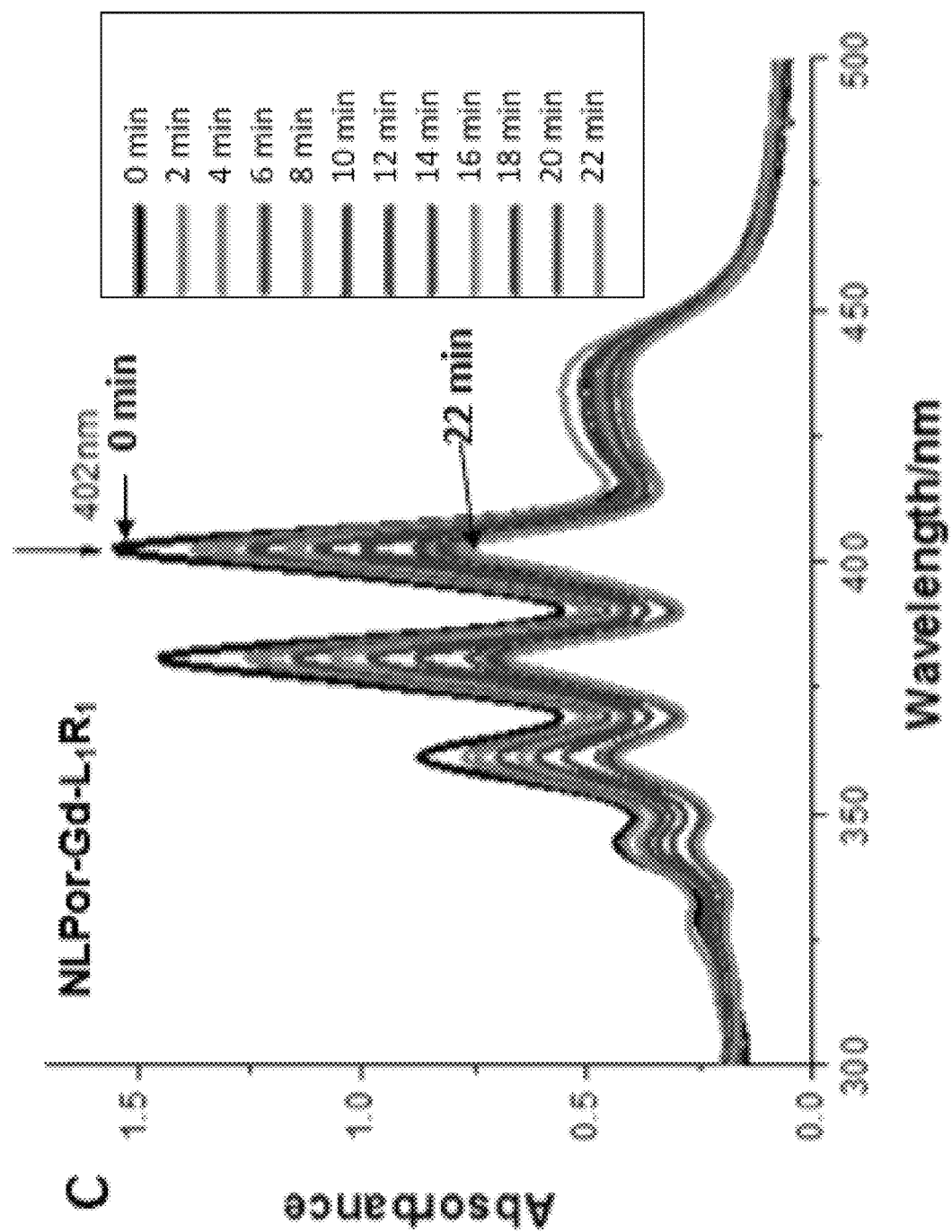
Figure 33:
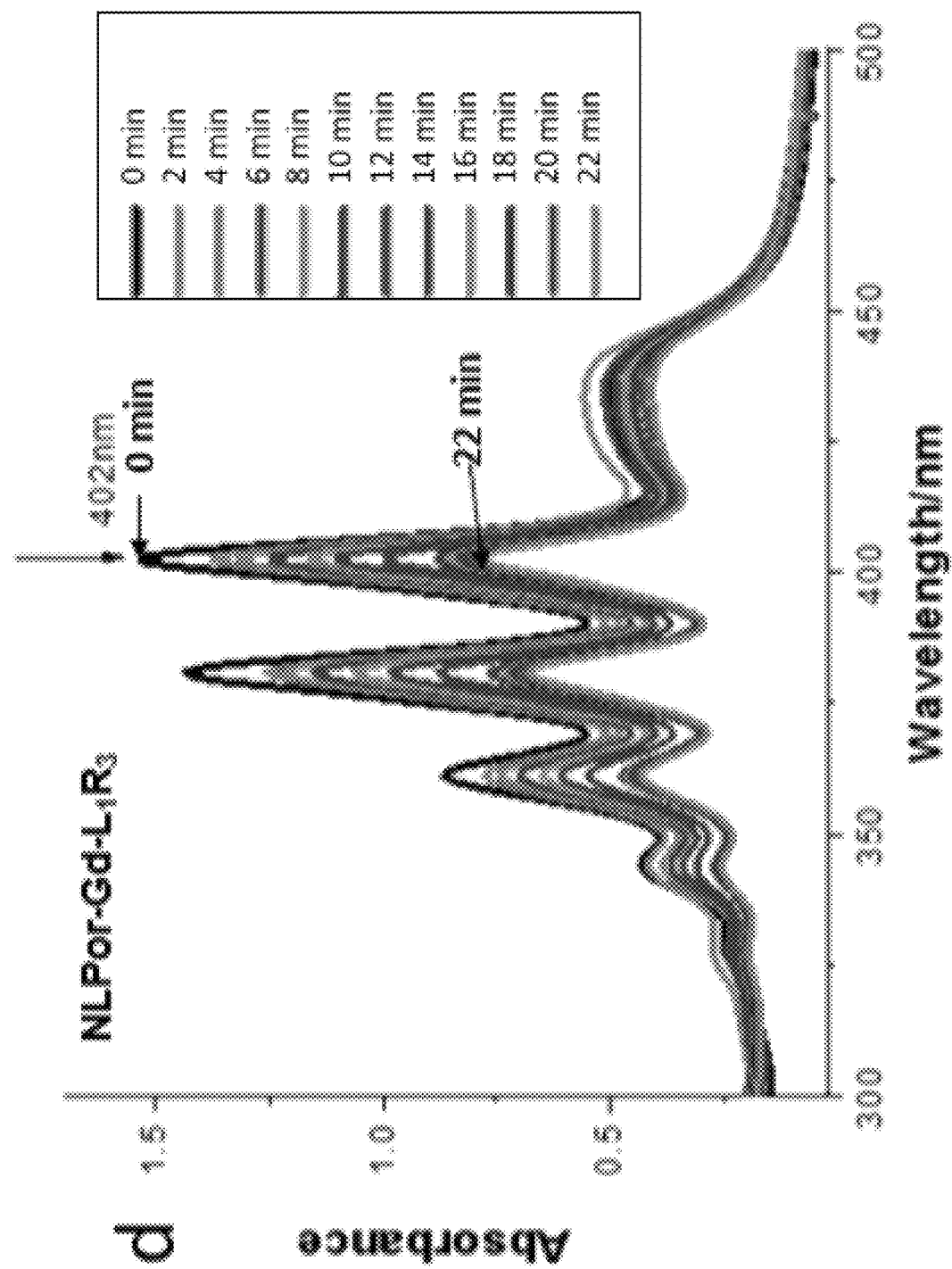
Figure 33:
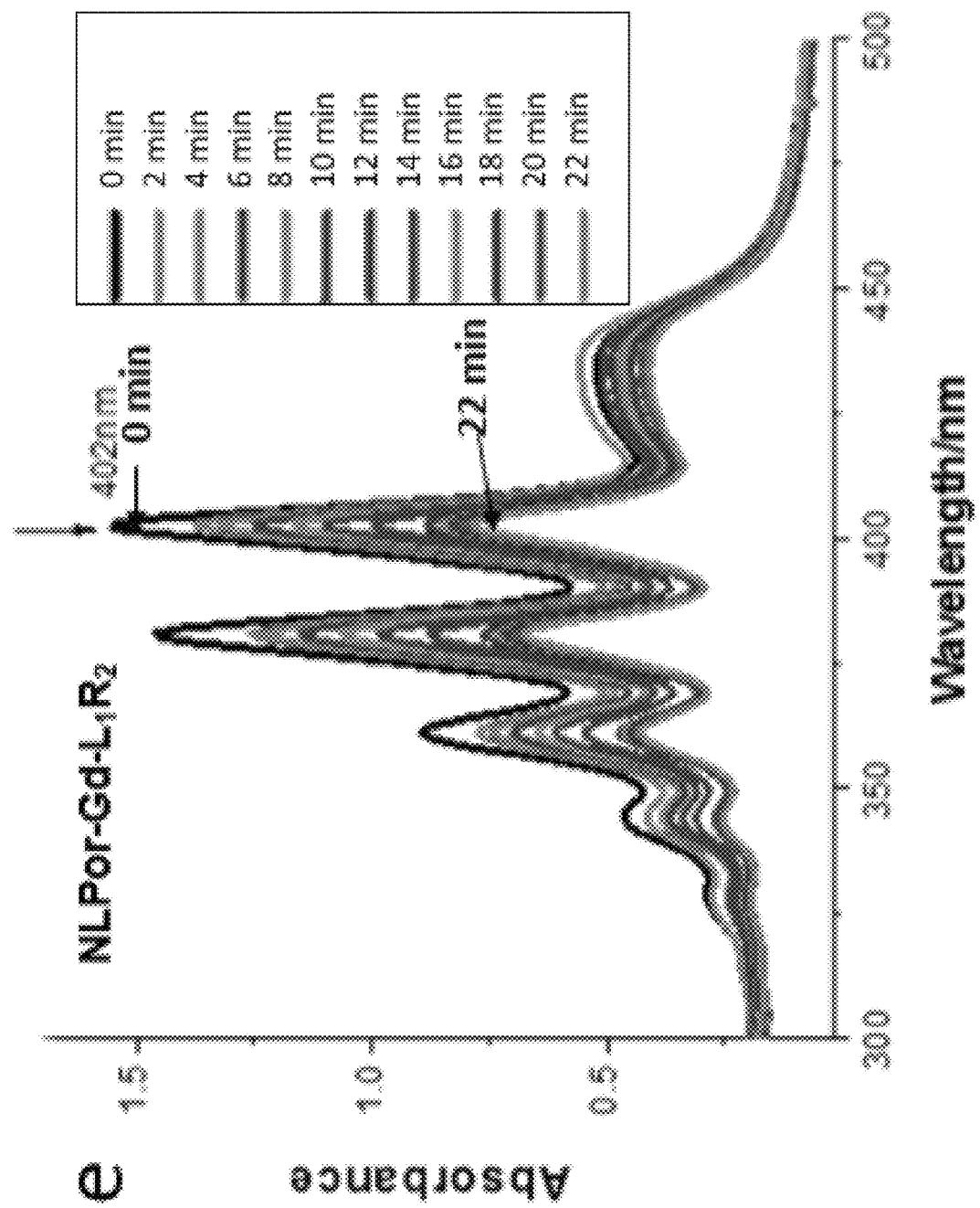
Figure 34:
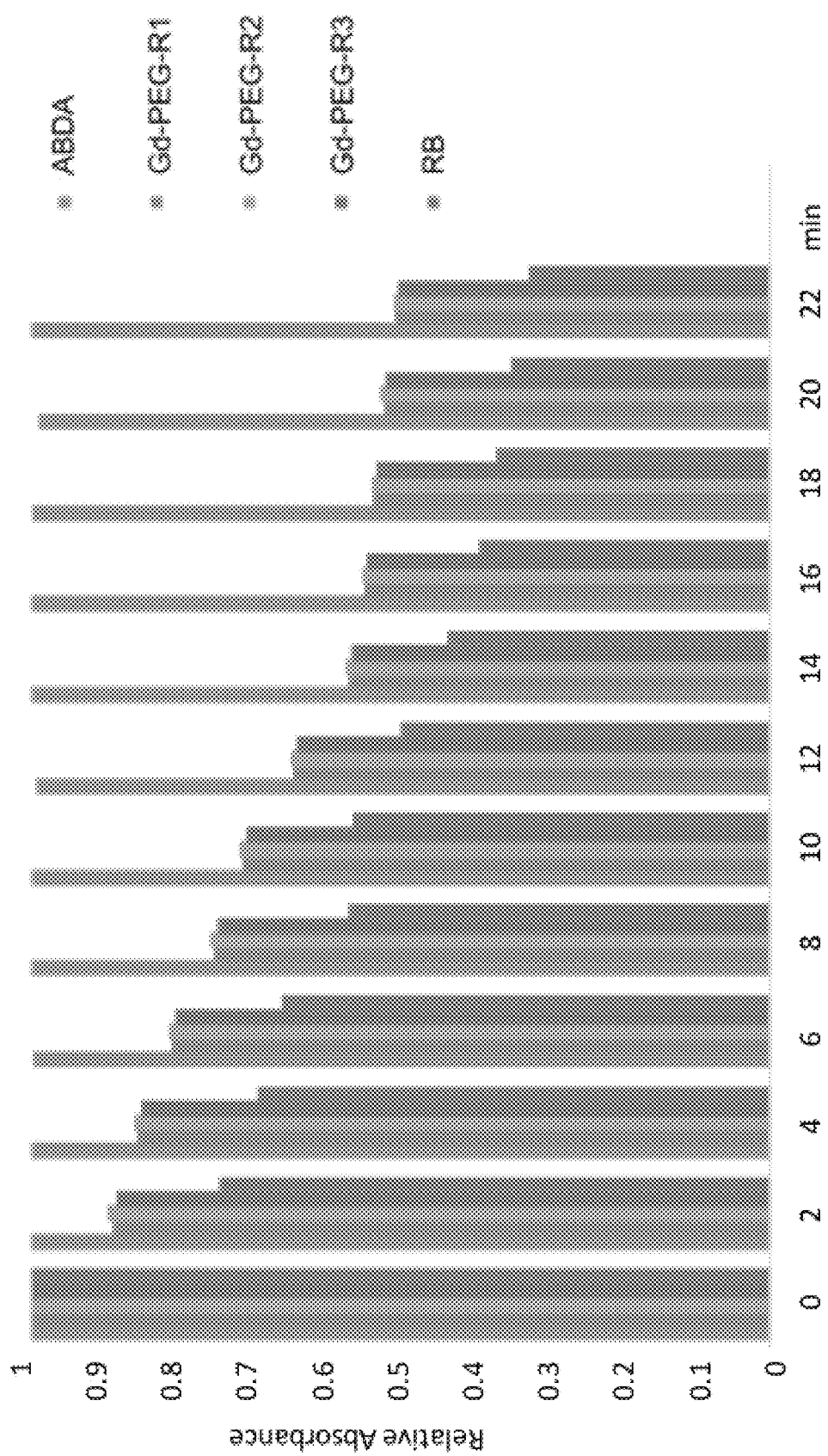
FIG. 34 shows the absorbance changes of ABDA at 402 nm upon illumination with LED lamp (with the power density 6 mWcm$^{-2}$) vs irradiation time in the presence of RB and NLPor-Gd-L$_1$R$_n$ (n=1-3).

As shown in FIG. 33a, ABDA as a control showed no changes of absorption under light irradiation (550 nm longpass filter, 6 mW·cm$^{-2}$). The ABDA absorbance decreased continuously due to the formation of its endoperoxide over the different amount of light exposure in the presence of singlet oxygen produced by Rose Bengal and NLPor-Gd-$L_1R_n$ (n=1-3) respectively (FIGS. 33b, 33c, 33d, and 33e). The absorbance changes of ABDA at 402 nm upon illumination with LED lamp is summarized in FIG. 34. As shown in FIG. 35, the $Φ_Δ$ values of NLPor-Gd-$L_1R_n$ (n=1-3) in PBS buffer are 0.39, 0.39 and 0.40 respectively. In addition, the evaluation of the singlet oxygen quantum yield of photosensitizers in aqueous solution is very important as the biological system mainly consists of water. The singlet oxygen quantum yield in aqueous solution is lower than that in an organic solvent because the photosensitizers aggregate easily in aqueous solution. Furthermore, water molecules will also quench singlet oxygen in some aspects.

III MR Relaxation Properties Measurements

In vitro $T_1$-weighted MR relaxivity measurements were conducted on a 3.0 Tesla MRI instrument (MAGNETOM Verio; Siemens Medical Solution, Erlangen, Germany) with a head coil. A $T_1$ map sequence was utilized for measurement of $T_1$ relaxation time with different Gd(III) concentrations (0, 0.05, 0.1, 0.2, 0.4, 0.8 mM). The $T_1$ measurement parameters were as follows: $T_R$=2250 ms, $T_E$=13 ms, and $T_I$=948.6 ms. The $r_1$ relaxivity values were obtained through the curve fitting of relaxation rate $1/T_1$ (S−1) vs. The concentration of $Gd^{3+}$ (mM) and the slope of the fitting line provides the $r_1$ value. The result is summarized in FIG. 36.

Figure 38:
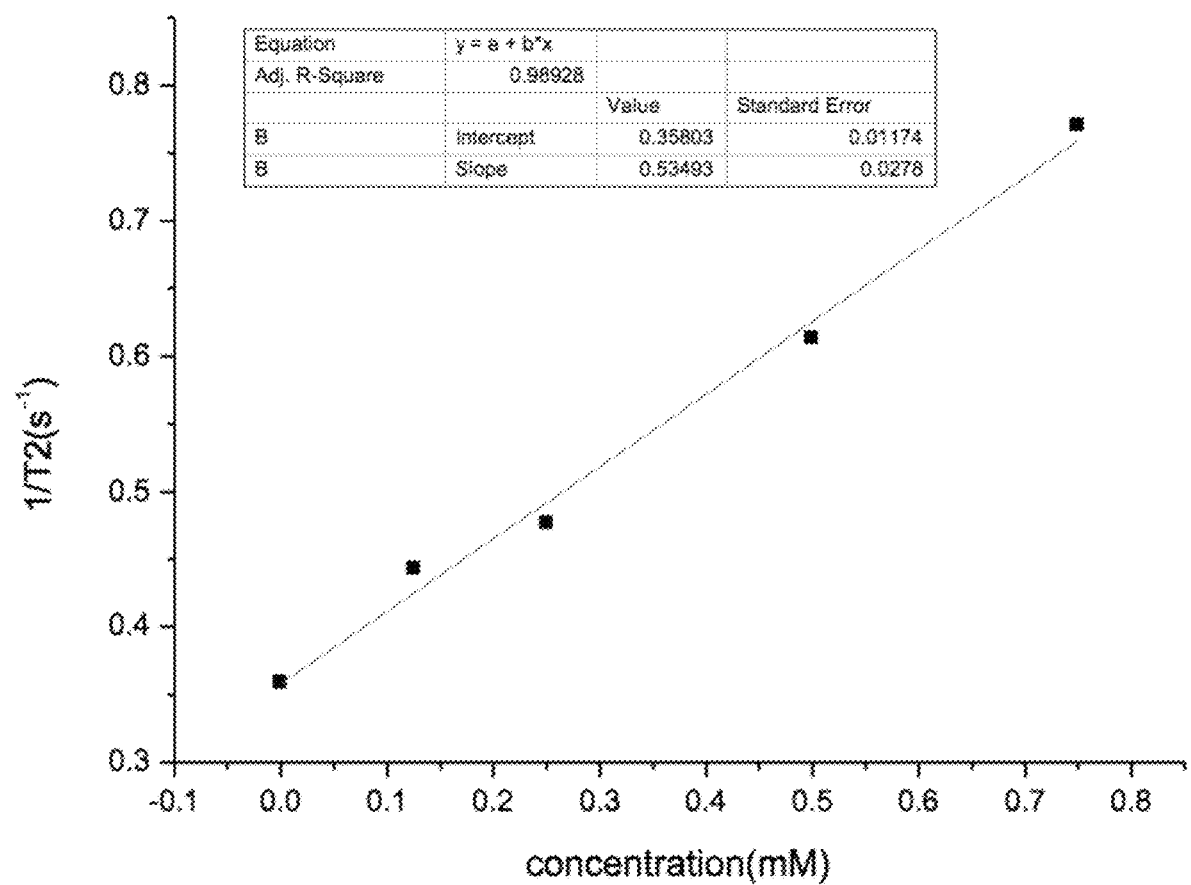
FIG. 38 shows the T$_2$ relativity of NLPor-Gd-L$_1$R$_3$ with the addition of α$_v$β$_3$.

In vitro T2-weighted MR relaxivity measurements were conducted at 37° C., 1.4T with the Mini Bruker Mq60 NMR Analyzer. Stock solution of NLPor-Gd-$L_1R_3$ was dissolved in water with 2% DMSO with concentration 1.23 mM and $α_vβ_3$ was dissolved in PBS buffer (pH 7.4) with concentration 100 μg/mL (FIGS. 37 and 38).

IV Flow Cytometry Measurements of Cellular Uptake

Figure 40:
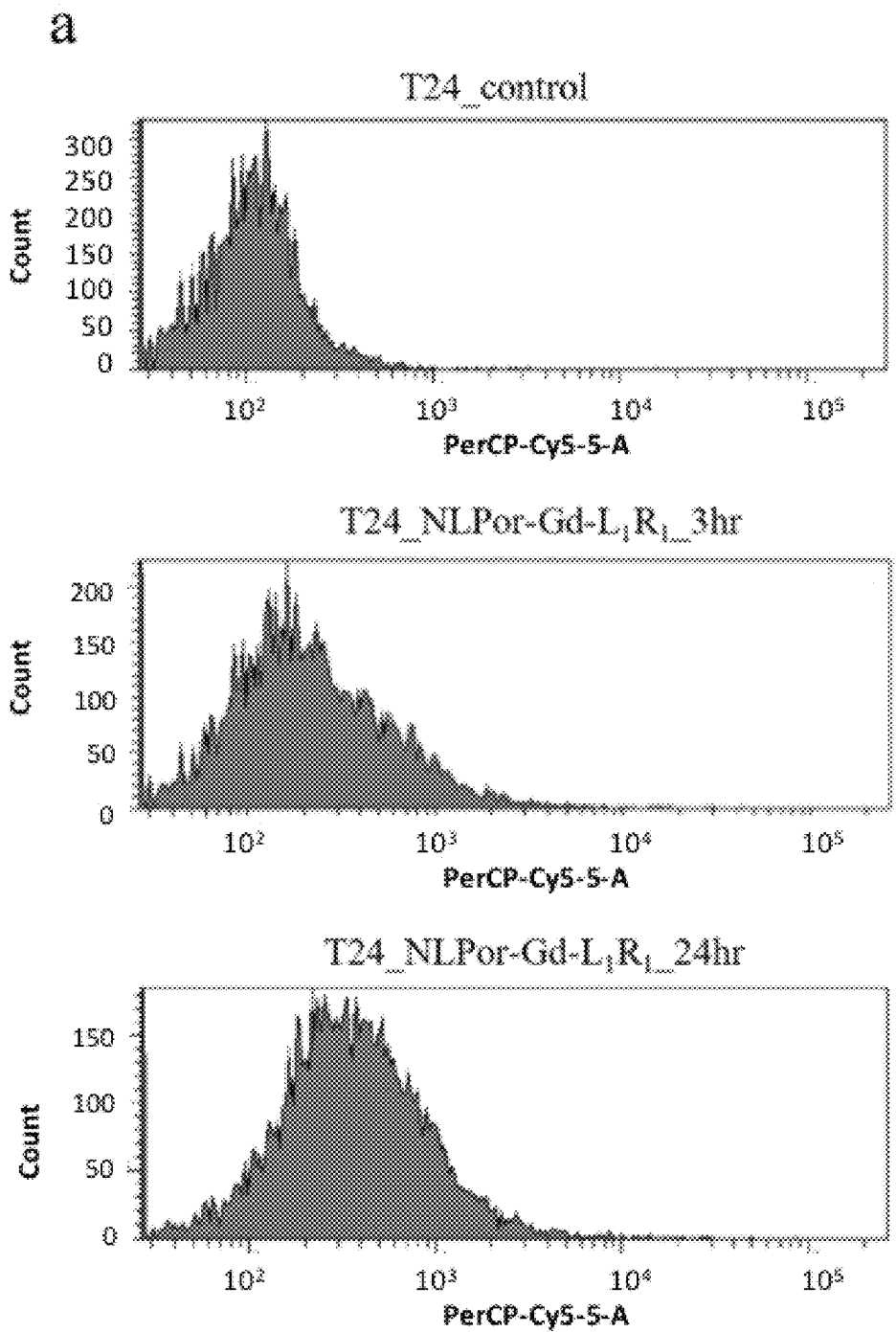
FIGS. 40 (a), (b), and (c) show flow cytometry of NLPor-Gd-L$_1$R$_n$ (n=1-3) in T24 with 3 hr and 24 hr incubation.
Figure 40:
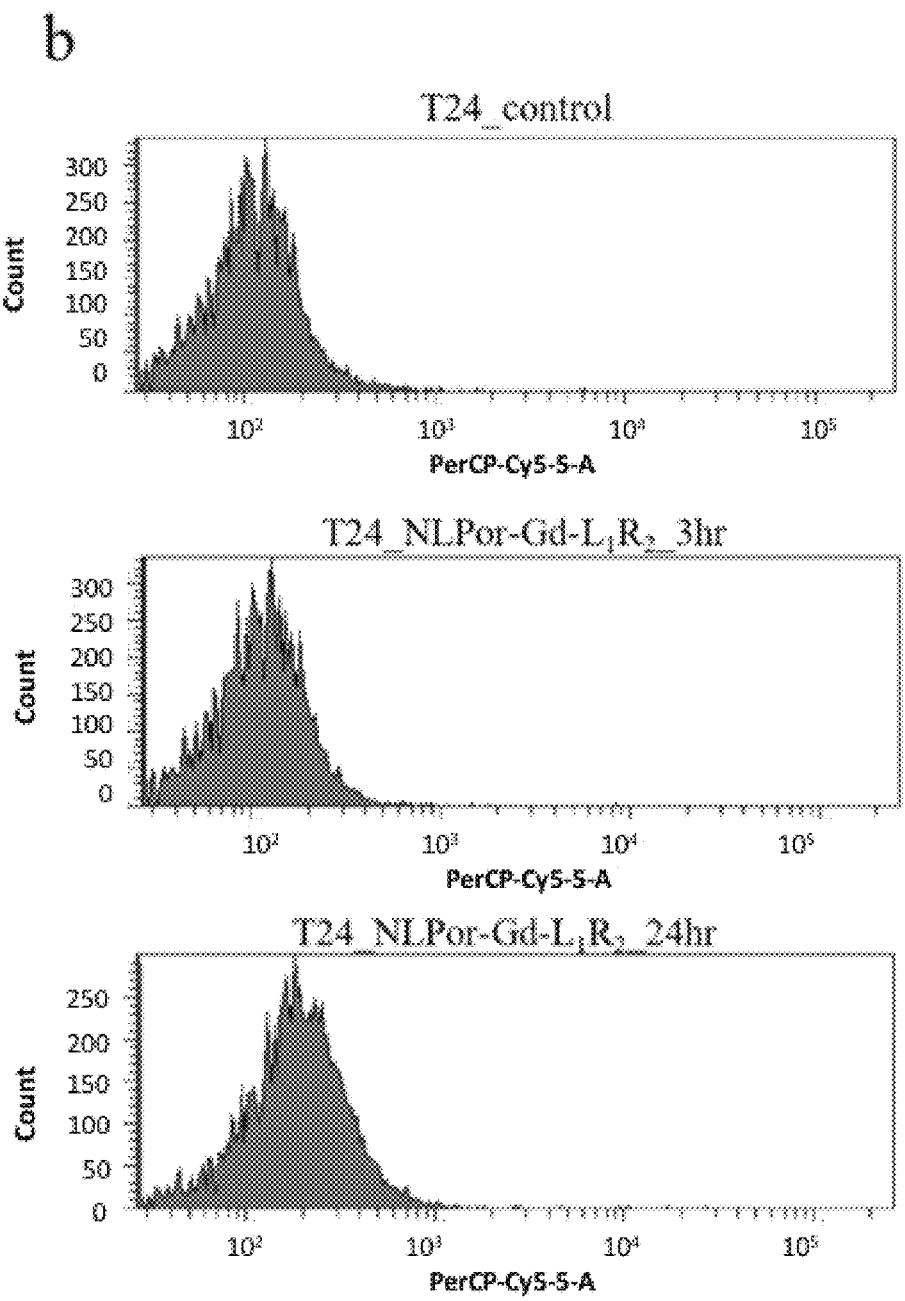
Figure 40:
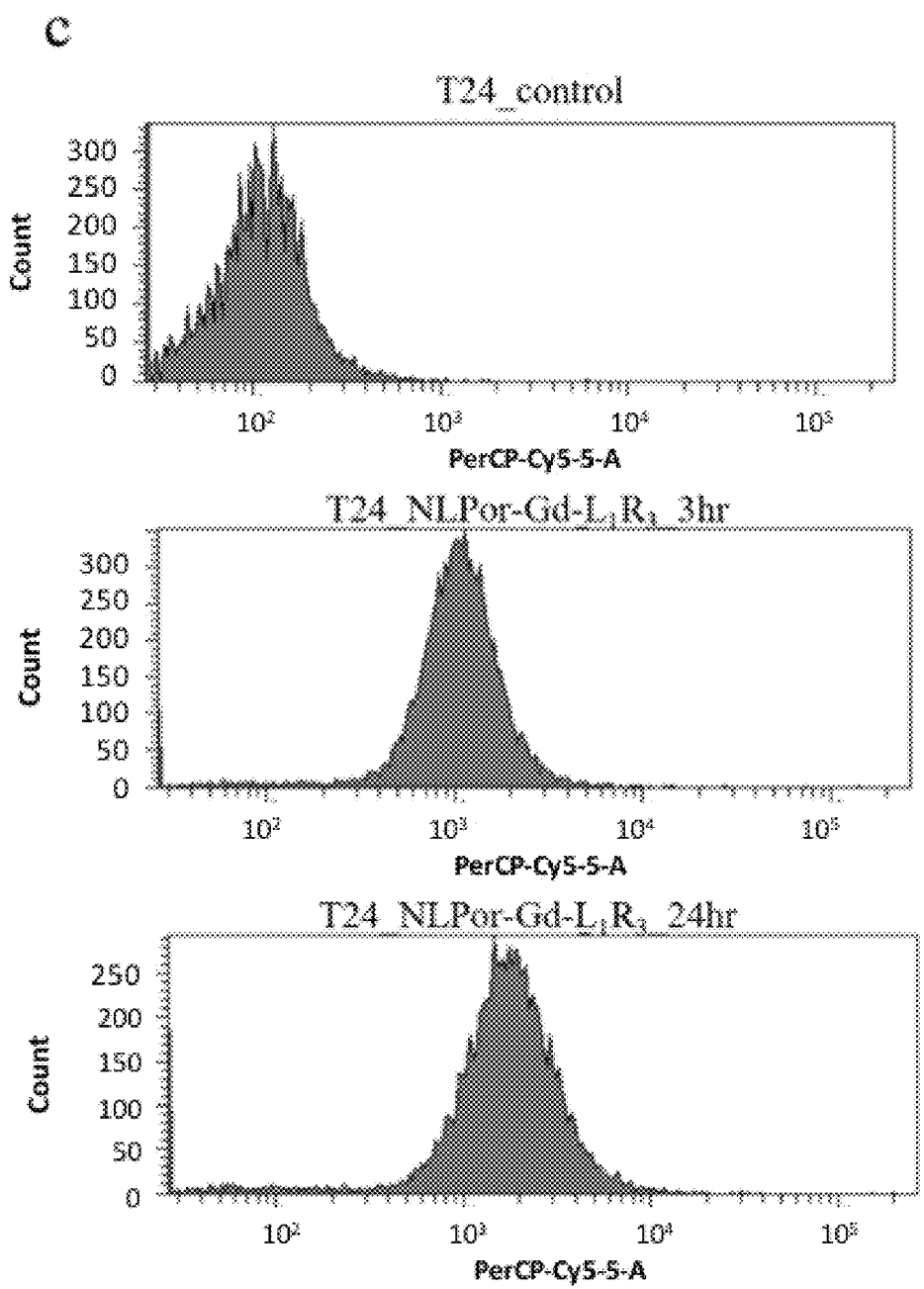

T24 bladder cancer cells were seeded onto 35 mm Petri dishes. Then incubated 5 μM porphyrin complexes in cells for 3 and 24 hours respectively. Harvested the cells with trypsin and washed the cells with PBS buffer twice. Flow cytometry was used to evaluate the uptake of the complexes within T24 cells. 488 nm was chosen as the excitation wavelength of cells and the FL-3 channel was used for the emission (FIG. 40).

Figure 41:
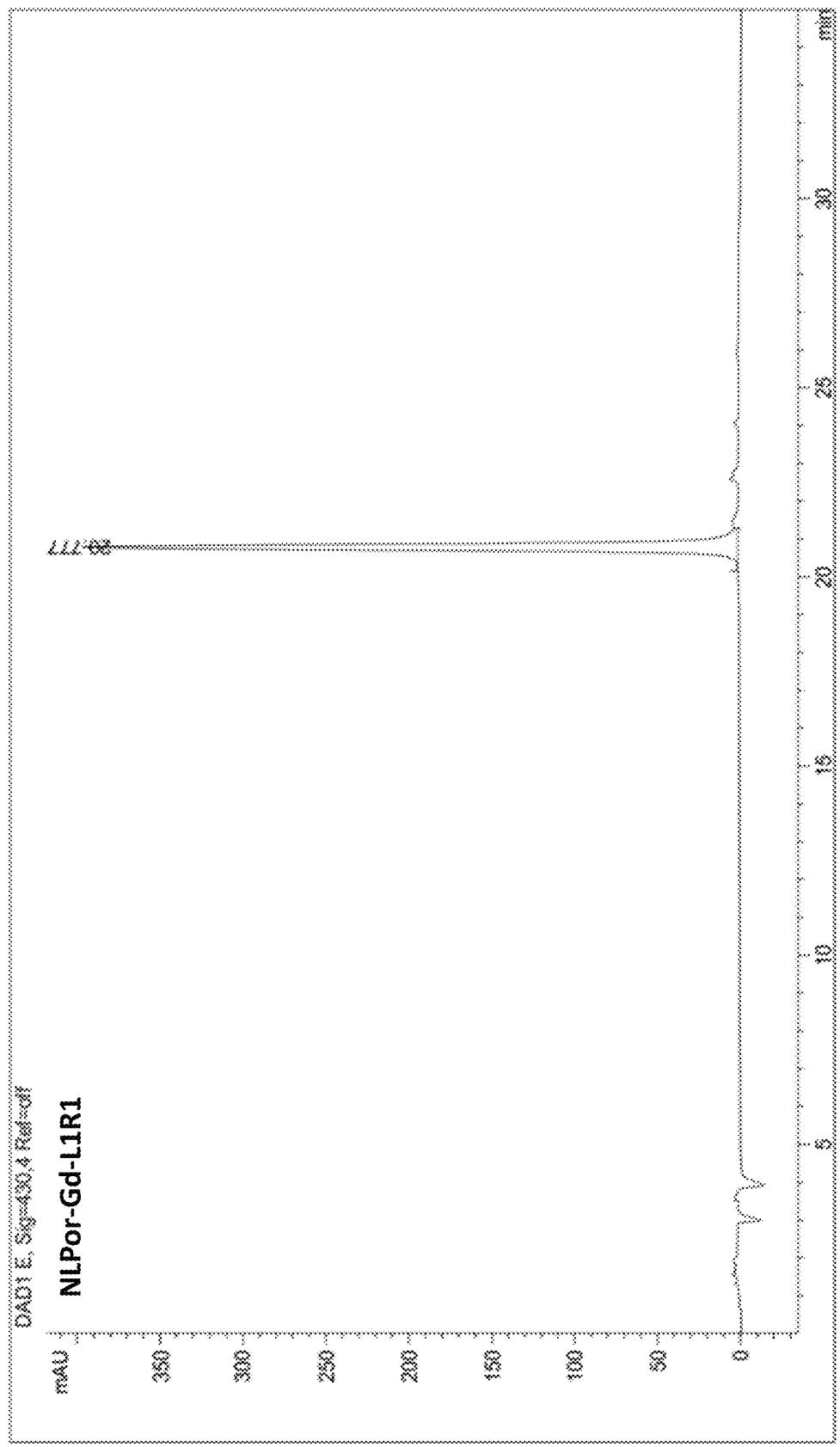
FIG. 41 shows analytical HPLC spectra of NLPor-Gd-L$_1$R$_n$. (n=1-3).
Figure 41:
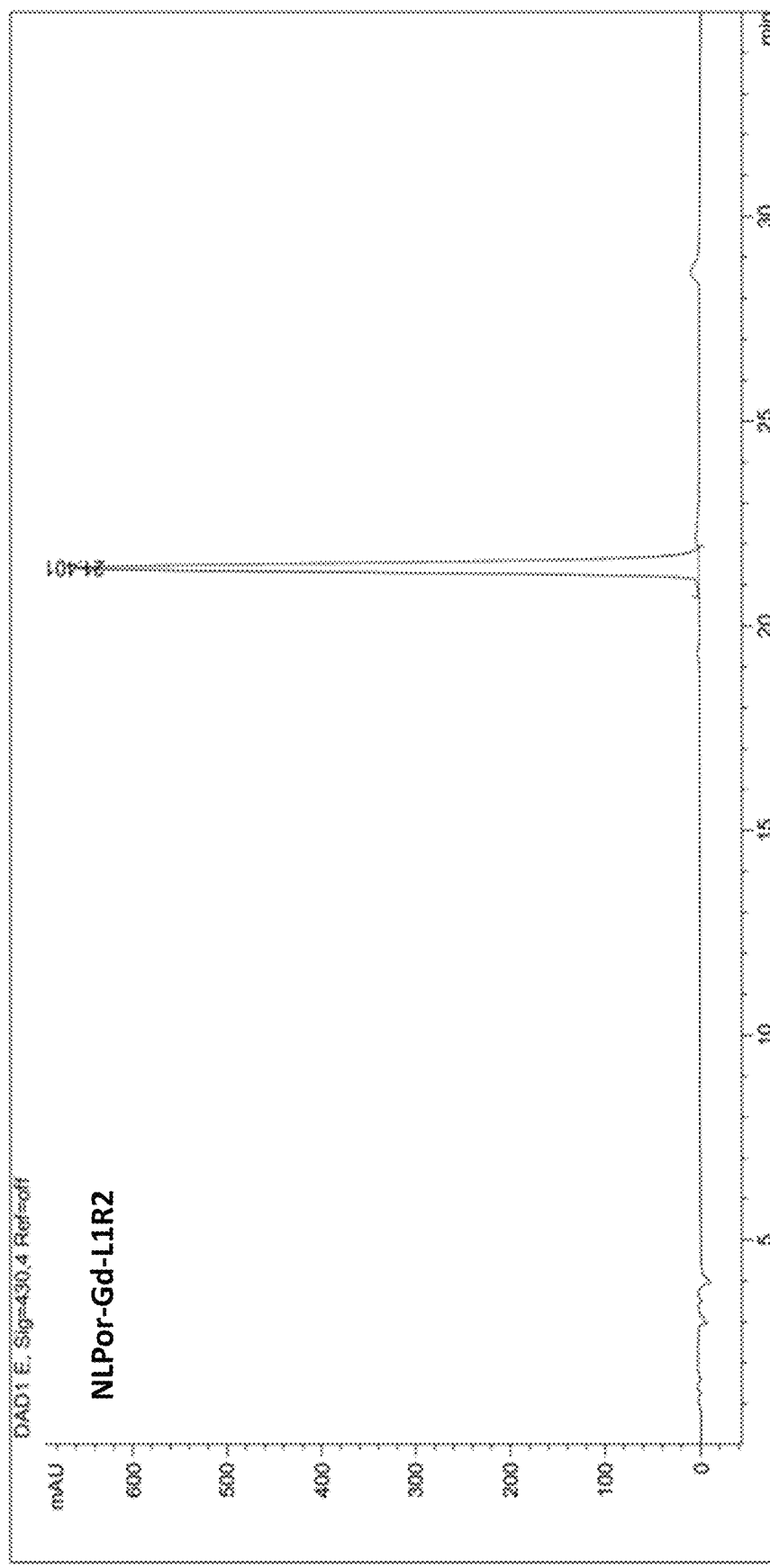
Figure 41:
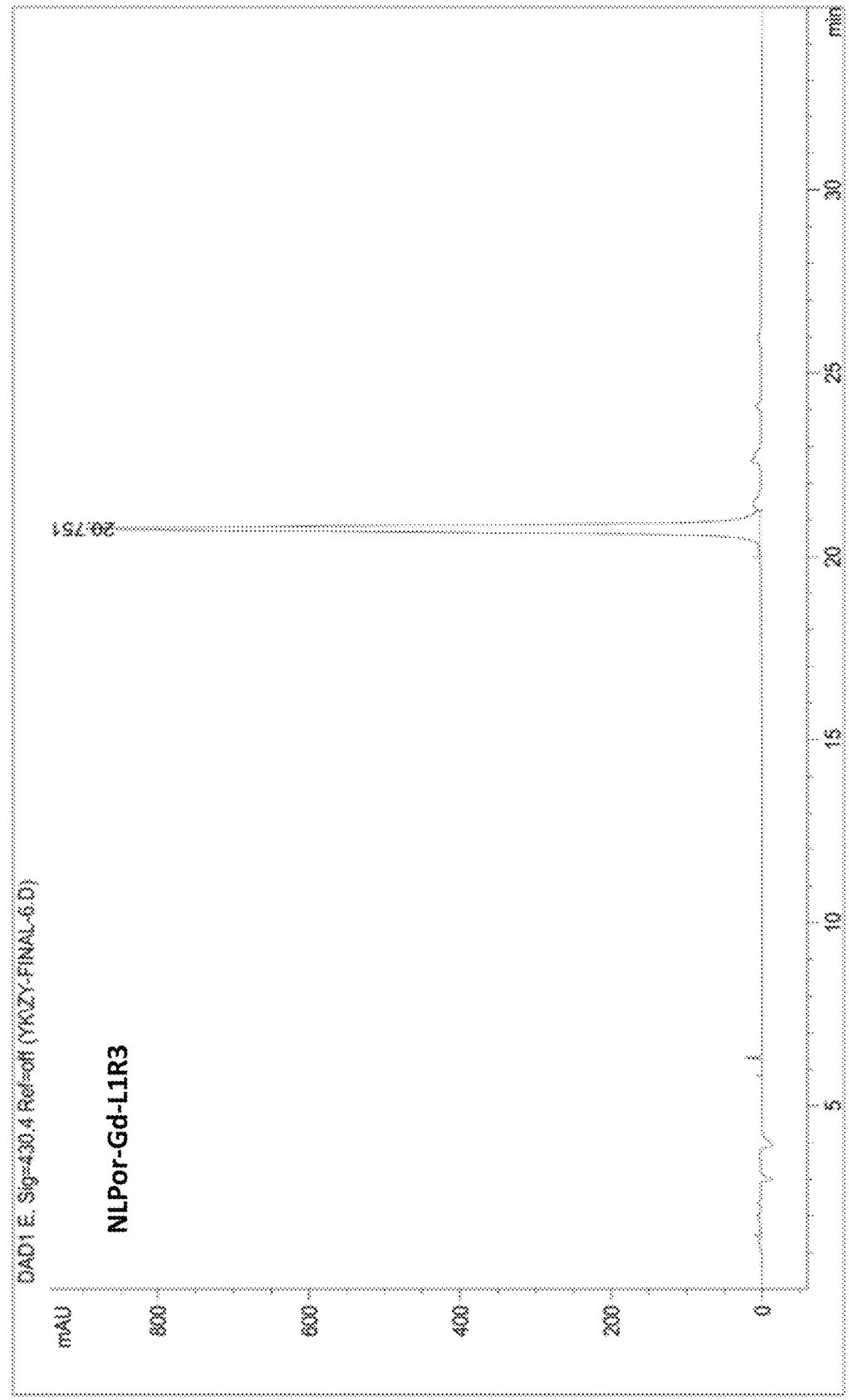
Figure 42:
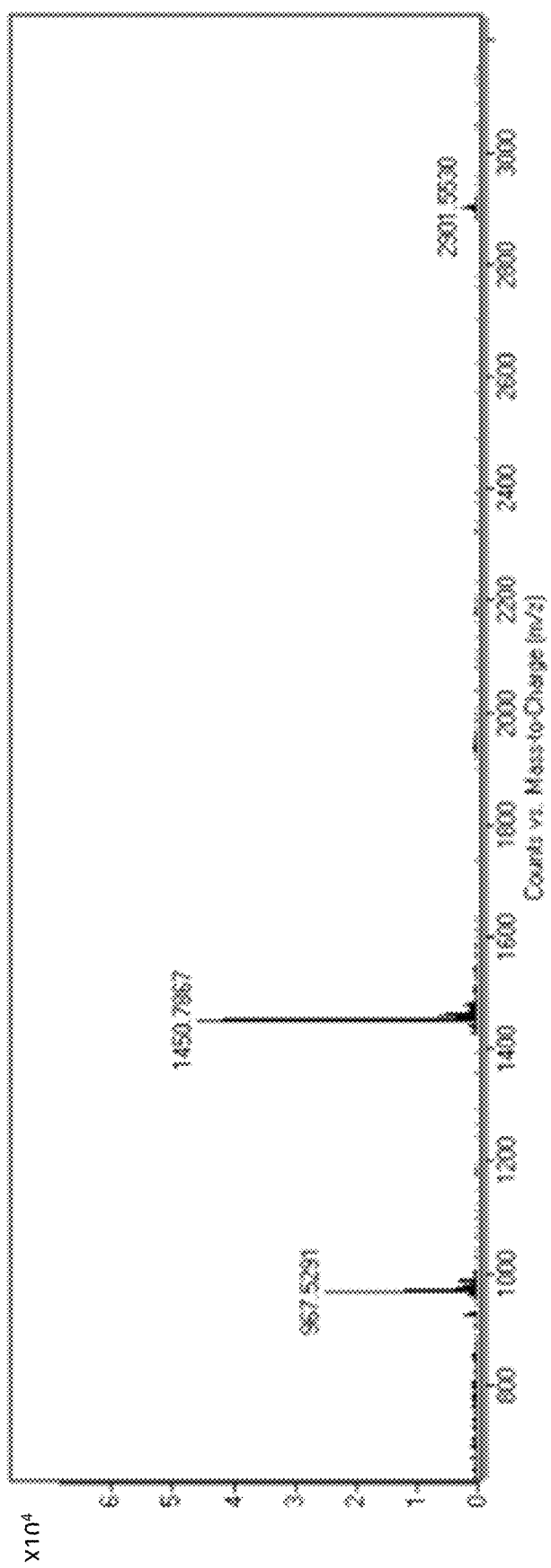
FIG. 42 shows LC-MS spectrum of NLPor-Gd-L$_1$R$_1$.
Figure 42:
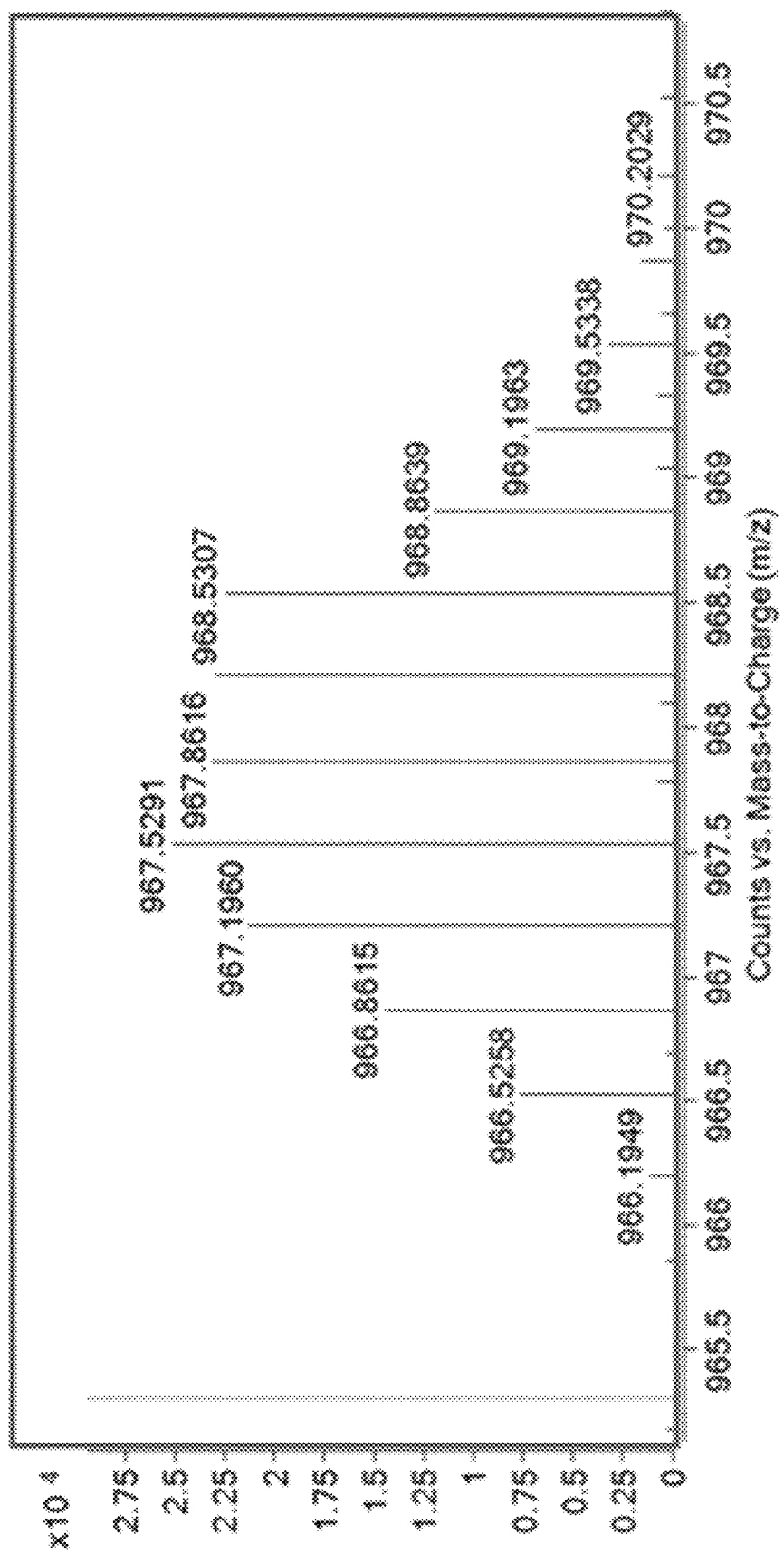
Figure 42:
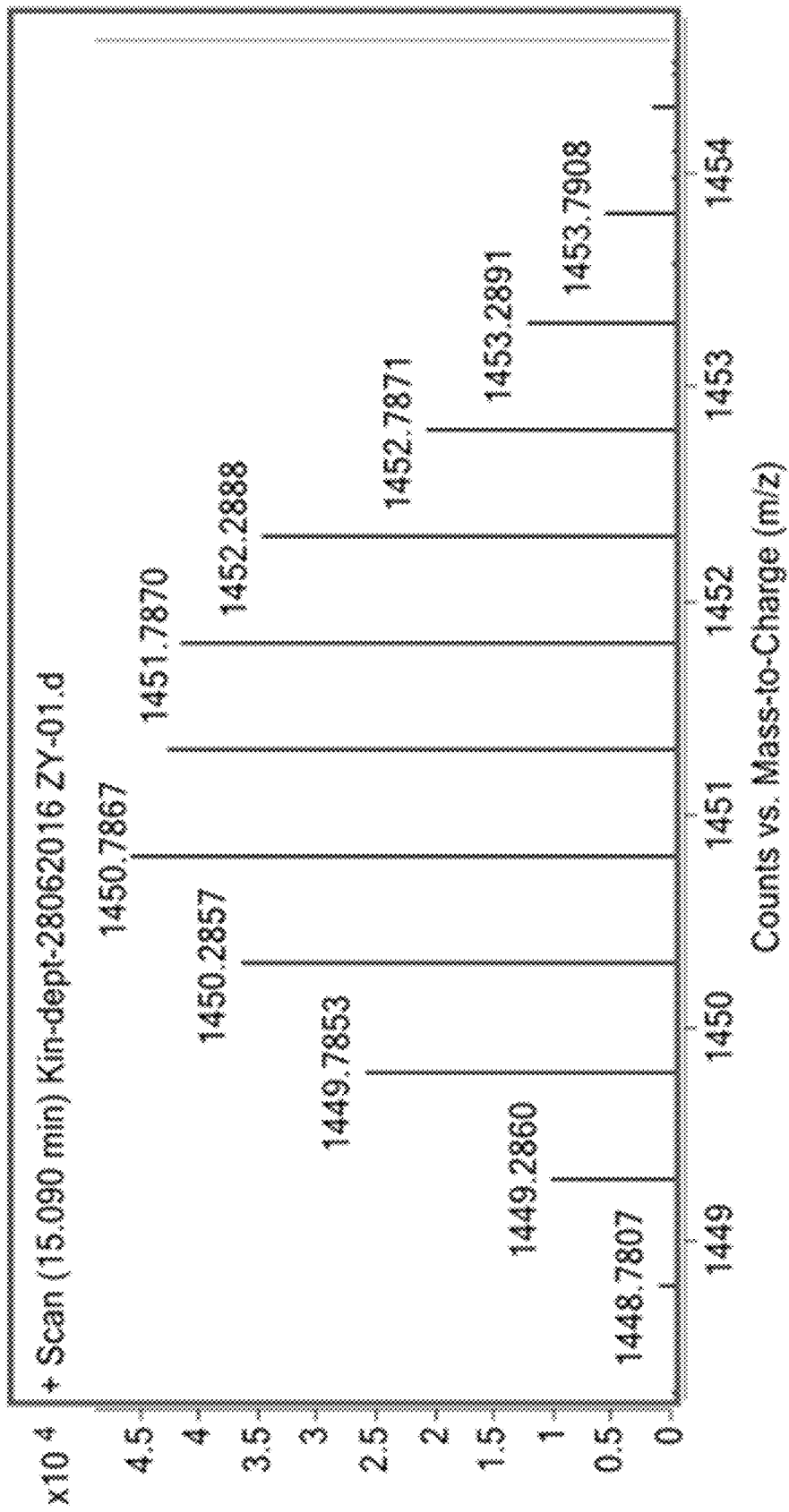
Figure 42:
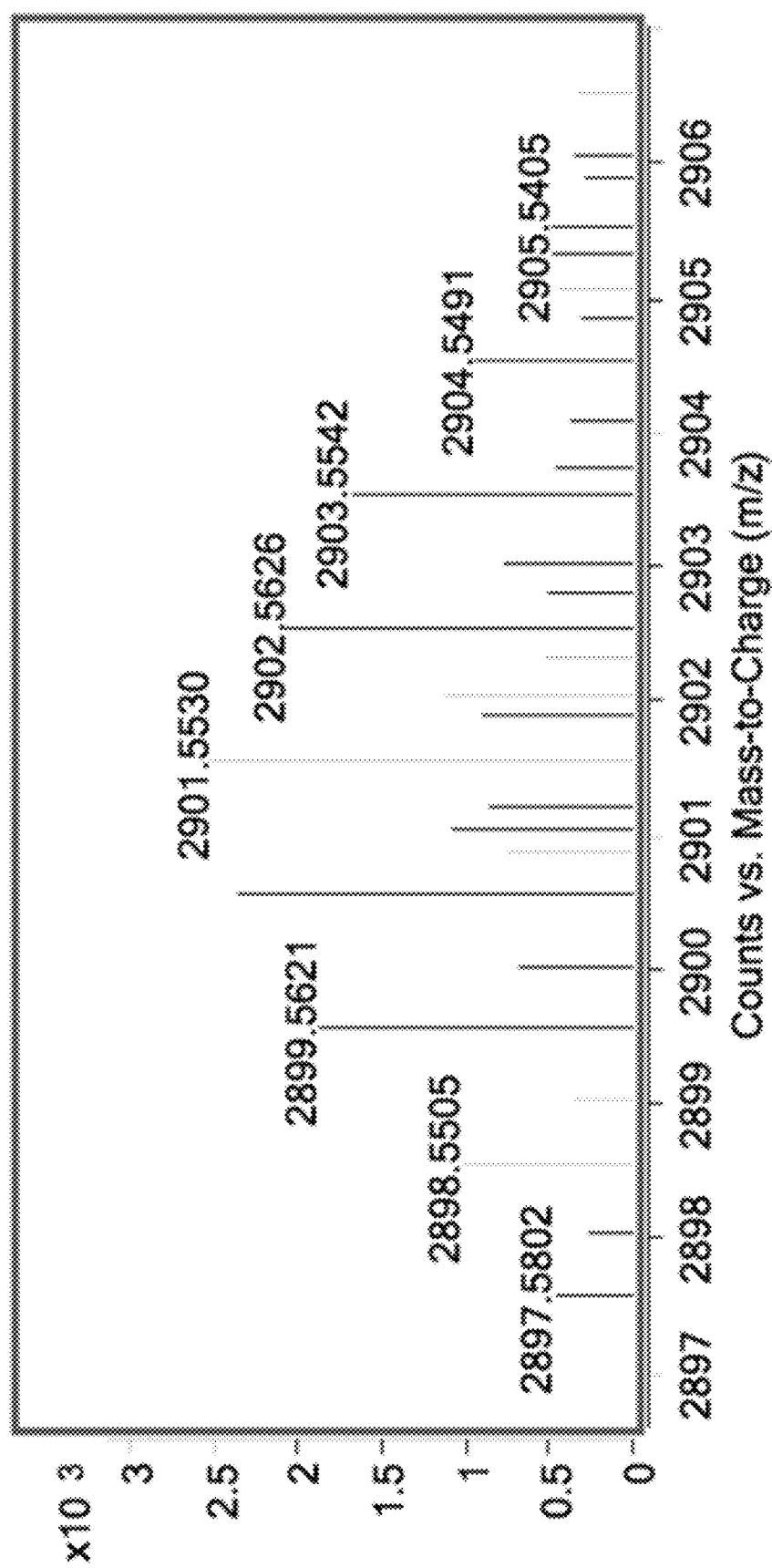

V Characterization of NLPor-Gd-$L_1R_n$ (n=1-3)

a) HPLC Characterization of NLPor-Gd-$L_1R_n$ (n=1-3).
Elution conditions: column, Agilent ZORBAXSB-C18 (4.6×150 mm, particle size 5; flow rate, 1.0 mL/min; gradient elution; detection wavelength, 430 nm. Retention time: NLPor-Gd-$L_1R_1$ 20.777 min, NLPor-Gd-$L_1R_2$ 21.401 min, NLPor-Gd-$L_1R_3$ 20.751 min) (FIG. 41). The methods used in running the HPLC is summarized in FIG. 39.

b) LC-MS analysis of NLPor-Gd-LxRn (n=1-3)
NLPor-Gd-$L_1R_1$: LC-MS: calcd. for $C_{112}H_{124}CoF_{15}N_{22}O_{27}P_3S_3Gd$ $[M+H]^+$ 2901.5212 found: 2901.5530. $[M+3H]^{3+}$ 967.1950, found: 967.5291, HPLC characterization: retention time=20.777 min. (FIG. 42)

Figure 43:
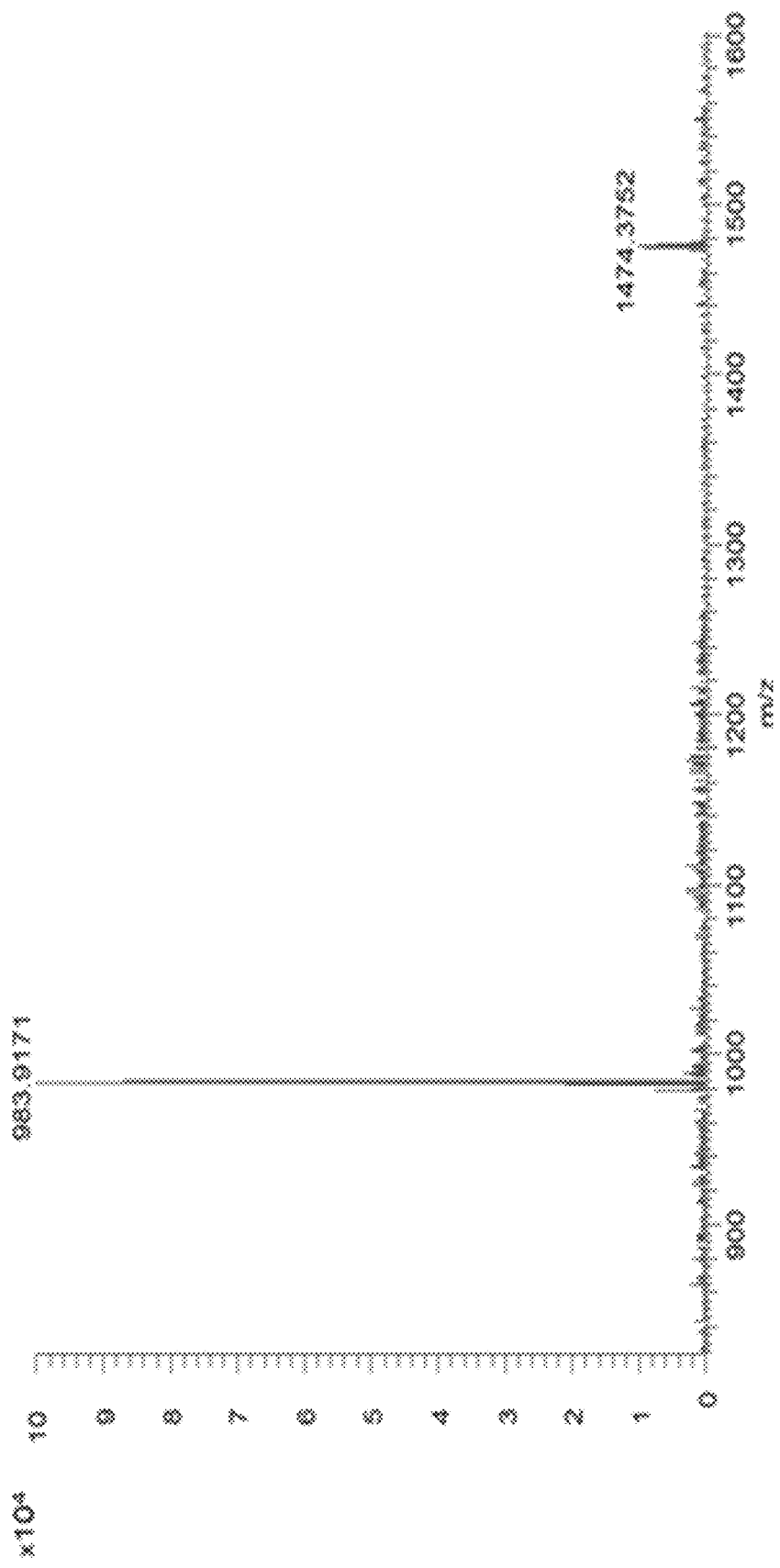
FIG. 43 shows LC-MS spectrum of NLPor-Gd-L$_1$R$_2$.
Figure 43:
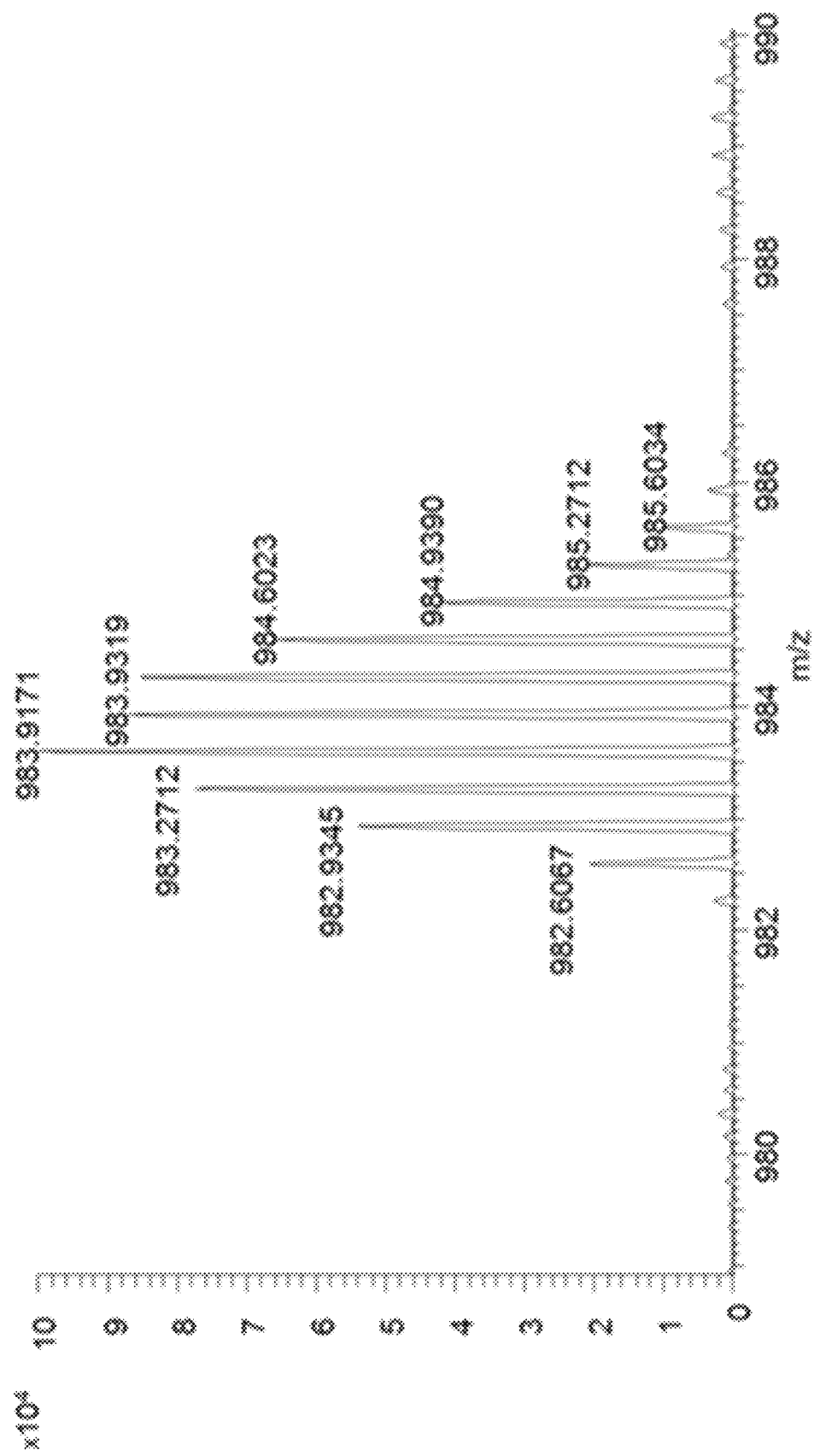
Figure 43:
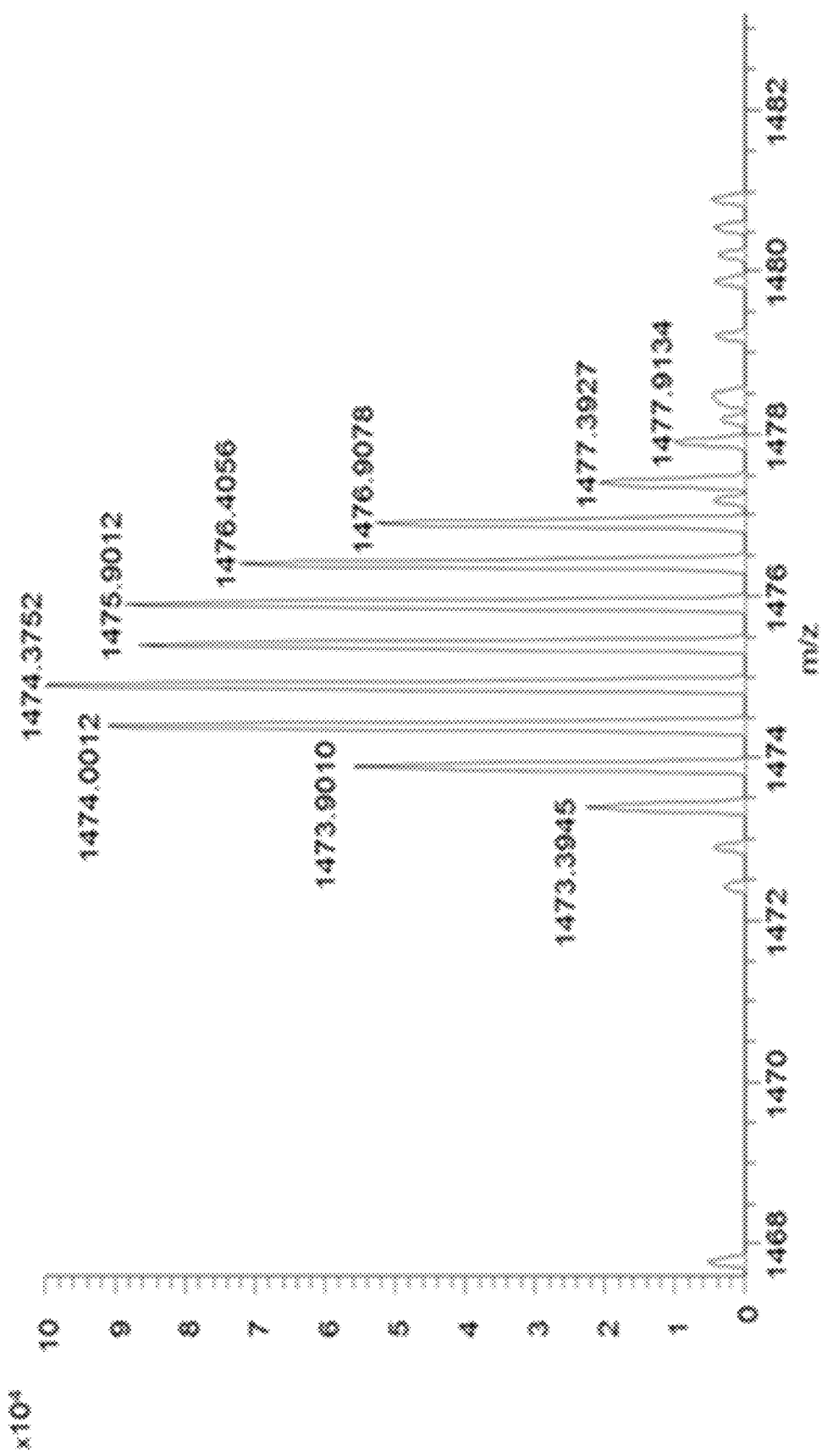

NLPor-Gd-$L_1R_2$: LC-MS: calcd, for $C_{116}H_{143}CoF_{15}N_{23}O_{27}P_3S_2Gd$ $[M+2H]^{2+}$ 1474.3525 found: 1474.3752. $[M+3H]^{3+}$ 983.9225 found: 983.9171. HPLC characterization: retention time=21.401 min. (FIG. 43)

Figure 44:
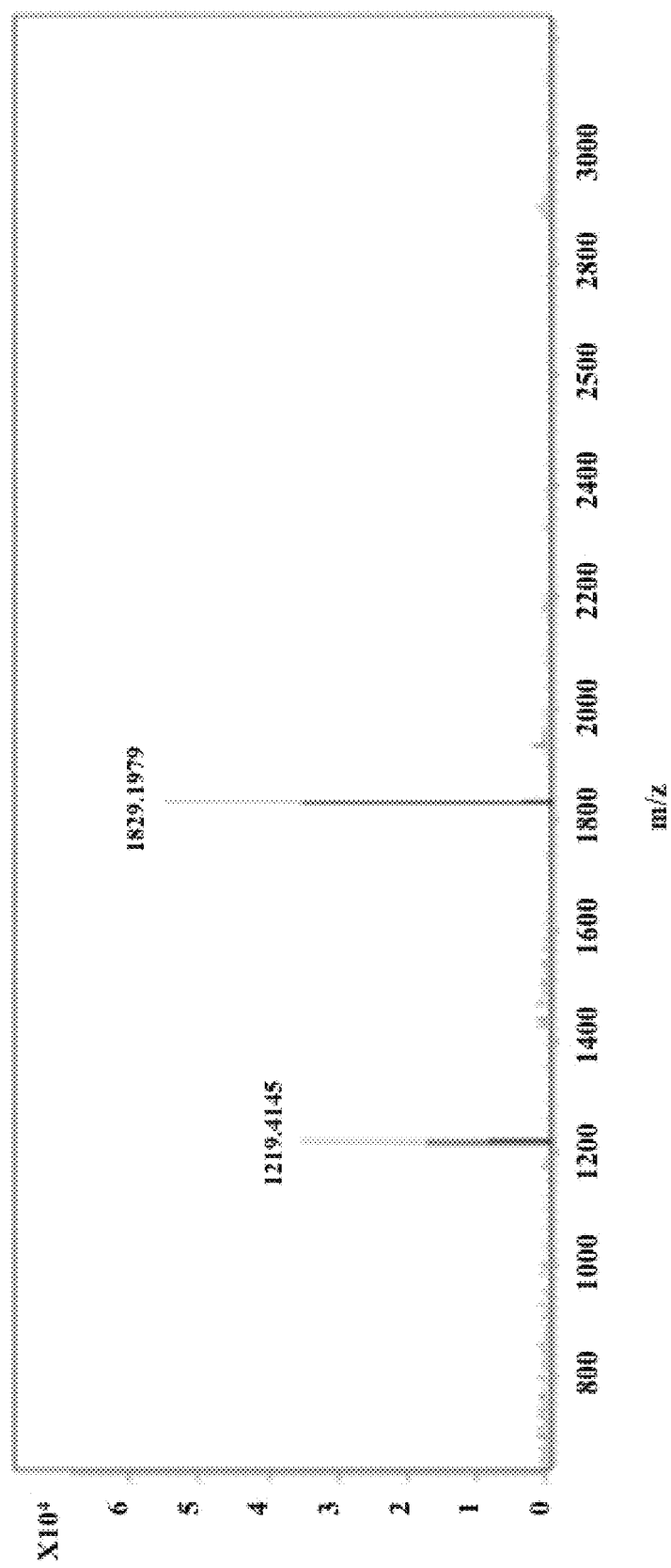
FIG. 44 shows LC-MS spectrum of NLPor-Gd-L$_1$R$_3$. NLPor-Gd-L$_1$R$_1$: LC-MS: calcd. for C$_{112}$H$_{124}$CoF$_{15}$N$_{22}$O$_{27}$P$_3$S$_3$Gd [M+H]$^+$ 2901.5212 found: 2901.5530. [M+3H]$^{3+}$ 967.1950, found: 967.5291. HPLC characterization: retention time=20.777 min. NLPor-Gd-L$_1$R$_2$: LC-MS: calcd. for C$_{116}$H$_{143}$CoF$_{15}$N$_{23}$O$_{27}$P$_3$S$_2$Gd [M+2H]$^{2+}$ 1474.3525 found: 1474.3752. [M+3H]$^{3+}$ 983.9225 found: 983.9171. HPLC characterization: retention time=21.401 min. NLPor-Gd-L$_1$R$_3$: LC-MS: calcd. for C$_{146}$H$_{202}$CoF$_{15}$N$_{38}$O$_{32}$P$_3$S$_2$Gd [M+2H]$^{2+}$ 1829.1728 found: 1829.1979. [M+3H]$^{3+}$ 1219.3333 found: 1219.4145. HPLC characterization: retention time=20.751 min.
Figure 44:
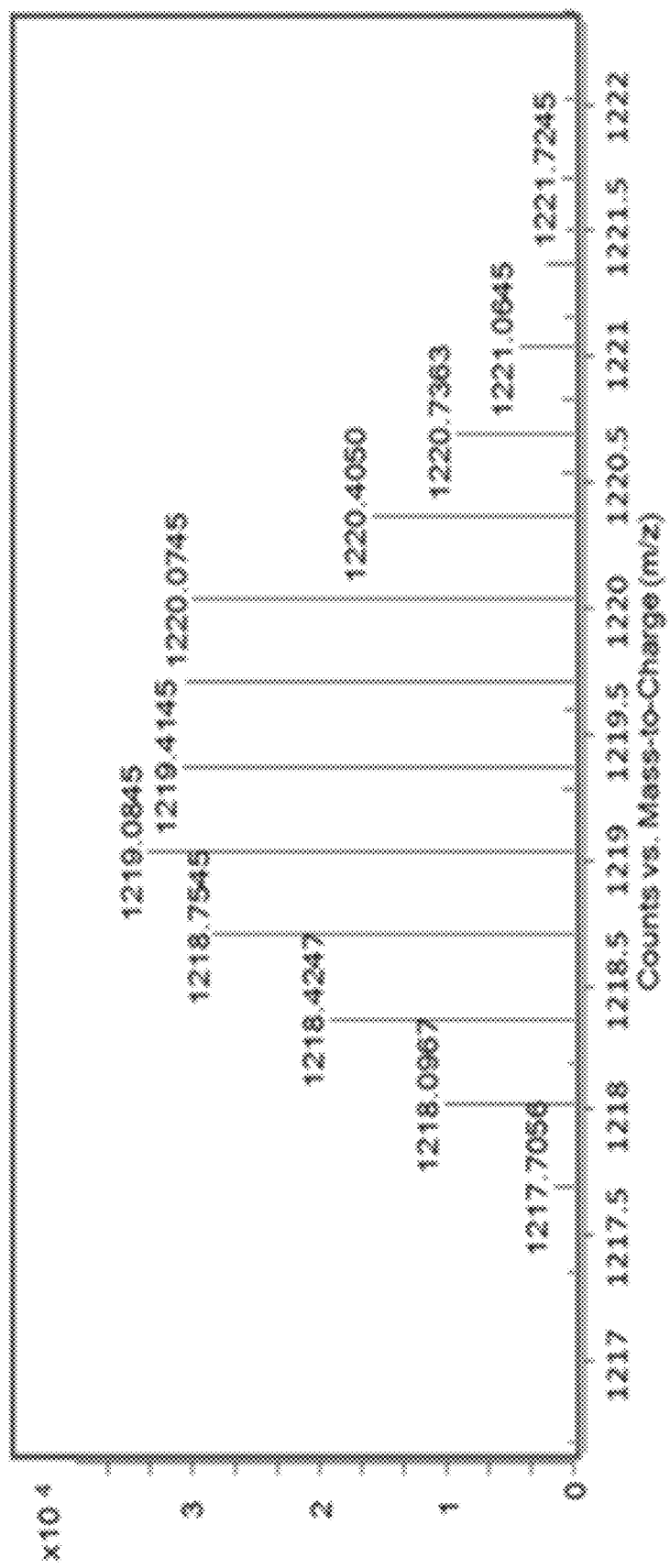
Figure 44:
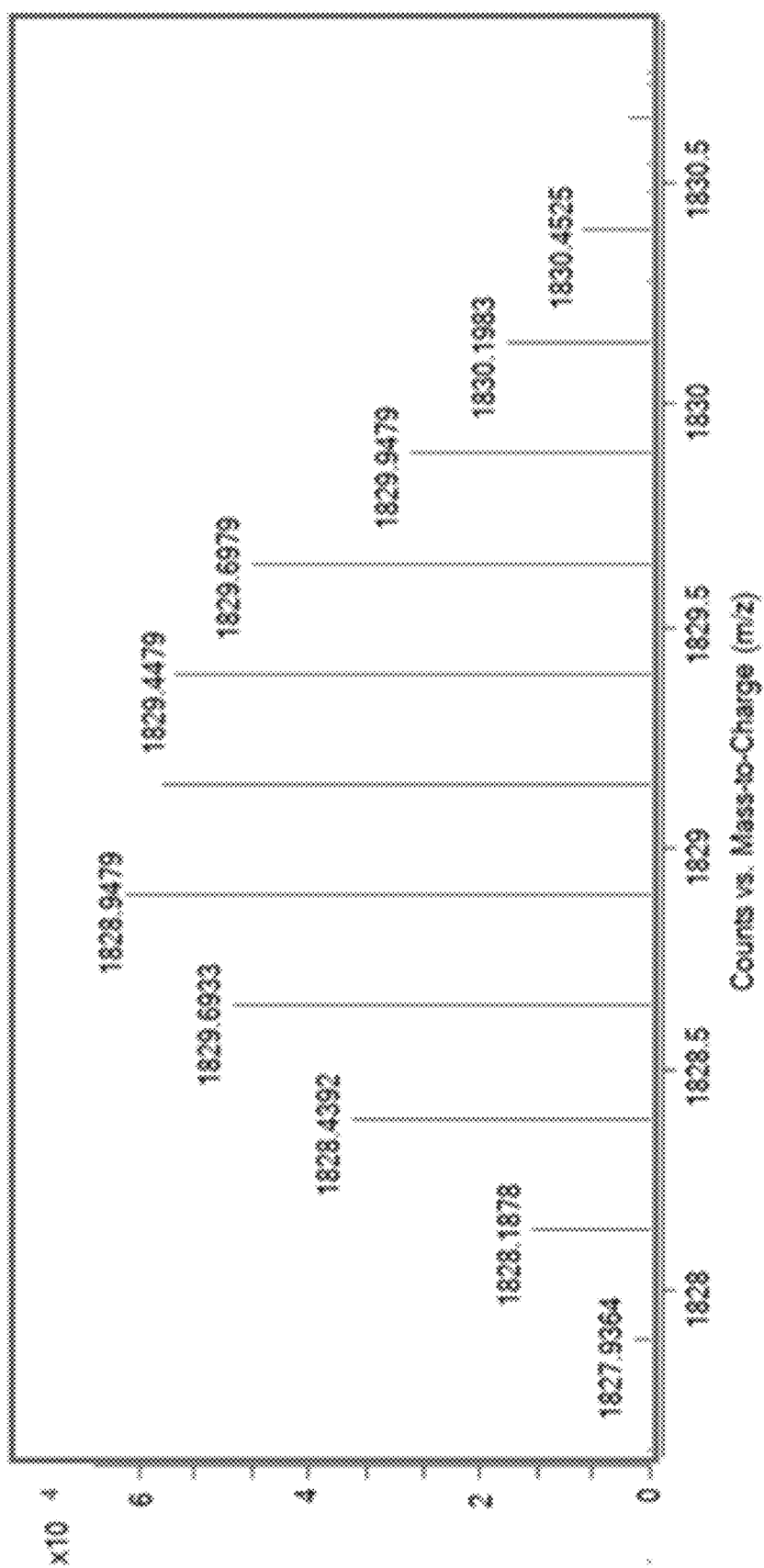

NLPor-Gd-$L_1R_3$: LC-MS: calcd., for $C_{146}H_{202}CoF_{15}N_{38}O_{32}P_3S_2Gd$ $[M+2H]^{2+}$ 1829.1728 found: 1829.1979. $[M+3H]^{3+}$ 1219.3333 found: 1219.4145. HPLC characterization: retention time=20.751 min. (FIG. 44)

c) Stability Test of NLPor-Gd-$L_1R_3$ in Different pH by HPLC

Figure 46:
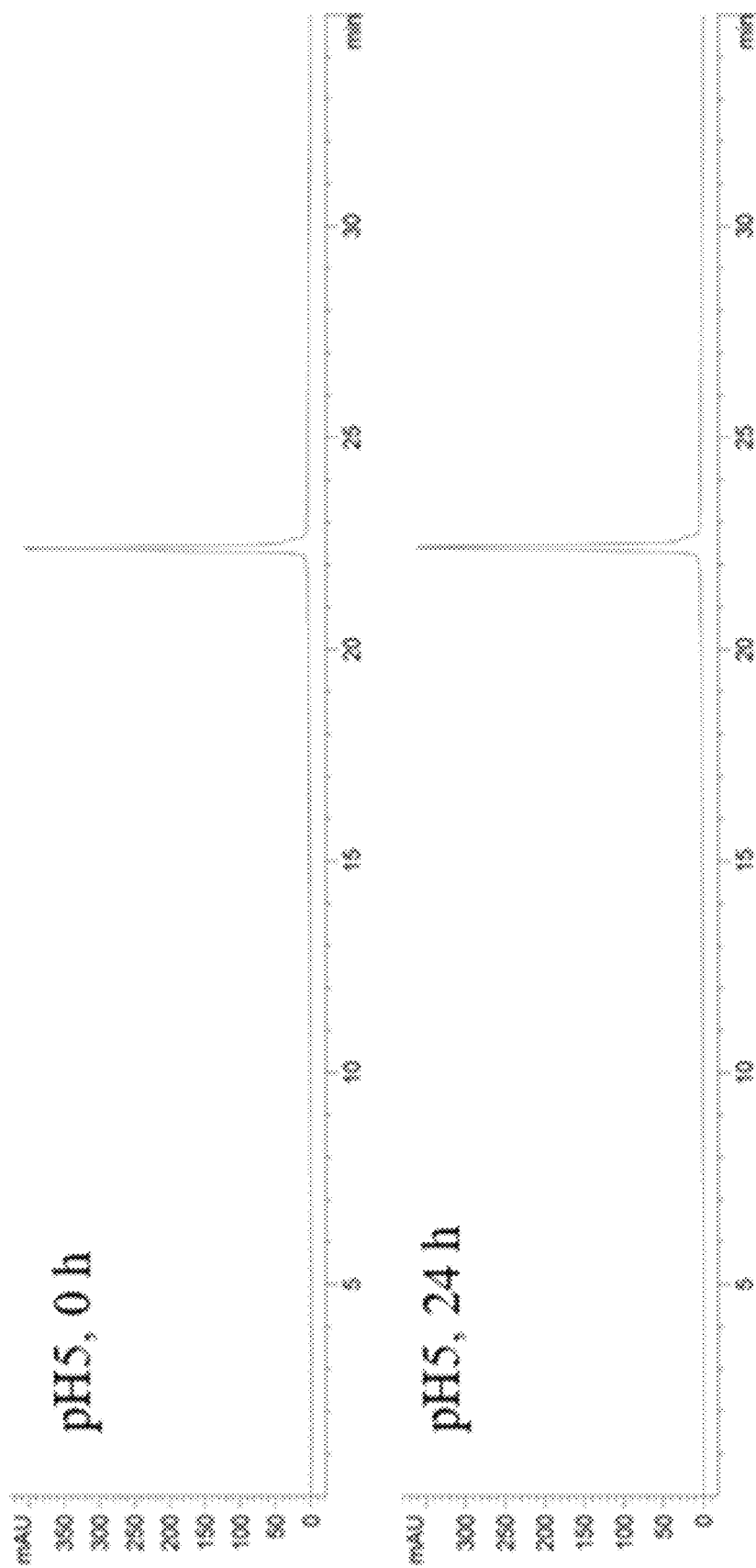
FIG. 46 shows analytical HPLC spectra of NLPor-Gd-L$_1$R$_3$ in pH 5 and pH 7 aqueous solution.
Figure 46:
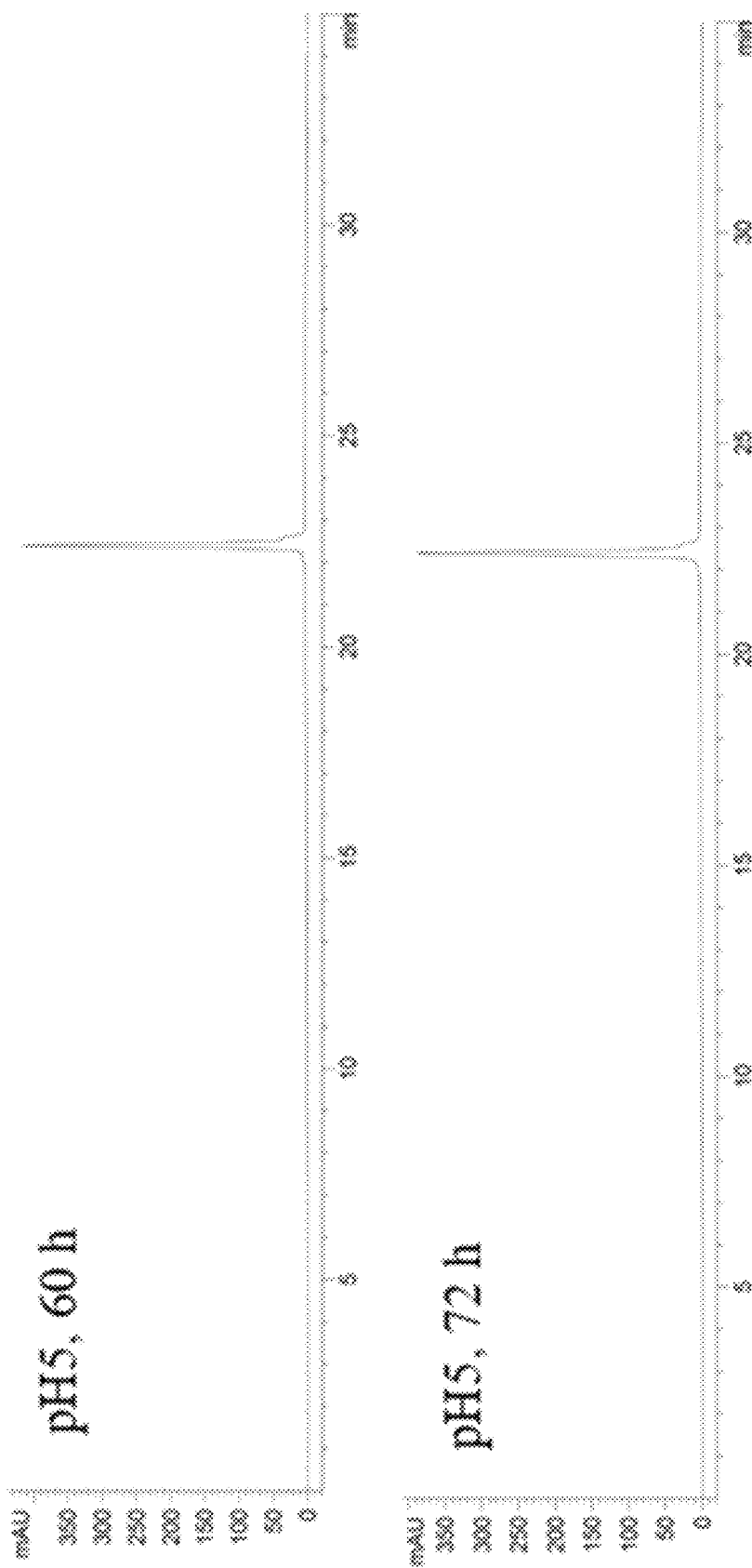
Figure 46:
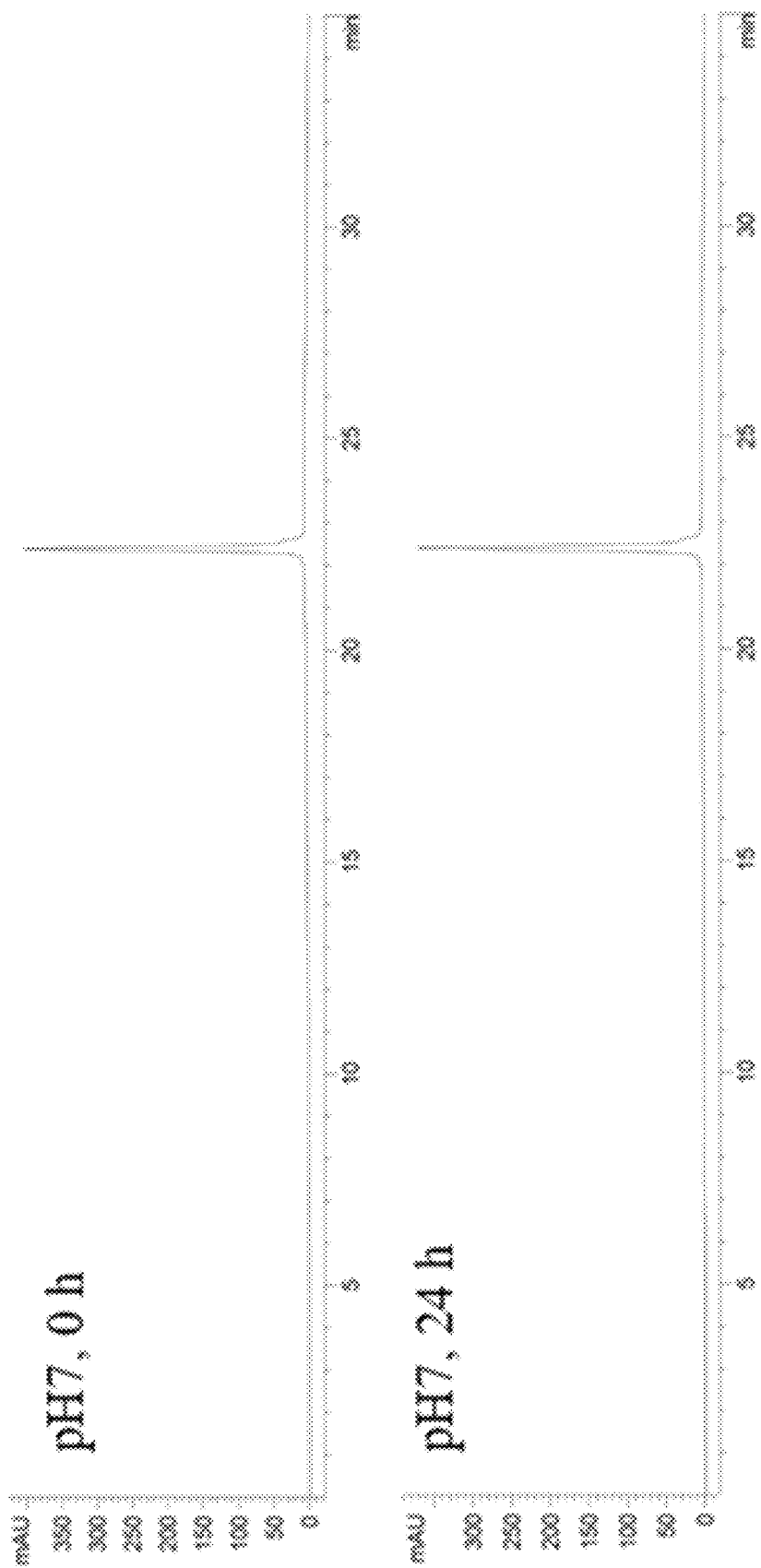
Figure 46:
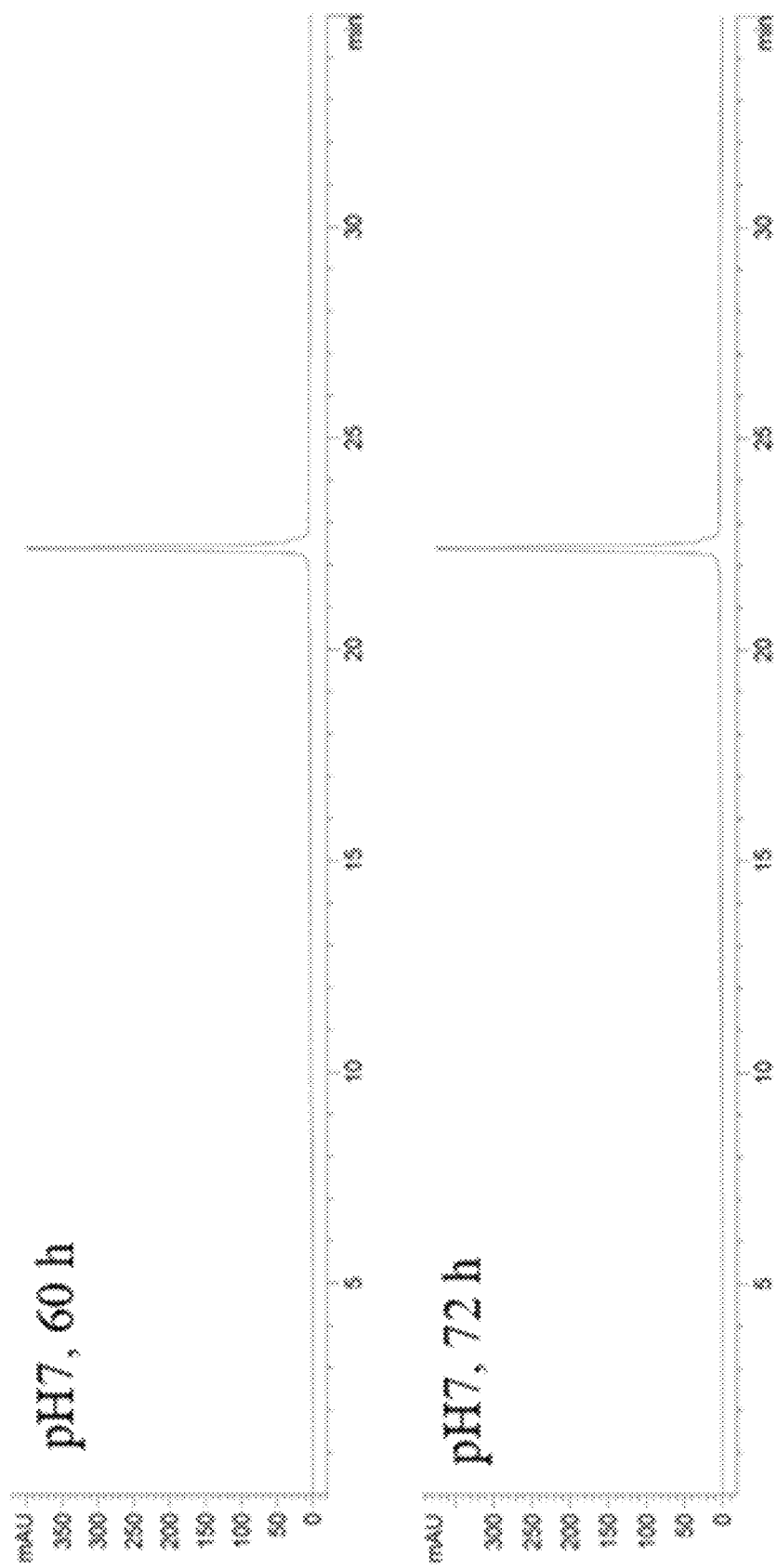
Figure 47:
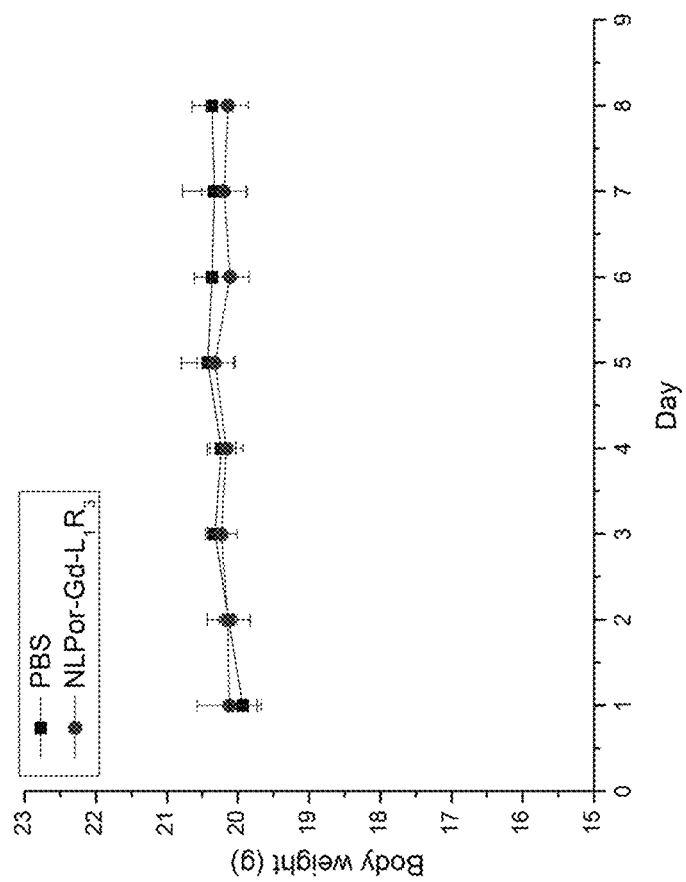
FIG. 47 shows the change in body weight of mice during in vivo PDT administered NLPor-Gd-L$_1$R$_3$.

The method of running the stability test is shown in FIG. 45, and FIG. 46-47 show the HPLC result of NLPor-Gd-$L_1R_3$ under pH 5 and pH 7. The results reveal that NLPor-Gd-L1R3 is very stable under different pH and so it is very safe to use owing to its inertness towards different pH condition and the metal Gd does not dissociate out from the complex.

VI Photodynamic Therapy (PDT) Assay

Figure 48:
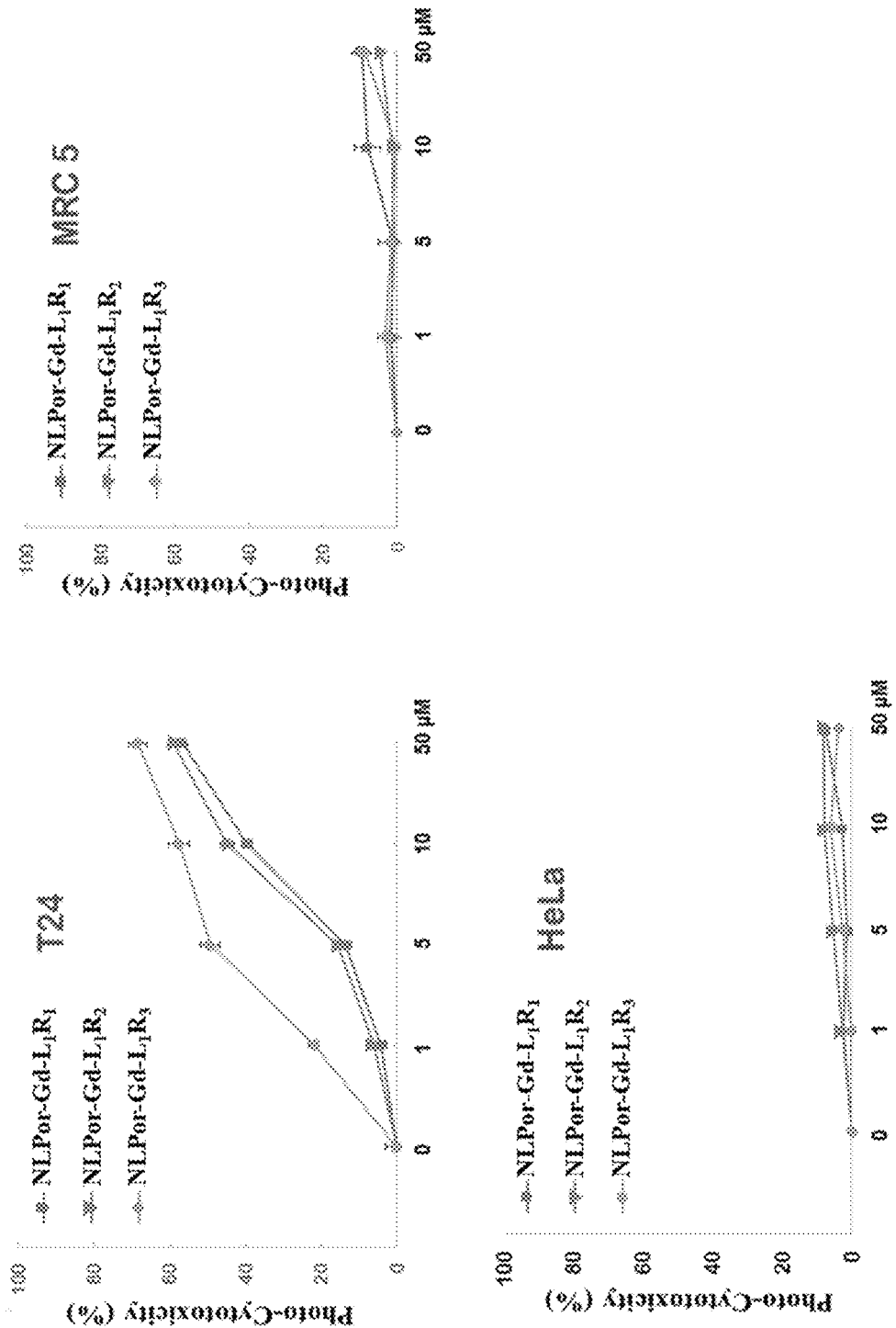
FIG. 48 shows the in vitro photo-cytotoxicity of NLPor-Gd-L$_1$R$_n$ (n=1-3) in T24, HeLa, and MRC-5 cells under 10 J cm$^{-2}$ irradiated with a 550 nm long-pass filter.

The three cell lines (HeLa, T24, and MRC-5) (1×10⁴ cells/mL) were seeded on 96-well plate overnight and different concentrations of NLPor-Gd-$L_1R_n$ (n=1-3) was added into the cells on the next day. After 24 hours incubation, the cells were exposed to blue light (1, 5, 10 J/cm²) produced from an LED lamp with power density 6 mWcm⁻². Then, MTT was added at 24 hours post-PDT and they were incubated at 37° C. for 3 hours. The formazan formed were dissolved in dimethyl sulfoxide (DMSO) and the absorbance of the solution was measured in a microplate reader at 540 nm wavelength (reference wavelength=690 nm) (FIG. 48).

What is claimed is:

1. A metal complex comprising a compound of Formula I:

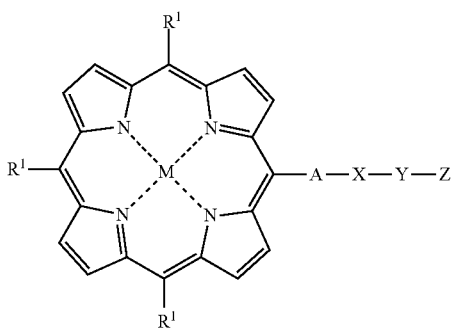

or a pharmaceutically acceptable salt thereof, wherein M has the structure:

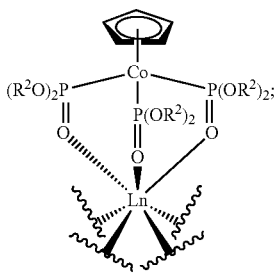

X is absent,

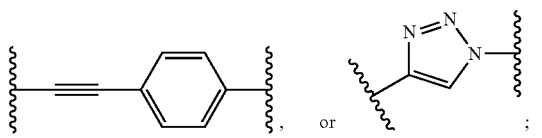 [SMILES: *C#Cc1ccc(*)cc1 ; *c1cn(*)nn1]

Y is —$(CH_2)_n$—; —$(CH_2CH_2O)_nCH_2$—; —$(CH_2CH_2O)_n$—; —$(OCH_2CH_2)_n$—; and Z is —(C=O)NHR$^3$; or M is 2H or Zn$^{2+}$;

X is absent;

Y is —$(OCH_2CH_2)_n$— or

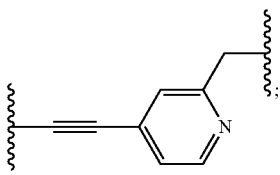 [SMILES: *C#Cc1ccnc(C*)c1]

and;

Z is

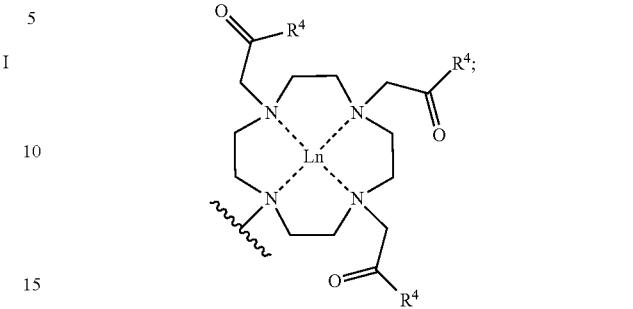

A is an optionally substituted phenyl;
n is a whole number selected between 1-10;
Ln for each instance is independently a paramagnetic metal ion;
each R$^1$ is independently optionally substituted aryl;
each R$^2$ is independently alkyl;
R$^3$ is SEQ ID NO:1, SEQ ID NO:2, or SEQ ID NO:3;
each R$^4$ is independently O$^-$, N(R$^5$)$_2$, or NHR$^3$; and
each R$^5$ is independently H or alkyl, with the proviso that at least one of M or Z comprises Ln and if M is 2H or Zn$^{2+}$; X is absent; and Y is —$(OCH_2CH_2)_n$—, then two instance of R$^4$ are each N(R$^5$)$_2$; and one instance of R$^4$ is NHR$^3$.

2. The metal complex of claim 1, wherein Ln is selected from Gd(III).

3. The metal complex of claim 1, wherein M has the structure:

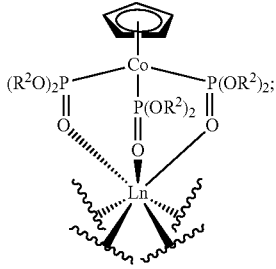

X is

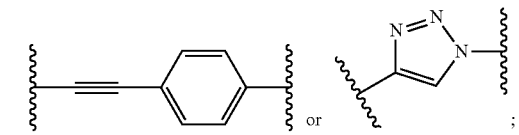

Y is —$(CH_2)_n$—; —$(CH_2CH_2O)_nCH_2$—; —$(CH_2CH_2O)_n$—; —$(OCH_2CH_2)_n$—; and
Z is —(C=O)NHR$^3$.

4. The metal complex of claim 3, wherein X is

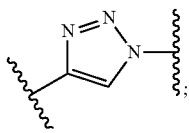 [SMILES: *c1cn(*)nn1]

Y is —$(CH_2CH_2O)_nCH_2$—; and R$^2$ C$_1$-C$_4$ alkyl.

5. The metal complex of claim 3, wherein X is
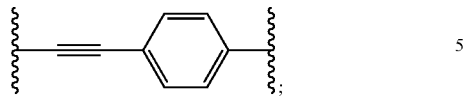
Y is —(CH$_2$CH$_2$O)$_n$—; and R$^2$ C$_1$-C$_4$ alkyl.
6. The metal complex of claim 1, wherein the compound of Formula I is selected from the group consisting of:
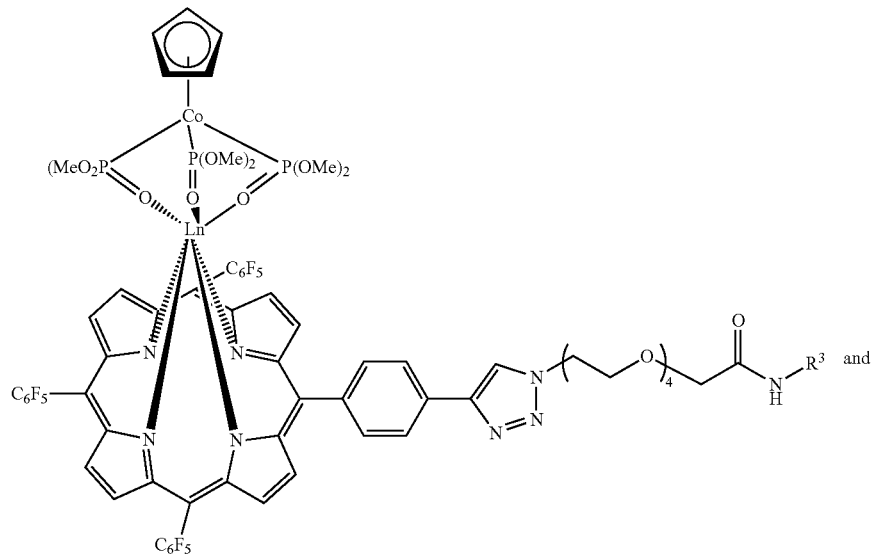
and
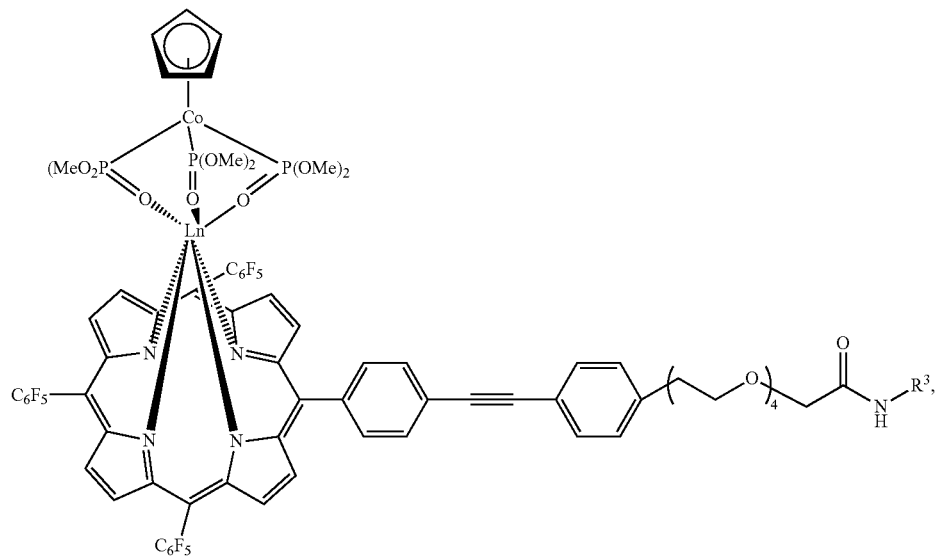
wherein Ln is Gd(III).

7. The metal complex of claim 1, wherein M is 2H or Zn²⁺; X is absent; Y is —(OCH₂CH₂)ₙ—; or

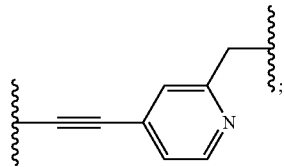 [SMILES: *C#Cc1ccnc(C*)c1]

and Z is

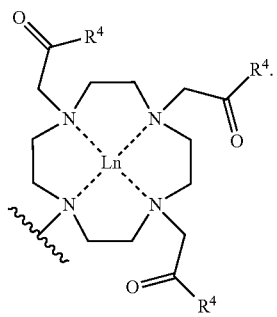

8. The metal complex of claim 7, wherein Y is

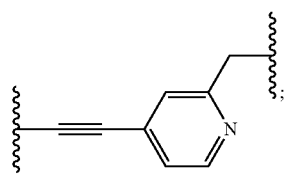 [SMILES: *C#Cc1ccnc(C*)c1]

and R⁴ is O— or NHR⁵.

9. The metal complex of claim 7, wherein Y is —(OCH₂CH₂)ₙ—; two instance of R⁴ are each N(R⁵)₂; and one instance of R⁴ is NHR³.

10. The metal complex of claim 1, wherein the compound of Formula I is selected from the group consisting of:

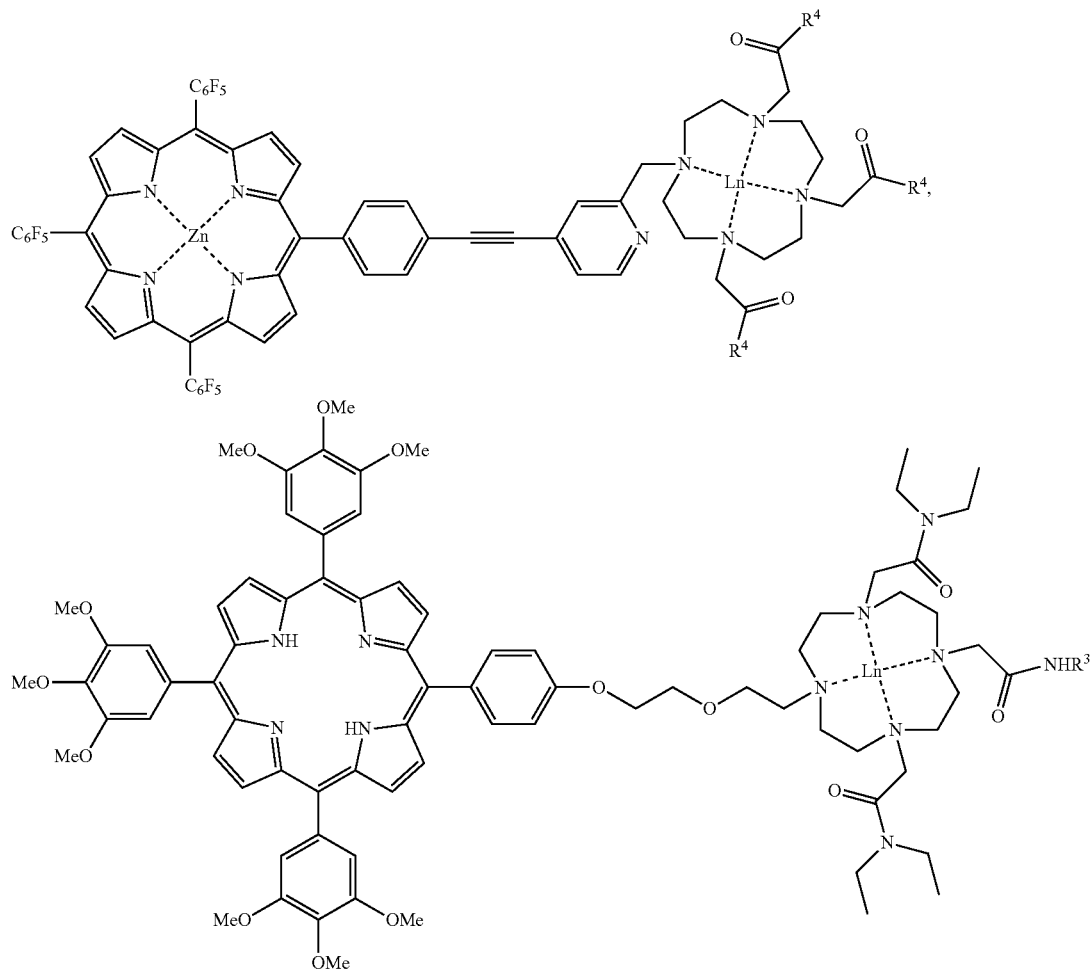

wherein Ln is Gd(III); and R⁴ is O⁻ or NH(tBu).

11. A pharmaceutical composition comprising the metal complex of claim 1 and at least one pharmaceutically acceptable excipient.

12. A method of imaging a subject by magnetic resonance imaging (MRI), the method comprising: administering a therapeutically effective amount of a metal complex of claim 1 to the subject; and imaging at least a portion of the subject by MRI.

13. The method claim 12, wherein the metal complex is selected from the group consisting of:

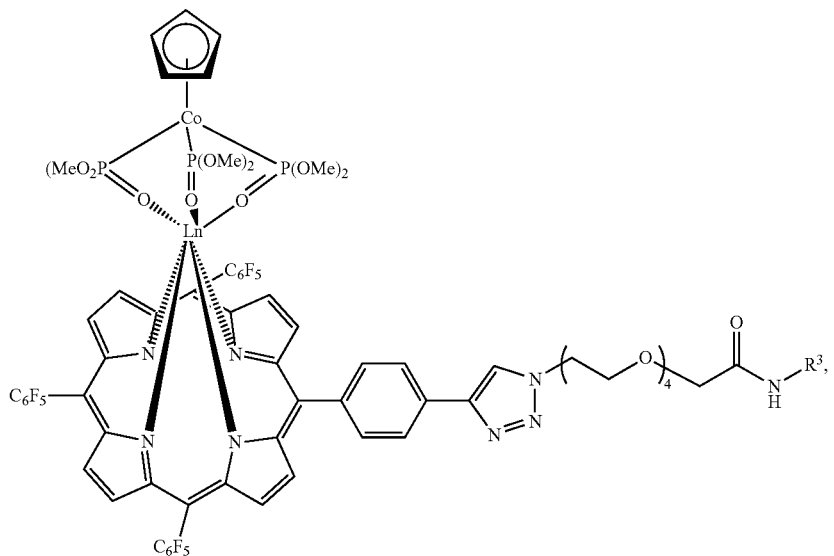

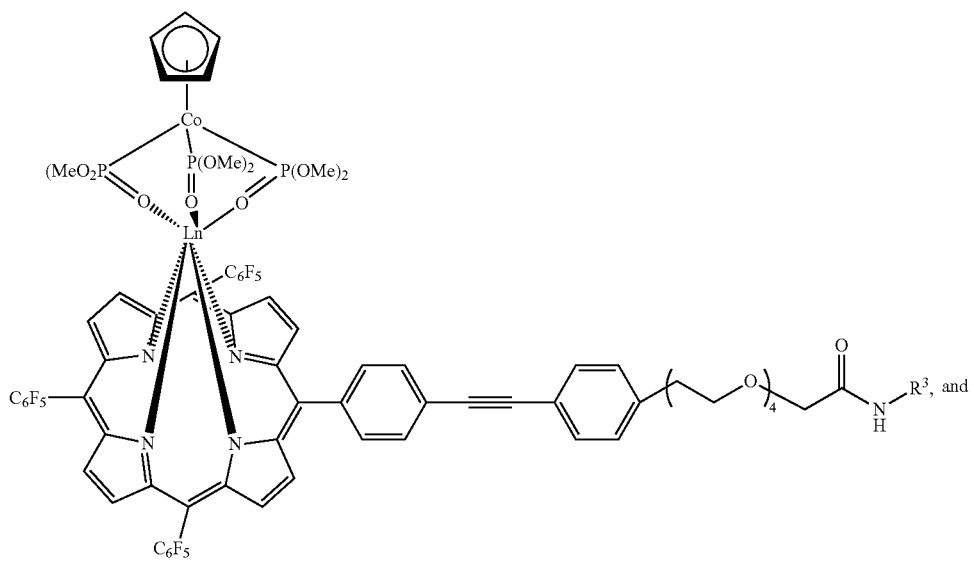

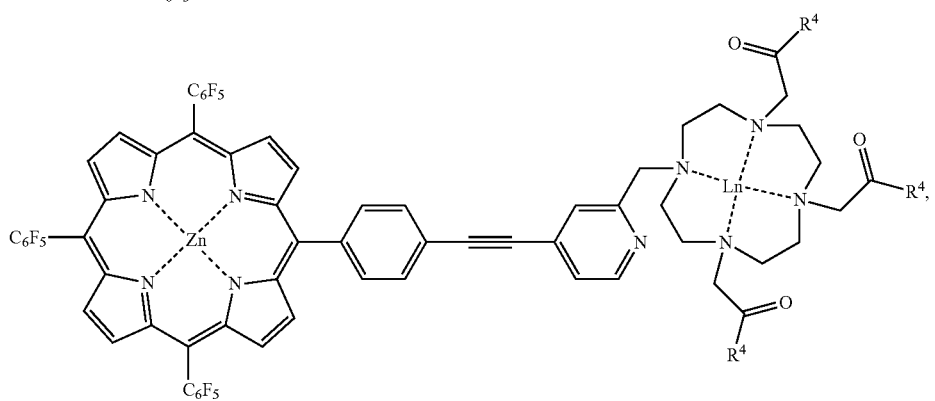

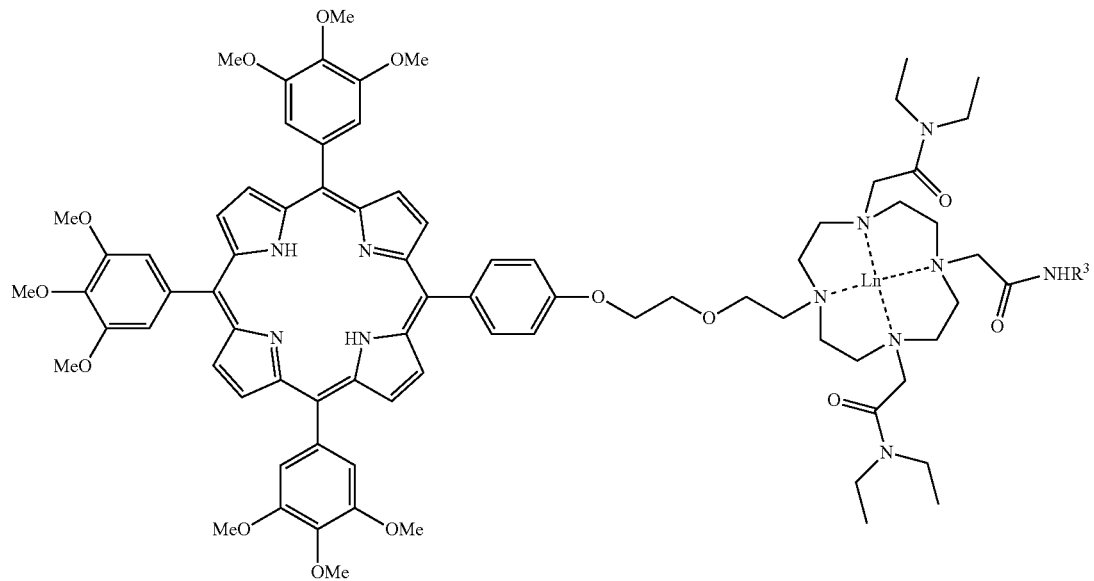

wherein Ln is Gd(III); and $R^4$ is $O^-$ or NH(tBu).

14. The method of claim 12 further comprising the step of administering a therapeutically effective amount of a cancer therapeutic to the subject.

15. A method of treating cancer in a subject in need thereof, the method comprising administering a therapeutically effective amount of a metal complex of claim 1; and irradiating a target tissue comprising the cancer with electromagnetic radiation having a wavelength within the activation wavelength of the metal complex.

16. The method of claim 15, wherein the cancer is bladder cancer.

17. The method claim 15, wherein the metal complex is selected from the group consisting of:

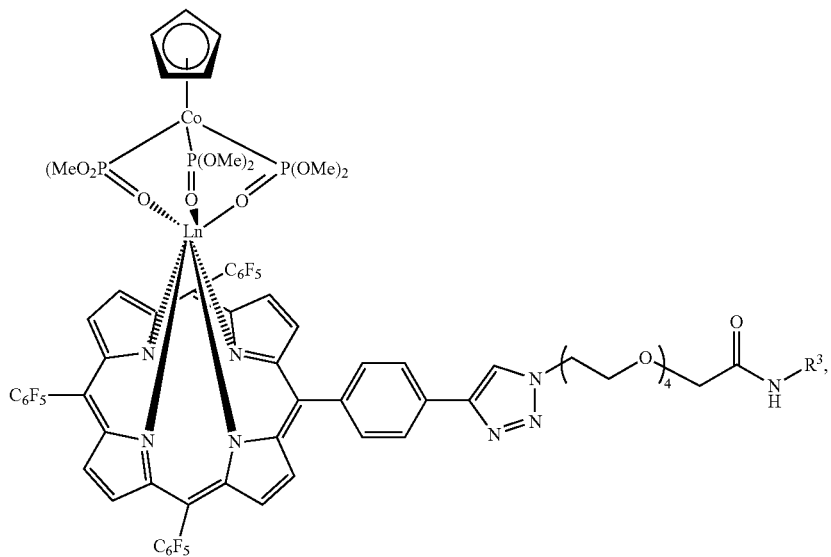

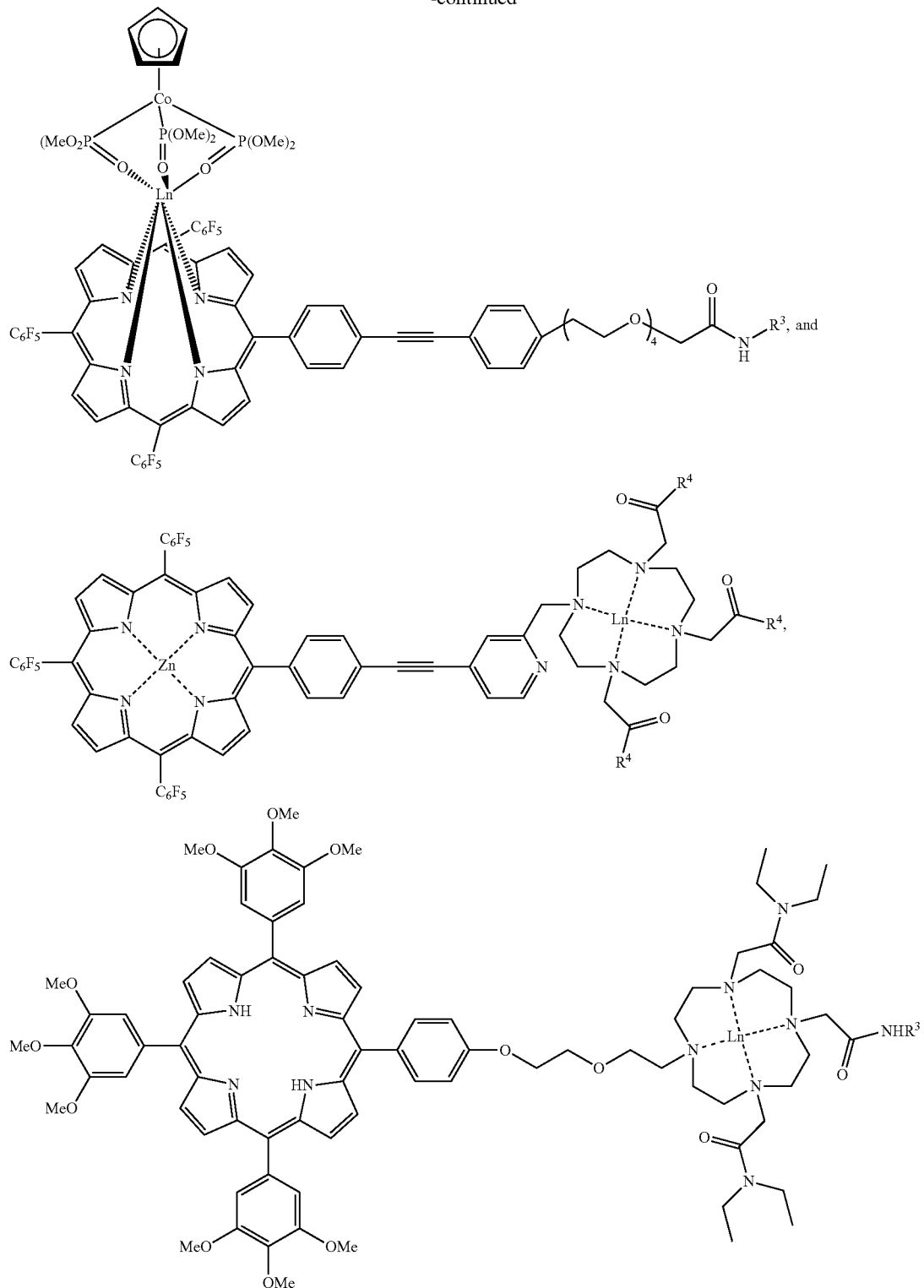

wherein Ln is Gd(III); and $R^4$ is $O^-$ or NH(tBu).

18. A method of imaging a subject by magnetic resonance imaging (MRI) and treating cancer in the subject, the method comprising: administering a therapeutically effective amount of a metal complex of claim 1 to the subject; irradiating a target tissue comprising the cancer with electromagnetic radiation having a wavelength within the activation wavelength of the metal complex; and imaging at least a portion of the subject by MRI.

19. The method claim 18, wherein the metal complex is selected from the group consisting of:

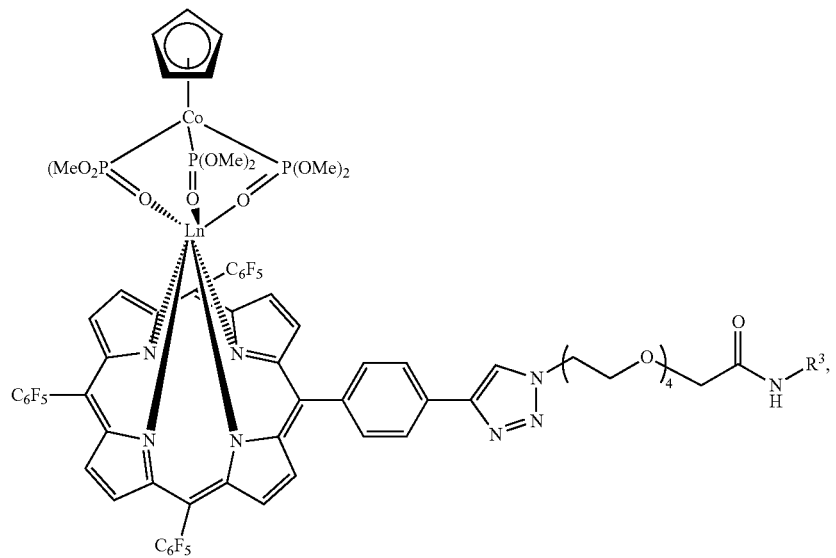
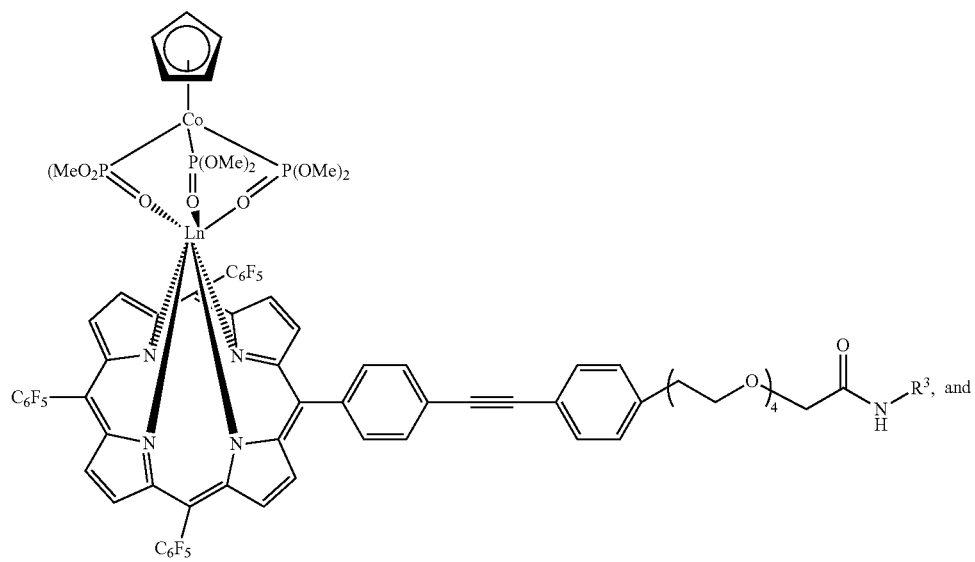
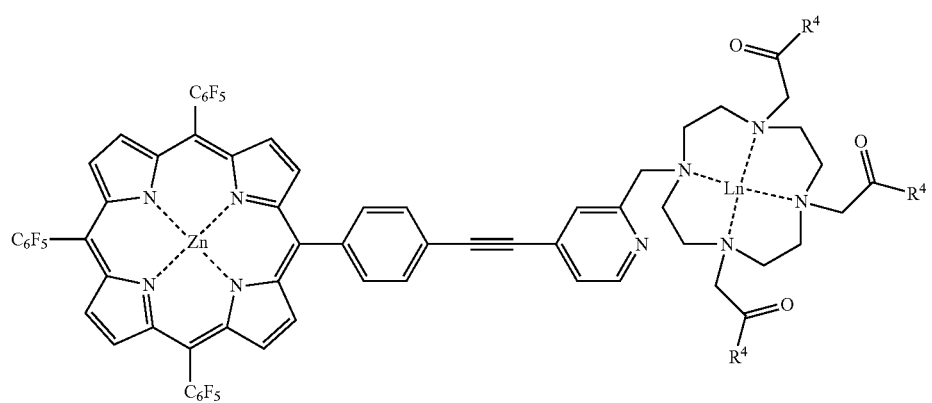

-continued
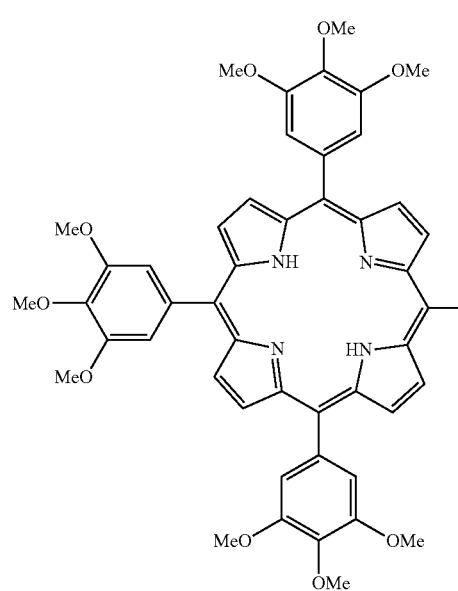 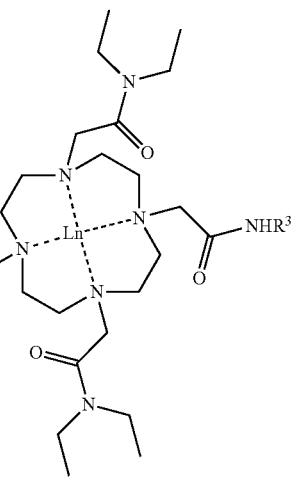
wherein Ln is Gd(III); and $R^4$ is $O^{31}$ or NH(tBu).
* * * * *

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: DISULFID
<222> LOCATION: (2)..(10)
<223> OTHER INFORMATION: The side chain of C in position two taken
      together with the side chain of C in position ten form a disulfide
      bond
<220> FEATURE:
<221> NAME/KEY: MISC_FEATURE
<222> LOCATION: (2)..(2)
<223> OTHER INFORMATION: C in position two is a D-amino acid
<220> FEATURE:
<221> NAME/KEY: MISC_FEATURE
<222> LOCATION: (10)..(10)
<223> OTHER INFORMATION: C in position ten is a D-amino acid
```

```
<400> SEQUENCE: 1

Xaa Cys Gln Asp Gly Arg Met Gly Phe Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: DISULFID
<222> LOCATION: (2)..(10)
<223> OTHER INFORMATION: The side chain of C in position two taken
      together with the side chain of C in position ten form a disulfide
      bond
<220> FEATURE:
<221> NAME/KEY: MISC_FEATURE
<222> LOCATION: (2)..(2)
<223> OTHER INFORMATION: C in position two is a D-amino acid
<220> FEATURE:
<221> NAME/KEY: MISC_FEATURE
<222> LOCATION: (10)..(10)
<223> OTHER INFORMATION: C in position ten is a D-amino acid

<400> SEQUENCE: 2

Xaa Cys Gly Arg Leu Lys Glu Lys Lys Cys
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: MISC_FEATURE
<222> LOCATION: (4)..(4)
<223> OTHER INFORMATION: Xaa in position four is a D-amino acid
<220> FEATURE:
<221> NAME/KEY: MISC_FEATURE
<222> LOCATION: (6)..(6)
<223> OTHER INFORMATION: Xaa in position six is 6-aminocaproic acid
<220> FEATURE:
<221> NAME/KEY: DISULFID
<222> LOCATION: (7)..(15)
<223> OTHER INFORMATION: The side chain of C in position seven taken
      together with the side chain of C in position fifteen form a
      disulfide bond CGR
<220> FEATURE:
<221> NAME/KEY: MISC_FEATURE
<222> LOCATION: (7)..(7)
<223> OTHER INFORMATION: C in position seven is a D-amino acid
<220> FEATURE:
<221> NAME/KEY: MISC_FEATURE
<222> LOCATION: (15)..(15)
<223> OTHER INFORMATION: C in position fifteen is a D-amino acid

<400> SEQUENCE: 3

Xaa Arg Arg Xaa Lys Xaa Cys Gly Arg Leu Lys Glu Lys Lys Cys
1               5                   10                  15
```